United States Patent
Avkin-Nachum et al.

(10) Patent No.: US 9,045,755 B2
(45) Date of Patent: Jun. 2, 2015

(54) DOUBLE STRANDED RNA COMPOUNDS TO RHOA AND USE THEREOF

(75) Inventors: Sharon Avkin-Nachum, Nes Zionna (IL); Elena Feinstein, Rehovot (IL); Hagar Kalinski, Rishon-le-Zion (IL); Igor Mett, Rehovot (IL)

(73) Assignee: QUARK PHARMACEUTICALS, INC., Fremont, CA (US)

(*) Notice: Subject to any disclaimer, the term of this patent is extended or adjusted under 35 U.S.C. 154(b) by 0 days.

(21) Appl. No.: 13/700,942

(22) PCT Filed: Jun. 23, 2011

(86) PCT No.: PCT/US2011/041562
§ 371 (c)(1),
(2), (4) Date: Nov. 29, 2012

(87) PCT Pub. No.: WO2011/163436
PCT Pub. Date: Dec. 29, 2011

(65) Prior Publication Data
US 2013/0137750 A1     May 30, 2013

Related U.S. Application Data

(60) Provisional application No. 61/358,012, filed on Jun. 24, 2010.

(51) Int. Cl.
*C07H 21/04* (2006.01)
*C12N 15/113* (2010.01)

(52) U.S. Cl.
CPC ........ *C12N 15/1137* (2013.01); *C12N 15/1135* (2013.01); *C12N 2310/14* (2013.01)

(58) Field of Classification Search
CPC .......................... C12N 2310/14; C12N 15/113
See application file for complete search history.

(56) References Cited

U.S. PATENT DOCUMENTS

| 5,945,290 A | 8/1999 | Cowsert |
|---|---|---|
| 6,410,323 B1 | 6/2002 | Roberts et al. |
| 2008/0108583 A1 | 5/2008 | Feinstein |
| 2013/0035368 A1* | 2/2013 | Avkin-Nachum et al. .. 514/44 A |

FOREIGN PATENT DOCUMENTS

| WO | WO 2005/113770 A1 | 12/2005 |
|---|---|---|
| WO | WO 2007/014075 A2 | 2/2007 |
| WO | WO 2007/014077 A2 | 2/2007 |
| WO | WO 2008/050329 A2 | 5/2008 |
| WO | WO 2009/044392 A2 | 4/2009 |
| WO | WO 2009/062199 A1 | 5/2009 |
| WO | WO 2010/058426 A2 | 5/2010 |
| WO | WO 2011/085056 A1 | 7/2011 |

OTHER PUBLICATIONS

Czauderna, F. et al. (2003). Structural variations and stabilising modifications of synthetic siRNAs in mammalian cells. *Nucleic Acids Research*, 31(11), 2705-2716.

International Search Report, mailed Nov. 28, 2011 in connection with PCT International Application No. PCT/US2011/041562, filed Jun. 23, 2011.

International Preliminary Report on Patentability (Chapter I of the Patent Cooperation Treaty), including Written Opinion of the International Searching Authority, issued Dec. 28, 2012 in connection with PCT International Application No. PCT/US2011/041562, filed Jun. 23, 2011.

* cited by examiner

*Primary Examiner* — Brian Whiteman
(74) *Attorney, Agent, or Firm* — John P. White; Cooper & Dunham LLP

(57) ABSTRACT

The present invention relates to compounds, pharmaceutical compositions comprising same, methods of use thereof and kits for the down-regulation of RhoA gene. The compounds, compositions, methods and kits are useful in the treatment of subjects suffering from diseases or conditions and or symptoms associated with diseases or conditions in which RhoA expression has adverse consequences and for conferring neuroprotection.

9 Claims, 13 Drawing Sheets

Figure 1

| siRNA_Name | Code Sense 5->3 (SEQ ID NO.) | Code AntiSense 5->3 (SEQ ID NO.) | 20 nM | 5 nM | 1 nM | 0.5 nM | 0.1 nM | 0.05 nM |
|---|---|---|---|---|---|---|---|---|
| RHOA_24_S75 | rG;mA;rA;mG;rG;mA;rU;mC;rU;mU;rC;mG;rG;mA;rA;mU;rG;mA;rU$ (SEQ ID NO: 164) | rA;rU;rC;rA;rU;rU;rC;rC;rG;rA;rA;rG;rA;rU;rC;rC;rU2p;rU2p;rC$ (SEQ ID NO: 168) | | | | | | |
| RHOA_24_S1245 | zc6Np;rG;rA;rA;rG;rG;rA;rU;rC;rU;rU;rC;rG;rG;rA;dA;yL;dA;rG;LdA;rU$ (SEQ ID NO: 164) | mA;rU;mC;rA;mU;rU;mC;rC;mG;rA;mA;rG;mA;rU;mC;rC;mU;rU;mC$ (SEQ ID NO: 168) | | | | | | |
| RHOA_29_S1585 | rU;rC;rG;rA;rC;rA;rG;rC;rC;rC;rU;rG;rA;rU;rA;rG;rU;rU;rU$ (SEQ ID NO: 166) | mA;rA;mA;rC;mU;rA;mU;rC;mA;rG;mG;rG;mC;rU;mG;rU;mC;rG;mA;zc3p;zc3p$ (SEQ ID NO: 170) | | | | | | |
| RHOA_29_S1602 | rU;rC;rG;rA;rC;rA;rG;rC;rC;rC;rU;rG;rA;rU;rA;rG;rU;rU;rU$ (SEQ ID NO: 166) | mA;rA;rA;mC;mU;rA;mU;mC;rA;rG;rG;rC;mU;rG;rU;mC;rG;rA;zc3p;zc3p$ (SEQ ID NO: 170) | | | | | | |
| RHOA_29_S992 | rU;rC;rG;rA;rC;rA;rG;rC;rC;rC;rU;rG;rA;rU;rA;rG;rU;rU;rU$ (SEQ ID NO: 166) | rA;mA;rA;mC;rU;mA;rU;mC;rA;rG;mG;rG;mC;rU;mG;rU;mC;rG;mA;zc3p;zc3p$ (SEQ ID NO: 170) | | | | | | |
| RHOA_29_S1625 | zc6Np;rU;rC;rG;rA;rC;rA;rG;rC;rC;rC;rU;rG;rA;rU;dA;dG;dT;dT;dT$ (SEQ ID NO: 166) | rA;mA;rA;mC;rU;mA;rU;mC;rA;rG;mG;rG;mC;rU;mG;rU;mC;rG;mA;zc3p;zc3p$ (SEQ ID NO: 170) | 12 | | | | | |
| RHOA_29_S1626 | zc6Np;rU;rC;rG;rA;rC;rA;rG;rC;rC;rC;rU;rG;rA;rU;dA;dG;dT;dT;dT$ (SEQ ID NO: 166) | mA;rA;mA;rC;mU;rA;mU;rC;mA;rG;mG;rG;mC;rU;mG;rU;mC;rG;mA;zc3p;zc3p$ (SEQ ID NO: 170) | 11 | | | | | |
| RHOA_29_S1636 | zc6Np;rU;rC;rG;rA;rC;rA;rG;rC;rC;rC;rU;rG;rA;rU;dA;dG;dT;dT;dT$ (SEQ ID NO: 166) | mA;rA;rA;mC;mU;rA;mU;mC;rA;rG;rG;rG;mC;mU;rG;mU;mC;rG;rA;zc3p;zc3p$ (SEQ ID NO: 170) | 100 | | | | | |
| RHOA_29_S1637 | zc6Np;rU;rC;rG;rA;rC;rA;rG;rC;rC;rC;rU;rG;rA;rU;dA;dG;dT;dT;dT$ (SEQ ID NO: 166) | mA;rA;rA;mC;mU;rA;mU;mC;rA;rG;rG;rG;rC;mU;rG;rU;mC;rG;rA;zc3p;zc3p$ (SEQ ID NO: 170) | 100 | | | | | |
| RHOA_29_S1638 | zc6Np;rU;rC;rG;rA;rC;rA;rG;rC;rC;rC;rU;rG;rA;rU;dA;dG;dT;dT;dT$ (SEQ ID NO: 166) | mA;rA;rA;mC;mU;rA;mU;mC;rA;rG;rG;rG;mC;mU;rG;rU;mC;rG;rA;zc3p;zc3p$ (SEQ ID NO: 170) | 37 | | | | | |
| RHOA_60_S1626 | zc6Np;rC;rA;rU;rC;rG;rA;rC;rA;rG;rC;rC;rC;rU;rG;dA;dT;dA;dG;dA$ (SEQ ID NO: 88) | mU;rC;mU;rA;mU;rC;mA;rG;mG;rG;mC;rU;mG;rU;mC;rG;mA;rU;mG;zc3p;zc3p$ (SEQ ID NO: 122) | 21 | | | | | |
| RHOA_60_S1585 | rC;rA;rU;rC;rG;rA;rC;rA;rG;rC;rC;rC;rU;rG;rA;rU;rA;rG;rA$ (SEQ ID NO: 88) | mU;rC;mU;rA;mU;rC;mA;rG;mG;rG;mC;rU;mG;rU;mC;rG;mA;rU;mG;zc3p;zc3p$ (SEQ ID NO: 122) | | | | | | |

Figure 1 (continued)

| siRNA_Name | Code Sense 5->3 (SEQ ID NO.) | Code AntiSense 5->3 (SEQ ID NO.) | 20 nM | 5 nM | 1 nM | 0.5 nM | 0.1 nM | 0.05 nM |
|---|---|---|---|---|---|---|---|---|
| RHOA_61 S1231 | rG;rA;rU;rC;rU;rU;rC;rG;rG;rA;rA;rU;rG;rA;rU;rG;rA;rG;rA;zc3p;zc3p$ (SEQ ID NO: 89) | rU;rC;rU;rC;rA;rU;rC;rA;rU;rU;rC;rC;rG;rA;rA;rG;rA;rU;rC;zc3p;zc3p$ (SEQ ID NO: 123) | | | | | | |
| RHOA_61 S1585 | rG;rA;rU;rC;rU;rU;rC;rG;rG;rA;rA;rU;rG;rA;rU;rG;rA;rG;rA$ (SEQ ID NO: 89) | mU;rC;mU;rC;mA;rU;mC;rA;mU;rU;mC;rC;mG;rA;mA;rG;mA;rU;mC;zc3p;zc3p$ (SEQ ID NO: 123) | | | | | | |
| RHOA_61 S1608 | rG;rA;rU;rC;rU;rU;rC;rG;rG;rA;rA;rU;rG;rA;rU;rG;rA;rG;rA$ (SEQ ID NO: 89) | mU;mC;mU;mC;rA;mU;mC;rA;mU;mU;mC;mC;rG;rA;rA;rG;rA;mU;rC;zc3p;zc3p$ (SEQ ID NO: 123) | | | | | | |
| RHOA_61 S1609 | rG;rA;rU;rC;rU;rU;rC;rG;rG;rA;rA;rU;rG;rA;rU;rG;rA;rG;rA$ (SEQ ID NO: 89) | mU;rC;mU;mC;rA;mU;mC;rA;mU;rU;mC;mC;rG;rA;rA;rG;rA;mU;rC;zc3p;zc3p$ (SEQ ID NO: 123) | | | | | | |
| RHOA_61 S1626 | zc6Np;rG;rA;rU;rC;rU;rU;rC;rG;rG;rA;rA;rU;rG;rA;dT;dG;dA;dG;dA$ (SEQ ID NO: 89) | mU;rC;mU;mC;rA;mU;mC;rA;mU;rU;mC;rC;mG;rA;mA;rG;mA;rU;mC;zc3p;zc3p$ (SEQ ID NO: 123) | | | | | | |
| RHOA_61 S1649 | rG;rA;rU;rC;rU;rU;rC;rG;rG;rA;rA;rU;rG;rA;rU;rG;rA;rG;y;rU;zc3p;zc3p$ (SEQ ID NO: 89) | yrA;rC;rU;rC;rA;rU;rC;rA;rU;rU;rC;rC;rG;rA;rA;rG;rA;rU;rC;zc3p;zc3p$ (SEQ ID NO: 123) | | | | | | |
| RHOA_61 S1650 | rG;rA;rU;rC;rU;rU;rC;rG;rG;rA;rA;rU;rG;rA;rU;rG;rA;rG;y;rC;zdT;zdT$ (SEQ ID NO: 89) | yrG;rC;rU;rC;rA;rU;rC;rA;rU;rU;rC;rC;rG;rA;rA;rG;rA;rU;rC;zdT;zdT$ (SEQ ID NO: 123) | | | | | | |
| RHOA_61 S1651 | rG;rA;rU;rC;rU;rU;rC;rG;rG;rA;rA;rU;rG;rA;rU;rG;rA;rG;rA;zc3p;zc3p$ (SEQ ID NO: 89) | dT;rC;rU;rC;rA;rU;rC;rA;rU;rU;rC;rC;rG;rA;rA;rG;rA;rU;rC;zc3p;zc3p$ (SEQ ID NO: 123) | | | | | | |
| RHOA_61 S1652 | rG;rA;rU;rC;rU;rU;rC;rG;rG;rA;rA;rU;rG;rA;rU;rG;rA;rG;rA;zc3p;zc3p$ (SEQ ID NO: 89) | dU;rC;rU;rC;rA;rU;rC;rA;rU;rU;rC;rC;rG;rA;rA;rG;rA;rU;rC;zc3p;zc3p$ (SEQ ID NO: 123) | | | | | | |
| RHOA_61 S1664 | rG;rA;rU;rC;rU;rU;rC;rG;rG;rA;rA;rU;rG;rA;rU;rG;rA;rG;rA;zc3p;zc3p$ (SEQ ID NO: 89) | mU;rC;rU;rC;rA;rU;rC;rA;rU;rU;rC;rC;rG;rA;rA;rG;rA;rU;rC;zc3p;zc3p$ (SEQ ID NO: 123) | | | | | | |
| RHOA_61 S1643 | zc6Np;rG;rA;rU;rC;rU;rU;rC;rG;rG;rA;rA;rU;rG;rA;dT;dG;dA;dG;dA$ (SEQ ID NO: 89) | mU;mC;mU;mC;rA;mU;mC;rA;mU;mU;mC;mC;rG;rA;rA;rG;rA;mU;rC;zc3p;zc3p$ (SEQ ID NO: 123) | 27 | | | | | |
| RHOA_61 S1644 | zc6Np;rG;rA;rU;rC;rU;rU;rC;rG;rG;rA;rA;rU;rG;rA;dT;dG;dA;dG;dA$ (SEQ ID NO: 89) | mU;rC;mU;mC;rA;mU;mC;rA;mU;rU;mC;mC;rG;rA;rA;rG;rA;mU;rC;zc3p;zc3p$ (SEQ ID NO: 123) | 37 | | | | | |

Figure 1 (continued)

| siRNA Name | Code Sense 5->3 (SEQ ID NO.) | Code AntiSense 5->3 (SEQ ID NO.) | 20 nM | 5 nM | 1 nM | 0.5 nM | 0.1 nM | 0.05 nM |
|---|---|---|---|---|---|---|---|---|
| RHOA_70_S1625 | zc6Np;rC;rA;rU;rC;rG;rA;rC;rA;rG;rC;rC;rC;rU;rG;dA;dT;dA;dG;dT$ (SEQ ID NO: 146) | rA;mC;rU;mA;rU;mC;rA;mG;rG;rG;mC;rU;mG;rU;mC;rG;mA;rU;mG;zc3p;zc3p$ (SEQ ID NO: 160) | 18 | | | | | |
| RHOA_70_S1626 | zc6Np;rC;rA;rU;rC;rG;rA;rC;rA;rG;rC;rC;rC;rU;rG;dA;dT;dA;dG;dT$ (SEQ ID NO: 146) | mA;rC;mU;rA;mU;rC;mA;rG;mG;rG;mC;rU;mG;rU;mC;rG;mA;rU;mG;zc3p;zc3p$ (SEQ ID NO: 160) | 28 | | | | | |
| RHOA_70_S1627 | zc6Np;rC;rA;rU;rC;rG;rA;rC;rA;rG;rC;rC;rC;rU;rG;dA;dT;dA;dG;dT$ (SEQ ID NO: 146) | rA;mC;mU;rA;mU;mC;rA;rG;rG;rG;mC;mU;rG;mU;mC;rG;rA;mU;rG;zc3p;zc3p$ (SEQ ID NO: 160) | 100 | | | | | |
| RHOA_70_S1628 | zc6Np;rC;rA;rU;rC;rG;rA;rC;rA;rG;rC;rC;rC;rU;rG;dA;dT;dA;dG;dT$ (SEQ ID NO: 146) | mA;rC;mU;rA;mU;mC;rA;rG;rG;rG;mC;mU;rG;mU;mC;rG;rA;mU;rG;zc3p;zc3p$ (SEQ ID NO: 160) | 100 | | | | | |
| RHOA_70_S1629 | zc6Np;rC;rA;rU;rC;rG;rA;rC;rA;rG;rC;rC;rC;rU;rG;dA;dT;dA;dG;dT$ (SEQ ID NO: 146) | mA;rC;mU;rA;mU;mC;rA;rG;rG;rG;mC;mU;rG;rU;mC;rG;rA;mU;rG;zc3p;zc3p$ (SEQ ID NO: 160) | 100 | | | | | |
| RHOA_75_S1626 | zc6Np;rU;rC;rG;rA;rC;rA;rG;rC;rC;rC;rU;rG;rA;rU;dA;dG;dT;dT;dA$ (SEQ ID NO: 100) | mU;rA;mA;rC;mU;rA;mU;rC;mA;rG;mG;rG;mC;rU;mG;rU;mC;rG;mA;zc3p;zc3p$ (SEQ ID NO: 134) | 8 | | | | | |
| RHOA_70_S992 | rC;rA;rU;rC;rG;rA;rC;rA;rG;rC;rC;rC;rU;rG;rA;rU;rA;rG;rU$ (SEQ ID NO: 146) | rA;mC;rU;mA;rU;mC;rA;mG;rG;rG;mC;rU;mG;rU;mC;rG;mA;rU;mG;zc3p;zc3p$ (SEQ ID NO: 160) | | | | | | |
| RHOA_70_S1585 | rC;rA;rU;rC;rG;rA;rC;rA;rG;rC;rC;rC;rU;rG;rA;rU;rA;rG;rU$ (SEQ ID NO: 146) | mA;rC;mU;rA;mU;rC;mA;rG;mG;rG;mC;rU;mG;rU;mC;rG;mA;rU;mG;zc3p;zc3p$ (SEQ ID NO: 160) | | | | | | |
| RHOA_70_S1586 | rC;rA;rU;rC;rG;rA;rC;rA;rG;rC;rC;rC;rU;rG;rA;rU;rA;rG;rU$ (SEQ ID NO: 146) | rA;mC;mU;rA;mU;mC;rA;rG;rG;rG;mC;mU;rG;mU;mC;rG;rA;mU;rG;zc3p;zc3p$ (SEQ ID NO: 160) | | | | | | |
| RHOA_70_S1587 | rC;rA;rU;rC;rG;rA;rC;rA;rG;rC;rC;rC;rU;rG;rA;rU;rA;rG;rU$ (SEQ ID NO: 146) | mA;rC;mU;rA;mU;mC;rA;rG;rG;rG;mC;mU;rG;mU;mC;rG;rA;mU;rG;zc3p;zc3p$ (SEQ ID NO: 160) | | | | | | |
| RHOA_70_S1588 | rC;rA;rU;rC;rG;rA;rC;rA;rG;rC;rC;rC;rU;rG;rA;rU;rA;rG;rU$ (SEQ ID NO: 146) | mA;rC;mU;rA;mU;mC;rA;rG;rG;rG;mC;mU;rG;rU;mC;rG;rA;mU;rG;zc3p;zc3p$ (SEQ ID NO: 160) | | | | | | |
| RHOA_70_S1589 | rC;rA;rU;rC;rG;rA;rC;rA;rG;rC;rC;rC;rU;rG;rA;rU;rA;rG;rU$ (SEQ ID NO: 146) | mA;rC;mU;rA;mU;mC;rA;rG;rG;rG;rC;mU;rG;rU;mC;rG;rA;mU;rG;zc3p;zc3p$ (SEQ ID NO: 160) | | | | | | |

Figure 1 (continued)

| siRNA_Name | Code Sense 5->3 (SEQ ID NO.) | Code AntiSense 5->3 (SEQ ID NO.) | 20 nM | 5 nM | 1 nM | 0.5 nM | 0.1 nM | 0.05 nM |
|---|---|---|---|---|---|---|---|---|
| RHOA_70_S1630 | zc6Np;rC;rA;rU;rC;rG;rA;rC;rA;rG;rC;rC;rC;rU;rG;dA;dT;dA;dG;dT$ (SEQ ID NO: 146) | mA;rC;mU;rA;mU;mC;rA;rG;rG;rG;rC;mU;rG;rU;mC;rG;rA;mU;rG;zc3p;zc3p$ (SEQ ID NO: 160) | | | | | | |
| RHOA_75_S1585 | rU;rC;rG;rA;rC;rA;rG;rC;rC;rC;rU;rG;rA;rU;rA;rG;rU;rU;rA$ (SEQ ID NO: 100) | mU;rA;mA;rC;mU;rA;mU;rC;mA;rG;mG;rG;mC;rU;mG;rU;mC;rG;mA;zc3p;zc3p$ (SEQ ID NO: 134) | | | | | | |
| RHOA_48_S1585 | rC;rA;rG;rA;rA;rG;rU;rC;rA;U;rC;rU;rU;rG;rC;rU;rA;rC;rA$ (SEQ ID NO: 79) | mU;rG;mU;rA;mG;rC;mA;rA;mG;rA;mU;rG;mA;rC;mU;rU;mC;rU;mG;zc3p;zc3p$ (SEQ ID NO: 113) | | | | | | |
| RHOA_48_S1591 | rC;rA;rG;rA;rA;rG;rU;rC;rA;U;rC;rU;rU;rG;rC;rU;rA;rC;rA$ (SEQ ID NO: 79) | mU;rG;mU;rA;rG;mC;rA;rA;rG;rA;mU;rG;rA;mC;mU;mU;mC;mU;rG;zc3p;zc3p$ (SEQ ID NO: 113) | | | | | | |
| RHOA_48_S1592 | rC;rA;rG;rA;rA;rG;rU;rC;rA;U;rC;rU;rU;rG;rC;rU;rA;rC;rA$ (SEQ ID NO: 79) | mU;rG;mU;rA;rG;mC;rA;rA;rG;rA;mU;rG;rA;mC;mU;rU;mC;mU;rG;zc3p;zc3p$ (SEQ ID NO: 113) | | | | | | |
| RHOA_48_S1593 | rC;rA;rG;rA;rA;rG;rU;rC;rA;U;rC;rU;rU;rG;rC;rU;rA;rC;rA$ (SEQ ID NO: 79) | mU;rG;mU;rA;rG;mC;rA;rA;rG;rA;mU;rG;rA;mC;rU;mU;mC;mU;rG;zc3p;zc3p$ (SEQ ID NO: 113) | | | | | | |
| RHOA_48_S1594 | rC;rA;rG;rA;rA;rG;rU;rC;rA;U;rC;rU;rU;rG;rC;rU;rA;rC;rA$ (SEQ ID NO: 79) | mU;rG;mU;rA;rG;mC;rA;rA;rG;rA;mU;rG;mA;rC;mU;rU;mC;rU;mG;zc3p;zc3p$ (SEQ ID NO: 113) | | | | | | |
| RHOA_48u_S1596 | rC;rA;rG;rA;rA;rG;rU;rC;rA;U;rC;rU;rU;rG;rC;rU;rA;rC;y;rU$ (SEQ ID NO: 80) | yrA;mG;rU;mA;rG;mC;rA;mA;rG;rA;mU;rG;mA;rC;mU;rU;mC;rU;mG;zc3p;zc3p$ (SEQ ID NO: 114) | | | | | | |
| RHOA_48_S1626 | zc6Np;rC;rA;rG;rA;rA;rG;rU;rC;rA;rU;rC;rU;rU;rG;dC;dT;dA;dC;dA$ (SEQ ID NO: 79) | mU;rG;mU;rA;mG;rC;mA;rA;mG;rA;mU;rG;mA;rC;mU;rU;mC;rU;mG;zc3p;zc3p$ (SEQ ID NO: 113) | | | | | | |
| RHOA_48_S1631 | zc6Np;rC;rA;rG;rA;rA;rG;rU;rC;rA;rU;rC;rU;rU;rG;dC;dT;dA;dC;dA$ (SEQ ID NO: 79) | mU;rG;mU;rA;rG;mC;rA;rA;rG;rA;mU;rG;rA;mC;mU;mU;mC;mU;rG;zc3p;zc3p$ (SEQ ID NO: 113) | | | | | | |
| RHOA_48_S1632 | zc6Np;rC;rA;rG;rA;rA;rG;rU;rC;rA;rU;rC;rU;rU;rG;dC;dT;dA;dC;dA$ (SEQ ID NO: 79) | mU;rG;mU;rA;rG;mC;rA;rA;rG;rA;mU;rG;rA;mC;mU;rU;mC;mU;rG;zc3p;zc3p$ (SEQ ID NO: 113) | | | | | | |
| RHOA_48_S1633 | zc6Np;rC;rA;rG;rA;rA;rG;rU;rC;rA;rU;rC;rU;rU;rG;dC;dT;dA;dC;dA$ (SEQ ID NO: 79) | mU;rG;mU;rA;rG;mC;rA;rA;rG;rA;mU;rG;rA;mC;rU;mU;mC;rU;mG;zc3p;zc3p$ (SEQ ID NO: 113) | | | | | | |

Figure 1 (continued)

| siRNA_Name | Code Sense 5->3 (SEQ ID NO.) | Code AntiSense 5->3 (SEQ ID NO.) | 20 nM | 5 nM | 1 nM | 0.5 nM | 0.1 nM | 0.05 nM |
|---|---|---|---|---|---|---|---|---|
| RHOA_48_S1634 | zc6Np;rC;rA;rG;rA;rA;rG;rU;rC;rA;rU;rC;rU;rU;rG;dC;dT;dA;dC;dA$ (SEQ ID NO: 79) | mU;rG;mU;rA;rG;mC;rA;rA;rG;rA;mU;rG;mA;rC;mU;rU;mC;rU;mG;zc3p;zc3p$ (SEQ ID NO: 113) | | | | | | |
| RHOA_48u_S1635 | zc6Np;rC;rA;rG;rA;rA;rG;rU;rC;rA;rU;rC;rU;rU;rG;dC;dT;dA;dC;ydT$ (SEQ ID NO: 80) | yrA;mG;rU;mA;rG;mC;rA;mA;rG;rA;mU;rG;mA;rC;mU;rU;mC;rU;mG;zc3p;zc3p$ (SEQ ID NO: 114) | | | | | | |
| RHOA_48u_S1812 | zidB;rC;rA;rG;rA;rA;rG;rU;rC;rA;rU;rC;rU;rU;rG;rC2p;rU2p;rA2p;rC2p;yrU2p;zc3p (SEQ ID NO: 80) | yrA;rG;mU;rA;rG;mC;rA2p;rA;rG;rA;mU;rG;rA;mC;mU;rU;mC;mU;rG;zc3p;zc3p$ (SEQ ID NO: 114) | 20 | 23 | 27 | 54 | | |
| RHOA_48u_S1813 | zidB;rC;rA;rG;rA;rA;rG;rU;rC;rA2p;rU;rC;rU;mU;rG;rC;mU;rA;rC;yrU;zc3p (SEQ ID NO: 80) | yrA;rG;mU;rA;rG;mC;rA2p;rA;rG;rA;mU;rG;rA;mC;mU;rU;mC;mU;rG;zc3p;zc3p$ (SEQ ID NO: 114) | 16 | 15 | 22 | 42 | | |
| RHOA_48_S1814 | zidB;rC;rA;rG;rA;rA;rG;rU;rC;rA;rU;rC;rU;rU;rG;rC2p;rU2p;rA2p;rC2p;rA2p;zc3p (SEQ ID NO: 79) | dU;rG;mU;rA;rG;mC;rA2p;rA;rG;rA;mU;rG;rA;mC;mU;rU;mC;mU;rG;zc3p;zc3p$ (SEQ ID NO: 113) | 32 | 59 | 48 | na | | |
| RHOA_48_S1815 | zidB;rC;rA;rG;rA;rA;rG;rU;rC;rA2p;rU;rC;rU;rU;rG;rC;mU;rA;mC;rA;zc3p (SEQ ID NO: 79) | dU;rG;mU;rA;rG;mC;rA2p;rA;rG;rA;mU;rG;rA;mC;mU;rU;mC;mU;rG;zc3p;zc3p$ (SEQ ID NO: 113) | 24 | 31 | 47 | 61 | | |
| RHOA_48_S1833 | zidB;rC;rA;rG;rA;rA;rG;rU;rC;rA;rU;rC;rU;rU;rG;rC2p;rU2p;rA2p;rC2p;rA2p;zc3p (SEQ ID NO: 79) | mU;rG;mU;rA;rG;mC;rA;rA;rG;rA;mU;rG;rA;mC;mU;rU;mC;mU;rG;zc3p;zc3p$ (SEQ ID NO: 113) | 16 | 22 | 25 | 35 | | |
| RHOA_48_S1834 | zidB;rC;rA;rG;rA;rA;rG;rU;rC;rA2p;rU;rC;rU;rU;rG;rC;mU;rA;mC;rA;zc3p (SEQ ID NO: 79) | mU;rG;mU;rA;rG;mC;rA;rA;rG;rA;mU;rG;rA;mC;mU;rU;mC;mU;rG;zc3p;zc3p$ (SEQ ID NO: 113) | 18 | 36 | 57 | 71 | | |
| RHOA_48_S1856 | zidB;mC;rA;rG;rA;rA;rG;rU;rC;rA;rU;rC;rU;rU;rG;rC2p;rU2p;rA2p;rC2p;rA2p;zc3p (SEQ ID NO: 79) | mU;rG;mU;rA;rG;mC;rA2p;rA;rG;rA;mU;rG;rA;mC;mU;rU;mC;mU;rG;zc3p;zc3p$ (SEQ ID NO: 113) | 32 | 28 | 48 | 64 | 69 | |
| RHOA_48_S1857 | zidB;mC;rA;rG;rA;rA;rG;rU;rC;rA;rU;rC;rU;rU;rG;rC2p;rU2p;rA2p;rC2p;rA2p;zc3p (SEQ ID NO: 79) | mU;rG;mU;rA;rG;rC2p;rA;rA;rG;rA;mU;rG;rA;mC;mU;rU;mC;mU;rG;zc3p;zc3p$ (SEQ ID NO: 113) | 8 | 10 | 14 | 14 | 32 | |
| RHOA_48_S1858 | zidB;mC;rA;rG;rA;rA;rG;rU;rC;rA;rU;rC;rU;rU;rG;rC2p;rU2p;rA2p;rC2p;rA2p;zc3p (SEQ ID NO: 79) | mU;rG;mU;rA;rG;rC2p;rA2p;rA;rG;rA;mU;rG;rA;mC;mU;rU;mC;mU;rG;zc3p;zc3p$ (SEQ ID NO: 113) | | | | | | |
| RHOA_48_S1859 | zidB;mC;rA;rG;rA;rA;rG;rU;rC;rA;rU;rC;rU;rU;rG;rC2p;rU2p;rA2p;rC2p;rA2p;zc3p (SEQ ID NO: 79) | mU;rG;mU;rA;rG;LdC;rA;rA;rG;rA;mU;rG;rA;mC;mU;rU;mC;mU;rG;zc3p;zc3p$ (SEQ ID NO: 113) | | | | | | |

Figure 1 (continued)

| siRNA_Name | Code Sense 5->3 (SEQ ID NO.) | Code AntiSense 5->3 (SEQ ID NO.) | 20 nM | 5 nM | 1 nM | 0.5 nM | 0.1 nM | 0.05 nM |
|---|---|---|---|---|---|---|---|---|
| RHOA_48_S1860 | zidB;mC;rA;rG;rA;rA;rG;rU;rC;rA;rU;rC;rU;rU;rG;rC2p;rU2p;rA2p;rC2p;rA2p;zc3p (SEQ ID NO: 79) | mU;rG;mU;rA;rG;mC;rA;LdC;rA;rG;rA;mU;rG;rA;mC;mU;rU;mC;mU;rG;zc3p;zc3p$ (SEQ ID NO: 113) | | | | | | |
| RHOA_48_S1870 | zLdG;mC;rA;rG;rA;rA;rG;rU;rC;rA;rU;rC;rU;rU;rG;rC2p;rU2p;rA2p;rC2p;yrU2p;zc3p (SEQ ID NO: 79) | yrA;rG;mU;rA;rG;mC;rA2p;rA;rG;rA;mU;rG;rA;mC;mU;rU;mC;mU;rG;zc3p;zc3p$ (SEQ ID NO: 113) | | | | 35 | 56 | 59 |
| RHOA_48_S1871 | zidB;mC;rA;rG;rA;rA;rG;rU;rC;rA;rU;rC;rU;rU;rG;rC2p;rU2p;rA2p;rC2p;yrU2p;zc3p (SEQ ID NO: 79) | yrA;rG;mU;rA;rG;mC;rA2p;rA;rG;rA;mU;rG;rA;mC;mU;rU;mC;mU;rG;zc3p;zc3p$ (SEQ ID NO: 113) | | | 27 | 26 | | 73 |
| RHOA_48_S1872 | zLdG;mC;rA;rG;rA;rA;rG;rU;rC;rA;rU;rC;rU;rU;rG;rC2p;rU2p;rA2p;rC2p;rA2p;zc3p (SEQ ID NO: 79) | mU;rG;mU;rA;rG;mC;rA2p;rA;rG;rA;mU;rG;rA;mC;mU;rU;mC;mU;rG;zc3p;zc3p$ (SEQ ID NO: 113) | | | 36 | 61 | 79 | 84 |
| RHOA_48_S1873 | zLdG;mC;rA;rG;rA;rA;rG;rU;rC;rA;rU;rC;rU;rU;rG;rC2p;rU2p;rA2p;rC2p;rA2p;zc3p (SEQ ID NO: 79) | mU;rG;mU;rA;rG;rC2p;rA;rA;rG;rA;mU;rG;rA;mC;mU;rU;mC;mU;rG;zc3p;zc3p$ (SEQ ID NO: 113) | | 16 | 15 | 18 | 22 | 31 |
| RHOA_48_S1874 | zLdG;mC;rA;rG;rA;rA;rG;rU;rC;rA;rU;rC;rU;rU;rG;rC2p;rU2p;rA2p;rC2p;rA2p;zc3p (SEQ ID NO: 79) | mU;rG;mU;rA;rG;rC2p;rA2p;rA;rG;rA;mU;rG;rA;mC;mU;rU;mC;mU;rG;zc3p;zc3p$ (SEQ ID NO: 113) | | | | | | |
| RHOA_48_S1875 | zLdG;mC;rA;rG;rA;rA;rG;rU;rC;rA;rU;rC;rU;rU;rG;rC2p;rU2p;rA2p;rC2p;rA2p;zc3p (SEQ ID NO: 79) | mU;rG;mU;rA;rG;LdC;rA;rA;rG;rA;mU;rG;rA;mC;mU;rU;mC;mU;rG;zc3p;zc3p$ (SEQ ID NO: 113) | | | | | | |
| RHOA_48_S1876 | zLdG;mC;rA;rG;rA;rA;rG;rU;rC;rA;rU;rC;rU;rU;rG;rC2p;rU2p;rA2p;rC2p;rA2p;zc3p (SEQ ID NO: 79) | mU;rG;mU;rA;rG;mC;rA;LdC;rA;rG;rA;mU;rG;rA;mC;mU;rU;mC;mU;rG;zc3p;zc3p$ (SEQ ID NO: 113) | | | | | | |
| RHOA_48_S1884 | zidB;mC;rA;rG;rA;rA;rG;rU;rC;rA;rU;rC;rU;rU;rG;rC2p;rU2p;rA2p;rC2p;rA2p;zc3p (SEQ ID NO: 79) | rp;LdT;rG;mU;rA;rG;mC;rA2p;rA;rG;rA;mU;rG;rA;mC;mU;rU;mC;mU;rG;zc3p;zc3p$ (SEQ ID NO: 113) | | | | | | |
| RHOA_48_S1885 | zidB;mC;rA;rG;rA;rA;rG;rU;rC;rA;rU;rC;rU;rU;rG;rC2p;rU2p;rA2p;rC2p;rA2p;zc3p (SEQ ID NO: 79) | rp;rU2p;rG;mU;rA;rG;mC;rA2p;rA;rG;rA;mU;rG;rA;mC;mU;rU;mC;mU;rG;zc3p;zc3p$ (SEQ ID NO: 113) | | | | | | |
| RHOA_48_S1886 | zidB;mC;rA;rG;rA;rA;rG;rU;rC;rA;rU;rC;rU;rU;rG;rC2p;rU2p;rA2p;rC2p;rA2p;zc3p (SEQ ID NO: 79) | rp;yc3p;rG;mU;rA;rG;mC;rA2p;rA;rG;rA;mU;rG;rA;mC;mU;rU;mC;mU;rG;zc3p;zc3p$ (SEQ ID NO: 113) | | | | | | |
| RHOA_48_S1887 | zidB;mC;rA;rG;rA;rA;rG;rU;rC;rA;rU;rC;rU;rU;rG;rC2p;rU2p;rA2p;rC2p;rA2p;zc3p (SEQ ID NO: 79) | rp;mU;rG;mU;rA;rG;mC;rA2p;rA;rG;rA;mU;rG;rA;mC;mU;rU;mC;mU;rG;zc3p;zc3p$ (SEQ ID NO: 113) | | | | | | |

Figure 1 (continued)

| siRNA Name | Code Sense 5->3 (SEQ ID NO.) | Code AntiSense 5->3 (SEQ ID NO.) | 20 nM | 5 nM | 1 nM | 0.5 nM | 0.1 nM | 0.05 nM |
|---|---|---|---|---|---|---|---|---|
| RHOA_48_S709 | (SEQ ID NO: 79) | (SEQ ID NO: 113) | | 18 | 26 | 31 (15) | 61 (23) | na (18) |
| RHOA_50_S1585 | rG;rU;rG;rG;rC;rA;rG;rA;rG;rU;rU;rA;rC;rA;rG;rU;rU;rC;rA$ (SEQ ID NO: 82) | mU;rG;mA;rA;mC;rU;mG;rU;mA;rA;mC;rU;mC;rU;mG;rC;mC;rA;mC;zc3p;zc3p$ (SEQ ID NO: 116) | | | | | | |
| RHOA_50_S1604 | rG;rU;rG;rG;rC;rA;rG;rA;rG;rU;rU;rA;rC;rA;rG;rU;rU;rC;rA$ (SEQ ID NO: 82) | mU;rG;rA;rA;mC;mU;rG;mU;rA;rA;mC;mU;mC;mU;rG;mC;mC;rA;rC;zc3p;zc3p$ (SEQ ID NO: 116) | | | | | | |
| RHOA_50_S1605 | rG;rU;rG;rG;rC;rA;rG;rA;rG;rU;rU;rA;rC;rA;rG;rU;rU;rC;rA$ (SEQ ID NO: 82) | mU;rG;rA;rA;mC;mU;rG;mU;rA;rA;rC;mU;mC;mU;rG;mC;mC;rA;rC;zc3p;zc3p$ (SEQ ID NO: 116) | | | | | | |
| RHOA_50_S1606 | rG;rU;rG;rG;rC;rA;rG;rA;rG;rU;rU;rA;rC;rA;rG;rU;rU;rC;rA$ (SEQ ID NO: 82) | mU;rG;rA;rA;mC;mU;rG;mU;rA;rA;mC;mU;rC;mU;rG;mC;mC;rA;rC;zc3p;zc3p$ (SEQ ID NO: 116) | | | | | | |
| RHOA_50_S1607 | rG;rU;rG;rG;rC;rA;rG;rA;rG;rU;rU;rA;rC;rA;rG;rU;rU;rC;rA$ (SEQ ID NO: 82) | mU;rG;rA;rA;mC;mU;rG;mU;rA;rA;mC;rU;rC;mU;rG;mC;mC;rA;rC;zc3p;zc3p$ (SEQ ID NO: 116) | | | | | | |
| RHOA_50_S1626 | zc6Np;rG;rU;rG;rG;rC;rA;rG;rA;rG;rU;rU;rA;rC;rA;dG;dT;dT;dC;dA$ (SEQ ID NO: 82) | mU;rG;mA;rA;mC;rU;mG;rU;mA;rA;mC;rU;mC;rU;mG;rC;mC;rA;mC;zc3p;zc3p$ (SEQ ID NO: 116) | | | | | | |
| RHOA_50_S1639 | zc6Np;rG;rU;rG;rG;rC;rA;rG;rA;rG;rU;rU;rA;rC;rA;dG;dT;dT;dC;dA$ (SEQ ID NO: 82) | mU;rG;rA;rA;mC;mU;rG;mU;rA;rA;mC;mU;mC;mU;rG;mC;mC;rA;rC;zc3p;zc3p$ (SEQ ID NO: 116) | | | | | | |
| RHOA_50_S1640 | zc6Np;rG;rU;rG;rG;rC;rA;rG;rA;rG;rU;rU;rA;rC;rA;dG;dT;dT;dC;dA$ (SEQ ID NO: 82) | mU;rG;rA;rA;mC;mU;rG;mU;rA;rA;rC;mU;mC;mU;rG;mC;mC;rA;rC;zc3p;zc3p$ (SEQ ID NO: 116) | | | | | | |
| RHOA_50_S1641 | zc6Np;rG;rU;rG;rG;rC;rA;rG;rA;rG;rU;rU;rA;rC;rA;dG;dT;dT;dC;dA$ (SEQ ID NO: 82) | mU;rG;rA;rA;mC;mU;rG;mU;rA;rA;mC;mU;rC;mU;rG;mC;mC;rA;rC;zc3p;zc3p$ (SEQ ID NO: 116) | | | | | | |
| RHOA_50_S1642 | zc6Np;rG;rU;rG;rG;rC;rA;rG;rA;rG;rU;rU;rA;rC;rA;dG;dT;dT;dC;dA$ (SEQ ID NO: 82) | mU;rG;rA;rA;mC;mU;rG;mU;rA;rA;mC;rU;rC;mU;rG;mC;mC;rA;rC;zc3p;zc3p$ (SEQ ID NO: 116) | | | | | | |
| RHOA_50_S1787 | zidB;rG;rU;rG;rG;rC;rA;rG;rA;rG;rU;rU;rA;rC;rA;rG2p;rU2p;rU2p;rC2p;rA2p;zc3p (SEQ ID NO: 82) | dU;mG;mA;rA;mC;rU;rG2p;rU;mA;rA;mC;rU;mC;rU;mG;rC;mC;rA;mC;zc3p;zc3p$ (SEQ ID NO: 116) | | 29 | 46 | 62 | 81 | |

Figure 1 (continued)

| siRNA_Name | Code Sense 5->3 (SEQ ID NO.) | Code AntiSense 5->3 (SEQ ID NO.) | 20 nM | 5 nM | 1 nM | 0.5 nM | 0.1 nM | 0.05 nM |
|---|---|---|---|---|---|---|---|---|
| RHOA_50_S1793 | zidB;rG;rU;rG;rG;rC;rA;rG;rA;rG;rU;rU;rA;rC;rA;rG2p;rU2p;rU2p;rC2p;rA2p;zc3p (SEQ ID NO: 82) | dU;rG;rA;mA;rC;mU;rG2p;mU;rA;rA;mC;rU;mC;rU;mG;rC;mC;rA;mC;zc3p;zc3p$ (SEQ ID NO: 116) | | 25 | 46 | 60 | 82 | |
| RHOA_50_S1794 | zidB;rG;rU;rG;rG;rC;rA;rG;rA;rG;rU;rU;rA;rC;rA;rG2p;rU2p;rU2p;rC2p;rA2p;zc3p (SEQ ID NO: 82) | dU;rG;rA;rA;mC;mU;rG2p;mU;rA;rA;mC;mU;rC;mU;rG;mC;mC;rA;rC;zc3p;zc3p$ (SEQ ID NO: 116) | | 73 | 72 | 137 | 99 | |
| RHOA_50_S1795 | zidB;rG;rU;rG;rG;rC;rA;rG;rA;rG2p;rU;mU;rA;mC;rA;rG;rU;rU;mC;rA;zc3p (SEQ ID NO: 82) | dU;rG;rA;mA;rC;mU;rG2p;mU;rA;rA;mC;rU;mC;rU;mG;rC;mC;rA;mC;zc3p;zc3p$ (SEQ ID NO: 116) | | 24 | 36 | 51 | 73 | |
| RHOA_50_S1796 | zidB;rG;rU;rG;rG;rC;rA;rG;rA;rG2p;rU;mU;rA;mC;rA;rG;rU;rU;mC;rA;zc3p (SEQ ID NO: 82) | dU;rG;mA;rA;mC;rU;rG2p;rU;mA;rA;mC;rU;mC;rU;mG;rC;mC;rA;mC;zc3p;zc3p$ (SEQ ID NO: 116) | | 16 | 26 | 32 | 42 | |
| RHOA_50_S1797 | zidB;rG;rU;rG;rG;rC;rA;rG;rA;rG2p;rU;mU;rA;mC;rA;rG;rU;rU;mC;rA;zc3p (SEQ ID NO: 82) | dU;rG;rA;rA;mC;mU;rG2p;mU;rA;rA;mC;mU;rC;mU;rG;mC;mC;rA;rC;zc3p;zc3p$ (SEQ ID NO: 116) | | 28 | 55 | 66 | 89 | |
| RHOA_50_S1798 | zidB;rG;rU;rG;rG;rC;rA;rG;rA;rG2p;rU;rU;rA;rC;rA;rG;rU;rU;mC;rA;zc3p (SEQ ID NO: 82) | dU;rG;rA;mA;rC;mU;rG2p;mU;rA;rA;mC;rU;mC;rU;mG;rC;mC;rA;mC;zc3p;zc3p$ (SEQ ID NO: 116) | | 15 | 28 | 26 | 51 | |
| RHOA_50_S1799 | zidB;rG;rU;rG;rG;rC;rA;rG;rA;rG2p;rU;rU;rA;rC;rA;rG;rU;rU;mC;rA;zc3p (SEQ ID NO: 82) | dU;rG;mA;rA;mC;rU;rG2p;rU;mA;rA;mC;rU;mC;rU;mG;rC;mC;rA;mC;zc3p;zc3p$ (SEQ ID NO: 116) | | 9 | 15 | 23 | 41 | |
| RHOA_50_S1800 | zidB;rG;rU;rG;rG;rC;rA;rG;rA;rG2p;rU;rU;rA;rC;rA;rG;rU;rU;mC;rA;zc3p (SEQ ID NO: 82) | dU;rG;rA;rA;mC;mU;rG2p;mU;rA;rA;mC;mU;rC;mU;rG;mC;mC;rA;rC;zc3p;zc3p$ (SEQ ID NO: 116) | | 24 | 39 | 57 | 74 | |
| RHOA_50_S1835 | zidB;rG;rU;rG;rG;rC;rA;rG;rA;rG;rU;rU;rA;rC;rA;rG2p;rU2p;rU2p;rC2p;rA2p;zc3p (SEQ ID NO: 82) | mU;rG;mA;rA;mC;rU;mG;rU;mA;rA;mC;rU;mC;rU;mG;rC;mC;rA;mC;zc3p;zc3p$ (SEQ ID NO: 116) | | 51 | 78 | 89 | 94 | |
| RHOA_50_S1836 | zidB;rG;rU;rG;rG;rC;rA;rG;rA;rG;rU;rU;rA;rC;rA;rG2p;rU2p;rU2p;rC2p;rA2p;zc3p (SEQ ID NO: 82) | mU;rG;rA;rA;mC;mU;rG;mU;rA;rA;mC;mU;rC;mU;rG;mC;mC;rA;rC;zc3p;zc3p$ (SEQ ID NO: 116) | | 36 | 54 | 58 | 86 | |
| RHOA_50_S1837 | zidB;rG;rU;rG;rG;rC;rA;rG;rA;rG2p;rU;mU;rA;mC;rA;rG;rU;rU;mC;rA;zc3p (SEQ ID NO: 82) | mU;rG;mA;rA;mC;rU;mG;rU;mA;rA;mC;rU;mC;rU;mG;rC;mC;rA;mC;zc3p;zc3p$ (SEQ ID NO: 116) | | 41 | 71 | 94 | 117 | |
| RHOA_50_S1838 | zidB;rG;rU;rG;rG;rC;rA;rG;rA;rG2p;rU;mU;rA;mC;rA;rG;rU;rU;mC;rA;zc3p (SEQ ID NO: 82) | mU;rG;rA;rA;mC;mU;rG;mU;rA;rA;mC;mU;rC;mU;rG;mC;mC;rA;rC;zc3p;zc3p$ (SEQ ID NO: 116) | | 34 | 69 | 63 | 92 | |

Figure 1 (continued)

| siRNA_Name | Code Sense 5->3 (SEQ ID NO.) | Code AntiSense 5->3 (SEQ ID NO.) | 20 nM | 5 nM | 1 nM | 0.5 nM | 0.1 nM | 0.05 nM |
|---|---|---|---|---|---|---|---|---|
| RHOA_50_S1839 | zidB;rG;rU;rG;rG;rC;rA;rG;rA;rG2p;rU;rU;rA;rC;rA;rG;rU;rU;mC;rA;zc3p (SEQ ID NO: 82) | mU;rG;mA;rA;mC;rU;mG;rU;mA;rA;mC;rU;mC;rU;mG;rC;mC;rA;mC;zc3p;zc3p$ (SEQ ID NO: 116) |  | 20 | 43 | 51 | 82 |  |
| RHOA_50_S1840 | zidB;rG;rU;rG;rG;rC;rA;rG;rA;rG2p;rU;rU;rA;rC;rA;rG;rU;rU;mC;rA;zc3p (SEQ ID NO: 82) | mU;rG;rA;rA;mC;mU;rG;mU;rA;rA;mC;mU;rC;mU;rG;mC;mC;rA;rC;zc3p;zc3p$ (SEQ ID NO: 116) |  | 21 | 33 | 50 | 82 |  |
| RHOA_50_S1865 | zidB;rG;rU;rG;rG;rC;rA;rG;rA;rG2p;rU;rU;rA;rC;rA;rG;rU;mU;mC;rA;zc3p (SEQ ID NO: 82) | dU;rG;rA;mA;rC;mU;rG2p;mU;rA;rA;mC;rU;mC;rU;mG;rC;mC;rA;mC;zc3p;zc3p$ (SEQ ID NO: 116) |  | 7 | 12 | 27 | 50 | 49 |
| RHOA_50_S1866 | zidB;rG;rU;rG;rG;rC;rA;rG;rA;rG2p;rU;rU;rA;rC;rA;rG;rU;mU;mC;rA;zc3p (SEQ ID NO: 82) | dU;rG;mA;rA;mC;rU;rG2p;rU;mA;rA;mC;rU;mC;rU;mG;rC;mC;rA;mC;zc3p;zc3p$ (SEQ ID NO: 116) |  | 5 | 10 | 22 | 39 | 49 |
| RHOA_50_S1882 | zLdG;rG;rU;rG;rG;rC;rA;rG;rA;rG2p;rU;rU;rA;rC;rA;rG;rU;mU;mC;rA;zc3p (SEQ ID NO: 82) | dU;rG;rA;mA;rC;mU;rG2p;mU;rA;rA;mC;rU;mC;rU;mG;rC;mC;rA;mC;zc3p;zc3p$ (SEQ ID NO: 116) |  | 11 | 13 | 57 | na | 78 |
| RHOA_50_S1883 | zLdG;rG;rU;rG;rG;rC;rA;rG;rA;rG2p;rU;rU;rA;rC;rA;rG;rU;mU;mC;rA;zc3p (SEQ ID NO: 82) | dU;rG;mA;rA;mC;rU;rG2p;rU;mA;rA;mC;rU;mC;rU;mG;rC;mC;rA;mC;zc3p;zc3p$ (SEQ ID NO: 116) |  | 16 | 23 | 34 | na | 56 |
| RHOA_50_709 | (SEQ ID NO: 82) | (SEQ ID NO: 116) |  | 13 | 25 | 30 | 43 | 62 |
| RHOA_58_S992 | rG;rU;rG;rG;rC;rA;rG;rA;rG;rU;rU;rA;rC;rA;rG;rU;rU;rC;rU$ (SEQ ID NO: 143) | rA;mG;rA;mA;rC;mU;rG;mU;rA;rA;mC;rU;mC;rU;mG;rC;mC;rA;mC;zc3p;zc3p$ (SEQ ID NO: 157) |  |  |  |  |  |  |
| RHOA_58_S1625 | zc6Np;rG;rU;rG;rG;rC;rA;rG;rA;rG;rU;rU;rA;rC;rA;dG;dT;dT;dC;dT$ (SEQ ID NO: 143) | rA;mG;rA;mA;rC;mU;rG;mU;rA;rA;mC;rU;mC;rU;mG;rC;mC;rA;mC;zc3p;zc3p$ (SEQ ID NO: 157) |  |  |  |  |  |  |
| RHOA_58_S1782 | zidB;rG;rU;rG;rG;rC;rA;rG;rA;rG;rU;rU;rA;rC;rA;rG2p;rU2p;rU2p;rC2p;rU2p;zc3p (SEQ ID NO: 143) | rA;rG;mA;rA;mC;rU;rG2p;rU;mA;rA;mC;rU;mC;rU;mG;rC;mC;rA;mC;zc3p;zc3p$ (SEQ ID NO: 157) |  | 18 | 31 | 53 | 63 |  |
| RHOA_58_S1801 | zidB;rG;rU;rG;rG;rC;rA;rG;rA;rG;rU;rU;rA;rC;rA;rG2p;rU2p;rU2p;rC2p;rU2p;zc3p (SEQ ID NO: 143) | rA;rG;rA;mA;rC;mU;rG2p;mU;rA;rA;mC;rU;mC;rU;mG;rC;mC;rA;mC;zc3p;zc3p$ (SEQ ID NO: 157) |  | 15 | 34 | 40 | 54 |  |
| RHOA_58_S1802 | zidB;rG;rU;rG;rG;rC;rA;rG;rA;rG;rU;rU;rA;rC;rA;rG2p;rU2p;rU2p;rC2p;rU2p;zc3p (SEQ ID NO: 143) | rA;rG;rA;rA;mC;mU;rG2p;mU;rA;rA;mC;mU;rC;mU;rG;mC;mC;rA;rC;zc3p;zc3p$ (SEQ ID NO: 157) |  | 32 | 60 | 64 | 76 |  |

Figure 1 (continued)

| siRNA_Name | Code Sense 5->3 (SEQ ID NO.) | Code AntiSense 5->3 (SEQ ID NO.) | 20 nM | 5 nM | 1 nM | 0.5 nM | 0.1 nM | 0.05 nM |
|---|---|---|---|---|---|---|---|---|
| RHOA_58_S1803 | zidB;rG;rU;rG;rG;rC;rA;rG;rA;rG2p;rU;rU;rA;rC;rA;rG2p;rU2p;rU2p;rC2p;rU2p;zc3p (SEQ ID NO: 143) | rA;rG;mA;rA;mC;rU;rG2p;rU;mA;rA;mC;rU;mC;rU;mG;rC;mC;rA;mC;zc3p;zc3p$ (SEQ ID NO: 157) |  | 35 | 54 | 68 | 92 |  |
| RHOA_58_S1804 | zidB;rG;rU;rG;rG;rC;rA;rG;rA;rG2p;rU;rU;rA;rC;rA;rG2p;rU2p;rU2p;rC2p;rU2p;zc3p (SEQ ID NO: 143) | rA;rG;rA;mA;rC;mU;rG2p;mU;rA;rA;mC;rU;mC;rU;mG;rC;mC;rA;mC;zc3p;zc3p$ (SEQ ID NO: 157) |  | 19 | 29 | 32 | 67 |  |
| RHOA_58_S1805 | zidB;rG;rU;rG;rG;rC;rA;rG;rA;rG2p;rU;rU;rA;rC;rA;rG2p;rU2p;rU2p;rC2p;rU2p;zc3p (SEQ ID NO: 143) | rA;rG;rA;rA;mC;mU;rG2p;mU;rA;rA;mC;mU;rC;mU;rG;mC;mC;rA;rC;zc3p;zc3p$ (SEQ ID NO: 157) |  | 28 | 44 | 48 | 95 |  |
| RHOA_58_S1806 | zidB;rG;rU;rG;rG;rC;rA;rG;rA;rG2p;rU;mU;rA;mC;rA;rG;rU;mU;rC;rU;zc3p (SEQ ID NO: 143) | rA;rG;mA;rA;mC;rU;rG2p;rU;mA;rA;mC;rU;mC;rU;mG;rC;mC;rA;mC;zc3p;zc3p$ (SEQ ID NO: 157) |  | 14 | 20 | 33 | 59 |  |
| RHOA_58_S1807 | zidB;rG;rU;rG;rG;rC;rA;rG;rA;rG2p;rU;mU;rA;mC;rA;rG;rU;mU;rC;rU;zc3p (SEQ ID NO: 143) | rA;rG;rA;mA;rC;mU;rG2p;mU;rA;rA;mC;rU;mC;rU;mG;rC;mC;rA;mC;zc3p;zc3p$ (SEQ ID NO: 157) |  | 13 | 25 | 36 | 78 |  |
| RHOA_58_S1808 | zidB;rG;rU;rG;rG;rC;rA;rG;rA;rG2p;rU;mU;rA;mC;rA;rG;rU;mU;rC;rU;zc3p (SEQ ID NO: 143) | rA;rG;rA;rA;mC;mU;rG2p;mU;rA;rA;mC;mU;rC;mU;rG;mC;mC;rA;rC;zc3p;zc3p$ (SEQ ID NO: 157) |  | 22 | 42 | 50 | 84 |  |
| RHOA_58_S1809 | zidB;rG;rU;rG;rG;rC;rA;rG;rA;rG2p;rU;rU;rA;rC;rA;rG;rU;mU;rC;rU;zc3p (SEQ ID NO: 143) | rA;rG;mA;rA;mC;rU;rG2p;rU;mA;rA;mC;rU;mC;rU;mG;rC;mC;rA;mC;zc3p;zc3p$ (SEQ ID NO: 157) |  | 15 | 20 | 33 | 65 |  |
| RHOA_58_S1810 | zidB;rG;rU;rG;rG;rC;rA;rG;rA;rG2p;rU;rU;rA;rC;rA;rG;rU;mU;rC;rU;zc3p (SEQ ID NO: 143) | rA;rG;rA;mA;rC;mU;rG2p;mU;rA;rA;mC;rU;mC;rU;mG;rC;mC;rA;mC;zc3p;zc3p$ (SEQ ID NO: 157) |  | 17 | 22 | 31 | 73 |  |
| RHOA_58_S1811 | zidB;rG;rU;rG;rG;rC;rA;rG;rA;rG2p;rU;rU;rA;rC;rA;rG;rU;mU;rC;rU;zc3p (SEQ ID NO: 143) | rA;rG;rA;rA;mC;mU;rG2p;mU;rA;rA;mC;mU;rC;mU;rG;mC;mC;rA;rC;zc3p;zc3p$ (SEQ ID NO: 157) |  | 24 | 36 | 62 | 98 |  |
| RHOA_58_S1861 | zidB;rG;rU;rG;rG;rC;rA;rG;rA;rG2p;rU;mU;rA;mC;rA;rG;rU;mU;rC;rU;zc3p (SEQ ID NO: 143) | rA;rG;rA;mA;rC;rU2p;rG;mU;rA;rA;mC;rU;mC;rU;mG;rC;mC;rA;mC;zc3p;zc3p$ (SEQ ID NO: 157) |  | 11 | 14 | 18 | 45 |  |
| RHOA_58_S1862 | zidB;rG;rU;rG;rG;rC;rA;rG;rA;rG2p;rU;mU;rA;mC;rA;rG;rU;mU;rC;rU;zc3p (SEQ ID NO: 143) | rA;rG;rA;mA;rC;LdT;rG;mU;rA;rA;mC;rU;mC;rU;mG;rC;mC;rA;mC;zc3p;zc3p$ (SEQ ID NO: 157) |  | 13 | 16 | 17 | 51 | 50 |
| RHOA_58_S1863 | zidB;rG;rU;rG;rG;rC;rA;rG;rA;rG2p;rU;mU;rA;mC;rA;rG;rU;mU;rC;rU;zc3p (SEQ ID NO: 143) | rA;rG;rA;mA;rC;mU;rG;LdT;rA;rA;mC;rU;mC;rU;mG;rC;mC;rA;mC;zc3p;zc3p$ (SEQ ID NO: 157) |  |  |  |  |  |  |

Figure 1 (continued)

| siRNA_Name | Code Sense 5->3 (SEQ ID NO.) | Code AntiSense 5->3 (SEQ ID NO.) | 20 nM | 5 nM | 1 nM | 0.5 nM | 0.1 nM | 0.05 nM |
|---|---|---|---|---|---|---|---|---|
| RHOA_58_S1864 | zidB;rG;rU;rG;rG;rC;rA;rG;rA;rG2p;rU;mU;rA;mC;rA;rG;rU;mU;rC;rU;zc3p (SEQ ID NO: 143) | rA;rG;rA;mA;rC;rU2p;rG2p;mU;rA;rA;mC;rU;mC;rU;mG;rC;mC;rA;mC;zc3p;zc3p$ (SEQ ID NO: 157) | | | | | | |
| RHOA_58_S1867 | zidB;rG;rU;rG;rG;rC;rA;rG;rA;rG;rU;mU;rA;mC;rA;rG;rU;mU;rC;rU;zc3p (SEQ ID NO: 143) | rA;rG;mA;rA;mC;rU;rG2p;rU;mA;rA;mC;rU;mC;rU;mG;rC;mC;rA;mC;zc3p;zc3p$ (SEQ ID NO: 157) | | | | | | |
| RHOA_58_S1877 | zLdG;rG;rU;rG;rG;rC;rA;rG;rA;rG2p;rU;mU;rA;mC;rA;rG;rU;mU;rC;rU;zc3p (SEQ ID NO: 143) | rA;rG;mA;rA;mC;rU;rG2p;rU;mA;rA;mC;rU;mC;rU;mG;rC;mC;rA;mC;zc3p;zc3p$ (SEQ ID NO: 157) | | 7 | 12 | 20 | 45 | 41 |
| RHOA_58_S1878 | zLdG;rG;rU;rG;rG;rC;rA;rG;rA;rG2p;rU;mU;rA;mC;rA;rG;rU;mU;rC;rU;zc3p (SEQ ID NO: 143) | rA;rG;rA;mA;rC;rU2p;rG;mU;rA;rA;mC;rU;mC;rU;mG;rC;mC;rA;mC;zc3p;zc3p$ (SEQ ID NO: 157) | | 7 | 17 | 19 | 43 | |
| RHOA_58_S1879 | zLdG;rG;rU;rG;rG;rC;rA;rG;rA;rG2p;rU;mU;rA;mC;rA;rG;rU;mU;rC;rU;zc3p (SEQ ID NO: 143) | rA;rG;rA;mA;rC;LdT;rG;mU;rA;rA;mC;rU;mC;rU;mG;rC;mC;rA;mC;zc3p;zc3p$ (SEQ ID NO: 157) | | 7 | 13 | 21 | | |
| RHOA_58_S1880 | zLdG;rG;rU;rG;rG;rC;rA;rG;rA;rG2p;rU;mU;rA;mC;rA;rG;rU;mU;rC;rU;zc3p (SEQ ID NO: 143) | rA;rG;rA;mA;rC;mU;rG;LdT;rA;rA;mC;rU;mC;rU;mG;rC;mC;rA;mC;zc3p;zc3p$ (SEQ ID NO: 157) | | | | | | |
| RHOA_58_S1881 | zLdG;rG;rU;rG;rG;rC;rA;rG;rA;rG2p;rU;mU;rA;mC;rA;rG;rU;mU;rC;rU;zc3p (SEQ ID NO: 143) | rA;rG;rA;mA;rC;rU2p;rG2p;mU;rA;rA;mC;rU;mC;rU;mG;rC;mC;rA;mC;zc3p;zc3p$ (SEQ ID NO: 157) | | | | | | |
| RHOA_58_S709 | (SEQ ID NO: 143) | (SEQ ID NO: 157) | | 15 | 21 | 24 | 33 | |

SEQUENCE LISTING

```
<160> NUMBER OF SEQ ID NOS: 184

<210> SEQ ID NO 1
<211> LENGTH: 1926
<212> TYPE: RNA
<213> ORGANISM: Homo sapiens

<400> SEQUENCE: 1
guggaugagc ugugagugcg cgcgcgugcg cggggccgcg accugugccg gcucgagccc      60
gcugggcacu cggaggcgcg cacgucguuc cccgcccucc cgccgccgcc cgcccucgcu     120
cucucgcgcu acccucccgc cgcccgcggu ccuccgucgg uucucucguu aguccacggu     180
cuggucuuca gcuacccgcc uucgucuccg aguuugcgac ucgcggaccg gcgucccgg     240 cgcgaagagg cuggacucgg auucguugcc ugagcaaugg cugccauccg gaagaaacug     300
gugauuguug gugauggagc cuguggaaag acaugcuugc ucauagucuu cagcaaggac     360
```

| | |
|---|---|
| caguucccag agguguaugu gcccacagug uuugagaacu auguggcaga uaucgaggug | 420 |
| gauggaaagc agguagaguu ggcuuugugg gacacagcug gcaggaaga uuaugaucgc | 480 |
| cugaggcccc ucuccuaccc agauaccgau guuauacuga uguguuuuc caucgacagc | 540 |
| ccugauaguu uagaaaacau cccagaaaag uggaccccag aagucaagca uuucuguccc | 600 |
| aacgugccca ucauccuggu ugggaauaag aaggaucuuc ggaaugauga gcacacaagg | 660 |
| cgggagcuag ccaagaugaa gcaggagccg gugaaaccug aagaaggcag agauauggca | 720 |
| aacaggauug gcgcuuuugg guacauggag guucagcaa agaccaaaga uggagugaga | 780 |
| gagguuuuug aaauggcuac gagagcugcu cugcaagcua gacgugggaa gaaaaaaucu | 840 |
| gggugccuug ucuugugaaa ccuugcugca agcacagccc uuaugcgguu aauuuugaag | 900 |
| ugcuguuuau uaaucuuagu guaugauuac uggccuuuuu cauuuaucua uaauuuaccu | 960 |
| aagauuacaa aucagaaguc aucuugcuac caguauuuag aagccaacua ugauuauuaa | 1020 |
| cgauguccaa cccgucuggc ccaccagggu ccuuuugaca cugcucuaac agcccuccuc | 1080 |
| ugcacuccca ccugacacac caggcgcuaa uucaaggaau ucuuaacuu cuugcuucuu | 1140 |
| ucuagaaaga gaaacaguug guaacuuuug ugaauuaggc uguaacuacu uuauaacuaa | 1200 |
| cauguccugc cuauuaucug ucagcugcaa gguacucugg ugagcacca cuucagggcu | 1260 |
| uuacuccgua acaguuuuug uuggcauagc ucggggugg gcaguuuuu gaaaaugggc | 1320 |
| ucaaccagaa aagcccaagu ucaugcagcu guggcagagu uacaguucug ugguuucaug | 1380 |
| uuaguuaccu uauaguuacu guguaauuag ugccacuuaa uguauguuac caaaaauaaa | 1440 |
| uauaucuacc ccagacuaga guaguauuu uuuguauaau uggauuuccu aauacuguca | 1500 |
| uccucaaaga aaguguauug guuuuuaaa aagaaagug uauuuggaaa uaaagucaga | 1560 |
| uggaaaauuc auuuuuaaa uucccguuuu gucacuuuuu cugauaaaag auggccauau | 1620 |
| uaccccuuuu cggcccccaug uaucucagua ccccauggag cugggcuaag uaaauaggaa | 1680 |
| uugguuucac gccugaggca auuagacacu uggaagaug gcauaaccug ucucaccugg | 1740 |
| acuuaagcau cuggcucuaa uucacagugc ucuuuucucc ucacuguauc cagguucccu | 1800 |
| cccagaggag ccaccaguuc ucauggguug cacucagucu cucuucucuc cagcugacua | 1860 |
| aacuuuuuuu cuguaccagu uaauuuuucc aacuacuaau agaauaaagg caguuuucua | 1920 |
| aaaaaa | 1926 |

<210> SEQ ID NO 2
<211> LENGTH: 193
<212> TYPE: PRT
<213> ORGANISM: Homo sapiens

<400> SEQUENCE: 2

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

-continued

```
Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Pro Val Lys Pro Glu Glu Gly
130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu

<210> SEQ ID NO 3
<211> LENGTH: 18
<212> TYPE: RNA
<213> ORGANISM: artificial
<220> FEATURE:
<223> OTHER INFORMATION: Chemically synthesized

<400> SEQUENCE: 3
ggaucuucgg aaugauga                                                 18

<210> SEQ ID NO 4
<211> LENGTH: 18
<212> TYPE: RNA
<213> ORGANISM: artificial
<220> FEATURE:
<223> OTHER INFORMATION: Chemically synthesized

<400> SEQUENCE: 4
caugcuugcu cauagucu                                                 18

<210> SEQ ID NO 5
<211> LENGTH: 18
<212> TYPE: RNA
<213> ORGANISM: artificial
<220> FEATURE:
<223> OTHER INFORMATION: Chemically synthesized

<400> SEQUENCE: 5
ggaagaaacu ggugauug                                                 18

<210> SEQ ID NO 6
<211> LENGTH: 18
<212> TYPE: RNA
<213> ORGANISM: artificial
<220> FEATURE:
<223> OTHER INFORMATION: Chemically synthesized

<400> SEQUENCE: 6
ggguacaugg aguguuca                                                 18

<210> SEQ ID NO 7
<211> LENGTH: 18
<212> TYPE: RNA
<213> ORGANISM: artificial
<220> FEATURE:
<223> OTHER INFORMATION: Chemically synthesized

<400> SEQUENCE: 7
```
gaaggaucuu cggaauga                                                    18

<210> SEQ ID NO 8
<211> LENGTH: 18
<212> TYPE: RNA
<213> ORGANISM: artificial
<220> FEATURE:
<223> OTHER INFORMATION: Chemically synthesized

<400> SEQUENCE: 8
ggaaugauga gcacacaa                                                    18

<210> SEQ ID NO 9
<211> LENGTH: 18
<212> TYPE: RNA
<213> ORGANISM: artificial
<220> FEATURE:
<223> OTHER INFORMATION: Chemically synthesized

<400> SEQUENCE: 9
cugaagaagg cagagaua                                                    18

<210> SEQ ID NO 10
<211> LENGTH: 18
<212> TYPE: RNA
<213> ORGANISM: artificial
<220> FEATURE:
<223> OTHER INFORMATION: Chemically synthesized

<400> SEQUENCE: 10
gcagagauau ggcaaaca                                                    18

<210> SEQ ID NO 11
<211> LENGTH: 18
<212> TYPE: RNA
<213> ORGANISM: artificial
<220> FEATURE:
<223> OTHER INFORMATION: Chemically synthesized

<400> SEQUENCE: 11
gaacuaugug gcagauau                                                    18

<210> SEQ ID NO 12
<211> LENGTH: 18
<212> TYPE: RNA
<213> ORGANISM: artificial
<220> FEATURE:
<223> OTHER INFORMATION: Chemically synthesized

<400> SEQUENCE: 12
ccaucgacag cccugaua                                                    18

<210> SEQ ID NO 13
<211> LENGTH: 18
<212> TYPE: RNA
<213> ORGANISM: artificial
<220> FEATURE:
<223> OTHER INFORMATION: Chemically synthesized

<400> SEQUENCE: 13
cccagaaguc aagcauuu                                                    18

<210> SEQ ID NO 14
<211> LENGTH: 18
<212> TYPE: RNA
<213> ORGANISM: artificial

```
<220> FEATURE:
<223> OTHER INFORMATION: Chemically synthesized

<400> SEQUENCE: 14
ggcgcuuuug gguacaug                                                 18

<210> SEQ ID NO 15
<211> LENGTH: 18
<212> TYPE: RNA
<213> ORGANISM: artificial
<220> FEATURE:
<223> OTHER INFORMATION: Chemically synthesized

<400> SEQUENCE: 15
cagaagucau cuugcuac                                                 18

<210> SEQ ID NO 16
<211> LENGTH: 18
<212> TYPE: RNA
<213> ORGANISM: artificial
<220> FEATURE:
<223> OTHER INFORMATION: Chemically synthesized

<400> SEQUENCE: 16
uaagaaggau cuucggaa                                                 18

<210> SEQ ID NO 17
<211> LENGTH: 18
<212> TYPE: RNA
<213> ORGANISM: artificial
<220> FEATURE:
<223> OTHER INFORMATION: Chemically synthesized

<400> SEQUENCE: 17
guggcagagu uacaguuc                                                 18

<210> SEQ ID NO 18
<211> LENGTH: 18
<212> TYPE: RNA
<213> ORGANISM: artificial
<220> FEATURE:
<223> OTHER INFORMATION: Chemically synthesized

<400> SEQUENCE: 18
cagagauaug gcaaacag                                                 18

<210> SEQ ID NO 19
<211> LENGTH: 18
<212> TYPE: RNA
<213> ORGANISM: artificial
<220> FEATURE:
<223> OTHER INFORMATION: Chemically synthesized

<400> SEQUENCE: 19
gauuggcgcu uuugggua                                                 18

<210> SEQ ID NO 20
<211> LENGTH: 18
<212> TYPE: RNA
<213> ORGANISM: artificial
<220> FEATURE:
<223> OTHER INFORMATION: Chemically synthesized

<400> SEQUENCE: 20
gacagcccug auaguuua                                                 18
```

<210> SEQ ID NO 21
<211> LENGTH: 18
<212> TYPE: RNA
<213> ORGANISM: artificial
<220> FEATURE:
<223> OTHER INFORMATION: Chemically synthesized

<400> SEQUENCE: 21
gaaugaugag cacacaag                                                 18

<210> SEQ ID NO 22
<211> LENGTH: 18
<212> TYPE: RNA
<213> ORGANISM: artificial
<220> FEATURE:
<223> OTHER INFORMATION: Chemically synthesized

<400> SEQUENCE: 22
caaacaggau uggcgcuu                                                 18

<210> SEQ ID NO 23
<211> LENGTH: 18
<212> TYPE: RNA
<213> ORGANISM: artificial
<220> FEATURE:
<223> OTHER INFORMATION: Chemically synthesized

<400> SEQUENCE: 23
caucgacagc ccugauag                                                 18

<210> SEQ ID NO 24
<211> LENGTH: 18
<212> TYPE: RNA
<213> ORGANISM: artificial
<220> FEATURE:
<223> OTHER INFORMATION: Chemically synthesized

<400> SEQUENCE: 24
gaucuucgga augaugag                                                 18

<210> SEQ ID NO 25
<211> LENGTH: 18
<212> TYPE: RNA
<213> ORGANISM: artificial
<220> FEATURE:
<223> OTHER INFORMATION: Chemically synthesized

<400> SEQUENCE: 25
cuguggcaga guuacagu                                                 18

<210> SEQ ID NO 26
<211> LENGTH: 18
<212> TYPE: RNA
<213> ORGANISM: artificial
<220> FEATURE:
<223> OTHER INFORMATION: Chemically synthesized

<400> SEQUENCE: 26
ucuucggaau gaugagca                                                 18

<210> SEQ ID NO 27
<211> LENGTH: 18
<212> TYPE: RNA
<213> ORGANISM: artificial
<220> FEATURE:
<223> OTHER INFORMATION: Chemically synthesized

```
<400> SEQUENCE: 27
uguggcagag uuacaguu                                                18

<210> SEQ ID NO 28
<211> LENGTH: 18
<212> TYPE: RNA
<213> ORGANISM: artificial
<220> FEATURE:
<223> OTHER INFORMATION: Chemically synthesized

<400> SEQUENCE: 28
ugaugagcac acaaggcg                                                18

<210> SEQ ID NO 29
<211> LENGTH: 18
<212> TYPE: RNA
<213> ORGANISM: artificial
<220> FEATURE:
<223> OTHER INFORMATION: Chemically synthesized

<400> SEQUENCE: 29
guuuuuccau cgacagcc                                                18

<210> SEQ ID NO 30
<211> LENGTH: 18
<212> TYPE: RNA
<213> ORGANISM: artificial
<220> FEATURE:
<223> OTHER INFORMATION: Chemically synthesized

<400> SEQUENCE: 30
uucggaauga ugagcaca                                                18

<210> SEQ ID NO 31
<211> LENGTH: 18
<212> TYPE: RNA
<213> ORGANISM: artificial
<220> FEATURE:
<223> OTHER INFORMATION: Chemically synthesized

<400> SEQUENCE: 31
cgauguuaua cugaugug                                                18

<210> SEQ ID NO 32
<211> LENGTH: 18
<212> TYPE: RNA
<213> ORGANISM: artificial
<220> FEATURE:
<223> OTHER INFORMATION: Chemically synthesized

<400> SEQUENCE: 32
guguuuuucc aucgacag                                                18

<210> SEQ ID NO 33
<211> LENGTH: 18
<212> TYPE: RNA
<213> ORGANISM: artificial
<220> FEATURE:
<223> OTHER INFORMATION: Chemically synthesized

<400> SEQUENCE: 33
agcuguggca gaguuaca                                                18

<210> SEQ ID NO 34
```

```
<211> LENGTH: 18
<212> TYPE: RNA
<213> ORGANISM: artificial
<220> FEATURE:
<223> OTHER INFORMATION: Chemically synthesized

<400> SEQUENCE: 34
ucgacagccc ugauaguu                                                 18

<210> SEQ ID NO 35
<211> LENGTH: 18
<212> TYPE: RNA
<213> ORGANISM: artificial
<220> FEATURE:
<223> OTHER INFORMATION: Chemically synthesized

<400> SEQUENCE: 35
ucaucauucc gaagaucc                                                 18

<210> SEQ ID NO 36
<211> LENGTH: 18
<212> TYPE: RNA
<213> ORGANISM: artificial
<220> FEATURE:
<223> OTHER INFORMATION: Chemically synthesized

<400> SEQUENCE: 36
agacuaugag caagcaug                                                 18

<210> SEQ ID NO 37
<211> LENGTH: 18
<212> TYPE: RNA
<213> ORGANISM: artificial
<220> FEATURE:
<223> OTHER INFORMATION: Chemically synthesized

<400> SEQUENCE: 37
caaucaccag uuucuucc                                                 18

<210> SEQ ID NO 38
<211> LENGTH: 18
<212> TYPE: RNA
<213> ORGANISM: artificial
<220> FEATURE:
<223> OTHER INFORMATION: Chemically synthesized

<400> SEQUENCE: 38
ugaacacucc auguaccc                                                 18

<210> SEQ ID NO 39
<211> LENGTH: 18
<212> TYPE: RNA
<213> ORGANISM: artificial
<220> FEATURE:
<223> OTHER INFORMATION: Chemically synthesized

<400> SEQUENCE: 39
ucauuccgaa gauccuuc                                                 18

<210> SEQ ID NO 40
<211> LENGTH: 18
<212> TYPE: RNA
<213> ORGANISM: artificial
<220> FEATURE:
<223> OTHER INFORMATION: Chemically synthesized

<400> SEQUENCE: 40
```
uugugugcuc aucauucc                                              18

<210> SEQ ID NO 41
<211> LENGTH: 18
<212> TYPE: RNA
<213> ORGANISM: artificial
<220> FEATURE:
<223> OTHER INFORMATION: Chemically synthesized

<400> SEQUENCE: 41
uaucucugcc uucuucag                                              18

<210> SEQ ID NO 42
<211> LENGTH: 18
<212> TYPE: RNA
<213> ORGANISM: artificial
<220> FEATURE:
<223> OTHER INFORMATION: Chemically synthesized

<400> SEQUENCE: 42
uguuugccau aucucugc                                              18

<210> SEQ ID NO 43
<211> LENGTH: 18
<212> TYPE: RNA
<213> ORGANISM: artificial
<220> FEATURE:
<223> OTHER INFORMATION: Chemically synthesized

<400> SEQUENCE: 43
auaucugcca cauaguuc                                              18

<210> SEQ ID NO 44
<211> LENGTH: 18
<212> TYPE: RNA
<213> ORGANISM: artificial
<220> FEATURE:
<223> OTHER INFORMATION: Chemically synthesized

<400> SEQUENCE: 44
uaucagggcu gucgaugg                                              18

<210> SEQ ID NO 45
<211> LENGTH: 18
<212> TYPE: RNA
<213> ORGANISM: artificial
<220> FEATURE:
<223> OTHER INFORMATION: Chemically synthesized

<400> SEQUENCE: 45
aaaugcuuga cuucuggg                                              18

<210> SEQ ID NO 46
<211> LENGTH: 18
<212> TYPE: RNA
<213> ORGANISM: artificial
<220> FEATURE:
<223> OTHER INFORMATION: Chemically synthesized

<400> SEQUENCE: 46
cauguaccca aaagcgcc                                              18

<210> SEQ ID NO 47
<211> LENGTH: 18
<212> TYPE: RNA

```
<213> ORGANISM: artificial
<220> FEATURE:
<223> OTHER INFORMATION: Chemically synthesized

<400> SEQUENCE: 47
guagcaagau gacuucug                                               18

<210> SEQ ID NO 48
<211> LENGTH: 18
<212> TYPE: RNA
<213> ORGANISM: artificial
<220> FEATURE:
<223> OTHER INFORMATION: Chemically synthesized

<400> SEQUENCE: 48
uuccgaagau ccuucuua                                               18

<210> SEQ ID NO 49
<211> LENGTH: 18
<212> TYPE: RNA
<213> ORGANISM: artificial
<220> FEATURE:
<223> OTHER INFORMATION: Chemically synthesized

<400> SEQUENCE: 49
gaacuguaac ucugccac                                               18

<210> SEQ ID NO 50
<211> LENGTH: 18
<212> TYPE: RNA
<213> ORGANISM: artificial
<220> FEATURE:
<223> OTHER INFORMATION: Chemically synthesized

<400> SEQUENCE: 50
cuguuugcca uaucucug                                               18

<210> SEQ ID NO 51
<211> LENGTH: 18
<212> TYPE: RNA
<213> ORGANISM: artificial
<220> FEATURE:
<223> OTHER INFORMATION: Chemically synthesized

<400> SEQUENCE: 51
uacccaaaag cgccaauc                                               18

<210> SEQ ID NO 52
<211> LENGTH: 18
<212> TYPE: RNA
<213> ORGANISM: artificial
<220> FEATURE:
<223> OTHER INFORMATION: Chemically synthesized

<400> SEQUENCE: 52
uaaacuauca gggcuguc                                               18

<210> SEQ ID NO 53
<211> LENGTH: 18
<212> TYPE: RNA
<213> ORGANISM: artificial
<220> FEATURE:
<223> OTHER INFORMATION: Chemically synthesized

<400> SEQUENCE: 53
cuugugugcu caucauuc                                               18
```

```
<210> SEQ ID NO 54
<211> LENGTH: 18
<212> TYPE: RNA
<213> ORGANISM: artificial
<220> FEATURE:
<223> OTHER INFORMATION: Chemically synthesized

<400> SEQUENCE: 54
aagcgccaau ccuguuug                                                    18

<210> SEQ ID NO 55
<211> LENGTH: 18
<212> TYPE: RNA
<213> ORGANISM: artificial
<220> FEATURE:
<223> OTHER INFORMATION: Chemically synthesized

<400> SEQUENCE: 55
cuaucagggc ugucgaug                                                    18

<210> SEQ ID NO 56
<211> LENGTH: 18
<212> TYPE: RNA
<213> ORGANISM: artificial
<220> FEATURE:
<223> OTHER INFORMATION: Chemically synthesized

<400> SEQUENCE: 56
cucaucauuc cgaagauc                                                    18

<210> SEQ ID NO 57
<211> LENGTH: 18
<212> TYPE: RNA
<213> ORGANISM: artificial
<220> FEATURE:
<223> OTHER INFORMATION: Chemically synthesized

<400> SEQUENCE: 57
acuguaacuc ugccacag                                                    18

<210> SEQ ID NO 58
<211> LENGTH: 18
<212> TYPE: RNA
<213> ORGANISM: artificial
<220> FEATURE:
<223> OTHER INFORMATION: Chemically synthesized

<400> SEQUENCE: 58
ugcucaucau uccgaaga                                                    18

<210> SEQ ID NO 59
<211> LENGTH: 18
<212> TYPE: RNA
<213> ORGANISM: artificial
<220> FEATURE:
<223> OTHER INFORMATION: Chemically synthesized

<400> SEQUENCE: 59
aacuguaacu cugccaca                                                    18

<210> SEQ ID NO 60
<211> LENGTH: 18
<212> TYPE: RNA
<213> ORGANISM: artificial
<220> FEATURE:
```

```
<223> OTHER INFORMATION: Chemically synthesized

<400> SEQUENCE: 60
cgccuugugu gcucauca                                                       18

<210> SEQ ID NO 61
<211> LENGTH: 18
<212> TYPE: RNA
<213> ORGANISM: artificial
<220> FEATURE:
<223> OTHER INFORMATION: Chemically synthesized

<400> SEQUENCE: 61
ggcugucgau ggaaaaac                                                       18

<210> SEQ ID NO 62
<211> LENGTH: 18
<212> TYPE: RNA
<213> ORGANISM: artificial
<220> FEATURE:
<223> OTHER INFORMATION: Chemically synthesized

<400> SEQUENCE: 62
ugugcucauc auuccgaa                                                       18

<210> SEQ ID NO 63
<211> LENGTH: 18
<212> TYPE: RNA
<213> ORGANISM: artificial
<220> FEATURE:
<223> OTHER INFORMATION: Chemically synthesized

<400> SEQUENCE: 63
cacaucagua uaacaucg                                                       18

<210> SEQ ID NO 64
<211> LENGTH: 18
<212> TYPE: RNA
<213> ORGANISM: artificial
<220> FEATURE:
<223> OTHER INFORMATION: Chemically synthesized

<400> SEQUENCE: 64
cugucgaugg aaaaacac                                                       18

<210> SEQ ID NO 65
<211> LENGTH: 18
<212> TYPE: RNA
<213> ORGANISM: artificial
<220> FEATURE:
<223> OTHER INFORMATION: Chemically synthesized

<400> SEQUENCE: 65
uguaacucug ccacagcu                                                       18

<210> SEQ ID NO 66
<211> LENGTH: 18
<212> TYPE: RNA
<213> ORGANISM: Artificial Sequence
<220> FEATURE:
<223> OTHER INFORMATION: Chemically synthesized

<400> SEQUENCE: 66
aacuaucagg gcugucga                                                       18
```

```
<210> SEQ ID NO 67
<211> LENGTH: 19
<212> TYPE: RNA
<213> ORGANISM: artificial
<220> FEATURE:
<223> OTHER INFORMATION: Chemically Synthesized

<400> SEQUENCE: 67
ggaucuucgg aaugaugaa                                                    19

<210> SEQ ID NO 68
<211> LENGTH: 19
<212> TYPE: RNA
<213> ORGANISM: artificial
<220> FEATURE:
<223> OTHER INFORMATION: Chemically Synthesized

<400> SEQUENCE: 68
caugcuugcu cauagucua                                                    19

<210> SEQ ID NO 69
<211> LENGTH: 19
<212> TYPE: RNA
<213> ORGANISM: artificial
<220> FEATURE:
<223> OTHER INFORMATION: Chemically Synthesized

<400> SEQUENCE: 69
ggaagaaacu ggugauuga                                                    19

<210> SEQ ID NO 70
<211> LENGTH: 19
<212> TYPE: RNA
<213> ORGANISM: artificial
<220> FEATURE:
<223> OTHER INFORMATION: Chemically Synthesized

<400> SEQUENCE: 70
ggguacaugg aguguucaa                                                    19

<210> SEQ ID NO 71
<211> LENGTH: 19
<212> TYPE: RNA
<213> ORGANISM: artificial
<220> FEATURE:
<223> OTHER INFORMATION: Chemically Synthesized

<400> SEQUENCE: 71
gaaggaucuu cggaaugaa                                                    19

<210> SEQ ID NO 72
<211> LENGTH: 19
<212> TYPE: RNA
<213> ORGANISM: artificial
<220> FEATURE:
<223> OTHER INFORMATION: Chemically Synthesized

<400> SEQUENCE: 72
ggaaugauga gcacacaaa                                                    19

<210> SEQ ID NO 73
<211> LENGTH: 19
<212> TYPE: RNA
<213> ORGANISM: artificial
<220> FEATURE:
<223> OTHER INFORMATION: Chemically Synthesized
```

```
<400> SEQUENCE: 73
cugaagaagg cagagauaa                                                19

<210> SEQ ID NO 74
<211> LENGTH: 19
<212> TYPE: RNA
<213> ORGANISM: artificial
<220> FEATURE:
<223> OTHER INFORMATION: Chemically Synthesized

<400> SEQUENCE: 74
gcagagauau ggcaaacaa                                                19

<210> SEQ ID NO 75
<211> LENGTH: 19
<212> TYPE: RNA
<213> ORGANISM: artificial
<220> FEATURE:
<223> OTHER INFORMATION: Chemically Synthesized

<400> SEQUENCE: 75
gaacuaugug gcagauaua                                                19

<210> SEQ ID NO 76
<211> LENGTH: 19
<212> TYPE: RNA
<213> ORGANISM: artificial
<220> FEATURE:
<223> OTHER INFORMATION: Chemically Synthesized

<400> SEQUENCE: 76
ccaucgacag cccugauaa                                                19

<210> SEQ ID NO 77
<211> LENGTH: 19
<212> TYPE: RNA
<213> ORGANISM: artificial
<220> FEATURE:
<223> OTHER INFORMATION: Chemically Synthesized

<400> SEQUENCE: 77
cccagaaguc aagcauuua                                                19

<210> SEQ ID NO 78
<211> LENGTH: 19
<212> TYPE: RNA
<213> ORGANISM: artificial
<220> FEATURE:
<223> OTHER INFORMATION: Chemically Synthesized

<400> SEQUENCE: 78
ggcgcuuuug gguacauga                                                19

<210> SEQ ID NO 79
<211> LENGTH: 19
<212> TYPE: RNA
<213> ORGANISM: artificial
<220> FEATURE:
<223> OTHER INFORMATION: Chemically Synthesized

<400> SEQUENCE: 79
cagaagucau cuugcuaca                                                19

<210> SEQ ID NO 80
<211> LENGTH: 19
```

```
<212> TYPE: RNA
<213> ORGANISM: artificial
<220> FEATURE:
<223> OTHER INFORMATION: Chemically Synthesized

<400> SEQUENCE: 80
cagaagucau cuugcuacu                                                    19

<210> SEQ ID NO 81
<211> LENGTH: 19
<212> TYPE: RNA
<213> ORGANISM: artificial
<220> FEATURE:
<223> OTHER INFORMATION: Chemically Synthesized

<400> SEQUENCE: 81
uaagaaggau cuucggaaa                                                    19

<210> SEQ ID NO 82
<211> LENGTH: 19
<212> TYPE: RNA
<213> ORGANISM: artificial
<220> FEATURE:
<223> OTHER INFORMATION: Chemically Synthesized

<400> SEQUENCE: 82
guggcagagu uacaguuca                                                    19

<210> SEQ ID NO 83
<211> LENGTH: 19
<212> TYPE: RNA
<213> ORGANISM: artificial
<220> FEATURE:
<223> OTHER INFORMATION: Chemically Synthesized

<400> SEQUENCE: 83
cagagauaug gcaaacaga                                                    19

<210> SEQ ID NO 84
<211> LENGTH: 19
<212> TYPE: RNA
<213> ORGANISM: artificial
<220> FEATURE:
<223> OTHER INFORMATION: Chemically Synthesized

<400> SEQUENCE: 84
gauuggcgcu uuuggguaa                                                    19

<210> SEQ ID NO 85
<211> LENGTH: 19
<212> TYPE: RNA
<213> ORGANISM: artificial
<220> FEATURE:
<223> OTHER INFORMATION: Chemically Synthesized

<400> SEQUENCE: 85
gacagcccug auaguuuaa                                                    19

<210> SEQ ID NO 86
<211> LENGTH: 19
<212> TYPE: RNA
<213> ORGANISM: artificial
<220> FEATURE:
<223> OTHER INFORMATION: Chemically Synthesized

<400> SEQUENCE: 86
```

```
gaaugaugag cacacaaga                                           19

<210> SEQ ID NO 87
<211> LENGTH: 19
<212> TYPE: RNA
<213> ORGANISM: artificial
<220> FEATURE:
<223> OTHER INFORMATION: Chemically Synthesized

<400> SEQUENCE: 87
caaacaggau uggcgcuua                                           19

<210> SEQ ID NO 88
<211> LENGTH: 19
<212> TYPE: RNA
<213> ORGANISM: artificial
<220> FEATURE:
<223> OTHER INFORMATION: Chemically Synthesized

<400> SEQUENCE: 88
caucgacagc ccugauaga                                           19

<210> SEQ ID NO 89
<211> LENGTH: 19
<212> TYPE: RNA
<213> ORGANISM: artificial
<220> FEATURE:
<223> OTHER INFORMATION: Chemically Synthesized

<400> SEQUENCE: 89
gaucuucgga augaugaga                                           19

<210> SEQ ID NO 90
<211> LENGTH: 19
<212> TYPE: RNA
<213> ORGANISM: artificial
<220> FEATURE:
<223> OTHER INFORMATION: Chemically Synthesized

<400> SEQUENCE: 90
gaucuucgga augaugagu                                           19

<210> SEQ ID NO 91
<211> LENGTH: 19
<212> TYPE: RNA
<213> ORGANISM: artificial
<220> FEATURE:
<223> OTHER INFORMATION: Chemically Synthesized

<400> SEQUENCE: 91
cuguggcaga guuacagua                                           19

<210> SEQ ID NO 92
<211> LENGTH: 19
<212> TYPE: RNA
<213> ORGANISM: artificial
<220> FEATURE:
<223> OTHER INFORMATION: Chemically Synthesized

<400> SEQUENCE: 92
ucuucggaau gaugagcaa                                           19

<210> SEQ ID NO 93
<211> LENGTH: 19
<212> TYPE: RNA
<213> ORGANISM: artificial
```

```
<220> FEATURE:
<223> OTHER INFORMATION: Chemically Synthesized

<400> SEQUENCE: 93
uguggcagag uuacaguua                                              19

<210> SEQ ID NO 94
<211> LENGTH: 19
<212> TYPE: RNA
<213> ORGANISM: artificial
<220> FEATURE:
<223> OTHER INFORMATION: Chemically Synthesized

<400> SEQUENCE: 94
ugaugagcac acaaggcga                                              19

<210> SEQ ID NO 95
<211> LENGTH: 19
<212> TYPE: RNA
<213> ORGANISM: artificial
<220> FEATURE:
<223> OTHER INFORMATION: Chemically Synthesized

<400> SEQUENCE: 95
guuuuuccau cgacagcca                                              19

<210> SEQ ID NO 96
<211> LENGTH: 19
<212> TYPE: RNA
<213> ORGANISM: artificial
<220> FEATURE:
<223> OTHER INFORMATION: Chemically Synthesized

<400> SEQUENCE: 96
uucggaauga ugagcacaa                                              19

<210> SEQ ID NO 97
<211> LENGTH: 19
<212> TYPE: RNA
<213> ORGANISM: artificial
<220> FEATURE:
<223> OTHER INFORMATION: Chemically Synthesized

<400> SEQUENCE: 97
cgauguuaua cugauguga                                              19

<210> SEQ ID NO 98
<211> LENGTH: 19
<212> TYPE: RNA
<213> ORGANISM: artificial
<220> FEATURE:
<223> OTHER INFORMATION: Chemically Synthesized

<400> SEQUENCE: 98
guguuuuccc aucgacaga                                              19

<210> SEQ ID NO 99
<211> LENGTH: 19
<212> TYPE: RNA
<213> ORGANISM: artificial
<220> FEATURE:
<223> OTHER INFORMATION: Chemically Synthesized

<400> SEQUENCE: 99
agcuguggca gaguuacaa                                              19
```

```
<210> SEQ ID NO 100
<211> LENGTH: 19
<212> TYPE: RNA
<213> ORGANISM: artificial
<220> FEATURE:
<223> OTHER INFORMATION: Chemically Synthesized

<400> SEQUENCE: 100
ucgacagccc ugauaguua                                              19

<210> SEQ ID NO 101
<211> LENGTH: 19
<212> TYPE: RNA
<213> ORGANISM: artificial
<220> FEATURE:
<223> OTHER INFORMATION: Chemically Synthesized

<400> SEQUENCE: 101
uucaucauuc cgaagaucc                                              19

<210> SEQ ID NO 102
<211> LENGTH: 19
<212> TYPE: RNA
<213> ORGANISM: artificial
<220> FEATURE:
<223> OTHER INFORMATION: Chemically Synthesized

<400> SEQUENCE: 102
uagacuauga gcaagcaug                                              19

<210> SEQ ID NO 103
<211> LENGTH: 19
<212> TYPE: RNA
<213> ORGANISM: artificial
<220> FEATURE:
<223> OTHER INFORMATION: Chemically Synthesized

<400> SEQUENCE: 103
ucaaucacca guuucuucc                                              19

<210> SEQ ID NO 104
<211> LENGTH: 19
<212> TYPE: RNA
<213> ORGANISM: artificial
<220> FEATURE:
<223> OTHER INFORMATION: Chemically Synthesized

<400> SEQUENCE: 104
uugaacacuc cauguaccc                                              19

<210> SEQ ID NO 105
<211> LENGTH: 19
<212> TYPE: RNA
<213> ORGANISM: artificial
<220> FEATURE:
<223> OTHER INFORMATION: Chemically Synthesized

<400> SEQUENCE: 105
uucauuccga agauccuuc                                              19

<210> SEQ ID NO 106
<211> LENGTH: 19
<212> TYPE: RNA
<213> ORGANISM: artificial
<220> FEATURE:
<223> OTHER INFORMATION: Chemically Synthesized
```

```
<400> SEQUENCE: 106 uugugugcu caucauucc                                          19

<210> SEQ ID NO 107
<211> LENGTH: 19
<212> TYPE: RNA
<213> ORGANISM: artificial
<220> FEATURE:
<223> OTHER INFORMATION: Chemically Synthesized

<400> SEQUENCE: 107
uuaucucugc cuucuucag                                         19

<210> SEQ ID NO 108
<211> LENGTH: 19
<212> TYPE: RNA
<213> ORGANISM: artificial
<220> FEATURE:
<223> OTHER INFORMATION: Chemically Synthesized

<400> SEQUENCE: 108
uuguuugcca uaucucugc                                         19

<210> SEQ ID NO 109
<211> LENGTH: 19
<212> TYPE: RNA
<213> ORGANISM: artificial
<220> FEATURE:
<223> OTHER INFORMATION: Chemically Synthesized

<400> SEQUENCE: 109
uauaucugcc acauaguuc                                         19

<210> SEQ ID NO 110
<211> LENGTH: 19
<212> TYPE: RNA
<213> ORGANISM: artificial
<220> FEATURE:
<223> OTHER INFORMATION: Chemically Synthesized

<400> SEQUENCE: 110
uuaucagggc ugucgaugg                                         19

<210> SEQ ID NO 111
<211> LENGTH: 19
<212> TYPE: RNA
<213> ORGANISM: artificial
<220> FEATURE:
<223> OTHER INFORMATION: Chemically Synthesized

<400> SEQUENCE: 111
uaaaugcuug acuucuggg                                         19

<210> SEQ ID NO 112
<211> LENGTH: 19
<212> TYPE: RNA
<213> ORGANISM: artificial
<220> FEATURE:
<223> OTHER INFORMATION: Chemically Synthesized

<400> SEQUENCE: 112
ucauguaccc aaaagcgcc                                         19

<210> SEQ ID NO 113
```

```
<211> LENGTH: 19
<212> TYPE: RNA
<213> ORGANISM: artificial
<220> FEATURE:
<223> OTHER INFORMATION: Chemically Synthesized

<400> SEQUENCE: 113
uguagcaaga ugacuucug                                                19

<210> SEQ ID NO 114
<211> LENGTH: 19
<212> TYPE: RNA
<213> ORGANISM: artificial
<220> FEATURE:
<223> OTHER INFORMATION: Chemically Synthesized

<400> SEQUENCE: 114
aguagcaaga ugacuucug                                                19

<210> SEQ ID NO 115
<211> LENGTH: 19
<212> TYPE: RNA
<213> ORGANISM: artificial
<220> FEATURE:
<223> OTHER INFORMATION: Chemically Synthesized

<400> SEQUENCE: 115
uuuccgaaga uccuucuua                                                19

<210> SEQ ID NO 116
<211> LENGTH: 19
<212> TYPE: RNA
<213> ORGANISM: artificial
<220> FEATURE:
<223> OTHER INFORMATION: Chemically Synthesized

<400> SEQUENCE: 116
ugaacuguaa cucugccac                                                19

<210> SEQ ID NO 117
<211> LENGTH: 19
<212> TYPE: RNA
<213> ORGANISM: artificial
<220> FEATURE:
<223> OTHER INFORMATION: Chemically Synthesized

<400> SEQUENCE: 117
ucuguuugcc auaucucug                                                19

<210> SEQ ID NO 118
<211> LENGTH: 19
<212> TYPE: RNA
<213> ORGANISM: artificial
<220> FEATURE:
<223> OTHER INFORMATION: Chemically Synthesized

<400> SEQUENCE: 118
uuacccaaaa gcgccaauc                                                19

<210> SEQ ID NO 119
<211> LENGTH: 19
<212> TYPE: RNA
<213> ORGANISM: artificial
<220> FEATURE:
<223> OTHER INFORMATION: Chemically Synthesized

<400> SEQUENCE: 119
```

-continued uuaaacuauc agggcuguc                                                19

<210> SEQ ID NO 120
<211> LENGTH: 19
<212> TYPE: RNA
<213> ORGANISM: artificial
<220> FEATURE:
<223> OTHER INFORMATION: Chemically Synthesized

<400> SEQUENCE: 120
ucuugugugc ucaucauuc                                                19

<210> SEQ ID NO 121
<211> LENGTH: 19
<212> TYPE: RNA
<213> ORGANISM: artificial
<220> FEATURE:
<223> OTHER INFORMATION: Chemically Synthesized

<400> SEQUENCE: 121
uaagcgccaa uccuguuug                                                19

<210> SEQ ID NO 122
<211> LENGTH: 19
<212> TYPE: RNA
<213> ORGANISM: artificial
<220> FEATURE:
<223> OTHER INFORMATION: Chemically Synthesized

<400> SEQUENCE: 122
ucuaucaggg cugucgaug                                                19

<210> SEQ ID NO 123
<211> LENGTH: 19
<212> TYPE: RNA
<213> ORGANISM: artificial
<220> FEATURE:
<223> OTHER INFORMATION: Chemically Synthesized

<400> SEQUENCE: 123
ucucaucauu ccgaagauc                                                19

<210> SEQ ID NO 124
<211> LENGTH: 19
<212> TYPE: RNA
<213> ORGANISM: artificial
<220> FEATURE:
<223> OTHER INFORMATION: Chemically Synthesized

<400> SEQUENCE: 124
acucaucauu ccgaagauc                                                19

<210> SEQ ID NO 125
<211> LENGTH: 19
<212> TYPE: RNA
<213> ORGANISM: artificial
<220> FEATURE:
<223> OTHER INFORMATION: Chemically Synthesized

<400> SEQUENCE: 125
uacuguaacu cugccacag                                                19

<210> SEQ ID NO 126
<211> LENGTH: 19
<212> TYPE: RNA

```
<213> ORGANISM: artificial
<220> FEATURE:
<223> OTHER INFORMATION: Chemically Synthesized

<400> SEQUENCE: 126
uugcucauca uuccgaaga                                                    19

<210> SEQ ID NO 127
<211> LENGTH: 19
<212> TYPE: RNA
<213> ORGANISM: artificial
<220> FEATURE:
<223> OTHER INFORMATION: Chemically Synthesized

<400> SEQUENCE: 127
uaacuguaac ucugccaca                                                    19

<210> SEQ ID NO 128
<211> LENGTH: 19
<212> TYPE: RNA
<213> ORGANISM: artificial
<220> FEATURE:
<223> OTHER INFORMATION: Chemically Synthesized

<400> SEQUENCE: 128
ucgccuugug ugcucauca                                                    19

<210> SEQ ID NO 129
<211> LENGTH: 19
<212> TYPE: RNA
<213> ORGANISM: artificial
<220> FEATURE:
<223> OTHER INFORMATION: Chemically Synthesized

<400> SEQUENCE: 129
uggcugucga uggaaaaac                                                    19

<210> SEQ ID NO 130
<211> LENGTH: 19
<212> TYPE: RNA
<213> ORGANISM: artificial
<220> FEATURE:
<223> OTHER INFORMATION: Chemically Synthesized

<400> SEQUENCE: 130
uugugcucau cauuccgaa                                                    19

<210> SEQ ID NO 131
<211> LENGTH: 19
<212> TYPE: RNA
<213> ORGANISM: artificial
<220> FEATURE:
<223> OTHER INFORMATION: Chemically Synthesized

<400> SEQUENCE: 131
ucacaucagu auaacaucg                                                    19

<210> SEQ ID NO 132
<211> LENGTH: 19
<212> TYPE: RNA
<213> ORGANISM: artificial
<220> FEATURE:
<223> OTHER INFORMATION: Chemically Synthesized

<400> SEQUENCE: 132
ucugucgaug gaaaacac                                                     19
```

<210> SEQ ID NO 133
<211> LENGTH: 19
<212> TYPE: RNA
<213> ORGANISM: artificial
<220> FEATURE:
<223> OTHER INFORMATION: Chemically Synthesized

<400> SEQUENCE: 133
uuguaacucu gccacagcu                                                19

<210> SEQ ID NO 134
<211> LENGTH: 19
<212> TYPE: RNA
<213> ORGANISM: Artificial Sequence
<220> FEATURE:
<223> OTHER INFORMATION: Chemically Synthesized

<400> SEQUENCE: 134
uaacuaucag ggcugucga                                                19

<210> SEQ ID NO 135
<211> LENGTH: 19
<212> TYPE: RNA
<213> ORGANISM: artificial
<220> FEATURE:
<223> OTHER INFORMATION: Chemically Synthesized

<400> SEQUENCE: 135
gcuucuuucu agaaagaga                                                19

<210> SEQ ID NO 136
<211> LENGTH: 19
<212> TYPE: RNA
<213> ORGANISM: artificial
<220> FEATURE:
<223> OTHER INFORMATION: Chemically Synthesized

<400> SEQUENCE: 136
accaguauuu agaagccaa                                                19

<210> SEQ ID NO 137
<211> LENGTH: 19
<212> TYPE: RNA
<213> ORGANISM: artificial
<220> FEATURE:
<223> OTHER INFORMATION: Chemically Synthesized

<400> SEQUENCE: 137
gcccugauag uuuagaaaa                                                19

<210> SEQ ID NO 138
<211> LENGTH: 19
<212> TYPE: RNA
<213> ORGANISM: artificial
<220> FEATURE:
<223> OTHER INFORMATION: Chemically Synthesized

<400> SEQUENCE: 138
cgacagcccu gauaguuua                                                19

<210> SEQ ID NO 139
<211> LENGTH: 19
<212> TYPE: RNA
<213> ORGANISM: artificial
<220> FEATURE:

```
<223> OTHER INFORMATION: Chemically Synthesized

<400> SEQUENCE: 139
cagcccugau aguuuagaa                                                19

<210> SEQ ID NO 140
<211> LENGTH: 19
<212> TYPE: RNA
<213> ORGANISM: artificial
<220> FEATURE:
<223> OTHER INFORMATION: Chemically Synthesized

<400> SEQUENCE: 140
agaaggaucu ucggaauga                                                19

<210> SEQ ID NO 141
<211> LENGTH: 19
<212> TYPE: RNA
<213> ORGANISM: artificial
<220> FEATURE:
<223> OTHER INFORMATION: Chemically Synthesized

<400> SEQUENCE: 141
uaagaaggau cuucggaau                                                19

<210> SEQ ID NO 142
<211> LENGTH: 19
<212> TYPE: RNA
<213> ORGANISM: artificial
<220> FEATURE:
<223> OTHER INFORMATION: Chemically Synthesized

<400> SEQUENCE: 142
ggaucuucgg aaugaugag                                                19

<210> SEQ ID NO 143
<211> LENGTH: 19
<212> TYPE: RNA
<213> ORGANISM: artificial
<220> FEATURE:
<223> OTHER INFORMATION: Chemically Synthesized

<400> SEQUENCE: 143
guggcagagu uacaguucu                                                19

<210> SEQ ID NO 144
<211> LENGTH: 19
<212> TYPE: RNA
<213> ORGANISM: artificial
<220> FEATURE:
<223> OTHER INFORMATION: Chemically Synthesized

<400> SEQUENCE: 144
cuucggaaug augagcaca                                                19

<210> SEQ ID NO 145
<211> LENGTH: 19
<212> TYPE: RNA
<213> ORGANISM: artificial
<220> FEATURE:
<223> OTHER INFORMATION: Chemically Synthesized

<400> SEQUENCE: 145
cuguggcaga guuacaguu                                                19
```

```
<210> SEQ ID NO 146
<211> LENGTH: 19
<212> TYPE: RNA
<213> ORGANISM: artificial
<220> FEATURE:
<223> OTHER INFORMATION: Chemically Synthesized

<400> SEQUENCE: 146
caucgacagc ccugauagu                                                    19

<210> SEQ ID NO 147
<211> LENGTH: 19
<212> TYPE: RNA
<213> ORGANISM: artificial
<220> FEATURE:
<223> OTHER INFORMATION: Chemically Synthesized

<400> SEQUENCE: 147
cagcuguggc agaguuaca                                                    19

<210> SEQ ID NO 148
<211> LENGTH: 19
<212> TYPE: RNA
<213> ORGANISM: artificial
<220> FEATURE:
<223> OTHER INFORMATION: Chemically Synthesized

<400> SEQUENCE: 148
gaucuucgga augaugagc                                                    19

<210> SEQ ID NO 149
<211> LENGTH: 19
<212> TYPE: RNA
<213> ORGANISM: artificial
<220> FEATURE:
<223> OTHER INFORMATION: Chemically Synthesized

<400> SEQUENCE: 149
ucucuuucua gaaagaagc                                                    19

<210> SEQ ID NO 150
<211> LENGTH: 19
<212> TYPE: RNA
<213> ORGANISM: artificial
<220> FEATURE:
<223> OTHER INFORMATION: Chemically Synthesized

<400> SEQUENCE: 150
uuggcuucua aauacuggu                                                    19

<210> SEQ ID NO 151
<211> LENGTH: 19
<212> TYPE: RNA
<213> ORGANISM: artificial
<220> FEATURE:
<223> OTHER INFORMATION: Chemically Synthesized

<400> SEQUENCE: 151
uuuucuaaac uaucagggc                                                    19

<210> SEQ ID NO 152
<211> LENGTH: 19
<212> TYPE: RNA
<213> ORGANISM: artificial
<220> FEATURE:
<223> OTHER INFORMATION: Chemically Synthesized
```

```
<400> SEQUENCE: 152
uaaacuauca gggcugucg                                          19

<210> SEQ ID NO 153
<211> LENGTH: 19
<212> TYPE: RNA
<213> ORGANISM: artificial
<220> FEATURE:
<223> OTHER INFORMATION: Chemically Synthesized

<400> SEQUENCE: 153
uucuaaacua ucagggcug                                          19

<210> SEQ ID NO 154
<211> LENGTH: 19
<212> TYPE: RNA
<213> ORGANISM: artificial
<220> FEATURE:
<223> OTHER INFORMATION: Chemically Synthesized

<400> SEQUENCE: 154
ucauuccgaa gauccuucu                                          19

<210> SEQ ID NO 155
<211> LENGTH: 19
<212> TYPE: RNA
<213> ORGANISM: artificial
<220> FEATURE:
<223> OTHER INFORMATION: Chemically Synthesized

<400> SEQUENCE: 155
auuccgaaga uccuucuua                                          19

<210> SEQ ID NO 156
<211> LENGTH: 19
<212> TYPE: RNA
<213> ORGANISM: artificial
<220> FEATURE:
<223> OTHER INFORMATION: Chemically Synthesized

<400> SEQUENCE: 156
cucaucauuc cgaagaucc                                          19

<210> SEQ ID NO 157
<211> LENGTH: 19
<212> TYPE: RNA
<213> ORGANISM: artificial
<220> FEATURE:
<223> OTHER INFORMATION: Chemically Synthesized

<400> SEQUENCE: 157
agaacuguaa cucugccac                                          19

<210> SEQ ID NO 158
<211> LENGTH: 19
<212> TYPE: RNA
<213> ORGANISM: artificial
<220> FEATURE:
<223> OTHER INFORMATION: Chemically Synthesized

<400> SEQUENCE: 158
ugugcucauc auuccgaag                                          19

<210> SEQ ID NO 159
<211> LENGTH: 19
```

```
<212> TYPE: RNA
<213> ORGANISM: artificial
<220> FEATURE:
<223> OTHER INFORMATION: Chemically Synthesized

<400> SEQUENCE: 159
aacuguaacu cugccacag                                                      19

<210> SEQ ID NO 160
<211> LENGTH: 19
<212> TYPE: RNA
<213> ORGANISM: artificial
<220> FEATURE:
<223> OTHER INFORMATION: Chemically Synthesized

<400> SEQUENCE: 160
acuaucaggg cugucgaug                                                      19

<210> SEQ ID NO 161
<211> LENGTH: 19
<212> TYPE: RNA
<213> ORGANISM: artificial
<220> FEATURE:
<223> OTHER INFORMATION: Chemically Synthesized

<400> SEQUENCE: 161
uguaacucug ccacagcug                                                      19

<210> SEQ ID NO 162
<211> LENGTH: 19
<212> TYPE: RNA
<213> ORGANISM: Artificial Sequence
<220> FEATURE:
<223> OTHER INFORMATION: Chemically Synthesized

<400> SEQUENCE: 162
gcucaucauu ccgaagauc                                                      19

<210> SEQ ID NO 163
<211> LENGTH: 19
<212> TYPE: RNA
<213> ORGANISM: artificial
<220> FEATURE:
<223> OTHER INFORMATION: Chemically Synthesized

<400> SEQUENCE: 163
cggaaugaug agcacacaa                                                      19

<210> SEQ ID NO 164
<211> LENGTH: 19
<212> TYPE: RNA
<213> ORGANISM: artificial
<220> FEATURE:
<223> OTHER INFORMATION: Chemically Synthesized

<400> SEQUENCE: 164
gaaggaucuu cggaaugau                                                      19

<210> SEQ ID NO 165
<211> LENGTH: 19
<212> TYPE: RNA
<213> ORGANISM: artificial
<220> FEATURE:
<223> OTHER INFORMATION: Chemically Synthesized

<400> SEQUENCE: 165
```
ucggaaugau gagcacaca                                                19

<210> SEQ ID NO 166
<211> LENGTH: 19
<212> TYPE: RNA
<213> ORGANISM: artificial
<220> FEATURE:
<223> OTHER INFORMATION: Chemically Synthesized

<400> SEQUENCE: 166
ucgacagccc ugauaguuu                                                19

<210> SEQ ID NO 167
<211> LENGTH: 19
<212> TYPE: RNA
<213> ORGANISM: artificial
<220> FEATURE:
<223> OTHER INFORMATION: Chemically Synthesized

<400> SEQUENCE: 167
uugugugcuc aucauuccg                                                19

<210> SEQ ID NO 168
<211> LENGTH: 19
<212> TYPE: RNA
<213> ORGANISM: artificial
<220> FEATURE:
<223> OTHER INFORMATION: Chemically Synthesized

<400> SEQUENCE: 168
aucauuccga agauccuuc                                                19

<210> SEQ ID NO 169
<211> LENGTH: 19
<212> TYPE: RNA
<213> ORGANISM: artificial
<220> FEATURE:
<223> OTHER INFORMATION: Chemically Synthesized

<400> SEQUENCE: 169
ugugugcuca ucauuccga                                                19

<210> SEQ ID NO 170
<211> LENGTH: 19
<212> TYPE: RNA
<213> ORGANISM: Artificial Sequence
<220> FEATURE:
<223> OTHER INFORMATION: Chemically Synthesized

<400> SEQUENCE: 170
aaacuaucag ggcugucga                                                19

<210> SEQ ID NO 171
<211> LENGTH: 19
<212> TYPE: RNA
<213> ORGANISM: artificial
<220> FEATURE:
<223> OTHER INFORMATION: Chemically Synthesized

<400> SEQUENCE: 171
aagucaucuu gcuaccagu                                                19

<210> SEQ ID NO 172
<211> LENGTH: 19
<212> TYPE: RNA
<213> ORGANISM: artificial

```
<220> FEATURE:
<223> OTHER INFORMATION: Chemically Synthesized

<400> SEQUENCE: 172
ggcagaguua caguucugu                                                19

<210> SEQ ID NO 173
<211> LENGTH: 19
<212> TYPE: RNA
<213> ORGANISM: artificial
<220> FEATURE:
<223> OTHER INFORMATION: Chemically Synthesized

<400> SEQUENCE: 173
agaagucauc uugcuacca                                                19

<210> SEQ ID NO 174
<211> LENGTH: 19
<212> TYPE: RNA
<213> ORGANISM: artificial
<220> FEATURE:
<223> OTHER INFORMATION: Chemically Synthesized

<400> SEQUENCE: 174
gcagaguuac aguucugug                                                19

<210> SEQ ID NO 175
<211> LENGTH: 19
<212> TYPE: RNA
<213> ORGANISM: artificial
<220> FEATURE:
<223> OTHER INFORMATION: Chemically Synthesized

<400> SEQUENCE: 175
uggcagaguu acaguucug                                                19

<210> SEQ ID NO 176
<211> LENGTH: 19
<212> TYPE: RNA
<213> ORGANISM: artificial
<220> FEATURE:
<223> OTHER INFORMATION: Chemically Synthesized

<400> SEQUENCE: 176
cagaguuaca guucugugg                                                19

<210> SEQ ID NO 177
<211> LENGTH: 19
<212> TYPE: RNA
<213> ORGANISM: artificial
<220> FEATURE:
<223> OTHER INFORMATION: Chemically Synthesized

<400> SEQUENCE: 177
gaagucaucu ugcuaccag                                                19

<210> SEQ ID NO 178
<211> LENGTH: 19
<212> TYPE: RNA
<213> ORGANISM: artificial
<220> FEATURE:
<223> OTHER INFORMATION: Chemically Synthesized

<400> SEQUENCE: 178
acugguagca agaugacuu                                                19
```

```
<210> SEQ ID NO 179
<211> LENGTH: 19
<212> TYPE: RNA
<213> ORGANISM: artificial
<220> FEATURE:
<223> OTHER INFORMATION: Chemically Synthesized

<400> SEQUENCE: 179
acagaacugu aacucugcc                                                19

<210> SEQ ID NO 180
<211> LENGTH: 19
<212> TYPE: RNA
<213> ORGANISM: artificial
<220> FEATURE:
<223> OTHER INFORMATION: Chemically Synthesized

<400> SEQUENCE: 180
ugguagcaag augacuucu                                                19

<210> SEQ ID NO 181
<211> LENGTH: 19
<212> TYPE: RNA
<213> ORGANISM: artificial
<220> FEATURE:
<223> OTHER INFORMATION: Chemically Synthesized

<400> SEQUENCE: 181
cacagaacug uaacucugc                                                19

<210> SEQ ID NO 182
<211> LENGTH: 19
<212> TYPE: RNA
<213> ORGANISM: artificial
<220> FEATURE:
<223> OTHER INFORMATION: Chemically Synthesized

<400> SEQUENCE: 182
cagaacugua acucugcca                                                19

<210> SEQ ID NO 183
<211> LENGTH: 19
<212> TYPE: RNA
<213> ORGANISM: artificial
<220> FEATURE:
<223> OTHER INFORMATION: Chemically Synthesized

<400> SEQUENCE: 183
ccacagaacu guaacucug                                                19

<210> SEQ ID NO 184
<211> LENGTH: 19
<212> TYPE: RNA
<213> ORGANISM: Artificial Sequence
<220> FEATURE:
<223> OTHER INFORMATION: Chemically Synthesized

<400> SEQUENCE: 184
cugguagcaa gaugacuuc                                                19
```

DOUBLE STRANDED RNA COMPOUNDS TO RHOA AND USE THEREOF

RELATED PATENT APPLICATIONS

This application is a §371 national stage of PCT International Application No. PCT/US2011/041562, filed Jun. 23, 2011, claiming the benefit of U.S. Provisional Application No. 61/358,012, filed Jun. 24, 2010, the contents of each of which are hereby incorporated by reference in their entirety.

SEQUENCE LISTING

This application incorporates-by-reference nucleotide and/or amino acid sequences which are present in the file named "121129_2094_84694_Substitute_Sequence_Listing_GC.txt," which is 37.8 kilobytes in size, and which was created Nov. 27, 2012 in the IBM-PC machine format, having an operating system compatibility with MS-Windows, which is contained in the text file filed Nov. 29, 2012 as part of this application.

Throughout this application various patents and publications are cited. The disclosures of these documents in their entireties are hereby incorporated by reference into this application to more fully describe the state of the art to which this invention pertains

FIELD OF THE INVENTION

The present application relates to double stranded nucleotide compounds, pharmaceutical compositions comprising same and methods of use thereof for the down-regulation of Ras homolog gene family, member A (RhoA) expression.

BACKGROUND OF THE INVENTION

PCT Patent Publication Nos. WO 2008/050329 and a WO 2009/044392 assigned to the assignee of the present invention disclose certain RhoA oligonucleotides and structural motifs useful in the preparation of chemically modified siRNA compounds.

SUMMARY OF THE INVENTION

Nucleic acid molecules for down-regulating expression of RhoA, compositions and kits comprising same and methods of use thereof are provided herein. The compositions, methods and kits may involve use of nucleic acid molecules (for example, short interfering nucleic acid (siNA), short interfering RNA (siRNA), double-stranded RNA (dsRNA), microRNA (miRNA) or short hairpin RNA (shRNA)) that bind a nucleotide sequence (such as an mRNA sequence) encoding RhoA, for example, the mRNA coding sequence (SEQ ID NO:1) for human RhoA protein exemplified by SEQ ID NO:2. In certain preferred embodiments, the compositions, methods and kits disclosed herein inhibit expression of RhoA. In various embodiments the nucleic acid molecule is selected from the group consisting of unmodified or chemically modified dsRNA compound or siRNA or shRNA that down-regulates RhoA expression. In the presently preferred embodiments the inhibitor is a synthetic, chemically modified double stranded RNA (dsRNA) compound that down-regulates RhoA expression. The chemically modified nucleic acid molecules and compositions exhibit beneficial properties including at least one of increased serum stability, improved cellular uptake, reduced off target activity, reduced immunogenicity, improved endosomal release, improved specific delivery to target tissue or cell and increased knock down activity when compared to unmodified molecules.

Further disclosed herein are methods for treating or preventing the incidence or severity of a disease or condition in a subject in need thereof wherein the disease or condition and/or a symptom associated therewith is associated with expression of the RhoA gene, such as a disease, injury, condition or pathology of the central nervous system (CNS). In some embodiments the subject is a mammal. In a preferred embodiment the subject is a human subject.

In particular embodiments, chemically modified dsRNA compounds that target RhoA, compositions and kits comprising same and methods of use thereof in the treatment of a CNS condition or pathology, particularly neuropatic pain (e.g., allodynia), spinal cord injury (SCI) and glaucoma are provided herein. Other conditions to be treated include any condition in which RhoA expression is detrimental to neuron survival, neuronal growth, neural regeneration or other cellular functions. Accordingly, conditions which require regeneration of neurons or protection of neurons or the nervous system, including but not limited to multiple sclerosis, stroke, traumatic brain injury, peripheral neuropathies and acute and chronic neurodegenerative diseases, are treated with the compounds of the present invention.

Stable and active dsRNA compounds and compositions comprising the same useful in treating the above mentioned diseases, conditions, injury and disorders would be of great therapeutic value.

In one aspect, provided are nucleic acid molecules (e.g., dsRNA molecules) in which (a) the nucleic acid molecule is a duplex which includes a sense strand and a complementary antisense strand; (b) each strand of the nucleic acid molecule is independently 18 to 49 nucleotides in length; (c) an 18 to 49 nucleotide sequence of the antisense strand is complementary to a consecutive sequence of a mRNA encoding mammalian RhoA (e.g., SEQ ID NO: 1); and (d) the sense strand and antisense strand comprise sequence pairs set forth in any of Tables I, II, III or IV.

In certain embodiments, the sequence of the antisense strand that is complementary to a consecutive sequence of a mRNA encoding human RhoA (set forth in SEQ ID NO:1) includes a sequence complimentary to a nucleotide sequence in the ranges 290-350; or 350-414; or 414-507; or 531-551; or 557-627; or 634-651; or 627-698; or 698-757; or 919-973; or 973-990, or 1134-1346; or 1346-1369; or 1804-1926; of SEQ ID NO: 1.

In certain embodiments, the antisense strand of a nucleic acid molecule (e.g., a dsRNA molecule) as disclosed herein includes a sequence corresponding to any one of the antisense sequences shown on Table III (SEQ ID NOS:149-162). In some embodiments the sense strand and the antisense strand are selected from the sequence pairs shown in Table III. In some embodiments the sense strands and the antisense strands are selected from the sequence pairs set forth in RHOA_31 (SEQ ID NOS:135 and 149), RHOA_33 (SEQ ID NOS:136 and 150), RHOA_37 (SEQ ID NOS:137 and 151), RHOA_38 (SEQ ID NOS:138 and 152), RHOA_43 (SEQ ID NOS:139 and 153), RHOA_52 (SEQ ID NOS:140 and 154), RHOA_56 (SEQ ID NOS:141 and 155), RHOA_57 (SEQ ID NOS:142 and 156), RHOA_58 (SEQ ID NOS: 143 and 157), RHOA_68 (SEQ ID NOS:144 and 158), RHOA_69 (SEQ ID NOS:145 and 159), RHOA_70 (SEQ ID NOS:146 and 160), RHOA_73 (SEQ ID NOS:147 and 161) and RHOA_76 (SEQ ID NOS:148 and 162).

In some embodiments the antisense and sense strands of a nucleic acid molecule (e.g., a dsRNA molecule) as disclosed herein includes the sequence pair set forth in RHOA_31

(SEQ ID NOS:135 and 149). In some embodiments the antisense and sense strands of a nucleic acid molecule (e.g., a dsRNA molecule) as disclosed herein include the sequence pair set forth in RHOA_33 (SEQ ID NOS:136 and 150). In some embodiments the antisense and sense strands of a nucleic acid molecule (e.g., a dsRNA molecule) as disclosed herein include the sequence pair set forth in RHOA_37 (SEQ ID NOS:137 and 151). In some embodiments the antisense and sense strands of a nucleic acid molecule (e.g., a dsRNA molecule) as disclosed herein include the sequence pair set forth in RHOA_38 (SEQ ID NOS:138 and 152). In some embodiments the antisense and sense strands of a nucleic acid molecule (e.g., a dsRNA molecule) as disclosed herein include the sequence pair set forth in RHOA_43 (SEQ ID NOS:139 and 153). In some embodiments the antisense and sense strands of a nucleic acid molecule (e.g., a dsRNA molecule) as disclosed herein include the sequence pair set forth in RHOA_52 (SEQ ID NOS:140 and 154). In some embodiments the antisense and sense strands of a nucleic acid molecule (e.g., a dsRNA molecule) as disclosed herein include the sequence pair set forth in RHOA_56 (SEQ ID NOS:141 and 155). In some embodiments the antisense and sense strands of a nucleic acid molecule (e.g., a dsRNA molecule) as disclosed herein include the sequence pair set forth in RHOA_57 (SEQ ID NOS:142 and 156). In some embodiments the antisense and sense strands of a nucleic acid molecule (e.g., a dsRNA molecule) as disclosed herein include the sequence pairs set forth in RHOA_58 (SEQ ID NOS:143 and 157). In some embodiments the antisense and sense strands of a nucleic acid molecule (e.g., a dsRNA molecule) as disclosed herein include the sequence pair set forth in RHOA_68 (SEQ ID NOS:144 and 158). In some embodiments the antisense and sense strands of a nucleic acid molecule (e.g., a dsRNA molecule) as disclosed herein include the sequence pair set forth in RHOA_69 (SEQ ID NOS:145 and 159). In some embodiments the antisense and sense strands of a nucleic acid molecule (e.g., a dsRNA molecule) as disclosed herein include the sequence pair set forth in RHOA_70 (SEQ ID NOS:146 and 160). In some embodiments the antisense and sense strands of a nucleic acid molecule (e.g., a dsRNA molecule) as disclosed herein include the sequence pair set forth in RHOA_73 (SEQ ID NOS:147 and 161). In some embodiments the antisense and sense strands of a nucleic acid molecule (e.g., a dsRNA molecule) as disclosed herein include the sequence pair set forth in RHOA_76 (SEQ ID NOS:148 and 162).

In some preferred embodiments the sense strand and the antisense strand comprise the sequence pair set forth in RHOA_58 (SEQ ID NOS:143 and 157). In some preferred embodiments the sense strand and the antisense strand comprise the sequence pair set forth in RHOA_70 (SEQ ID NOS:146 and 160).

In certain embodiments, the antisense strand of a nucleic acid molecule (e.g., a dsRNA molecule) as disclosed herein includes a sequence corresponding to any one of the antisense sequences shown on Table IV (SEQ ID NOS:167-170). In some embodiments the sense strand and the antisense strand are selected from the sequence pairs shown in Table IV and are selected from the sequence pairs set forth in RHOA_23 (SEQ ID NOS:163 and 167), RHOA_24 (SEQ ID NOS:164 and 168), RHOA_26 (SEQ ID NOS:165 and 169) or RHOA_29 (SEQ ID NOS:166 and 170).

In certain embodiments, the antisense strand of a nucleic acid molecule (e.g., a dsRNA molecule) as disclosed herein includes a sequence corresponding to any one of the antisense sequences shown in Table II. In certain preferred embodiments the antisense strand and the strand are selected from the sequence pairs shown in Table II.

In some embodiments a nucleic acid molecule disclosed herein includes the antisense and sense strands selected from the sequence pairs set forth in RHOA_32 (SEQ ID NOS:67 and 101), RHOA_34 (SEQ ID NOS:68 and 102), RHOA_35 (SEQ ID NOS:69 and 103), RHOA_36 (SEQ ID NOS:70 and 104), RHOA_39 (SEQ ID NOS:71 and 105), RHOA_40 (SEQ ID NOS:72 and 106), RHOA_41 (SEQ ID NOS:73 and 107), RHOA_42 (SEQ ID NOS:74 and 108), RHOA_44 (SEQ ID NOS:75 and 109), RHOA_45 (SEQ ID NOS:76 and 110), RHOA_46 (SEQ ID NOS:77 and 111), RHOA_47 (SEQ ID NOS:78 and 112), RHOA_48 (SEQ ID NOS:79 and 113), RHOA_48u (SEQ ID NOS:80 and 114), RHOA_49 (SEQ ID NOS:81 and 115), RHOA_50 (SEQ ID NOS:82 and 116) RHOA_51 (SEQ ID NOS:83 and 117), RHOA_53 (SEQ ID NOS:84 and 118), RHOA_54 (SEQ ID NOS:85 and 119), RHOA_55 (SEQ ID NOS:86 and 120), RHOA_59 (SEQ ID NOS:87 and 121), RHOA_60 (SEQ ID NOS:88 and 122), RHOA_61 (SEQ ID NOS:89 and 123), RHOA_61u (SEQ ID NOS:90 and 124), RHOA_62 (SEQ ID NOS:91 and 125), RHOA_63 (SEQ ID NOS:92 and 126) RHOA_64 (SEQ ID NOS:93 and 127), RHOA_65 (SEQ ID NO:94 and 128), RHOA_66 (SEQ ID NOS:95 and 129) RHOA_67 (SEQ ID NOS:96 and 130), RHOA_71 (SEQ ID NOS:97 and 131), RHOA_72 (SEQ ID NOS:98 and 132), RHOA_74 (SEQ ID NOS:99 and 133) and RHOA_75 (SEQ ID NOS:100 and 134).

In some embodiments the antisense and sense strands of a nucleic acid molecule (e.g., a dsRNA molecule) as disclosed herein include the sequence pair set forth in RHOA_32 (SEQ ID NOS:67 and 101). In some embodiments the antisense and sense strands of a nucleic acid molecule (e.g., a dsRNA molecule) as disclosed herein include the sequence pair set forth in RHOA_34 (SEQ ID NOS:68 and 102). In some embodiments the antisense and sense strands of a nucleic acid molecule (e.g., a dsRNA molecule) as disclosed herein include the sequence pair set forth in RHOA_35 (SEQ ID NOS:69 and 103). In some embodiments the antisense and sense strands of a nucleic acid molecule (e.g., a dsRNA molecule) as disclosed herein include the sequence pair set forth in RHOA_36 (SEQ ID NOS:70 and 104). In some embodiments the antisense and sense strands of a nucleic acid molecule (e.g., a dsRNA molecule) as disclosed herein include the sequence pair set forth in RHOA_39 (SEQ ID NOS:71 and 105). In some embodiments the antisense and sense strands of a nucleic acid molecule (e.g., a dsRNA molecule) as disclosed hereininclude the sequence pair set forth in RHOA_40 (SEQ ID NOS:72 and 106). In some embodiments the antisense and sense strands of a nucleic acid molecule (e.g., a dsRNA molecule) as disclosed herein include the sequence pair set forth in RHOA_41 (SEQ ID NOS:73 and 107). In some embodiments the antisense and sense strands of a nucleic acid molecule (e.g., a dsRNA molecule) as disclosed herein include the sequence pair set forth in RHOA_42 (SEQ ID NOS:74 and 108). In some embodiments the antisense and sense strands of a nucleic acid molecule (e.g., a dsRNA molecule) as disclosed hereininclude the sequence pair set forth in RHOA_44 (SEQ ID NOS:75 and 109). In some embodiments the antisense and sense strands of a nucleic acid molecule (e.g., a dsRNA molecule) as disclosed herein include the sequence pair set forth in RHOA_45 (SEQ ID NOS:76 and 110). In some embodiments the antisense and sense strands of a nucleic acid molecule (e.g., a dsRNA molecule) as disclosed herein include the sequence pair set forth in RHOA_46 (SEQ ID NOS:77 and 111) In some embodiments the antisense and sense strands of a nucleic acid molecule (e.g., a dsRNA molecule) as disclosed herein include the sequence pair set forth in RHOA_47 (SEQ ID NOS:78 and 112). In some embodiments the antisense and sense strands of a nucleic acid molecule (e.g., a dsRNA molecule) as disclosed herein include the sequence pair set forth in RHOA_48 (SEQ ID NOS:79 and 113), RHOA_48u (SEQ ID NOS:80 and 114), RHOA_49 (SEQ ID NOS:81 and 115). In some embodiments the antisense and sense strands of a nucleic acid molecule (e.g., a dsRNA molecule) as disclosed herein include the sequence pair set forth in RHOA_50 (SEQ ID NOS:82 and 116). In some embodiments the antisense and sense strands of a nucleic acid molecule (e.g., a dsRNA molecule) as disclosed herein include the sequence pair set forth in RHOA_51 (SEQ ID NOS:83 and 117). In some embodiments the antisense and sense strands of a nucleic acid molecule (e.g., a dsRNA molecule) as disclosed herein include the sequence pair set forth in RHOA_53 (SEQ ID NOS:84 and 118). In some embodiments the antisense and sense strands of a nucleic acid molecule (e.g., a dsRNA molecule) as disclosed herein include the sequence pair set forth in RHOA_54 (SEQ ID NOS:85 and 119). In some embodiments the antisense and sense strands of a nucleic acid molecule (e.g., a dsRNA molecule) as disclosed herein include the sequence pair set forth in RHOA_55 (SEQ ID NOS:86 and 120). In some embodiments the antisense and sense strands of a nucleic acid molecule (e.g., a dsRNA molecule) as disclosed herein include the sequence pair set forth in RHOA_59 (SEQ ID NOS:87 and 121). In some embodiments the antisense and sense strands of a nucleic acid molecule (e.g., a dsRNA molecule) as disclosed herein include the sequence pair set forth in RHOA_60 (SEQ ID NOS:88 and 122). In some embodiments the antisense and sense strands of a nucleic acid molecule (e.g., a dsRNA molecule) as disclosed herein include the sequence pair set forth in RHOA_61 (SEQ ID NOS:89 and 123). In some embodiments the antisense and sense strands of a nucleic acid molecule (e.g., a dsRNA molecule) as disclosed herein include the sequence pair set forth in RHOA_61u (SEQ ID NOS:90 and 124). In some embodiments the antisense and sense strands of a nucleic acid molecule (e.g., a dsRNA molecule) as disclosed herein include the sequence pair set forth in RHOA_62 (SEQ ID NOS:91 and 125). In some embodiments the antisense and sense strands of a nucleic acid molecule (e.g., a dsRNA molecule) as disclosed herein include the sequence pair set forth in RHOA_63 (SEQ ID NOS:92 and 126). In some embodiments the antisense and sense strands of a nucleic acid molecule (e.g., a dsRNA molecule) as disclosed herein include the sequence pair set forth in RHOA_64 (SEQ ID NOS:93 and 127). In some embodiments the antisense and sense strands of a nucleic acid molecule (e.g., a dsRNA molecule) as disclosed herein include the sequence pair set forth in RHOA_65 (SEQ ID NO:94 and 128). In some embodiments the antisense and sense strands of a nucleic acid molecule (e.g., a dsRNA molecule) as disclosed herein include the sequence pair set forth in RHOA_66 (SEQ ID NOS:95 and 129). In some embodiments the antisense and sense strands of a nucleic acid molecule (e.g., a dsRNA molecule) as disclosed herein include the sequence pair set forth in RHOA_67 (SEQ ID NOS:96 and 130). In some embodiments the antisense and sense strands of a nucleic acid molecule (e.g., a dsRNA molecule) as disclosed herein include the sequence pair set forth in RHOA_71 (SEQ ID NOS:97 and 131), RHOA_72 (SEQ ID NOS:98 and 132), RHOA_74 (SEQ ID NOS:99 and 133). In some embodiments the antisense and sense strands of a nucleic acid molecule (e.g., a dsRNA molecule) as disclosed herein include the sequence pair set forth in RHOA_75 (SEQ ID NOS:100 and 134).

In some preferred embodiments the antisense and sense strands of a nucleic acid molecule (e.g., a dsRNA molecule) as disclosed herein include the sequence pair set forth in RHOA_48 (SEQ ID NOS: 79 and 113), RHOA_48u (SEQ ID NOS: 80 and 114), RHOA_50 (SEQ ID NOS: 82 and 116), RHOA_61 (SEQ ID NOS: 89 and 123), RHOA_61u (SEQ ID NOS: 90 and 124) or RHOA_75 (SEQ ID NOS: 100 and 134).

In some preferred embodiments the antisense and sense strands comprise the sequence pair set forth in RHOA_48 (SEQ ID NOS: 79 and 113). In some preferred embodiments the antisense and sense strands comprise the sequence pair set forth in RHOA_48u (SEQ ID NOS: 80 and 114). In some preferred embodiments the antisense and sense strands comprise the sequence pair set forth in RHOA_50 (SEQ ID NOS: 82 and 116).

In various embodiments of nucleic acid molecules (e.g., dsRNA molecules) as disclosed herein, the antisense strand may be 18 to 49 nucleotides in length (e.g., 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 nucleotides in length); or 18-35 nucleotides in length; or 18-30 nucleotides in length; or 18-25 nucleotides in length; or 18-23 nucleotides in length; or 19-21 nucleotides in length; or 25-30 nucleotides in length; or 26-28 nucleotides in length. In some embodiments of nucleic acid molecules (e.g., dsRNA molecules) as disclosed herein, the antisense strand is 19 nucleotides in length. Similarly the sense strand of nucleic acid molecules (e.g., dsRNA molecules) as disclosed herein may be 18 to 49 nucleotides in length (e.g., 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 nucleotides in length); or 18-35 nucleotides in length; or 18-30 nucleotides in length; or 18-25 nucleotides in length; or 18-23 nucleotides in length; or 19-21 nucleotides in length; or 25-30 nucleotides in length; or 26-28 nucleotides in length. In some embodiments of nucleic acid molecules (e.g., dsRNA molecules) as disclosed herein, the sense strand is 19 nucleotides in length. In some embodiments of nucleic acid molecules (e.g., dsRNA molecules) as disclosed herein, each of the antisense strand and the sense strand are 19 nucleotides in length. The duplex region of the nucleic acid molecules (e.g., dsRNA molecules) as disclosed herein may be 18-49 nucleotides in length (e.g., about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 nucleotides in length), 18-35 nucleotides in length; or 18-30 nucleotides in length; or about 18-25 nucleotides in length; or 18-25 nucleotides in length; or 18-23 nucleotides in length; or 18-21 nucleotides in length; or 25-30 nucleotides in length; or 25-28 nucleotides in length. In various embodiments of nucleic acid molecules (e.g., dsRNA molecules) as disclosed herein, the duplex region is 19 nucleotides in length.

In certain embodiments, the sense strand and the antisense strand of a nucleic acid (e.g., an dsRNA nucleic acid molecule) as provided herein are separate polynucleotide strands. In some embodiments, the separate sense and antisense strands form a double stranded structure, also known as a duplex, via hydrogen bonding, for example, Watson-Crick base pairing. In some embodiments one or more nucleotide pairs form non-Watson-Crick base pairing. In some embodiments the sense and antisense strands are two separate strands that are covalently linked to each other. In other embodiments, the sense and antisense strands are part of a single polynucleotide strand having both a sense and antisense region; in some preferred embodiments the polynucleotide strand has a hairpin structure.

In certain embodiments, the nucleic acid molecule is a double stranded nucleic acid (dsRNA) molecule that is symmetrical with regard to overhangs, and has a blunt end on both ends. In other embodiments the nucleic acid molecule is a dsRNA molecule that is symmetrical with regard to overhangs, and has a nucleotide or a non-nucleotide or a combination of a nucleotide and non-nucleotide overhang on both ends of the dsRNA molecule. In certain preferred embodiments, the nucleic acid molecule is a dsRNA molecule that is asymmetrical with regard to overhangs, and has a blunt end on one end of the molecule and an overhang on the other end of the molecule. In some embodiments an asymmetrical dsRNA molecule has a 3'-overhang on one side of a duplex occurring on the sense strand; and a blunt end on the other side of the molecule. In some embodiments an asymmetrical dsRNA molecule has a 5'-overhang on one side of a duplex occurring on the sense strand; and a blunt end on the other side of the molecule. In other embodiments an asymmetrical dsNA molecule has a 3'-overhang on one side of a duplex occurring on the antisense strand; and a blunt end on the other side of the molecule. In some embodiments an asymmetrical dsRNA molecule has a 5'-overhang on one side of a duplex occurring on the antisense strand; and a blunt end on the other side of the molecule. In some embodiments the overhangs are nucleotide overhangs, in other embodiments the overhangs are non-nucleotide overhangs. In some embodiments the overhangs are 5' overhangs; in alternative embodiments the overhangs are 3' overhangs.

In some embodiments, the nucleic acid molecule has a hairpin structure (having the sense strand and antisense strand on one polynucleotide), with a loop structure on one end and a blunt end on the other end. In some embodiments, the nucleic acid molecule has a hairpin structure, with a loop structure on one end and an overhang end on the other end; in certain embodiments, the overhang is a 3'-overhang; in certain embodiments the overhang is a 5'-overhang; in certain embodiments the overhang is on the sense strand; in certain embodiments the overhang is on the antisense strand.

The nucleic acid molecules (e.g., dsRNA molecule) disclosed herein may include one or more modifications or modified nucleotides such as described herein. For example, a nucleic acid molecule (e.g., dsRNA molecule) as provided herein may include a modified nucleotide having a modified sugar; a modified nucleotide having a modified nucleobase; or a modified nucleotide having a modified phosphate group. Similarly, a nucleic acid molecule (e.g., dsRNA molecule) as provided herein may include a modified phosphodiester backbone and/or may include a modified terminal phosphate group.

Nucleic acid molecules (e.g., dsRNA molecules) as provided may have one or more nucleotides that include a modified sugar moiety, for example a 2' alkoxy modified sugar moiety. In some preferred embodiments the modified sugar comprises a 2'-O-methyl.

Nucleic acid molecules (e.g., dsRNA molecules) as provided may have one or more modified nucleobase(s) for example as described herein, which may be selected from the group consisting of xanthine, hypoxanthine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine, and acyclonucleotides.

Nucleic acid molecules (e.g., dsRNA molecules) as provided may have one or more modifications to the phosphodiester backbone, for example as described herein. In some preferred embodiments the phosphodiester bond is modified by substituting the phosphodiester bond with a phosphorothioate, 3'-(or -5')deoxy-3'-(or -5')thio-phosphorothioate, phosphorodithioate, phosphoroselenate, 3'-(or -5')deoxy phosphinate, borano phosphate, 3'-(or -5')deoxy-3'-(or 5'-) amino phosphoramidate, hydrogen phosphonate, borano phosphate ester, phosphoramidate, alkyl or aryl phosphonate and a phosphotriester.

In various embodiments, the provided nucleic acid molecules (e.g., dsRNA molecules) may include an unmodified antisense strand and a sense strand having one or more modifications. In some embodiments the provided nucleic acid molecules (e.g., dsRNA molecules) include an unmodified sense strand and one an antisense strand having or more modifications. In preferred embodiments the provided nucleic acid molecules (e.g., dsRNA molecules) include one or more modified nucleotides in the both the sense strand and the antisense strand.

The nucleic acid molecules (e.g., dsRNA molecules) as provided herein may include a phosphate group at the 5' end of the sense and/or the antisense strand. In some embodiments the dsRNA molecules disclosed herein include a phosphate group at the 5' terminus of the antisense strand.

In some embodiments provided are double stranded nucleic acid compounds useful for down-regulating expression of RhoA. In some embodiments provided herein is a double stranded RNA compound having the structure (A1):

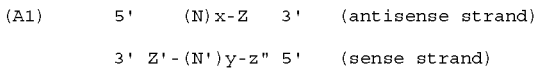

```
(A1)     5'    (N)x-Z    3'    (antisense strand)

3' Z'-(N')y-z"   5'    (sense strand)
``` wherein each N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein each of Z and Z' is independently present or absent, but if present independently comprises 1-5 consecutive nucleotides, 1-5 consecutive non-nucleotide moieties or a combination thereof covalently attached at the 3' terminus of the strand in which it is present;

wherein z" may be present or absent, but if present is a capping moiety covalently attached at the 5' terminus of (N')y;

each of x and y is independently an integer from 18 to 40;

wherein the sequence of (N')y is complementary to the sequence of (N)x; and wherein (N)x comprises an antisense sequence set forth in Table III or Table IV.

The sense and antisense sequences useful in generating dsRNA compounds provided in Table III are RHOA_31 (SEQ ID NOS:135 and 149), RHOA_33 (SEQ ID NOS:136 and 150), RHOA_37 (SEQ ID NOS:137 and 151), RHOA_38 (SEQ ID NOS:138 and 152), RHOA_43 (SEQ ID NOS: 139 and 153), RHOA_52 (SEQ ID NOS:140 and 154), RHOA_56 (SEQ ID NOS:141 and 155), RHOA_57 (SEQ ID NOS:142 and 156), RHOA_58 (SEQ ID NOS:143 and 157), RHOA_68 (SEQ ID NOS:144 and 158), RHOA_69 (SEQ ID NOS:145 and 159), RHOA_70 (SEQ ID NOS:146 and 160), RHOA_73 (SEQ ID NOS:147 and 161) and RHOA_76 (SEQ ID NOS:148 and 162). The sense and antisense sequences useful in generating dsRNA compounds provided in Table IV are set forth in RHOA_23 (SEQ ID NOS:

163 and 167), RHOA_24 (SEQ ID NOS:164 and 168), RHOA_26 (SEQ ID NOS:165 and 169) or RHOA_29 (SEQ ID NOS:166 and 170).

In some embodiments the covalent bond joining each consecutive N and/or N' is a phosphodiester bond.

In some embodiments x=y and each of x and y is 19, 20, 21, 22 or 23. In preferred embodiments x=y=19.

In some embodiments of nucleic acid molecules (e.g., dsRNA molecules) as disclosed herein, the double stranded nucleic acid molecule is a siRNA, siNA or a miRNA.

In some embodiments the sense and antisense strands comprise the sequence pairs set forth in RHOA_58 (SEQ ID NOS: 143 and 157). In some embodiments the sense and antisense strands comprise the sequence pairs set forth in RHOA_70 (SEQ ID NOS: 146 and 160).

In some embodiments the double stranded nucleic acid molecules comprise a DNA moiety or a mismatch to the target at position 1 of the antisense strand (5' terminus). Such a duplex structure is described herein. According to one embodiment provided are double stranded siRNA compounds having a structure (A2) set forth below:

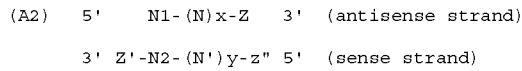

wherein each N1, N2, N and N' is independently an unmodified or modified nucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein N2 is covalently bound to (N')y;

wherein N1 is covalently bound to (N)x and is mismatched to the target mRNA (SEQ ID NO:1) or is a complementary DNA moiety to the target mRNA;

wherein N1 is a moiety selected from the group consisting of natural or modified: uridine, deoxyribouridine, ribothymidine, deoxyribothymidine, adenosine or deoxyadenosine, an abasic ribose moiety and an abasic deoxyribose moiety;

wherein z" may be present or absent, but if present is a capping moiety covalently attached at the 5' terminus of N2-(N')y;

wherein each of Z and Z' is independently present or absent, but if present is independently 1-5 consecutive nucleotides, 1-5 consecutive non-nucleotide moieties or a combination thereof covalently attached at the 3' terminus of the strand in which it is present; and wherein the sequence of (N')y is complementary to the sequence of (N)x; and wherein the sequence of (N)x comprises an antisense sequence set forth in Table I.

In various embodiments the sequence of N1-(N)x comprises an antisense sequence set forth in Table II. In some embodiments the N2-(N')y and N1-(N)x useful in generating dsRNA compounds are presented in Table II and set forth in RHOA_32 (SEQ ID NOS:67 and 101), RHOA_34 (SEQ ID NOS:68 and 102), RHOA_35 (SEQ ID NOS:69 and 103), RHOA_36 (SEQ ID NOS:70 and 104), RHOA_39 (SEQ ID NOS:71 and 105), RHOA_40 (SEQ ID NOS:72 and 106), RHOA_41 (SEQ ID NOS:73 and 107), RHOA_42 (SEQ ID NOS:74 and 108), RHOA_44 (SEQ ID NOS:75 and 109), RHOA_45 (SEQ ID NOS:76 and 110), RHOA_46 (SEQ ID NOS:77 and 111), RHOA_47 (SEQ ID NOS:78 and 112), RHOA_48 (SEQ ID NOS:79 and 113), RHOA_48u (SEQ ID NOS:80 and 114), RHOA_49 (SEQ ID NOS:81 and 115), RHOA_50 (SEQ ID NOS:82 and 116) RHOA_51 (SEQ ID NOS:83 and 117), RHOA_53 (SEQ ID NOS:84 and 118), RHOA_54 (SEQ ID NOS:85 and 119), RHOA_55 (SEQ ID NOS:86 and 120), RHOA_59 (SEQ ID NOS:87 and 121), RHOA_60 (SEQ ID NOS:88 and 122), RHOA_61 (SEQ ID NOS:89 and 123), RHOA_61u (SEQ ID NOS:90 and 124), RHOA_62 (SEQ ID NOS:91 and 125), RHOA_63 (SEQ ID NOS:92 and 126) RHOA_64 (SEQ ID NOS:93 and 127), RHOA_65 (SEQ ID NO:94 and 128), RHOA_66 (SEQ ID NOS:95 and 129) RHOA_67 (SEQ ID NOS:96 and 130), RHOA_71 (SEQ ID NOS:97 and 131), RHOA_72 (SEQ ID NOS:98 and 132), RHOA_74 (SEQ ID NOS:99 and 133) and RHOA_75 (SEQ ID NOS:100 and 134).

In certain embodiments, (N)x of a nucleic acid molecule (e.g., a dsRNA molecule) as disclosed herein includes a sequence corresponding to any one of the antisense sequences shown in Table I. In certain preferred embodiments (N)x and (N')y are selected from the sequence pairs shown in Table I.

In some embodiments a nucleic acid molecule disclosed herein include an (N)x and an (N')y selected from the sequence pairs set forth in RHOA_32-1 (SEQ ID NOS:3 and 35), RHOA_34-1 (SEQ ID NOS:4 and 36), RHOA_35-1 (SEQ ID NOS:5 and 37), RHOA_36-1 (SEQ ID NOS:6 and 38), RHOA_39-1 (SEQ ID NOS:7 and 39), RHOA_40-1 (SEQ ID NOS:8 and 40), RHOA_41-1 (SEQ ID NOS:9 and 41), RHOA_42-1 (SEQ ID NOS:10 and 42), RHOA_44-1 (SEQ ID NOS:11 and 43), RHOA_45-1 (SEQ ID NOS:12 and 44), RHOA_46-1 (SEQ ID NOS:13 and 45), RHOA_47-1 (SEQ ID NOS:14 and 46), RHOA_48-1 (SEQ ID NOS:15 and 47), RHOA_49-1 (SEQ ID NOS:16 and 48), RHOA_50-1 (SEQ ID NOS:17 and 49), RHOA_51-1 (SEQ ID NOS:18 and 50), RHOA_53-1 (SEQ ID NOS:19 and 51), RHOA_54-1 (SEQ ID NOS:20 and 52), RHOA_55-1 (SEQ ID NOS:21 and 53), RHOA_59-1 (SEQ ID NOS:22 and 54), RHOA_60-1 (SEQ ID NOS:23 and 55), RHOA_61-1 (SEQ ID NOS:24 and 56), RHOA_62-1 (SEQ ID NOS:25 and 57), RHOA_63-1 (SEQ ID NOS:26 and 58) RHOA_64-1 (SEQ ID NOS:27 and 59), RHOA_65-1 (SEQ ID NO:28 and 60), RHOA_66-1 (SEQ ID NOS:29 and 61), RHOA_67-1 (SEQ ID NOS:30 and 62), RHOA_71-1 (SEQ ID NOS:31 and 63), RHOA_72-1 (SEQ ID NOS:32 and 64), RHOA_74-1 (SEQ ID NOS:33 and 65) and RHOA_75-1 (SEQ ID NOS:34 and 66).

In some embodiments the sequence of (N')y is fully complementary to the sequence of (N)x. In various embodiments sequence of N2-(N')y is complementary to the sequence of N1-(N)x. In some embodiments (N)x comprises an antisense that is fully complementary to about 17 to about 39 consecutive nucleotides in a target mRNA. In other embodiments (N)x comprises an antisense that is substantially complementary to about 17 to about 39 consecutive nucleotides in a target mRNA set forth in SEQ ID NO:1.

In some embodiments N1 and N2 form a Watson-Crick base pair. In other embodiments N1 and N2 form a non-Watson-Crick base pair. In some embodiments a base pair is formed between a ribonucleotide and a deoxyribonucleotide.

In some embodiments x=y=18, x=y=19 or x=y=20. In preferred embodiments x=y=18. When x=18 in N1-(N)x, N1 refers to position 1 and positions 2-19 are included in (N)18. When y=18 in N2-(N')y, N2 refers to position 19 and positions 1-18 are included in (N')18.

In some embodiments N1 is covalently bound to (N)x and is mismatched to the target mRNA. In various embodiments N1 is covalently bound to (N)x and is a DNA moiety complementary to the target mRNA.

In some embodiments a uridine in position 1 of the antisense strand is substituted with an N1 selected from natural or modified: adenosine, deoxyadenosine, uridine, deoxyuridine (dU), ribothymidine or deoxythymidine. In various embodiments N1 is selected from natural or modified: adenosine, deoxyadenosine or deoxyuridine. For example, in some embodiments a cytidine in position 1 is replaced with an adenine or a uridine; a guanosine in position 1 is replaced with an adenine or a uridine; or an adenine is replaced with a uridine.

In some embodiments guanosine in position 1 (N1) of the antisense strand is substituted with a natural or modified: adenosine, deoxyadenosine, uridine, deoxyuridine, ribothymidine or deoxythymidine. In various embodiments N1 is selected from natural or modified: adenosine, deoxyadenosine, uridine or deoxyuridine.

In some embodiments cytidine in position 1 (N1) of the antisense strand is substituted with a natural or modified: adenosine, deoxyadenosine, uridine, deoxyuridine, ribothymidine or deoxythymidine. In various embodiments N1 is selected from natural or modified: adenosine, deoxyadenosine, uridine or deoxyuridine.

In some embodiments adenosine in position 1 (N1) of the antisense strand is substituted with a natural or modified: deoxyadenosine, deoxyuridine, ribothymidine or deoxythymidine.

In some embodiments N1 and N2 form a base pair between natural or modified: uridine or deoxyuridine, and adenosine or deoxyadenosine. In other embodiments N1 and N2 form a base pair between natural or modified: deoxyuridine and adenosine.

In some embodiments the double stranded nucleic acid molecule is a siRNA, siNA or a miRNA. The double stranded nucleic acid molecules as provided herein are also referred to as "duplexes".

In certain preferred embodiments of Structure A2 x=y=18. In some embodiments x=y=18 and (N)x consists of an antisense oligonucleotide present in Table I. In some embodiments N1 is selected from a natural uridine and a modified uridine. In some embodiments N1 is a natural uridine. In some embodiments N1-(N)x consists of an antisense oligonucleotide present in Table II. In some embodiments x=y=19 or x=y=20. In some embodiments x=y=19 or x=y=20 and (N)x comprises an antisense oligonucleotide present in Table I.

In some embodiments the preferred sense and antisense sequences useful in generating dsRNA compounds are selected from the sequence pairs set forth in Table II: RHOA_48 (SEQ ID NOS: 79 and 113), RHOA_48u (SEQ ID NOS: 80 and 114), RHOA_50 (SEQ ID NOS: 82 and 116), RHOA_61 (SEQ ID NOS: 89 and 123), RHOA_61u (SEQ ID NOS: 90 and 124), and RHOA_75 (SEQ ID NOS: 100 and 134).

In some embodiments of Structure (A2), N1 is a 2'OMe sugar-modified uridine or a 2'OMe sugar-modified adenosine. In certain embodiments of structure (A2), $N^2$ is a 2'OMe sugar modified ribonucleotide or deoxyribonucleotide.

In some embodiments of Structure (A1) and/or Structure (A2) each N consists of an unmodified ribonucleotide. In some embodiments of Structure (A1) and/or Structure (A2) each N' consists of an unmodified nucleotide. In preferred embodiments at least one of N and/or N' comprises a chemically modified nucleotide or an unconventional moiety. In some embodiments the unconventional moiety is selected from a mirror nucleotide, an abasic ribose moiety and an abasic deoxyribose moiety. In some embodiments the unconventional moiety is a mirror nucleotide, preferably an L-DNA moiety. In some embodiments at least one of N or N' comprises a 2'OMe sugar-modified ribonucleotide.

In some embodiments of Structure (A1) and/or Structure (A2) the sequence of (N')y is fully complementary to the sequence of (N)x. In other embodiments of Structure (A1) and/or Structure (A2) the sequence of (N')y is substantially complementary to the sequence of (N)x.

In some embodiments of Structure (A1) and/or Structure (A2) (N)x includes an antisense sequence that is fully complementary to about 17 to about 39 consecutive nucleotides in a target mRNA. In other embodiments of Structure A1 and/or Structure A2 (N)x includes an antisense that is substantially complementary to about 17 to about 39 consecutive nucleotides in a target mRNA. In some embodiments of Structure (A1) and/or Structure (A2) the dsRNA compound is blunt ended, for example, wherein each of z", Z and Z' is absent. In an alternative embodiment, at least one of z", Z or Z' is present.

In various embodiments Z and Z' independently include one or more covalently linked modified and or unmodified nucleotides, including deoxyribonucleotides and ribonucleotides, or one or more unconventional moieties for example inverted abasic deoxyribose moiety or abasic ribose moiety or a mirror nucleotide; one or more non-nucleotide C3, C4 or C5 moiety, an amino-C6 moiety, and the like. In some embodiments Z' is absent and Z is present and includes one or more non-nucleotide C3 moieties. In some embodiments Z is absent and Z' is present and includes one or more non-nucleotide C3 moieties. In some embodiments each of Z and Z' independently comprises one or more non-nucleotide C3 moieties or one or more amino-C6 moieties. In some embodiments z" is present and is selected from a mirror nucleotide, an abasic moiety and an inverted abasic moiety. In some embodiments of Structures A1 and A2 each of Z and Z' includes an abasic moiety, for example a deoxyriboabasic moiety (referred to herein as "dAb") or riboabasic moiety (referred to herein as "rAb"). In some embodiments each of Z and/or Z' comprises two covalently linked abasic moieties and is for example dAb-dAb or rAb-rAb or dAb-rAb or rAb-dAb, wherein each moiety is covalently attached to an adjacent moiety, preferably via a phospho-based bond. In some embodiments the phospho-based bond includes a phosphorothioate, a phosphonoacetate or a phosphodiester bond. In preferred embodiments the phospho-based bond includes a phosphodiester bond.

In some embodiments each of Z and/or Z' independently includes an alkyl moiety, optionally propane [$(CH2)_3$] moiety (C3) or a derivative thereof including propanol (C3OH) and phospho derivative of propanediol ("C3Pi"). In some embodiments each of Z and/or Z' includes two alkyl moieties and in some examples is C3Pi-C3OH. The 3' terminus of the antisense strand and/or the 3' terminus of the sense strand is covalently attached to a C3 moiety via a phospho-based bond and the C3 moiety is covalently conjugated a C3OH moiety via a phospho-based bond. In some embodiments the phospho-based bonds include a phosphorothioate, a phosphonoacetate or a phosphodiester bond. In preferred embodiments the phospho-based bond includes a phosphodiester bond.

In specific embodiments of Structures A1 and A2, Z comprises C3Pi-C3OH. In specific embodiments of Structures A1 and A2, Z' comprises C3Pi or C3OH. In some embodiments of Structures A1 and A2, a double stranded nucleic acid molecule includes a C3Pi-C3OH moiety covalently attached to the 3' terminus of the antisense strand and a C3Pi or C3OH moiety covalently attached to the 3' terminus of the sense strand.

In some embodiments of Structure (A1) and/or Structure (A2) each N consists of an unmodified nucleotide. In some embodiments of Structure (A1) and/or Structure (A2) each N' consists of an unmodified nucleotide. In preferred embodiments, at least one of N and/or N' is a modified ribonucleotide or an unconventional moiety.

In other embodiments a compound of Structure A1 and/or Structure A2 includes at least one ribonucleotide modified in its sugar residue. In some embodiments the compound comprises a modification at the 2' position of the sugar residue. In some embodiments the modification in the 2' position comprises the presence of an amino, a fluoro, an alkoxy or an alkyl moiety. In certain embodiments the 2' modification includes an alkoxy moiety. In preferred embodiments the alkoxy moiety is a methoxy moiety (also known as 2'-O-methyl; 2'OMe; 2'-OCH$_3$). In some embodiments a nucleic acid compound includes 2'OMe sugar modified alternating ribonucleotides in one or both of the antisense strand and the sense strand. In other embodiments a compound includes 2'OMe sugar modified ribonucleotides in the antisense strand, (N)x or N$^1$—(N)x, only. In certain embodiments the middle ribonucleotide of the antisense strand; e.g. ribonucleotide in position 10 in a 19-mer strand, is unmodified. In various embodiments the nucleic acid compound includes at least 5 alternating 2'OMe sugar modified ribonucleotides and unmodified ribonucleotides. In additional embodiments a compound of Structure A1 and/or Structure A2 includes modified ribonucleotides in alternating positions wherein each ribonucleotide at the 5' and 3' termini of (N)x or N$^1$—(N)x are modified in their sugar residues, and each ribonucleotide at the 5' and 3' termini of (N')y or N$^2$—(N)y are unmodified in their sugar residues. In various embodiments the ribonucleotides in alternating positions are modified at the 2' position of the sugar residue.

In some embodiments the nucleic acid compound includes at least 5 alternating 2'OMe sugar modified ribonucleotides and unmodified ribonucleotides, for example at positions 1, 3, 5, 7 and 9 or positions 11, 13, 15, 17, 19 (5'>3'). In some embodiments, (N)x of Structure (A1) or N1-(N)x of Structure (A2) includes 2'OMe modified ribonucleotides in positions 2, 4, 6, 8, 11, 13, 15, 17 and 19. In some embodiments, (N)x of Structure (A1) or N1-(N)x of Structure (A2) includes 2'OMe modified ribonucleotides in positions 1, 3, 5, 7, 9, 11, 13, 15, 17 and 19. In some embodiments, (N)x of Structure (A1) or N1-(N)x of Structure (A2) includes 2'OMe modified ribonucleotides in one or pyrimidines.

In some embodiments of Structure A1 and/or Structure A2, neither of the sense strand nor the antisense strand is phosphorylated at the 3' and 5' termini. In other embodiments one or both of the sense strand or the antisense strand are phosphorylated at the 3' termini. In other embodiments one or both of the sense strand or the antisense strand are phosphorylated at the 5' termini.

In some embodiments the double stranded molecules disclosed herein include one or more of the following modifications:

N in at least one of positions 5, 6, 7, 8, or 9 from the 5' terminus of the antisense strand is selected from a DNA, TNA, a 2'5' nucleotide or a mirror nucleotide;

N' in at least one of positions 9 or 10 from the 5' terminus of the sense strand is selected from a TNA, 2'5' nucleotide and a pseudoUridine; and N' in 4, 5, or 6 consecutive positions at the 3' terminus positions of (N')y comprises a 2'5' nucleotide.

In some embodiments the double stranded molecules include a combination of the following modifications the antisense strand includes a DNA, TNA, a 2'5' nucleotide or a mirror nucleotide in at least one of positions 5, 6, 7, 8, or 9 from the 5' terminus; and the sense strand includes at least one of a TNA, a 2'5' nucleotide and a pseudoUridine in positions 9 or 10 from the 5' terminus.

In some embodiments the double stranded molecules include a combination of the following modifications the antisense strand includes a DNA, 2'5' nucleotide or a mirror nucleotide in at least one of positions 5, 6, 7, 8, or 9 from the 5' terminus; and the sense strand includes 4, 5, or 6 consecutive 2'5' nucleotides at the 3' penultimate or 3' terminal positions.

In some embodiments of Structure A1 and/or Structure A2 (N)y includes at least one unconventional moiety selected from a mirror nucleotide, a 2'5' nucleotide and a TNA. In some embodiments the unconventional moiety is a mirror nucleotide. In various embodiments the mirror nucleotide is selected from an L-ribonucleotide (L-RNA) and an L-deoxyribonucleotide (L-DNA). In preferred embodiments the mirror nucleotide is L-DNA. In certain embodiments the sense strand comprises an unconventional moiety in position 9 or 10 (from the 5' terminus). In preferred embodiments the sense strand includes an unconventional moiety in position 9 (from the 5' terminus). In some embodiments the sense strand is 19 nucleotides in length and comprises 4, 5, or 6 consecutive unconventional moieties in positions 15, (from the 5' terminus). In some embodiments the sense strand includes 4 consecutive 2'5' ribonucleotides in positions 15, 16, 17, and 18. In some embodiments the sense strand includes 5 consecutive 2'5' ribonucleotides in positions 15, 16, 17, 18 and 19. In various embodiments the sense strand further comprises Z'. In some embodiments Z' includes a C3OH moiety or a C3Pi moiety.

In some embodiments of Structure A1 and/or Structure A2 (N)y comprises at least one unconventional moiety selected from a mirror nucleotide and a nucleotide joined to an adjacent nucleotide by a 2'-5' internucleotide phosphate bond. In some embodiments the unconventional moiety is a mirror nucleotide. In various embodiments the mirror nucleotide is selected from an L-ribonucleotide (L-RNA) and an L-deoxyribonucleotide (L-DNA). In preferred embodiments the mirror nucleotide is L-DNA.

In some embodiments of Structure A1 (N')y comprises at least one L-DNA moiety. In some embodiments x=y=19 and (N')y, consists of unmodified ribonucleotides at positions 1-17 and 19 and one L-DNA at the 3' penultimate position (position 18). In other embodiments x=y=19 and (N')y consists of unmodified ribonucleotides at position 1-16 and 19 and two consecutive L-DNA at the 3' penultimate position (positions 17 and 18). In various embodiments the unconventional moiety is a nucleotide joined to an adjacent nucleotide by a 2'-5' internucleotide phosphate linkage. According to various embodiments (N')y comprises 2, 3, 4, 5, or 6 consecutive ribonucleotides at the 3' terminus linked by 2'-5' internucleotide linkages. In one embodiment, four consecutive nucleotides at the 3' terminus of (N')y are joined by three 2'-5' phosphodiester bonds. In one embodiment, five consecutive nucleotides at the 3' terminus of (N')y are joined by four 2'-5' phosphodiester bonds. In some embodiments, wherein one or more of the 2'-5' nucleotides form a 2'-5' phosphodiester bonds the nucleotide further comprises a 3'-β-methyl (3'OMe) sugar modification. In some embodiments the 3' terminal nucleotide of (N')y comprises a 3'OMe sugar modification. In certain embodiments x=y=19 and (N')y comprises two or more consecutive nucleotides at positions 15, 16, 17, 18 and 19 comprise a nucleotide joined to an adjacent nucleotide by a 2'-5' internucleotide bond. In various embodiments the nucleotide forming the 2'-5' internucleotide bond comprises a 3' deoxyribose nucleotide or a 3' methoxy nucleotide. In some embodiments x=y=19 and (N')y comprises nucleotides joined to the adjacent nucleotide by a 2'-5' internucleotide bond between positions 15-16, 16-17 and 17-18 or between positions 16-17, 17-18 and 18-19. In some embodiments x=y=19 and (N')y comprises nucleotides joined to the adjacent nucleotide by a 2'-5' internucleotide bond between positions 16-17 and 17-18 or between positions 17-18 and 18-19 or between positions 15-16 and 17-18. In other embodiments the pyrimidine ribonucleotides (rU, rC) in (N')y are substituted with nucleotides joined to the adjacent nucleotide by a 2'-5' internucleotide bond.

In some embodiments of Structure A2 (N)y comprises at least one L-DNA moiety. In some embodiments x=y=18 and $N^2$—(N')y, consists of unmodified ribonucleotides at positions 1-17 and 19 and one L-DNA at the 3' penultimate position (position 18). In other embodiments x=y=18 and $N^2$—(N')y consists of unmodified ribonucleotides at position 1-16 and 19 and two consecutive L-DNA at the 3' penultimate position (positions 17 and 18). In various embodiments the unconventional moiety is a nucleotide joined to an adjacent nucleotide by a 2'-5' internucleotide phosphate linkage. According to various embodiments $N^2$—(N')y comprises 2, 3, 4, 5, or 6 consecutive ribonucleotides at the 3' terminus linked by 2'-5' internucleotide linkages. In one embodiment, four consecutive nucleotides at the 3' terminus of $N^2$—(N')y are joined by three 2'-5' phosphodiester bonds, wherein one or more of the 2'-5' nucleotides which form the 2'-5' phosphodiester bonds further comprises a 3'-O-methyl (3'OMe) sugar modification. In some embodiments the 3' terminal nucleotide of $N^2$—(N')y comprises a 2'OMe sugar modification. In certain embodiments x=y=18 and $N^2$—(N')y comprises two or more consecutive nucleotides at positions 15, 16, 17, 18 and 19 comprise a nucleotide joined to an adjacent nucleotide by a 2'-5' internucleotide bond. In various embodiments the nucleotide forming the 2'-5' internucleotide bond comprises a 3' deoxyribose nucleotide or a 3' methoxy nucleotide. In some embodiments x=y=18 and $N^2$—(N')y comprises nucleotides joined to the adjacent nucleotide by a 2'-5' internucleotide bond between positions 16-17 and 17-18 or between positions 17-18 and 18-19 or between positions 15-16 and 17-18. In other embodiments the pyrimidine ribonucleotides (rU, rC) in (N')y comprise nucleotides joined to the adjacent nucleotide by a 2'-5' internucleotide bond.

In further embodiments of Structures A1 and A2 (N')y comprises 1-8 modified ribonucleotides wherein the modified ribonucleotide is a deoxyribose (DNA) nucleotide. In certain embodiments (N')y comprises 1, 2, 3, 4, 5, 6, 7, or up to 8 DNA moieties.

In some embodiments provided herein is a double stranded RNA molecule which includes a sense strand and an antisense strand selected from the oligonucleotide pairs set forth in Table II and identified herein as RHOA_48 (SEQ ID NOS: 79 and 113), RHOA_48u (SEQ ID NOS: 80 and 114), RHOA_50 (SEQ ID NOS: 82 and 116), RHOA_61 (SEQ ID NOS: 89 and 123) and RHOA_61u (SEQ ID NOS: 90 and 124).

In some embodiments provided herein is a double stranded RNA molecule which includes a sense strand and an antisense strand selected from the oligonucleotide pairs set forth in Table II and identified herein as RHOA_48 (SEQ ID NOS: 79 and 113), RHOA_48u (SEQ ID NOS: 80 and 114), RHOA_50 (SEQ ID NOS: 82 and 116), RHOA_61 (SEQ ID NOS: 89 and 123) and RHOA_61u (SEQ ID NOS: 90 and 124). Unless otherwise stated all positions along a sense strand or antisense strand are counted from the 5' to the 3' (5'>3').

In some embodiments a double stranded nucleic acid molecule includes the antisense strand set forth in SEQ ID NO:113 and sense strand set forth in SEQ ID NO:79; identified herein as RHOA_48. In some embodiments the double stranded nucleic acid molecule has the structure

```
5'  UGUAGCAAGAUGACUUCUG-Z 3'  (antisense SEQ ID NO: 113)
    ||||||||||||||||||
3'  Z'-ACAUCGUUCUACUGAAGAC-z"5'  (sense SEQ ID NO: 79)
``` wherein each "|" represents base pairing between the ribonucleotides;
wherein each of A, C, G, U is independently an unmodified or modified ribonucleotide, or an unconventional moiety;
wherein each of Z and Z' is independently present or absent, but if present is independently 1-5 consecutive nucleotides or non-nucleotide moieties or a combination thereof covalently attached at the 3' terminus of the strand in which it is present; and
wherein z" may be present or absent, but if present is a capping moiety covalently attached at the 5' terminus of the sense strand.

In preferred embodiments the double stranded nucleic acid molecule comprises modified ribonucleotides and unconventional moieties.

In some embodiments provided is a double stranded nucleic acid molecule wherein the antisense strand (SEQ ID NO:113) includes a mirror nucleotide or a 2'-5' linked nucleotide in one or more of positions 5, 6, 7 or 8 (5'>3'), and a nucleotide or non-nucleotide moiety covalently attached at the 3' terminus. In some embodiments the antisense strand further includes one or more 2'OMe sugar modified ribonucleotides. In some embodiments the sense strand (SEQ ID NO:79) includes 4 or 5 consecutive 2'-5' linked nucleotides at the 3' terminal or penultimate positions, a nucleotide or non-nucleotide moiety covalently attached at the 3' terminus, one or more 2'OMe sugar modified nucleotides, and a cap moiety covalently attached at the 5' terminus. The molecule may include a 5' phosphate on the antisense strand.

In some embodiments provided is a double stranded nucleic acid molecule wherein the antisense strand (SEQ ID NO:113) includes (5'>3') 2'OMe sugar modified ribonucleotides at positions 1, 3, 11, 14, 15, 17 and 18, and a C3Pi-C3OH moiety covalently attached to the 3' terminus; and the sense strand (SEQ ID NO:79) includes (5'>3') 2'-5' linked ribonucleotides at positions 15, 16, 17, 18 and 19, a 3' terminal nucleotide or non-nucleotide overhang; and a cap moiety covalently attached at the 5' terminus. In some embodiments the antisense strand further includes a 2'-5' linked ribonucleotide at position 6, at position 7 or at positions 6 and 7.

In some embodiments provided is a double stranded nucleic acid molecule wherein the antisense strand (SEQ ID NO:113) includes (5'>3') 2'OMe sugar modified ribonucleotides at positions 1, 3, 6, 11, 14, 15, 17 and 18, and a C3Pi-C3OH moiety covalently attached to the 3' terminus; and the sense strand (SEQ ID NO:79) includes (5'>3') 2'-5' linked ribonucleotides at positions 15, 16, 17, 18 and 19, a C3Pi or C3OH moiety covalently attached to the 3' terminus; and a cap moiety covalently attached at the 5' terminus.

In some embodiments provided is a double stranded nucleic acid molecule wherein the antisense strand (SEQ ID NO:113) includes (5'>3') 2'OMe sugar modified ribonucleotides at positions 1, 3, 6, 11, 14, 15, 17 and 18, and a C3Pi-C3OH moiety covalently attached to the 3' terminus; and the sense strand (SEQ ID NO:79) includes (5'>3') 2'-5' linked ribonucleotides at positions 15, 16, 17, 18 and 19, a C3Pi covalently attached to the 3 terminus and an inverted abasic deoxyribonucleotide cap moiety covalently attached at the 5' terminus, as set forth in compound RHOA_48_S1833.

In some embodiments provided is a double stranded nucleic acid molecule wherein the antisense strand (SEQ ID NO:113) includes (5'>3') 2'OMe sugar modified ribonucleotides at positions 1, 3, 11, 14, 15, 17 and 18, a 2'-5' linked nucleotide or a mirror nucleotide in one or more of positions 6, 7 and 8, and a C3Pi-C3OH moiety covalently attached to the 3' terminus; and the sense strand (SEQ ID NO:79) includes (5'>3') 2'-5' linked ribonucleotides at positions 15, 16, 17, 18 and 19, a 3' terminal nucleotide or non-nucleotide overhang; and a cap moiety covalently attached at the 5' terminus.

In some embodiments provided is a double stranded nucleic acid molecule wherein the antisense strand (SEQ ID NO:113) includes (5'>3') 2'OMe sugar modified ribonucleotides at positions 1, 3, 11, 14, 15, 17 and 18, a 2'-5' linked ribonucleotide at position 6, and a C3Pi-C3OH moiety covalently attached to the 3' terminus; and the sense strand (SEQ ID NO:79) includes (5'>3') 2'-5' linked ribonucleotides at positions 15, 16, 17, 18 and 19, a C3Pi or C3OH moiety covalently attached to the 3' terminus; and a cap moiety selected from an abasic moiety, an inverted abasic moiety, a C6 amino and a mirror nucleotide covalently attached at the 5' terminus.

In some embodiments provided is a double stranded nucleic acid molecule wherein the antisense strand (SEQ ID NO:113) includes (5'>3') 2'OMe sugar modified ribonucleotides at positions 1, 3, 11, 14, 15, 17 and 18, a 2'-5' linked ribonucleotide at position 6, and a C3Pi-C3OH moiety covalently attached to the 3' terminus; and the sense strand (SEQ ID NO:79) includes (5'>3') 2'-5' linked ribonucleotides at positions 15, 16, 17, 18 and 19, a C3Pi covalently attached to the 3 terminus and an inverted abasic deoxyribonucleotide cap moiety covalently attached at the 5' terminus, set forth in compound RHOA_48_S1857.

In some embodiments provided is a double stranded nucleic acid molecule wherein the antisense strand (SEQ ID NO:113) includes (5'>3') 2'OMe sugar modified ribonucleotides at positions 1, 3, 11, 14, 15, 17 and 18, a 2'-5' linked ribonucleotide at position 6, and a C3Pi-C3OH moiety covalently attached to the 3' terminus; and the sense strand (SEQ ID NO:79) includes (5'>3') 2'-5' linked ribonucleotides at positions 15, 16, 17, 18 and 19, a C3Pi covalently attached to the 3 terminus and a mirror nucleotide (L-deoxyriboguanosine-3'-phosphate) covalently attached at the 5' terminus, set forth in compound RHOA_48_S1873.

In some embodiments provided is a double stranded nucleic acid molecule wherein the antisense strand (SEQ ID NO:113) includes (5'>3') 2'OMe sugar modified ribonucleotides at positions 1, 3, 6, 11, 14, 15, 17 and 18, a 2'-5' linked ribonucleotide at position 7, and a C3Pi-C3OH moiety covalently attached to the 3' terminus; and the sense strand (SEQ ID NO:79) includes (5'>3') an optional 2'OMe sugar modified ribonucleotide at position 1, 2'-5' linked ribonucleotides at positions 15, 16, 17, 18 and 19, a C3Pi or C3OH moiety covalently attached to the 3' terminus; and a cap moiety selected from an abasic moiety, an inverted abasic moiety, a C6 amino and a mirror nucleotide covalently attached at the 5' terminus.

In some embodiments provided is a double stranded nucleic acid molecule wherein the antisense strand (SEQ ID NO:113) includes (5'>3') 2'OMe sugar modified ribonucleotides at positions 1, 3, 6, 11, 14, 15, 17 and 18, a 2'-5' linked ribonucleotide at position 7, and a C3Pi-C3OH moiety covalently attached to the 3' terminus; and the sense strand (SEQ ID NO:79) includes (5'>3') a 2'OMe sugar modified ribonucleotide at position 1, a C3Pi moiety covalently attached to the 3 terminus and an inverted abasic deoxyribonucleotide cap moiety covalently attached at the 5' terminus; as set forth in compound RHOA_48_S1856.

In some embodiments provided is a double stranded nucleic acid molecule wherein the antisense strand (SEQ ID NO:113) includes (5'>3') 2'OMe sugar modified ribonucleotides at positions 1, 3, 6, 11, 14, 15, 17 and 18, a 2'-5' linked ribonucleotide at position 7, and a C3Pi-C3OH moiety covalently attached to the 3' terminus; and the sense strand (SEQ ID NO:79) includes (5'>3') includes a 2'OMe sugar modified ribonucleotide at position 1, and 2'-5' linked ribonucleotides at positions 15, 16, 17, 18 and 19, a C3Pi covalently attached to the 3 terminus and a mirror nucleotide (L-deoxyriboguanosine-3'-phosphate) covalently attached at the 5' terminus, as set forth in compound RHOA_48_S1872.

In some embodiments provided is a double stranded nucleic acid molecule wherein the antisense strand (SEQ ID NO:113) includes (5'>3') 2'OMe sugar modified ribonucleotides at positions 1, 3, 11, 14, 15, 17 and 18, and 2'-5' linked ribonucleotide at positions 6 and 7 and a C3Pi-C3OH moiety covalently attached to the 3' terminus; and the sense strand (SEQ ID NO:79) includes (5'>3') an optional 2'OMe sugar modified ribonucleotide at position 1, and 2'-5' linked ribonucleotides at positions 15, 16, 17, 18 and 19, a C3Pi or C3OH moiety covalently attached to the 3' terminus and a cap moiety selected from an abasic moiety, an inverted abasic moiety and a mirror nucleotide covalently attached at the 5' terminus.

In some embodiments provided is a double stranded nucleic acid molecule wherein the antisense strand (SEQ ID NO:113) includes (5'>3') 2'OMe sugar modified ribonucleotides at positions 1, 3, 11, 14, 15, 17 and 18, a 2'-5' linked ribonucleotide at positions 6 and 7 and a C3Pi-C3OH moiety covalently attached to the 3' terminus; and the sense strand (SEQ ID NO:79) includes (5'>3') includes a 2'OMe sugar modified ribonucleotide at position 1, and 2'-5' linked ribonucleotides at positions 15, 16, 17, 18 and 19, a C3Pi moiety covalently attached to the 3 terminus and an inverted abasic deoxyribonucleotide cap moiety covalently attached at the 5' terminus, as set forth in compound RHOA_48_S1858.

In some embodiments provided is a double stranded nucleic acid molecule wherein the antisense strand (SEQ ID NO:113) includes (5'>3') 2'OMe sugar modified ribonucleotides at positions 1, 3, 11, 14, 15, 17 and 18, a mirror nucleotide at position 6 and a C3Pi-C3OH moiety covalently attached to the 3' terminus; and the sense strand (SEQ ID NO:79) includes (5'>3') a 2'OMe sugar modified ribonucleotide at position 1, and 2'-5' linked ribonucleotides at positions 15, 16, 17, 18 and 19, a C3Pi moiety covalently attached to the 3 terminus and an inverted abasic deoxyribonucleotide cap moiety covalently attached at the 5' terminus as set forth in compound RHOA_48 S1859.

In some embodiments provided is a double stranded nucleic acid molecule wherein the antisense strand (SEQ ID NO:113) includes (5'>3') 2'OMe sugar modified ribonucleotides at positions 1, 3, 11, 14, 15, 17 and 18, a mirror nucleotide at position 8 and a C3Pi-C3OH moiety covalently attached to the 3' terminus; and the sense strand (SEQ ID NO:79) includes (5'>3') a 2'OMe sugar modified ribonucleotide at position 1, and 2'-5' linked ribonucleotides at positions 15, 16, 17, 18 and 19, a C3Pi moiety covalently attached to the 3 terminus and an inverted abasic deoxyribonucleotide cap moiety covalently attached at the 5' terminus, as set forth in compound RHOA_48_S1860.

In some embodiments provided is a double stranded nucleic acid molecule wherein the sense strand (SEQ ID NO:79) includes (5'>3') a 2'OMe sugar modified ribonucleotide at position 1, and 2'-5' linked ribonucleotides at positions 15, 16, 17, 18 and 19, a C3Pi moiety covalently attached to the 3 terminus and an inverted abasic deoxyribonucleotide cap moiety covalently attached at the 5' terminus, and the antisense strand (SEQ ID NO:113) is selected from an antisense oligonucleotide which includes (5'>3') a U to dT substitution in position 1, a 5' phosphate covalently attached to the deoxyribothymidine in position 1, 2'OMe sugar modified ribonucleotides at positions 3, 11, 14, 15, 17 and 18, a 2'-5' linked ribonucleotide at position 7 and a C3Pi-C3OH moiety covalently attached to the 3' terminus; and as set forth in compound RHOA_48_S1884; or an antisense oligonucleotide which includes (5'>3') a a 5' phosphate covalently attached to the uridine in position 1, 2'OMe sugar modified ribonucleotides at positions 3, 11, 14, 15, 17 and 18, a 2'-5' linked ribonucleotide at position 7 and a C3Pi-C3OH moiety covalently attached to the 3' terminus; and as set forth in compound RHOA_48_S1885; or an antisense oligonucleotide which includes (5'>3') a U to C3 substitution in position 1, a 5' phosphate covalently attached to the C3 in position 1, 2'OMe sugar modified ribonucleotides at positions 3, 11, 14, 15, 17 and 18, a 2'-5' linked ribonucleotide at position 7 and a C3Pi-C3OH moiety covalently attached to the 3' terminus; and as set forth in compound RHOA_48_S1886; or an antisense oligonucleotide which includes (5'>3') a 5' phosphate covalently attached to the uridine in position 1, 2'OMe sugar modified ribonucleotides at positions 1, 3, 11, 14, 15, 17 and 18, a 2'-5' linked ribonucleotide at position 7 and a C3Pi-C3OH moiety covalently attached to the 3' terminus; and as set forth in compound RHOA_48_S1887.

In some embodiments the double stranded nucleic acid molecule includes the antisense strand set forth in SEQ ID NO:114 and sense strand set forth in SEQ ID NO:80; identified herein as RHOA_48u. In some embodiments the double stranded nucleic acid molecule has the structure

```
5'  AGUAGCAAGAUGACUUCUG-Z 3' (antisense SEQ ID NO: 114)
    |||||||||||||||||||
3' Z'-UCAUCGUUCUACUGAAGAC-z" 5' (sense SEQ ID NO: 80)
``` wherein each "|" represents base pairing between the ribonucleotides;
wherein each of A, C, G, U is independently an unmodified or modified ribonucleotide, or an unconventional moiety;
wherein each of Z and Z' is independently present or absent, but if present is independently 1-5 consecutive nucleotides or non-nucleotide moieties or a combination thereof covalently attached at the 3' terminus of the strand in which it is present; and wherein z" may be present or absent, but if present is a capping moiety covalently attached at the 5' terminus of the sense strand.

In preferred embodiments the double stranded nucleic acid molecule comprises modified ribonucleotides and unconventional moieties.

In some embodiments provided is a double stranded nucleic acid molecule wherein the antisense strand (SEQ ID NO:114) includes (5'>3') one or more 2'OMe sugar modified ribonucleotides, a mirror nucleotide or a 2'-5' linked ribonucleotide in one or more of positions 5, 6, 7 or 8 (5'>3'), and a 3' terminal nucleotide or non-nucleotide overhang. The antisense strand may further include a 5' terminal phosphate. In some embodiments the sense strand (SEQ ID NO:80) includes (5'>3') 4 or 5 consecutive 2'-5' linked nucleotides at the 3' terminal or penultimate positions, a nucleotide or non-nucleotide moiety covalently attached at the 3' terminus and a cap moiety covalently attached at the 5' terminus. In other embodiments the sense strand (SEQ ID NO:80) further includes one or more 2'OMe sugar modified ribonucleotides.

In some embodiments provided is a double stranded nucleic acid molecule wherein the antisense strand (SEQ ID NO:114) includes (5'>3') 2'OMe sugar modified ribonucleotides at positions (5'>3') 3, 6, 11, 14, 15, 17 and 18, a 2'-5' ribonucleotide at position 7, and a C3Pi-C3OH moiety covalently attached to the 3' terminus; and the sense strand (SEQ ID NO:80) includes (5'>3') 2'-5' ribonucleotides at positions 15, 16, 17, 18 and 19, a C3Pi moiety covalently attached at the 3' terminus; and an inverted abasic deoxyribonucleotide moiety covalently attached at the 5' terminus, set forth in compound RHOA_48u_S1812.

In some embodiments provided is a double stranded nucleic acid molecule wherein the antisense strand (SEQ ID NO:114) includes (5'>3') 2'OMe sugar modified ribonucleotides at positions (5'>3') 3, 6, 11, 14, 15, 17 and 18, a 2'-5' ribonucleotide at position 7, and a C3Pi-C3OH moiety covalently attached to the 3' terminus; and the sense strand (SEQ ID NO:80) includes (5'>3') 2'OMe sugar modified ribonucleotides at positions 13 and 16, a 2'-5' linked ribonucleotide at position 9, a C3Pi moiety covalently attached at the 3' terminus; and an inverted abasic deoxyribonucleotide moiety covalently attached at the 5' terminus, set forth in compound RHOA_48u_S1813.

In some embodiments provided is a double stranded nucleic acid molecule wherein the antisense strand (SEQ ID NO:114) includes (5'>3') 2'OMe sugar modified ribonucleotides at positions (5'>3') 3, 6, 11, 14, 15, 17 and 18, a 2'-5' ribonucleotide at position 7, and a C3Pi-C3OH moiety covalently attached to the 3' terminus; and the sense strand (SEQ ID NO:80) includes (5'>3') a 2'OMe sugar modified ribonucleotide at position 1, and 2'-5' ribonucleotides at positions 15, 16, 17, 18 and 19, a C3Pi moiety covalently attached at the 3' terminus; and a mirror nucleotide (L-deoxyriboguanosine-3'-phosphate) covalently attached at the 5' terminus, set forth in compound RHOA_48u_S1870.

In some embodiments provided is a double stranded nucleic acid molecule wherein the antisense strand (SEQ ID NO:114) includes (5'>3') 2'OMe sugar modified ribonucleotides at positions (5'>3') 3, 6, 11, 14, 15, 17 and 18, a 2'-5' ribonucleotide at position 7, and a C3Pi-C3OH moiety covalently attached to the 3' terminus; and the sense strand (SEQ ID NO:80) includes (5'>3') a 2'OMe sugar modified ribonucleotide at position 1, and 2'-5' ribonucleotides at positions 15, 16, 17, 18 and 19, a C3Pi moiety covalently attached at the 3' terminus; and an inverted abasic deoxyribonucleotide covalently attached at the 5' terminus, set forth in compound RHOA_48u_S1871.

In some embodiments a double stranded nucleic acid molecule includes the antisense strand set forth in SEQ ID NO:116 and sense strand set forth in SEQ ID NO:82; identified herein as RHOA_50. In some embodiments the double stranded nucleic acid molecule has the structure

```
5'   UGAACUGUAACUCUGCCAC-Z 3' (antisense SEQ ID NO: 116)
     |||||||||||||||||||
3' Z'-ACUUGACAUUGAGACGGUG-z" 5' (sense SEQ ID NO: 82)
``` wherein each "|" represents base pairing between the ribonucleotides;
wherein each of A, C, G, U is independently an unmodified or modified ribonucleotide, or an unconventional moiety;
wherein each of Z and Z' is independently present or absent, but if present is independently 1-5 consecutive nucleotides or non-nucleotide moieties or a combination thereof covalently attached at the 3' terminus of the strand in which it is present; and
wherein z" may be present or absent, but if present is a capping moiety covalently attached at the 5' terminus of the sense strand.

In some embodiments provided is a double stranded nucleic acid molecule wherein the antisense strand (SEQ ID NO:116) includes (5'>3') a DNA, a mirror nucleotide or a 2'-5' linked nucleotide in one or more of positions 5, 6, 7 or 8, a nucleotide or non-nucleotide moiety covalently attached at the 3' terminus and one or more 2'OMe sugar modified nucleotides. In some embodiments the antisense strand (SEQ ID NO:116) includes (5'>3') alternating 2'OMe sugar modified ribonucleotides, a mirror nucleotide or a 2'-5' linked ribonucleotide in one or more of positions 5, 6, 7 or 8, and a nucleotide or non-nucleotide moiety covalently attached at the 3' terminus. In some embodiments the antisense strand further includes a U (uridine) to dU (deoxyuridine) substitution in position 1. The antisense strand may further include a 5' terminal phosphate.

In some embodiments the sense strand (SEQ ID NO:82) includes (5'>3') a mirror nucleotide or a 2'-5' linked nucleotide in one or more of positions 9 or 10, a nucleotide or non-nucleotide moiety covalently attached at the 3' terminus, one or more 2' OMe sugar modified nucleotides, and a cap moiety covalently attached at the 5' terminus.

In some embodiments provided is a double stranded nucleic acid molecule wherein the antisense strand (SEQ ID NO:116) includes (5'>3') 2'OMe sugar modified ribonucleotides in positions 3, 5, 9, 11, 13, 15, 17 and 19, a 2'-5' linked ribonucleotide in position 7, C3Pi-C3OH non-nucleotide moiety covalently attached at the 3' terminus and a U (uridine) to dU (deoxyuridine) substitution in position 1; and the sense strand (SEQ ID NO:82) includes (5'>3') a C3Pi non-nucleotide moiety covalently attached at the 3' terminus, 2'OMe sugar modified nucleotides at positions 11, 13 and 18, a 2'-5' linked nucleotide at position 9 and an inverted abasic deoxyribonucleotide cap moiety covalently attached at the 5' terminus, set forth in RHOA_50_S1796.

In some embodiments provided is a double stranded nucleic acid molecule wherein the antisense strand (SEQ ID NO:116) includes (5'>3') 2'OMe sugar modified ribonucleotides in positions 4, 6, 8, 11, 13, 15, 17 and 19, a 2'-5' linked ribonucleotide in position 7, a C3Pi-C3OH non-nucleotide moiety covalently attached at the 3' terminus and a U (uridine) to dU (deoxyuridine) substitution in position 1; and the sense strand (SEQ ID NO:82) includes (5'>3') a C3Pi non-nucleotide moiety covalently attached at the 3' terminus, a 2'OMe sugar modified nucleotides at position 18, a 2'-5' linked nucleotide at position 9 and an inverted abasic deoxyribonucleotide cap moiety covalently attached at the 5' terminus, set forth in RHOA_50_S1798.

In some embodiments provided is a double stranded nucleic acid molecule wherein the antisense strand (SEQ ID NO:116) includes (5'>3') 2'OMe sugar modified ribonucleotides in positions 3, 5, 9, 11, 13, 15, 17 and 19, a 2'-5' linked ribonucleotide in position 7, a C3Pi-C3OH non-nucleotide moiety covalently attached at the 3' terminus and a U (uridine) to dU (deoxyuridine) substitution in position 1; and the sense strand (SEQ ID NO:82) includes (5'>3') a C3Pi non-nucleotide moiety covalently attached at the 3' terminus, a 2'OMe sugar modified nucleotides at position 18, a 2'-5' linked nucleotide at position 9 and an inverted abasic deoxyribonucleotide cap moiety covalently attached at the 5' terminus, set forth in RHOA_50_S1799.

In some embodiments provided is a double stranded nucleic acid molecule wherein the antisense strand (SEQ ID NO:116) includes (5'>3') 2' OMe sugar modified ribonucleotides in positions 4, 6, 8, 11, 13, 15, 17 and 19, a 2'-5' linked ribonucleotide in position 7, a C3Pi-C3OH non-nucleotide moiety covalently attached at the 3' terminus and a U (uridine) to dU (deoxyuridine) substitution in position 1; and the sense strand (SEQ ID NO:82) includes (5'>3') a C3Pi non-nucleotide moiety covalently attached at the 3' terminus, a 2'OMe sugar modified nucleotides at positions 17 and 18, a 2'-5' linked nucleotide at position 9 and an inverted abasic deoxyribonucleotide cap moiety covalently attached at the 5' terminus, set forth in RHOA_50_S1865.

In some embodiments provided is a double stranded nucleic acid molecule wherein the antisense strand (SEQ ID NO:116) includes (5'>3') 2' OMe sugar modified ribonucleotides in positions 3, 5, 9, 11, 13, 15, 17 and 19, a 2'-5' linked ribonucleotide in position 7, a C3Pi-C3OH non-nucleotide moiety covalently attached at the 3' terminus and a U (uridine) to dU (deoxyuridine) substitution in position 1; and the sense strand (SEQ ID NO:82) includes (5'>3') a C3Pi non-nucleotide moiety covalently attached at the 3' terminus, a 2'OMe sugar modified nucleotides at positions 17 and 18, a 2'-5' linked nucleotide at position 9 and an inverted abasic deoxyribonucleotide cap moiety covalently attached at the 5' terminus, set forth in RHOA_50_S1866.

In some embodiments a double stranded nucleic acid molecule includes the antisense strand set forth in SEQ ID NO:123 and sense strand set forth in SEQ ID NO:89; identified herein as RHOA_61. In some embodiments the double stranded nucleic acid molecule has the structure

```
5'    UCUCAUCAUUCCGAAGAUC-Z 3' (antisense SEQ ID NO: 123)
      ||||||||||||||||||
3' Z'-AGAGUAGUAAGGCUUCUAG-z" 5' (sense SEQ ID NO: 89)
``` wherein each "|" represents base pairing between the ribonucleotides;

wherein each of A, C, G, U is independently an unmodified or modified ribonucleotide, or an unconventional moiety;

wherein each of Z and Z' is independently present or absent, but if present is independently 1-5 consecutive nucleotides or non-nucleotide moieties or a combination thereof covalently attached at the 3' terminus of the strand in which it is present; and wherein z" may be present or absent, but if present is a capping moiety covalently attached at the 5' terminus of the sense strand.

In preferred embodiments the double stranded nucleic acid molecule comprises modified ribonucleotides and unconventional moieties.

In some embodiments provided is a double stranded nucleic acid molecule wherein the antisense strand (SEQ ID NO:123) includes a DNA, a mirror nucleotide or a 2'-5' linked nucleotide in one or more of positions 5, 6, 7 or 8 (5'>3'), a nucleotide or non-nucleotide moiety covalently attached at the 3' terminus and one or more 2'OMe sugar modified nucleotides. In some embodiments the sense strand (SEQ ID NO:89) includes 4 or 5 consecutive 2'-5' linked nucleotides at the 3' terminal or penultimate positions or one or more 2'OMe sugar modified nucleotides, a nucleotide or non-nucleotide moiety covalently attached at the 3' terminus, and a cap moiety covalently attached at the 5' terminus. In some embodiments the sense strands further includes a DNA, a mirror nucleotide or a 2'5' linked nucleotide in one or both positions 9 and 10.

In some embodiments a double stranded nucleic acid molecule includes the antisense strand set forth in SEQ ID NO:124 and sense strand set forth in SEQ ID NO:90; identified herein as RHOA_61U. In some embodiments the double stranded nucleic acid molecule has the structure

```
5'    ACUCAUCAUUCCGAAGAUC-Z 3' (antisense SEQ ID NO: 124)
      ||||||||||||||||||
3' Z'-UGAGUAGUAAGGCUUCUAG-z" 5' (sense SEQ ID NO: 90)
``` wherein each "|" represents base pairing between the ribonucleotides;

wherein each of A, C, G, U is independently an unmodified or modified ribonucleotide, or an unconventional moiety;

wherein each of Z and Z' is independently present or absent, but if present is independently 1-5 consecutive nucleotides or non-nucleotide moieties or a combination thereof covalently attached at the 3' terminus of the strand in which it is present; and wherein z" may be present or absent, but if present is a capping moiety covalently attached at the 5' terminus of the sense strand.

In preferred embodiments the double stranded nucleic acid molecule comprises modified ribonucleotides and unconventional moieties.

In some embodiments provided is a double stranded nucleic acid molecule wherein the antisense strand (SEQ ID NO:124) includes a DNA, a mirror nucleotide or a 2'-5' linked nucleotide in one or more of positions 5, 6, 7 or 8 (5'>3'), a nucleotide or non-nucleotide moiety covalently attached at the 3' terminus and one or more 2'OMe sugar modified nucleotides. In some embodiments the sense strand (SEQ ID NO:90) includes 4 or 5 consecutive 2'-5' linked nucleotides at the 3' terminal or penultimate positions or one or more 2'OMe sugar modified nucleotides, a nucleotide or non-nucleotide moiety covalently attached at the 3' terminus, and a cap moiety covalently attached at the 5' terminus. In some embodiments the sense strands further includes a DNA, a mirror nucleotide or a 2'5' linked nucleotide in one or both positions 9 and 10.

In some embodiments provided herein is a double stranded RNA molecule which includes a sense strand and an antisense strand selected from the oligonucleotide pairs set forth in Table III and identified herein as RHOA_58 (SEQ ID NOS: 143 and 157) and RHOA_70 (SEQ ID NOS: 146 and 160).

In some embodiments a double stranded nucleic acid molecule includes the antisense strand set forth in SEQ ID NO:157 and sense strand set forth in SEQ ID NO:143; identified herein as RHOA_58. In some embodiments the double stranded nucleic acid molecule has the structure

```
5'    AGAACUGUAACUCUGCCAC-Z 3' (antisense SEQ ID NO: 157)
      ||||||||||||||||||
3' Z'-UCUUGACAUUGAGACGGUG-z" 5' (sense SEQ ID NO: 143)
``` wherein each "|" represents base pairing between the ribonucleotides;

wherein each of A, C, G, U is independently an unmodified or modified ribonucleotide, or an unconventional moiety;

wherein each of Z and Z' is independently present or absent, but if present is independently 1-5 consecutive nucleotides or non-nucleotide moieties or a combination thereof covalently attached at the 3' terminus of the strand in which it is present; and wherein z" may be present or absent, but if present is a capping moiety covalently attached at the 5' terminus of the sense strand.

In preferred embodiments the double stranded nucleic acid molecule comprises modified ribonucleotides and unconventional moieties.

In some embodiments provided is a double stranded nucleic acid molecule wherein the antisense strand (SEQ ID NO:157) includes a mirror nucleotide or a 2'-5' linked ribonucleotide in one or more of positions 5, 6, 7 or 8 (5'>3'), a nucleotide or non-nucleotide moiety covalently attached at the 3' terminus and one or more 2'OMe sugar modified nucleotides. In some embodiments the antisense strand further includes a 5' terminal phosphate. In some embodiments the sense strand (SEQ ID NO:143) includes 4 or 5 consecutive 2'-5' linked nucleotides at the 3' terminal or penultimate positions or one or more 2'OMe sugar modified nucleotides, a nucleotide or non-nucleotide moiety covalently attached at the 3' terminus, and a cap moiety covalently attached at the 5' terminus. In some embodiments the sense strands further includes (5'>3') a DNA, a mirror nucleotide or a 2'-5' linked nucleotide in one or both positions 9 and 10.

In some embodiments provided is a double stranded nucleic acid molecule wherein the antisense strand (SEQ ID NO:157) includes (5'>3') 2'OMe sugar modified ribonucleotides at positions 4, 6, 8, 11, 13, 15, 17 and 19, a 2'-5' linked ribonucleotide at position 7, and a C3Pi-C3OH non-nucleotide moiety covalently attached at the 3' terminus and the sense strand (SEQ ID NO:143) includes (5'>3') 5 consecutive 2'-5' linked nucleotides at positions 15, 16, 17, 18 and 19, a C3Pi non-nucleotide moiety covalently attached at the 3' terminus and an inverted abasic deoxyribonucleotide cap moiety covalently attached at the 5' terminus, set forth in RHOA__58_S1801.

In some embodiments provided is a double stranded nucleic acid molecule wherein the antisense strand (SEQ ID NO:157) includes (5'>3') 2'OMe sugar modified ribonucleotides at positions 4, 6, 8, 11, 13, 15, 17 and 19, a 2'-5' linked ribonucleotide at position 7, and a C3Pi-C3OH non-nucleotide moiety covalently attached at the 3' terminus and the sense strand (SEQ ID NO:143) includes (5'>3') 5 consecutive 2'-5' linked nucleotides at positions 15, 16, 17, 18 and 19, a C3Pi non-nucleotide moiety covalently attached at the 3' terminus, a 2'-5' linked nucleotide at position 9 and an inverted abasic deoxyribonucleotide cap moiety covalently attached at the 5' terminus, set forth in RHOA__58_S1804.

In some embodiments provided is a double stranded nucleic acid molecule wherein the antisense strand (SEQ ID NO:1157) includes (5'>3') 2'OMe sugar modified ribonucleotides at positions 3, 5, 9, 11, 13, 15, 17 and 19, a 2'-5' linked ribonucleotide in positions 7, and a C3Pi-C3OH non-nucleotide moiety covalently attached at the 3' terminus and the sense strand (SEQ ID NO:143) includes (5'>3') a C3Pi non-nucleotide moiety covalently attached at the 3' terminus, 2'OMe sugar modified nucleotides at positions 11, 13 and 17, a 2'-5' linked nucleotide at position 9 and an inverted abasic deoxyribonucleotide cap moiety covalently attached at the 5' terminus, set forth in RHOA__58_S1806.

In some embodiments provided is a double stranded nucleic acid molecule wherein the antisense strand (SEQ ID NO:157) includes (5'>3') 2' OMe sugar modified ribonucleotides in positions 4, 8, 11, 13, 15, 17 and 19, a 2'-5' linked nucleotide in position 6, and a C3Pi-C3OH non-nucleotide moiety covalently attached at the 3' terminus; and the sense strand (SEQ ID NO:143) includes (5'>3') a C3Pi non-nucleotide moiety covalently attached at the 3' terminus, 2'OMe sugar modified nucleotides at positions 11, 13 and 17, a 2'-5' linked nucleotide at position 9 and an inverted abasic deoxyribonucleotide cap moiety covalently attached at the 5' terminus, set forth in RHOA__58_S1861.

In some embodiments provided is a double stranded nucleic acid molecule wherein the antisense strand (SEQ ID NO:157) includes (5'>3') 2' OMe sugar modified ribonucleotides in positions 4, 8, 11, 13, 15, 17 and 19, a U to dT substitution in position 6, and a C3Pi-C3OH non-nucleotide moiety covalently attached at the 3' terminus; and the sense strand (SEQ ID NO:143) includes (5'>3') a C3Pi non-nucleotide moiety covalently attached at the 3' terminus, 2'OMe sugar modified nucleotides at positions 11, 13 and 17, a 2'-5' linked nucleotide at position 9 and an inverted abasic deoxyribonucleotide cap moiety covalently attached at the 5' terminus, set forth in RHOA__58_S1862.

In some embodiments provided is a double stranded nucleic acid molecule wherein the antisense strand (SEQ ID NO:157) includes (5'>3') 2' OMe sugar modified ribonucleotides at positions 3, 5, 9, 11, 13, 15, 17 and 19, a 2'-5' linked ribonucleotide in positions 7, and a C3Pi-C3OH non-nucleotide moiety covalently attached at the 3' terminus and the sense strand (SEQ ID NO:143) includes (5'>3') a C3Pi non-nucleotide moiety covalently attached at the 3' terminus, 2'OMe sugar modified nucleotides at positions 11, 13 and 17, a 2'-5' linked nucleotide at position 9 and a mirror nucleotide (L-deoxyriboguanosine-3'-phosphate) cap moiety covalently attached at the 5' terminus, set forth in RHOA__58_S1877.

In some embodiments provided is a double stranded nucleic acid molecule wherein the antisense strand (SEQ ID NO:157) includes (5'>3') 2' OMe sugar modified ribonucleotides in positions 4, 8, 11, 13, 15, 17 and 19, a 2'-5' linked nucleotide in position 6, and a C3Pi-C3OH non-nucleotide moiety covalently attached at the 3' terminus; and the sense strand (SEQ ID NO:143) includes (5'>3') a C3Pi non-nucleotide moiety covalently attached at the 3' terminus, 2'OMe sugar modified nucleotides at positions 11, 13 and 17, a 2'-5' linked nucleotide at position 9 and a mirror nucleotide (L-deoxyriboguanosine-3'-phosphate) cap moiety covalently attached at the 5' terminus, set forth in RHOA__58_S1878.

In some embodiments provided is a double stranded nucleic acid molecule wherein the antisense strand (SEQ ID NO:157) includes (5'>3') 2' OMe sugar modified ribonucleotides in positions 4, 8, 11, 13, 15, 17 and 19, a dT in position 6, and a C3Pi-C3OH non-nucleotide moiety covalently attached at the 3' terminus; and the sense strand (SEQ ID NO:143) includes (5'>3') a C3Pi non-nucleotide moiety covalently attached at the 3' terminus, 2'OMe sugar modified nucleotides at positions 11, 13 and 17, a 2'-5' linked nucleotide at position 9 and a mirror nucleotide (L-deoxyriboguanosine-3'-phosphate) cap moiety covalently attached at the 5' terminus, set forth in RHOA__58_S1879.

In some embodiments a double stranded nucleic acid molecule includes the antisense strand set forth in SEQ ID NO:160 and sense strand set forth in SEQ ID NO:146; identified herein as RHOA__70. In some embodiments the double stranded nucleic acid molecule has the structure

```
5'    ACUAUCAGGGCUGUCGAUG-Z 3'  (antisense SEQ ID NO: 160)
      ||||||||||||||||||
3' Z'-UGAUAGUCCCGACAGCUAC-z" 5' (sense SEQ ID NO: 146)
``` wherein each "|" represents base pairing between the ribonucleotides;

wherein each of A, C, G, U is independently an unmodified or modified ribonucleotide, or an unconventional moiety;

wherein each of Z and Z' is independently present or absent, but if present is independently 1-5 consecutive nucleotides or non-nucleotide moieties or a combination thereof covalently attached at the 3' terminus of the strand in which it is present; and wherein z" may be present or absent, but if present is a capping moiety covalently attached at the 5' terminus of the sense strand.

In preferred embodiments the double stranded nucleic acid molecule comprises modified ribonucleotides and unconventional moieties.

In some embodiments provided is a double stranded nucleic acid molecule wherein the antisense strand (SEQ ID NO:160) includes a DNA, a mirror nucleotide or a 2'-5' linked nucleotide in one or more of positions 5, 6, 7 or 8 (5'>3'), a nucleotide or non-nucleotide moiety covalently attached at the 3' terminus and one or more 2'OMe sugar modified nucleotides. In some embodiments the antisense strand further includes a 5' terminal phosphate. In some embodiments the sense strand (SEQ ID NO:146) includes 4 or 5 consecutive 2'-5' linked nucleotides at the 3' terminal or penultimate positions or one or more 2'OMe sugar modified nucleotides, a nucleotide or non-nucleotide moiety covalently attached at the 3' terminus, and a cap moiety covalently attached at the 5' terminus. In some embodiments the sense strands further includes (5'>3') a DNA, a mirror nucleotide or a 2'5' linked nucleotide in one or both positions 9 and 10.

In a second aspect the present invention provides pharmaceutical compositions comprising one or more such nucleic acid compounds according to the present invention; and a pharmaceutically acceptable excipient. In some embodiments the dsRNA is administered as naked dsRNA. In other embodiments the compound is encapsulated in a drug carrier.

In a third aspect the present invention relates to a compound according to the present application for use in treating a subject suffering from disease or disorder in the CNS, PNS, vestibular sensory system, visual system and/or circulatory (vascular, arterial) system or for use in treating a subject suffering from a malignant disease or disorder, e.g. cancer. Provided herein is a method for prevention, inhibition or treatment of neuronal degeneration caused by injury, disease, disorder or condition in the central nervous system (CNS) and/or the peripheral nervous system (PNS), comprising administering to an individual in need thereof an amount effective to treat said injury, disease, disorder or condition, of a nucleic acid compound according to Structure A1 and/or Structure A2. Also provided is a method for conferring neuroprotection to an individual afflicted with a neurological injury, which comprises administering to said individual a compound according to Structure A1 and/or Structure A2 or pharmaceutically acceptable salt thereof in an amount effective to ameliorate the neurodegeneration associated with said neurological injury.

In another aspect provided is use of a nucleic acid compound disclosed herein for the preparation of a medicament for the treatment of a disease or disorder in the CNS, PNS, vestibular sensory system, visual system and/or circulatory (vascular, arterial) system. In another aspect provided is use of a nucleic acid compound disclosed herein for the preparation of a medicament for the treatment of a malignant disease or disorder, e.g. cancer. In particular embodiments, the invention provides chemically modified dsRNA oligonucleotides, compositions comprising same and methods of use thereof in the treatment of diseases, disorders, injuries and conditions of the central nervous system (CNS) including, without being limited to, conditions related to neuroregeneration and neuroprotection, injury of the central nervous system (CNS), spinal cord injury (SCI), brain injury, peripheral nerve injury (PNI), neurological disorders, ocular diseases and disorders and diseases and disorders of the vestibular system. In some embodiments the compounds disclosed herein attenuate neuronal degeneration. Neuronal degeneration includes for example degeneration of the optic nerve and retina including retinal ganglion cells. It also includes degeneration of the auditory nerve, (also known as the vestibulocochlear nerve or acoustic nerve) responsible for transmitting sound and equilibrium information from the inner ear to the brain. The hair cells of the inner ear transmit information to the brain via the auditory nerve, which consists of the cochlear nerve, and the vestibular nerve, and emerges from the medulla oblongata and enters the inner skull via the internal acoustic meatus (or internal auditory meatus) in the temporal bone, along with the facial nerve.

In some embodiments the present invention provides a method of attenuating neuronal degeneration in the optic nerve and or retinal ganglion cells of a subject comprising administering to the subject a therapeutically effective amount of a nucleic acid molecule disclosed herein. In some embodiments the subject is afflicted with glaucoma or NAION.

In some embodiments the present invention provides a method of attenuating neuronal degeneration in the auditory nerve of a subject comprising administering to the subject a therapeutically effective amount of a nucleic acid molecule disclosed herein. In some embodiments the subject is afflicted with Meniere's disease.

In some embodiments the present invention provides a method of conferring neuroprotection to the optic nerve and or retinal ganglion cells in a subject comprising administering to the subject a therapeutically effective amount of a nucleic acid molecule disclosed herein. In some embodiments the subject is afflicted with glaucoma or NAION.

In some embodiments the present invention provides a method of conferring neuroprotection to the auditory nerve and or spiral ganglion cells in a subject comprising administering to the subject a therapeutically effective amount of a nucleic acid molecule disclosed herein. In some embodiments the subject is afflicted with Meniere's disease.

In some embodiments the present invention provides a method of treating a neuropathy in a subject comprising administering to the subject a therapeutically effective amount of a nucleic acid molecule disclosed herein. In some embodiments the subject is afflicted with autonomic neuropathy, cancer-related neuropathy, compressive neuropathy, diabetic neuropathy, drug-induced neuropathy, toxic neuropathy, chemotherapy-induced neuropathy, gastrointestinal neuropathy, nutrition-related neuropathy, hereditary neuropathy, immune-mediated neuropathy and chronic immune-mediated poly neuropathy, infectious neuropathy or neuropatic pain. In some embodiments the subject is afflicted with diabetic neuropathy. In some embodiments the subject is afflicted with allodynia. In some embodiments the present invention provides a method of treating a subject suffering from a disease or disorder associated with aberrant and/or disrupted cell motility, cytoskeleton regulation and/or microtubule organization comprising administering to the subject a therapeutically effective amount of a nucleic acid molecule disclosed herein. In some embodiments the subject is afflicted with angiogenic disorder, vascular diseases and/or arterial diseases. In some embodiments the subject is suffering from ocular angiogenic disease or disorder, sleeted from corneal angiogenic disease or disorder, retinal angiogenic disease or disorder, choroidal angiogenic disease or disorder or a combination thereof. In some embodiments the subject is suffering from retinopathy, e.g., diabetic retinopathy. In some embodiments the subject is a corneal transplant patient at risk of or suffering from corneal graft rejection. In some embodiments the subject is at risk of or suffering from restenosis.

Such methods involve administering to a mammal in need of such treatment a prophylactically or therapeutically effective amount of one or more nucleic acid molecules disclosed herein which inhibit or reduce expression or activity of RhoA.

In another aspect, the present invention relates to a method for the treatment of a subject in need of treatment for a disease or disorder or symptoms associated with the disease or disorder, associated with the expression of RhoA, comprising administering to the subject an amount of nucleic acid molecule which reduces or inhibits expression of RhoA set forth in SEQ ID NO:1.

BRIEF DESCRIPTION OF THE FIGURES

FIG. 1 provides a table of exemplary dsRNA that were synthesized. Some of the molecules were tested in vitro at different concentrations and the % residual mRNA is provided.

DETAILED DESCRIPTION OF THE INVENTION

Figure 2:
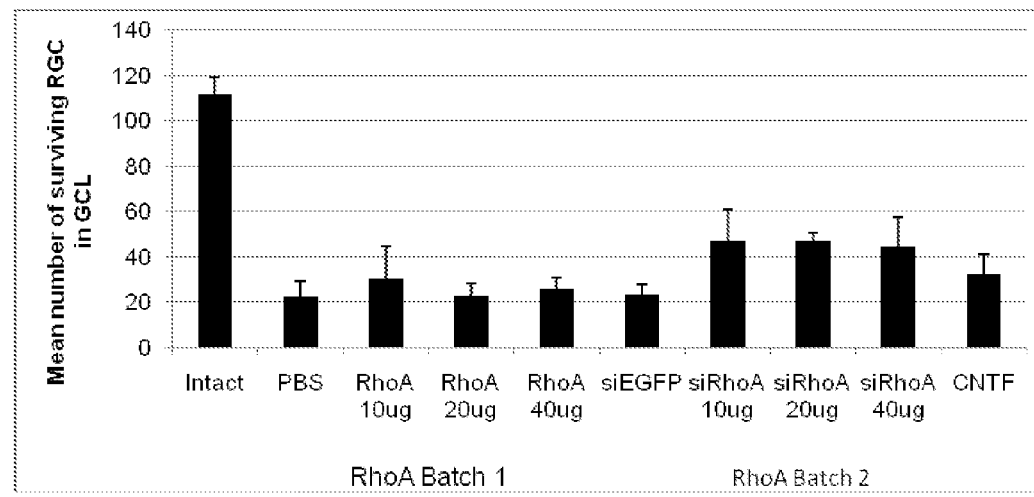
FIG. 2: Mean RGC survival after dsRhoA treatment in in-vivo Study Measuring the Ability of Escalating Doses of dsRhoA Compound to Induce RGC Axon Regeneration Following Optic Nerve Crush in Rats

Disclosed herein are compounds which down-regulate expression of RhoA, particularly to novel chemically modified double stranded RNA oligonucleotides (dsRNAs), and to the use of these novel dsRNAs in the treatment of various diseases and medical conditions, particularly diseases and disorders of the central nervous system (CNS). According to one aspect the present invention provides inhibitory oligonucleotide compounds comprising unmodified and modified nucleotides and or unconventional moieties. The compound includes at least one modified nucleotide selected from the group consisting of a sugar modification, a base modification and an internucleotide linkage modification and may further include DNA, and modified nucleotides or unconventional moieties including LNA (locked nucleic acid), ENA (ethylene-bridged nucleic acid), PNA (peptide nucleic acid), arabinoside, PACE, mirror nucleotide, a nucleotide joined to an adjacent nucleotide by a 2'-5' internucleotide bond or a nucleotide with a 6 carbon sugar.

RhoA is a small GTPase protein that controls cellular functions such as motility, growth, differentiation, and apoptosis in CNS neurons, including RGC. RhoA is also involved in the secondary inflammatory and scarring CNS injury responses by signalling in neural immune cells (microglia and macrophages) and astrocytes. Particular diseases and conditions to be treated include SCI, glaucoma, AMD, neurodegenerative diseases including Alzheimer's disease and Parkinson's disease, ALS, stoke, TBI and the like.

Lists of preferred sense and antisense sequences useful in generating siRNA compounds according to this disclosure are provided in Table I, Table II, and Table III.

Methods, nucleic acid molecules and compositions, which down-regulate RhoA are discussed herein at length, and any of said molecules and/or compositions may be beneficially employed in the treatment of a subject suffering from any of said conditions.

The nucleic acid compounds provided herein possess structures and modifications, which may increase activity, increase stability, and or minimize toxicity; the novel modifications useful in generating dsRNA compounds disclosed herein can be beneficially applied to double stranded RNA useful in preventing or attenuating RhoA expression.

In some embodiments provided herein is a double stranded RNA compound having the structure (A1):

```
(A1)      5'    (N)x-Z     3'    (antisense strand)

3' Z'-(N')y-z"  5'     (sense strand)
``` wherein each N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein each of Z and Z' is independently present or absent, but if present independently comprises 1-5 consecutive nucleotides, 1-5 consecutive non-nucleotide moieties or a combination thereof covalently attached at the 3' terminus of the strand in which it is present;

wherein z" may be present or absent, but if present is a capping moiety covalently attached at the 5' terminus of (N')y;

each of x and y is independently an integer from 18 to 40;

wherein the sequence of (N')y is complementary to the sequence of (N)x; and wherein (N)x comprises an antisense sequence set forth in Table III or Table IV.

The sense and antisense sequences useful in generating dsRNA compounds provided in Table III are RHOA_31 (SEQ ID NOS:135 and 149), RHOA_33 (SEQ ID NOS:136 and 150), RHOA_37 (SEQ ID NOS:137 and 151), RHOA_38 (SEQ ID NOS:138 and 152), RHOA_43 (SEQ ID NOS: 139 and 153), RHOA_52 (SEQ ID NOS:140 and 154), RHOA_56 (SEQ ID NOS:141 and 155), RHOA_57 (SEQ ID NOS:142 and 156), RHOA_58 (SEQ ID NOS:143 and 157), RHOA_68 (SEQ ID NOS:144 and 158), RHOA_69 (SEQ ID NOS:145 and 159), RHOA_70 (SEQ ID NOS:146 and 160), RHOA_73 (SEQ ID NOS:147 and 161) and RHOA_76 (SEQ ID NOS:148 and 162). The sense and antisense sequences useful in generating dsRNA compounds provided in Table IV are set forth in RHOA_23 (SEQ ID NOS: 163 and 167), RHOA_24 (SEQ ID NOS:164 and 168), RHOA_26 (SEQ ID NOS:165 and 169) or RHOA_29 (SEQ ID NOS:166 and 170).

In some embodiments the covalent bond joining each consecutive N and/or N' is a phosphodiester bond.

In some embodiments x=y and each of x and y is 19, 20, 21, 22 or 23. In preferred embodiments x=y=19.

In some embodiments of nucleic acid molecules (e.g., dsRNA molecules) as disclosed herein, the double stranded nucleic acid molecule is a siRNA, siNA or a miRNA.

In some embodiments the sense and antisense strands comprise the sequence pairs set forth in RHOA_58 (SEQ ID NOS: 143 and 157). In some embodiments the sense and antisense strands comprise the sequence pairs set forth in RHOA_70 (SEQ ID NOS: 146 and 160).

In some embodiments the double stranded nucleic acid molecules comprise a DNA moiety or a mismatch to the target at position 1 of the antisense strand (5' terminus). Such a duplex structure is described herein. According to one embodiment provided are double stranded siRNA compounds having a structure (A2) set forth below:

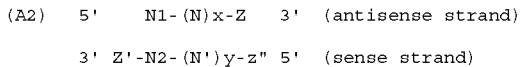

wherein each N1, N2, N and N' is independently an unmodified or modified nucleotide, or an unconventional moiety;
wherein each of (N)x and (N')y is an oligonucleotide in which each consecutive N or N' is joined to the adjacent N or N' by a covalent bond;
wherein each of x and y is independently an integer between 17 and 39;
wherein N2 is covalently bound to (N')y;
wherein N1 is covalently bound to (N)x and is mismatched to the target mRNA (SEQ ID NO:1) or is a complementary DNA moiety to the target mRNA;
wherein N1 is a moiety selected from the group consisting of natural or modified: uridine, deoxyribouridine, ribothymidine, deoxyribothymidine, adenosine or deoxyadenosine, an abasic ribose moiety and an abasic deoxyribose moiety;
wherein z" may be present or absent, but if present is a capping moiety covalently attached at the 5' terminus of N2-(N')y;
wherein each of Z and Z' is independently present or absent, but if present is independently 1-5 consecutive nucleotides, 1-5 consecutive non-nucleotide moieties or a combination thereof covalently attached at the 3' terminus of the strand in which it is present; and
wherein the sequence of (N')y is complementary to the sequence of (N)x; and
wherein the sequence of (N)x comprises an antisense sequence set forth in Table I.

In various embodiments the sequence of N1-(N)x comprises an antisense sequence set forth in Table II. In some embodiments the N2-(N')y and N1-(N)x useful in generating dsRNA compounds are presented in Table II and set forth in RHOA_32 (SEQ ID NOS:67 and 101), RHOA_34 (SEQ ID NOS:68 and 102), RHOA_35 (SEQ ID NOS:69 and 103), RHOA_36 (SEQ ID NOS:70 and 104), RHOA_39 (SEQ ID NOS:71 and 105), RHOA_40 (SEQ ID NOS:72 and 106), RHOA_41 (SEQ ID NOS:73 and 107), RHOA_42 (SEQ ID NOS:74 and 108), RHOA_44 (SEQ ID NOS:75 and 109), RHOA_45 (SEQ ID NOS:76 and 110), RHOA_46 (SEQ ID NOS:77 and 111), RHOA_47 (SEQ ID NOS:78 and 112), RHOA_48 (SEQ ID NOS:79 and 113), RHOA_48u (SEQ ID NOS:80 and 114), RHOA_49 (SEQ ID NOS:81 and 115), RHOA_50 (SEQ ID NOS:82 and 116) RHOA_51 (SEQ ID NOS:83 and 117), RHOA_53 (SEQ ID NOS:84 and 118), RHOA_54 (SEQ ID NOS:85 and 119), RHOA_55 (SEQ ID NOS:86 and 120), RHOA_59 (SEQ ID NOS:87 and 121), RHOA_60 (SEQ ID NOS:88 and 122), RHOA_61 (SEQ ID NOS:89 and 123), RHOA_61u (SEQ ID NOS:90 and 124), RHOA_62 (SEQ ID NOS:91 and 125), RHOA_63 (SEQ ID NOS:92 and 126) RHOA_64 (SEQ ID NOS:93 and 127), RHOA_65 (SEQ ID NO:94 and 128), RHOA_66 (SEQ ID NOS:95 and 129) RHOA_67 (SEQ ID NOS:96 and 130), RHOA_71 (SEQ ID NOS:97 and 131), RHOA_72 (SEQ ID NOS:98 and 132), RHOA_74 (SEQ ID NOS:99 and 133) and RHOA_75 (SEQ ID NOS:100 and 134).

Novel dsRNA compounds utilizing the sense (passenger strand) and antisense (guide strand) sequences are set forth herein

DEFINITIONS

For convenience certain terms employed in the specification, examples and claims are described herein.

It is to be noted that, as used herein, the singular forms "a", "an" and "the" include plural forms unless the content clearly dictates otherwise.

Where aspects or embodiments of the invention are described in terms of Markush groups or other grouping of alternatives, those skilled in the art will recognize that the invention is also thereby described in terms of any individual member or subgroup of members of the group.

An "inhibitor" is a compound, which is capable of down-regulating or reducing (partially or fully) the expression of a gene or the activity of the product of such gene to an extent sufficient to achieve a desired biological or physiological effect. The term "inhibitor" as used herein refers to one or more of an oligonucleotide or nucleic acid inhibitor, including dsRNA, siRNA, shRNA, synthetic shRNA; miRNA, antisense RNA and DNA and ribozymes.

A "dsRNA inhibitor" is a compound, which is capable of down-regulating or reducing the expression of a gene or the activity of the product of such gene to an extent sufficient to achieve a desired biological or physiological effect. The term "dsRNA inhibitor" as used herein refers to one or more of a dsRNA, siRNA, shRNA, synthetic shRNA; miRNA. Inhibition may also be referred to as down-regulation or, for RNAi, silencing.

The term "inhibit" as used herein refers to down-regulating or reducing the expression of a gene or the activity of the product of such gene to an extent sufficient to achieve a desired biological or physiological effect. Inhibition may be complete or partial.

As used herein, the term "inhibition" or "down-regulation" of RhoA means down-regulation or inhibition of gene expression (transcription or translation) or polypeptide activity. The polynucleotide sequence of the target mRNA sequence, refers to the mRNA sequences, or any homologous sequences thereof preferably having at least 70% identity, more preferably 80% identity, even more preferably 90% or 95% identity to RhoA mRNA, set forth in SEQ ID NO:1. Therefore, polynucleotide sequences, which have undergone mutations, alterations or modifications as described herein are encompassed in the present invention. The terms "mRNA polynucleotide sequence" and "mRNA" are used interchangeably. RhoA is a GTPase that regulates the actin cytoskeleton and it is upregulated following spinal cord injury and has been shown to be expressed in the trabecular meshwork of the eye.

As used herein, the terms "polynucleotide" and "nucleic acid" may be used interchangeably and refer to nucleotide sequences comprising deoxyribonucleic acid (DNA), and ribonucleic acid (RNA). The terms should also be understood to include, as equivalents, analogs of either RNA or DNA made from nucleotide analogs. Throughout this application, mRNA sequences are set forth as representing the corresponding genes.

"Oligonucleotide" or "oligomer" refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The compounds disclosed herein encompass molecules comprising deoxyribonucleotides, ribonucleotides, modified deoxyribonucleotides, modified ribonucleotides and combinations thereof.

"Nucleotide" is meant to encompass deoxyribonucleotides and ribonucleotides, which may be natural or synthetic, and or modified or unmodified. Modifications include changes to the sugar moiety, the base moiety and or the linkages between ribonucleotides in the oligoribonucleotide. As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide.

According to some embodiments inhibitory oligonucleotide compounds comprising unmodified and modified nucleotides and or unconventional moieties are provided. The compound comprises at least one modified nucleotide selected from the group consisting of a sugar modification, a base modification and an internucleotide linkage modification and may contain DNA, and modified nucleotides such as LNA (locked nucleic acid), ENA (ethylene-bridged nucleic acid, PNA (peptide nucleic acid), arabinoside, PACE, mirror nucleotide, or nucleotides with a 6 carbon sugar.

All analogs of, or modifications to, a nucleotide/oligonucleotide may be employed with the modifications disclosed herein, provided that said analog or modification does not substantially adversely affect the function of the nucleotide/oligonucleotide. Acceptable modifications include modifications of the sugar moiety, modifications of the base moiety, modifications in the inter-nucleotide linkages and combinations thereof.

In one embodiment the compound comprises a 2' modification on the sugar moiety of at least one ribonucleotide ("2' sugar modification"). In certain embodiments the compound comprises 2'O-alkyl or 2'-fluoro or 2'O-allyl or any other 2' modification, optionally on alternate positions. Other stabilizing modifications are also possible (e.g. terminal modifications). In some embodiments a preferred 2'O-alkyl is 2'O-methyl (methoxy, 2' OMe) sugar modification. A sugar modification includes a modification on the 2' moiety of the sugar residue and encompasses amino, fluoro, alkoxy e.g. methoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1.

In some embodiments the backbone of the oligonucleotides is modified and comprises phosphate-D-ribose entities but may also contain thiophosphate-D-ribose entities, triester, thioate, 2'-5' bridged backbone (also may be referred to as 5'-2'), PACE and the like.

As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide.

Other modifications include terminal modifications on the 5' and/or 3' part of the oligonucleotides and are also known as capping moieties. Such terminal modifications are selected from a nucleotide, a modified nucleotide, a lipid, a peptide, and a sugar.

An "alkyl moiety or derivative thereof" refers to straight chain or branched carbon moieties and moieties per se or further comprising a functional group including alcohols, phosphodiester, phosphorothioate, phosphonoacetate and also includes amines, carboxylic acids, esters, amides aldehydes. "Hydrocarbon moiety" and "alkyl moiety" are used interchangeably.

"Terminal functional group" includes halogen, alcohol, amine, carboxylic, ester, amide, aldehyde, ketone, ether groups.

Nucleotide" is meant to encompass deoxyribonucleotides and ribonucleotides, which may be natural or synthetic, and be modified or unmodified. Modifications include changes and substitutions to the sugar moiety, the base moiety and/or the internucleotide linkages.

Modified ribonucleotides include deoxyribonucleotides and modified deoxyribonucleotides. Modified deoxyribonucleotide includes, for example 5'OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate. Additionally provided herein are methods and compositions for inhibiting expression of RhoA in vivo. In general, the method includes administering oligoribonucleotides, in particular double stranded RNAs (i.e. dsRNAs) or a nucleic acid material that can produce dsRNA in a cell, that target an mRNA transcribed from RhoA in an amount sufficient to downregulate expression of RhoA by e.g., an RNA interference mechanism. In particular, the subject method can be used to down-regulate expression of RhoA for treatment of a disease, disorder or injury. In accordance with the present invention, the nucleic acid molecules or inhibitors of RhoA are used as drugs to treat various pathologies. In accordance with the present invention, the nucleic acid molecules or inhibitors of RhoA are used as drugs to treat various disease or disorder in the CNS, PNS, vestibular sensory system, visual system and/or circulatory (vascular, arterial) system.

dsRNAs and RNA Interference

RNA interference (RNAi) is a phenomenon involving double-stranded (ds) RNA-dependent gene-specific posttranscriptional silencing. Initial attempts to study this phenomenon and to manipulate mammalian cells experimentally were frustrated by an active, non-specific antiviral defense mechanism which was activated in response to long dsRNA molecules (Gil et al., Apoptosis, 2000. 5:107-114). Later, it was discovered that synthetic duplexes of 21 nucleotide RNAs could mediate gene specific RNAi in mammalian cells, without stimulating the generic antiviral defense mechanisms Elbashir et al. Nature 2001, 411:494-498 and Caplen et al. PNAS 2001, 98:9742-9747). As a result, small interfering RNAs (siRNAs), which are short double-stranded RNAs, have been widely used to inhibit gene expression and understand gene function.

RNA interference (RNAi) is mediated by small interfering RNAs (siRNAs) (Fire et al, Nature 1998, 391:806) or microRNAs (miRNAs) (Ambros V. Nature 2004, 431:350-355); and Bartel D P. Cell. 2004 116(2):281-97). The corresponding process is commonly referred to as specific post-transcriptional gene silencing when observed in plants and as quelling when observed in fungi.

A siRNA compound is a double-stranded RNA which down-regulates or silences (i.e. fully or partially inhibits) the expression of an endogenous or exogenous gene/mRNA. RNA interference is based on the ability of certain dsRNA species to enter a specific protein complex, where they are then targeted to complementary cellular RNAs and specifically degrades them. Thus, the RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir, et al., Genes Dev., 2001, 15:188). In more detail, longer dsRNAs are digested into short (17-29 bp) dsRNA fragments (also referred to as short inhibitory RNAs or "siRNAs") by type III RNAses (DICER, DROSHA, etc., (see Bernstein et al., Nature, 2001, 409:363-6 and Lee et al., Nature, 2003, 425:415-9). The RISC protein complex recognizes these fragments and complementary mRNA. The whole process is culminated by endonuclease cleavage of target mRNA (McManus and Sharp, Nature Rev Genet, 2002, 3:737-47; Paddison and Hannon, Curr Opin Mol. Ther. 2003, 5(3): 217-24). (For additional information on these terms and proposed mechanisms, see for example, Bernstein, et al., RNA. 2001, 7(11):1509-21; Nishikura, Cell. 2001, 107(4):415-8 and PCT Publication No. WO 01/36646).

Studies have revealed that siRNA can be effective in vivo in both mammals and humans. Specifically, Bitko et al., showed that specific siRNAs directed against the respiratory syncytial virus (RSV) nucleocapsid N gene are effective in treating mice when administered intranasally (Nat. Med. 2005, 11(1): 50-55). For reviews of therapeutic applications of siRNAs see for example Barik (Mol. Med. 2005, 83: 764-773) and Chakraborty (Current Drug Targets 2007 8(3):469-82). In addition, clinical studies with short siRNAs that target the VEGFR1 receptor in order to treat age-related macular degeneration (AMD) have been conducted in human patients (Kaiser, Am J. Ophthalmol. 2006 142(4):660-8). Further information on the use of siRNA as therapeutic agents may be found in Durcan, 2008. Mol. Pharma. 5(4):559-566; Kim and Rossi, 2008. BioTechniques 44:613-616; Grimm and Kay, 2007, JCI, 117(12):3633-41.

Chemical Synthesis

The compounds of the present invention can be synthesized by any of the methods that are well-known in the art for synthesis of ribonucleic (or deoxyribonucleic) oligonucleotides. Such synthesis is, among others, described in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Annu Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et. al., in IRL Press 1989 edited by Oliver R. W. A.; Kap. 7: 183-208.

Other synthetic procedures are known in the art e.g. the procedures as described in Usman et al., 1987, J. Am. Chem. Soc., 109, 7845; Scaringe et al., 1990, NAR., 18, 5433; Wincott et al., 1995, NAR. 23, 2677-2684; and Wincott et al., 1997, Methods Mol. Bio., 74, 59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides of the present invention can be synthesized separately and joined together post-synthetically, for example, by ligation (Moore et al., 1992, Science 256, 9923; Draper et al., International Patent Publication No. WO 93/23569; Shabarova et al., 1991, NAR 19, 4247; Bellon et al., 1997, Nucleosides & Nucleotides, 16, 951; Bellon et al., 1997, Bioconjugate Chem. 8, 204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via tandem synthesis methodology, as described for example in US Patent Publication No. US 2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

The present invention further provides for a pharmaceutical composition comprising two or more siRNA molecules for the treatment of any of the diseases and conditions mentioned herein, whereby said two molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. In one embodiment, the siRNA molecules are comprised of a double-stranded nucleic acid structure as described herein, wherein the two siRNA sequences are selected from the nucleic acids set forth in Tables I, II, III or IV. Thus, the siRNA molecules may be covalently or non-covalently bound or joined by a linker to form a tandem siRNA compound. Such tandem siRNA compounds comprising two siRNA sequences are typically of 38-150 nucleotides in length, more preferably 38 or 40-60 nucleotides in length, and longer accordingly if more than two siRNA sequences are included in the tandem molecule. A longer tandem compound comprised of two or more longer sequences which encode siRNA produced via internal cellular processing, e.g., long dsRNAs, is also envisaged, as is a tandem molecule encoding two or more shRNAs. Such tandem molecules are also considered to be a part of the disclosure. A compound comprising two (tandem) or more (RNAistar") dsRNA sequences disclosed herein is envisaged. Examples of such "tandem" or "star" molecules are provided in PCT patent publication no. WO 2007/091269, assigned to the assignee of the present application and incorporated herein by reference in its entirety.

The dsRNA molecules that target RhoA may be the main active component in a pharmaceutical composition, or may be one active component of a pharmaceutical composition containing two or more dsRNAs (or molecules which encode or endogenously produce two or more dsRNAs, be it a mixture of molecules or one or more tandem molecules which encode two or more dsRNAs), said pharmaceutical composition further being comprised of one or more additional dsRNA molecule which targets one or more additional gene. Simultaneous inhibition of said additional gene(s) will likely have an additive or synergistic effect for treatment of the diseases disclosed herein.

Additionally, the dsRNA disclosed herein or any nucleic acid molecule comprising or encoding such dsRNA can be linked or bound (covalently or non-covalently) to antibodies (including aptamer molecules) against cell surface internalizable molecules expressed on the target cells, in order to achieve enhanced targeting for treatment of the diseases disclosed herein. For example, anti-Fas antibody (preferably a neutralizing antibody) may be combined (covalently or non-covalently) with any dsRNA. In another example, an aptamer which can act like a ligand/antibody may be combined (covalently or non-covalently) with any dsRNA.

The nucleic acid compounds of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell. Vectors optionally used for delivery of the compounds of the present invention are commercially available, and may be modified for the purpose of delivery of the compounds of the present invention by methods known to one of skill in the art.

Chemical Modifications

All analogues of, or modifications to, a nucleotide/oligonucleotide All analogs of, or modifications to, a nucleotide/oligonucleotide may be employed with the present invention, provided that said analogue or modification does not substantially affect the function of the nucleotide/oligonucleotide. The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiuracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine. In some embodiments one or more nucleotides in an oligomer is substituted with inosine.

In addition, analogues of polynucleotides can be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to enzymatic degradation and to have extended stability in vivo and in vitro. Other modifications that can be made to oligonucleotides include polymer backbones, cyclic backbones, acyclic backbones, thiophosphate-D-ribose backbones, triester backbones, thioate backbones, 2'-5' bridged backbone, artificial nucleic acids, morpholino nucleic acids, locked nucleic acid (LNA), glycol nucleic acid (GNA), threose nucleic acid (TNA), arabinoside, and mirror nucleoside (for example, beta-L-deoxynucleoside instead of beta-D-deoxynucleoside). Examples of siRNA compounds comprising LNA nucleotides are disclosed in Elmen et al., (NAR 2005, 33(1): 439-447).

The nucleic acid compounds of the present invention can be synthesized using one or more inverted nucleotides, for example inverted thymidine or inverted adenine (see, for example, Takei, et al., 2002, JBC 277(26):23800-06).

The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide joined to an adjacent nucleotide by a 2'-5' internucleotide phosphate bond; C3, C4, C5 and C6 moieties; bridged nucleic acids including LNA and ethylene bridged nucleic acids.

The term "capping moiety" as used herein includes abasic ribose moiety, abasic deoxyribose moiety, modifications abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyriboabasic 5'-phosphate.

A "mirror" nucleotide is a nucleotide with reversed chirality to the naturally occurring or commonly employed nucleotide, i.e., a mirror image (L-nucleotide) of the naturally occurring (D-nucleotide). The nucleotide can be a ribonucleotide or a deoxyribonucleotide and my further comprise at least one sugar, base and or backbone modification. U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU).

In various embodiments of Structure A1 or Structure A2, Z and Z' are absent. In other embodiments Z or Z' is present. In some embodiments each of Z and/or Z' independently includes a C2, C3, C4, C5 or C6 alkyl moiety, optionally a C3 [propane, —(CH2)3-] moiety or a derivative thereof including propanol (C3-OH/C3OH), propanediol, and phosphodiester derivative of propanediol ("C3Pi"). In preferred embodiments each of Z and/or Z' includes two hydrocarbon moieties and in some examples is C3Pi-C3OH or C3Pi-C3Pi. Each C3 is covalently conjugated to an adjacent C3 via a covalent bond, preferably a phospho-based bond. In some embodiments the phospho-based bond is a phosphorothioate, a phosphonoacetate or a phosphodiester bond.

In specific embodiments of Structure A1 x=y=19 and Z comprises at least one C3 alkyl overhang. In specific embodiments of Structure A2 x=y=18 and Z comprises at least one C3 alkyl overhang. In some embodiments the C3-C3 overhang is covalently attached to the 3' terminus of (N)x or (N')y via a covalent linkage, preferably a phosphodiester linkage. In some embodiments the linkage between a first C3 and a second C3 is a phosphodiester linkage. In some embodiments the 3' non-nucleotide overhang is C3Pi-C3Pi. In some embodiments the 3' non-nucleotide overhang is C3Pi-C3Ps. In some embodiments the 3' non-nucleotide overhang is C3Pi-C3OH(OH is hydroxy). In some embodiments the 3' non-nucleotide overhang is C3Pi-C3OH.

In various embodiments the alkyl moiety comprises an alkyl derivative including a C3 alkyl, C4 alkyl, C5 alky or C6 alkyl moiety comprising a terminal hydroxyl, a terminal amino, or terminal phosphate group. In some embodiments the alkyl moiety is a C3 alkyl or C3 alkyl derivative moiety. In some embodiments the C3 alkyl moiety comprises propanol, propylphosphate, propylphosphorothioate or a combination thereof. The C3 alkyl moiety is covalently linked to the 3' terminus of (N')y and/or the 3' terminus of (N)x via a phosphodiester bond. In some embodiments the alkyl moiety comprises propanol, propyl phosphate or propyl phosphorothioate. In some embodiments each of Z and Z' is independently selected from propanol, propyl phosphate propyl phosphorothioate, combinations thereof or multiples thereof in particular 2 or 3 covalently linked propanol, propyl phosphate, propyl phosphorothioate or combinations thereof. In some embodiments each of Z and Z' is independently selected from propyl phosphate, propyl phosphorothioate, propyl phosphopropanol; propyl phospho-propyl phosphorothioate; propylphospho-propyl phosphate; (propyl phosphate)3, (propyl phosphate)2-propanol, (propyl phosphate)2-propyl phosphorothioate. Any propane or propanol conjugated moiety can be included in Z or Z'.

The structures of exemplary 3' terminal non-nucleotide moieties are as follows:

Indications

The molecules and compositions disclosed herein are useful in the treatment of diseases and disorders of the CNS, PNS, vestibular sensory system, visual system and/or circulatory (vascular, arterial) system, as well as disease and disorders associated with cell motility, cytoskeleton regulation and microtubular organization and other diseases and conditions herein described.

CNS Disorders and Injury

In various aspects and embodiments the nucleic acid compounds and pharmaceutical compositions disclosed herein are useful for treating diseases, disorders and injury associates with RhoA gene, such as diseases, disorders and injury of the central nervous system (CNS) that are related to or will respond to the levels of RhoA in a cell or tissue, alone or in combination with other therapies, particularly for treating a subject suffering from or affected by or susceptible to disease or injury of the CNS.

Conditions Related to Neuroregeneration and Neuroprotection

The dsRhoA compounds disclosed herein can be used for protection of spinal cord neurons form secondary damage and promotion of axonal (nerve) regeneration leading to restoration of function.

There are many indications in which axon regeneration would be beneficial. Axon loss contributes to neurological symptoms in disorders such as multiple sclerosis, stroke, traumatic brain injury, peripheral neuropathies and chronic neurodegenerative diseases.

Injury of the Central Nervous System (CNS)

In various embodiments the nucleic acid compounds and pharmaceutical compositions disclosed herein are useful for treating injury of the central nervous system (CNS), particu-

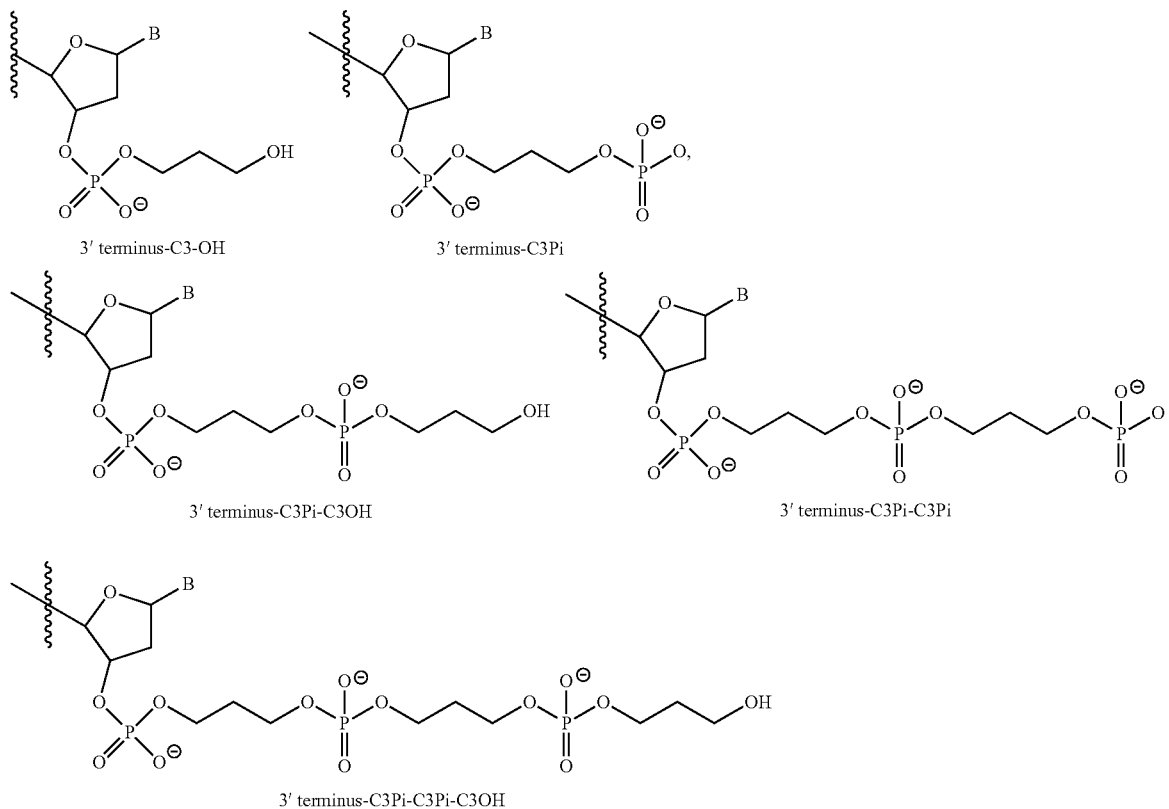

larly for treating a subject suffering from or affected by or susceptible to injury of the CNS, including, without being limited to, traumatic and non-traumatic spinal cord injury, and brain injury (e.g. Traumatic Brain Injury (TBI)), that is caused by fracture or penetration of the skull (i.e. a vehicle accident, fall, gunshot wound), a disease process (i.e. neurotoxins, infections, tumors, metabolic abnormalities, etc.) or a closed head injury such as in the case of rapid acceleration or deceleration of the head (i.e. Shaken Baby Syndrome, blast), blunt trauma, concussions, and concussion syndrome.

Additionally, an ischemic episode may be caused by a mechanical injury to the Central Nervous System, such as results from a blow to the head or spine. Trauma can involve a tissue insult such as an abrasion, incision, contusion, puncture, compression, etc., such as can arise from traumatic contact of a foreign object with any locus of or appurtenant to the head, neck, or vertebral column. Other forms of traumatic injury can arise from constriction or compression of CNS tissue by an inappropriate accumulation of fluid (for example, a blockade or dysfunction of normal cerebrospinal fluid or vitreous humor fluid production, turnover, or volume regulation, or a subdural or intracranial hematoma or edema). Similarly, traumatic constriction or compression can arise from the presence of a mass of abnormal tissue, such as a metastatic or primary tumor.

Spinal Cord Injury (SCI)

There are an estimated 10,000-12,000 spinal cord injuries (SCI) every year in the United States alone with over a quarter of a million Americans that are currently living with spinal cord injuries according to the Spinal Cord Injury Facts and Figures at a Glance from April 2009 written by the National Spinal Cord Injury Statistical Center. Of the people suffering from SCI, more than half (57.5%) reported being employed at the time of their injury. The cost of managing the care of spinal cord injury patients approaches $4 billion/year, but does not include any indirect costs such as losses in wages, fringe benefits and productivity which averages $64,443 per year in December 2008 dollars.

Currently there is no effective treatment for SCI, and since the National Acute Spinal Cord Injury Studies (NASCIS) I, II and III, a high dose of the steroid methylprednisolone (MP) given for 24 hours, administered within 8 hours post injury, is the current standard of care. However, its effect is small and controversial and in many countries, such as Canada, MP has been discontinued as the standard of care and is now classified only as a treatment option (Hugenholtz, 2003). Recently there have been studies showing that early surgical intervention (spinal decompression surgery) after SCI shows promising results. According to the Surgical Treatment of Acute Spinal Cord Injury Study (STASCIS), 24% of people who underwent decompressive surgery within a day of their initial injury showed significant improvement when measured by the American Spinal Injury Association (ASIA) scale, however it is still too early for a definitive decision on these results. Today there are close to 250 clinical trials listed dealing with SCI, however, the vast majority of these deal with patient rehabilitation. Thus, there is a need for new therapies, which requires development of novel therapies in model systems and their translation to the clinic.

In one embodiment the injury to the CNS is Spinal Cord Injury (SCI) or myelopathy. SCI or myelopathy, is a disturbance of the spinal cord that results in loss of sensation and/or mobility. The two common types of spinal cord injury are due to trauma and disease. Traumatic injury can be due to automobile accidents, falls, gunshot, diving accidents inter alia, and diseases that can affect the spinal cord include polio, spina bifida, tumors, Amyotrophic Lateral Sclerosis (ALS), Multiple Sclerosis (MS) syringomyelia, transverse myelitis and Friedreich's ataxia.

In various embodiments, the nucleic acid compounds and pharmaceutical compositions of the invention are used for treating or preventing the damage caused by spinal-cord injury especially spinal cord trauma caused by motor vehicle accidents, falls, sports injuries, industrial accidents, gunshot wounds, spinal cord trauma caused by spine weakening (such as from rheumatoid arthritis or osteoporosis) or if the spinal canal protecting the spinal cord has become too narrow (spinal stenosis) due to the normal aging process, direct damage that occur when the spinal cord is pulled, pressed sideways, or compressed, damage to the spinal-cord following bleeding, fluid accumulation, and swelling inside the spinal cord or outside the spinal cord (but within the spinal canal).

Thus the present invention further provides a method of treating SCI in a subject in need of treatment that comprises administering to the subject a pharmaceutical composition which comprises a therapeutically effective amount of at least one oligonucleotide compound, which down-regulates RhoA expression in the CNS of the subject in an amount effective to treat SCI.

Brain Injury

In one embodiment the injury to the CNS is brain injury. Brain injury such as trauma and stroke are among the leading causes of mortality and disability in the western world. Traumatic brain injury (TBI) is one of the most serious reasons for hospital admission and disability in modern society. Clinical experience suggests that TBI may be classified into primary damage occurring immediately after injury, and secondary damage, which occurs during several days post injury. Current therapy of TBI is either surgical or else mainly symptomatic.

Thus the present invention provides a method of treating brain injury in a subject in need of treatment that comprises administering to the subject a pharmaceutical composition which comprises a therapeutically effective amount of at least one oligonucleotide compound, which down-regulates RhoA expression in the CNS of the subject in an amount effective to treat brain injury.

Peripheral Nerve Injuries (PNI)

PNIs may result in loss of motor function, sensory function, or both. Peripheral nerve injuries may occur as a result of trauma (eg, a blunt or penetrating wound, trauma) or acute compression. Stretch-related injuries are the most common type. Lacerations such as those created by a knife blade are also common. In North America it is believed that approximately 2-3% of trauma patients have a major nerve injury. Based on retrospective studied the incidence of limb trauma is some 1.4% of the population seeking medical assistance, 83% less than 55 yrs old, and 50% male. The total incidence of nerve injuries within 90 days of upper- or lower-limb trauma was 1.64% in the same population. Peripheral nerve injury may result in demyelination or axonal degeneration. Clinically, both demyelination and axonal degeneration result in disruption of the sensory and/or motor function of the injured nerve. Recovery of function occurs with remyelination and with axonal regeneration and re-innervation of the sensory receptors, muscle end plates, or both. The pattern of recovery is mixed and incomplete. 4th to 6th degree injuries require surgery. Indications for nerve injury surgery are:

Closed nerve injury: With no evidence of recovery either clinically or with electrodiagnostic studies at 3 months following injury.

Open nerve injury (ie, laceration): Surgical exploration is recommended as soon as possible. All lacerations with a reported loss of sensation or motor weakness should be surgically explored.

Crush nerve injury: After 3 months with no evidence of re-innervation electrically or clinically, surgical reconstruction with repair or graft is indicated.

Perioperative nerve damage. Nerve damage can occur even during and as a result of surgery. Perioperative nerve injuries are relatively rare but devastating to patients. Permanent damage is believed to occur in 1 of 5000 cases. Nerve damage can (rarely) occur with major orthopedic surgery as well such as knee replacement. The most common nerve damaged in knee replacement surgery is the nerve to the muscles that bring the foot up toward the face (the peroneal nerve). The odds of this occurring are probably one in many hundreds. Currently in the US, there are more than 550,000 joint replacement procedures performed each year—most often involving the hip and knee, with total joint replacement of the ankle, elbow, shoulder, and fingers performed less often. More than 193,000 artificial hip replacement surgeries are performed yearly. The demand is expected to increase drastically in the next 25 years, as presented at the 73rd Annual Meeting of the American Academy of Orthopaedic Surgeons (AAOS), with estimates of 3.48 million hip and knee replacement procedures to be performed in the USA in 2030.

Diseases and Disorders of the Vestibular System

In various embodiments the nucleic acid compounds and pharmaceutical compositions of the invention are useful for treating disorders and diseases affecting the vestibular system in which expression of RhoA is detrimental, for example Meniere's Disease. The vestibular sensory system in most mammals, including humans, contributes to balance, and to a sense of spatial orientation and stability. Together with the cochlea it constitutes the labyrinth of the inner ear. The vestibular system comprises two components: the semicircular canal system, which indicate rotational movements; and the otoliths, which indicate linear accelerations.

Meniere's Disease

Meniere's disease, also known as idiopathic endolymphatic hydrops (ELH), is a disorder of the inner ear resulting in vertigo and tinnitus, and eventual neuronal damage leading to hearing loss. The exact cause of Meniere's disease is unknown but the underlying mechanism is believed to be distortion of the membranous labyrinth due to accumulation of endolymph. Endolymph is produced primarily by the stria vascularis in the cochlea and also by the planum semilunatum and the dark cells in the vestibular labyrinth (Sajjadi H, Paparella M M. Meniere's disease. Lancet. 372(9636):406-14). If the flow of endolymph from the endolymphatic fluid space through the vestibular aqueduct to the endolymphatic sac is obstructed, endolymphatic hydrops will occur. Meniere's disease may affect one or both of a subject's ears. The primary morbidity associated with Ménière's disease is the debilitating nature of vertigo and the progressive hearing loss. Current therapies have not been successful at preventing progression of neuronal degeneration and associated hearing loss. A therapeutic treatment, which would protect the neurons of the inner ear including the vestibulocochlear nerve from damage and or induce regeneration of the vestibulocochlear nerve and thereby attenuate or prevent hearing loss in Meniere's patients would be highly desirable.

The nucleic acids, compositions, methods and kits provided herein are useful in treating subjects at risk of or suffering from Meniere's disease.

Neurological Disorders

In various embodiments the nucleic acid compounds and pharmaceutical compositions of the invention are useful for treating neurological disorders.

In various embodiments the neurological disorder is selected from, without being limited to, stroke, stroke-like situations (e.g. cerebral, renal, cardiac failure), neuronal cell death, epilepsy, Parkinsonism, Gluten Ataxia, cerebral ischemia and cerebrovascular accident.

Epilepsy

In one embodiment the neurological disorder is epilepsy. Epilepsy is a group of disorders marked by problems in the normal functioning of the brain. These problems can produce seizures, unusual body movements, loss of consciousness or changes in consciousness, as well as mental problems or problems with the senses.

Thus the present invention further provides a method of treating epilepsy in a subject in need of treatment that comprises administering to the subject a pharmaceutical composition which comprises a therapeutically effective amount of at least one oligonucleotide compound, which down-regulates RhoA expression in the CNS of the subject in an amount effective to treat epilepsy.

Stroke

In another embodiment the neurological disorder is stroke. Stroke is an acute neurological injury occurring as a result of interrupted blood supply, resulting in an insult to the brain. Most cerebrovascular diseases present as the abrupt onset of focal neurological deficit. The deficit may remain fixed, or it may improve or progressively worsen, leading usually to irreversible neuronal damage at the core of the ischemic focus, whereas neuronal dysfunction in the penumbra may be treatable and/or reversible. Prolonged periods of ischemia result in frank tissue necrosis. Cerebral edema follows and progresses over the subsequent 2 to 4 days. If the region of the infarction is large, the edema may produce considerable mass effect with all of its attendant consequences.

Damage to neuronal tissue can lead to severe disability and death. The extent of the damage is primarily affected by the location and extent of the injured tissue. Endogenous cascades activated in response to the acute insult play a role in the functional outcome. Efforts to minimize, limit and/or reverse the damage have the great potential of alleviating the clinical consequences.

Thus the present invention further provides a method of treating cerebrovascular condition in a subject in need of treatment that comprises administering to the subject a pharmaceutical composition which comprises a therapeutically effective amount of at least one oligonucleotide compound, which down-regulates RhoA expression in the CNS of the subject in an amount effective to treat cerebrovascular condition.

Parkinsonism

In one embodiment the neurological disorder is Parkinsonism—a group of disorders which feature impaired motor control characterized by bradykinesia, muscle rigidity; tremor; and postural instability. Parkinsonian diseases are generally divided into primary parkinsonism, secondary parkinsonism and inherited forms. These conditions are associated with dysfunction of dopaminergic or closely related motor integration neuronal pathways in the basal ganglia.

Thus the present invention further provides a method of treating parkinsonism in a subject in need of treatment that comprises administering to the subject a pharmaceutical composition which comprises a therapeutically effective amount of at least one oligonucleotide compound, which down-regulates RhoA expression in the CNS of the subject in an amount effective to treat parkinsonism.

Neurodegenerative Disease

Neurodegenerative diseases are conditions in which cells of the CNS (the brain and/or the spinal cord and/or the eye) are lost. The CNS cells are not readily regenerated en masse, so excessive damage can be devastating. Neurodegenerative diseases result from deterioration of neurons or their myelin sheath, which over time leads to dysfunction and disabilities. They are crudely divided into two groups according to phenotypic effects, although these are not mutually exclusive: conditions affecting movement, such as ataxia; and conditions affecting memory and related to dementia. Dementia is marked by loss of intellectual functions such as memory, learning, reasoning, problem solving, and abstract thinking while vegetative functions remain intact. Non-limiting examples of neurodegenerative disease are Alzheimer's disease, Amyotrophic lateral sclerosis (ALS, also known as Lou Gehrig's Disease), Huntington's disease, Lewy body dementia and Parkinson's disease.

Another type of neurodegenerative diseases includes diseases caused by misfolded proteins, or prions. Non-limiting examples of prion diseases in humans are Creutzfeldt-Jakob disease (CJD) and variant CJD (Mad Cow Disease).

Non-limiting examples of ocular neurodegenerative disease include photoreceptor loss in the retina in subjects afflicted with macular degeneration, diabetic retinopathy, retinitis pigmentosa, glaucoma, and similar diseases.

In various embodiments the nucleic acid compounds and pharmaceutical compositions disclosed herein are useful for treating neurodegenerative diseases and conditions.

The pharmaceutical compositions of the present invention are particularly useful in treating a subject suffering from or affected by or susceptible to neurodegenerative disorders, including, without being limited to, Parkinson's disease, Amyotrophic Lateral Sclerosis (ALS), Prion disease dementia, Alzheimer's disease, Lewy body dementia, Pick's disease, Ataxia-telangiectasia (AT), Frontotemporal dementia (FTD), Frontotemporal lobar degeneration (FTLD), Huntington's disease, HIV-associated dementia, post-stroke dementia or any other disease-induced dementia; and ocular neurodegenerative diseases.

Alzheimer's Disease (AD)

In one embodiment the neurodegenerative disorder is Alzheimer's disease (AD). AD is progressive, neurodegenerative disease characterized by loss of function and death of nerve cells in several areas of the brain leading to loss of cognitive function such as memory and language.

Thus the present invention further provides a method of treating AD in a subject in need of treatment that comprises administering to the subject an pharmaceutical composition which comprises a therapeutically effective amount of at least one oligonucleotide compound, which i down-regulates expression of RhoA in the CNS of the subject in an amount effective to treat AD.

Amyotrophic Lateral Sclerosis (ALS)

In one embodiment the neurodegenerative disorder is Amyotrophic Lateral Sclerosis (ALS). ALS a progressive, usually fatal, neurodegenerative disease caused by the degeneration of motor neurons, the nerve cells in the central nervous system that control voluntary muscle movement. The disorder causes muscle weakness and atrophy throughout the body as both the upper and lower motor neurons degenerate, ceasing to send messages to muscles. Unable to function, the muscles gradually weaken, develop fasciculations (twitches) because of denervation, and eventually atrophy because of that denervation. Subject suffering from ALS may ultimately lose the ability to initiate and control all voluntary movement; bladder and bowel sphincters and the muscles responsible for eye movement are usually (but not always) spared.

Thus the present invention further provides a method of treating ALS in a subject in need of treatment that comprises administering to the subject a pharmaceutical composition which comprises a therapeutically effective amount of at least one oligonucleotide compound, which down-regulates expression of RhoA in the CNS of the subject in an amount effective to treat ALS. In certain embodiments down-regulation of RhoA confers upon the CNS neuroprotective properties.

Parkinson's Disease (PD)

In one embodiment the neurodegenerative disorder is Parkinson's Disease (PD). Parkinson's disease is a progressive disorder of the nervous system marked by muscle tremors, muscle rigidity, decreased mobility, stooped posture, slow voluntary movements, and a mask-like facial expression.

Thus the present invention further provides a method of treating PD in a subject in need of treatment that comprises administering to the subject a pharmaceutical composition which comprises a therapeutically effective amount of at least one oligonucleotide compound, which down-regulates expression of RhoA in the CNS of the subject in an amount effective to treat PD.

Ataxia-Telangiectasia (AT)

In one embodiment the neurodegenerative disorder is Ataxia-telangiectasia (AT). AT is a rare, neurodegenerative, inherited disease, which affects many parts of the body and causes severe disability. Ataxia refers to poor coordination and telangiectasia to small, dilated blood vessels, both of which are hallmarks of the disease. AT affects the cerebellum (the body's motor coordination control center) and also weakens the immune system in about 70% of the cases, leading to respiratory disorders and increased risk of cancer.

Thus the present invention further provides a method of treating AT in a subject in need of treatment that comprises administering to the subject a pharmaceutical composition which comprises a therapeutically effective amount of at least one oligonucleotide compound, which down-regulates expression of RhoA in the CNS of the subject in an amount effective to treat AT.

Post Stroke Dementia (PSD)

In one embodiment the disorder is Post Stroke Dementia (PSD). About 25% of people have dementia after a stroke with many others developing dementia over the following 5 to 10 years. In addition, many individuals experience more subtle impairments of their higher brain functions (such as planning skills and speed of processing information) and are at very high risk of subsequently developing dementia. Very small strokes in the deep parts of the brain in this process (called microvascular disease) seem to be essential in the process leading to an identified pattern of brain atrophy specific to post-stroke dementia.

Thus the present invention further provides a method of treating PSD in a subject in need of treatment that comprises administering to the subject a pharmaceutical composition which comprises a therapeutically effective amount of at least one oligonucleotide compound, which down-regulates expression of RhoA in the CNS of the subject in an amount effective to treat PSD.

Ocular Neurodegenerative Diseases

In one embodiment the neurodegenerative disease is a neurodegenerative disease of the eye, including, without being limited to, Retinal Ganglion Cell (RGC) and/or photoreceptor cell loss in the retina in subjects afflicted with macular degeneration, diabetic retinopathy, retinitis pigmentosa, glaucoma, and other ocular diseases.

Thus the present invention further provides a method of treating an ocular neurodegenerative disease in a subject in need of treatment that comprises administering to the subject a pharmaceutical composition which comprises a therapeutically effective amount of at least one oligonucleotide compound, which down-regulates RhoA expression in the CNS of the subject in an amount effective to treat an ocular neurodegenerative disease.

Neuroprotection

In further embodiments, the nucleic acid compounds and pharmaceutical compositions disclosed herein are directed to providing neuroprotection, and/or to providing cerebroprotection, and/or to attenuating acute or chronic neuronal damage in diseases, disorders or injury of the CNS.

Cerebrovascular Disorders

In one embodiment the neurological disorder is cerebrovascular disorder, Cerebrovascular accident is a sudden, nonconvulsive loss of neurological function due to an ischemic or hemorrhagic intracranial vascular event. In general, cerebrovascular accidents are classified by anatomic location in the brain, vascular distribution, etiology, age of the affected individual, and hemorrhagic vs. nonhemorrhagic nature (for additional information see Adams et al., Principles of Neurology, 6th ed, pp 777-810).

Cerebrovascular diseases occur predominately in the middle and late years of life. They cause approximately 200,000 deaths in the United States each year as well as considerable neurological disability. The incidence of stroke increases with age and affects many elderly people, a rapidly growing segment of the population. These diseases cause either ischemia-infarction or intracranial hemorrhage.

Ocular Ischemic Conditions

Ischemic optic neuropathy (ION) includes a variety of disorders that produce ischemia to the optic nerve. By definition, ION is termed anterior if disc edema is present acutely, suggesting infarction of the portion of the optic nerve closest to the globe. ION also may be posterior, lying several centimeters behind the globe. Ischemic optic neuropathy usually occurs only in people older than 60 years of age. Most cases are nonarteritic and attributed to the effects of atherosclerosis, diabetes, or hypertension on optic nerve perfusion. Temporal arteritis causes about 5% of cases (arteritic ION).

Symptoms and signs are sudden, partial or complete vision loss, accompanied by swelling of the optic nerve head and often hemorrhage. Visual field defects may manifest as loss of half the visual field with a horizontal demarcation or as central or centrocecal (surrounding the natural blind spot) scotomata. Decreased vision is soon followed by pallor of the optic disk.

Anterior Ischemic Optic Neuropathy

Nonarteritic Anterior Ischemic Optic Neuropathy (NAION) is one of two main types of Anterior Ischemic Optic Neuropathy (AION), a condition in which insufficient blood supply to the optic nerve damages it, resulting in loss of vision. NAION results from a combination of certain cardiovascular risk factors in a patient with crowded optic discs. Arteritic Anterior Ischemic Optic Neuropathy (AAION), the other main type of AION on the other hand, is a less commonly occurring inflammatory condition of medium-sized blood vessels that occurs in those generally slightly older than in those who get NAION.

While the mechanism behind what causes the condition is not fully understood, neuro-ophthalmologists generally agree that the convergence of two problems is to blame. In most people, the diameter of the hole in the eye wall through which the optic nerve penetrates through is 20-30 percent larger than that of the optic nerve. The first of the two problems in those who tend to develop NAION is that they do not have this 20-30 percent margin of error. The second problem involves cardiovascular risk factors that lead to a poor blood supply, or ischemia, to the optic disk, which is in the forward portion of the optic nerve. The disc swells as a result, and since there is no room for this, the resulting compression of the optic nerve leads to more ischemia.

The most common of these cardiovascular risk factors include diabetes, hypertension and high cholesterol levels. There are genetic factors at play in the potential for developing these risk factors. There is evidence that other genetic factors may also play a role in the potential for developing NAION.

In various aspects and embodiments the nucleic acid compounds and pharmaceutical compositions disclosed herein are useful for treating NAION, alone or in combination with other therapies.

Glaucoma

Glaucoma is one of the leading causes of blindness in the world. It affects approximately 66.8 million people worldwide and at least 12,000 Americans are blinded by this disease each year (Kahn and Milton, Am J. Epidemiol. 1980, 111(6):769-76). Glaucoma is the second most common cause of blindness in the United States, accounting for >11% of all cases of blindness.

Glaucoma is characterized by the degeneration of axons in the optic nerve head, due to elevated intraocular pressure (IOP), interference of the immune system and lack of delivery of trophic factors. One of the most common forms of glaucoma, known as primary open-angle glaucoma (POAG), results from the increased resistance of aqueous humor outflow in the trabecular meshwork (TM), causing IOP elevation and eventual optic nerve damage.

Currently there are many drugs that target glaucoma and are administered via eye drops or ointments, however, all of them are focused on lowering of IOP alone and do not address prevention of the damage to the neural retina. Some of the available drugs have rather severe side effects such as increased heart rate, elevated blood pressure, headaches, blurry vision, fatigue, dry mouth, and redness in or around the eye, as in the case of alpha-2-adrenergic receptor agonists. Many of these side effects stem not only from systemic exposure to the drugs but also due to low specificity of alpha-adrenergic receptor small molecule agonists. The assignee of the instant application proposes inhibiting human RhoA mRNA and protein as a novel multifaceted treatment for glaucoma.

In primary, open angle glaucoma, raised intraocular pressure (IOP) develops as a result of compromised aqueous humour drainage, and this is associated with optic neuropathy, subsequent progressive retinal ganglion cell (RGC) axon degeneration, and RGC apoptosis. The current treatments for glaucoma focus on lowering IOP. However, there are types of glaucoma that are not accompanied with increased IOP; and vision loss is actually caused by the damage to the optic nerve and RGC. Currently there are very few drugs in clinical trials that address neuroprotection and/or neuroregeneration in glaucoma patients. The FDA-approved neuroprotective drug for Alzheimer's disease, Namenda (memantine), has recently completed Phase III clinical trials for glaucoma with disappointing results, as it appeared to have no benefit in glaucoma patients when compared to a placebo. RhoA is a small GTPase protein that controls cellular functions such as motility, growth, differentiation, and apoptosis in CNS neurons, including RGC. RhoA is also involved in the secondary inflammatory and scarring CNS injury responses by signalling in neural immune cells (microglia and macrophages) and astrocytes. Optic nerve crush (ONC) injury activates RhoA in axotomised RGC and this signals apoptosis and inhibition of axon regeneration. By contrast, treatment of injured RGC with RhoA antagonists, including siRhoA and C3 transferase exoenzyme, significantly enhances RGC survival and neurotrophin-driven axon regeneration. It was shown that RhoA activation is also involved in regulating the resistance of the trabecular meshwork of the eye to aqueous humor outflow by modulating cell contraction and extracellular matrix production, leading to increased IOP (Zhang et al., Am J Physiol Cell Physiol, 259:1057. 2008). Without being bound to theory, blockade of RhoA signaling in the glaucomatous eye can be of therapeutic benefit by multiple effects: (A) correcting homeostasis of aqueous humour drainage; (B) blocking RGC apoptotic signaling; and (C) enhancing RGC axon regeneration.

In some embodiments, the dsRNA molecules, compositions, methods and kits provided herein are useful in treating subjects at risk of or suffering from glaucoma. Without being bound by theory, it is believed that the therapeutic dsRhoA molecules provided herein, treat glaucoma by multiple mechanisms, leading to retinal ganglion cells (RGCs) neuroprotection, enhanced RGC axon regeneration and lowered intraocular pressure (IOP).

Neuropathy

Autonomic Neuropathy

Autonomic neuropathy is a group of symptoms that occur when there is damage to the nerves that manage every day body functions such as blood pressure, heart rate, bowel and bladder emptying, and digestion.

The autonomic nervous system is composed of nerves serving the heart, GI tract and urinary system. Autonomic neuropathy can affect any of these organ systems. The most commonly recognized autonomic dysfunction in diabetics is orthostatic hypotension, or the uncomfortable sensation of fainting when a patient stands up. In the case of diabetic autonomic neuropathy, it is due to the failure of the heart and arteries to appropriately adjust heart rate and vascular tone to keep blood continually and fully flowing to the brain. This symptom is usually accompanied by a loss of sinus respiratory variation, that is, the usual change in heart rate seen with normal breathing. When these two findings are present, cardiac autonomic neuropathy is present.

GI tract manifestations include delayed gastric emptying, gastroparesis, nausea, bloating, and diarrhea. Because many diabetics take oral medication for their diabetes, absorption of these medicines is greatly affected by the delayed gastric emptying. This can lead to hypoglycemia when an oral diabetic agent is taken before a meal and does not get absorbed until hours, or sometimes days later, when there is normal or low blood sugar already. Sluggish movement of the small intestine can cause bacterial overgrowth, made worse by the presence of hyperglycemia. This leads to bloating, gas and diarrhea.

Urinary symptoms include urinary frequency, urgency, incontinence and retention. Again, because of the retention of sweet urine, urinary tract infections are frequent. Urinary retention can lead to bladder diverticula, stones, reflux nephropathy.

In some embodiments, the nucleic acids, compositions, methods and kits provided herein are useful in treating subjects at risk of or suffering from autonomic neuropathy.

Cranial Neuropathy

When cranial nerves are affected, oculomotor (3rd) neuropathies are most common. The oculomotor nerve controls all of the muscles that move the eye with the exception of the lateral rectus and superior oblique muscles. It also serves to constrict the pupil and open the eyelid. The onset of a diabetic third nerve palsy is usually abrupt, beginning with frontal or periorbital pain and then diplopia. All of the oculomotor muscles innervated by the third nerve may be affected, except for those that control pupil size. The sixth nerve, the abducens nerve, which innervates the lateral rectus muscle of the eye (moves the eye laterally), is also commonly affected but fourth nerve, the trochlear nerve, (innervates the superior oblique muscle, which moves the eye downward) involvement is unusual. Mononeuropathies of the thoracic or lumbar spinal nerves can occur and lead to painful syndromes that mimic myocardial infarction, cholecystitis or appendicitis. Diabetics have a higher incidence of entrapment neuropathies, such as carpal tunnel syndrome.

In some embodiments, the nucleic acids, compositions, methods and kits provided herein are useful in treating subjects at risk of or suffering from cranial neuropathy.

Cancer-Related Neuropathies

Peripheral neuropathies are among the most common neurologic complications of cancer. The differential diagnosis of peripheral nervous system dysfunction in cancer patients is broad and includes: direct nerve compression or infiltration by tumor; neurotoxicity of cancer treatment; nutritional deficiencies; metabolic derangements; and paraneoplastic disorders. In patients presenting with a peripheral neuropathy but no known cancer diagnosis, it is important to consider the possibility that the neuropathy is a remote effect of a previously undiagnosed neoplasm.

In some embodiments, the dsRNA molecules, compositions, methods and kits provided herein are useful in treating subjects at risk of or suffering from cancer-related neuropathy.

Compressive Neuropathy

Entrapment Neuropathies: The term entrapment neuropathies refers to isolated peripheral nerve injuries occurring at specific locations where a nerve is mechanically constricted in a fibrous or fibro-osseous tunnel or deformed by a fibrous band. In some instances the nerve is injured by chronic direct compression, and in other instances angulation or stretching forces cause mechanical damage to the nerve. Common examples of nerve compression in a fibro-osseous tunnel are the carpal tunnel syndrome and ulnar neuropathy at the cubital tunnel. Angulation and stretch injury are important mechanisms of nerve injury for ulnar neuropathies associated with gross deformity of the elbow joint ("tardy ulnar palsy") and neurogenic thoracic outlet syndrome. Recurrent compression of nerves by external forces may also cause focal nerve injuries such as ulnar neuropathy at the elbow and deep branch lesions of the ulnar nerve in the hand. Although these latter neuropathies do not satisfy the strict definition of "entrapment neuropathies", they are often considered in a discussion of the topic. The pathological features of all of these isolated neuropathies include a varying combination of focal demyelination and wallerian axonal degeneration.

In various aspects and embodiments the nucleic acid compounds and pharmaceutical compositions disclosed herein are useful for treating compressive neuropathy and/or entrapment neuropathy, alone or in combination with other therapies.

Diabetic Neuropathy

Diabetic neuropathy is a common complication of diabetes, in which nerves are damaged as a result of high blood sugar levels (hyperglycemia). Diabetic neuropathy may occur in both type I and type II diabetes.

People with diabetes commonly develop temporary or permanent damage to nerve tissue. Nerve injuries are caused by decreased blood flow and high blood sugar levels, and are more likely to develop if blood sugar levels are not well controlled. On average, symptoms begin 10 to 20 years after the diabetes diagnosis. Approximately 50% of people with diabetes will eventually develop nerve damage. Peripheral nerve injuries may affect nerves in the skull (cranial nerves) or nerves from the spinal column and their branches. This type of nerve injury (neuropathy) tends to develop in stages. Autonomic neuropathies affect the nerves that regulate vital functions, including the heart muscle and smooth muscles.

Microvascular Disease in Diabetic Neuropathy

Vascular and neural diseases are closely related and intertwined. Blood vessels depend on normal nerve function, and nerves depends on adequate blood flow. The first pathological change in the microvasculature is vasoconstriction. As the disease progresses, neuronal dysfunction correlates closely with the development of vascular abnormalities, such as capillary basement membrane thickening and endothelial hyperplasia, which contribute to diminished oxygen tension and hypoxia. Neuronal ischemia is a well-established characteristic of diabetic neuropathy. Vasodilator agents (e.g., angiotensin-converting-enzyme inhibitors, alpha1-antagonists) can lead to substantial improvements in neuronal blood flow, with corresponding improvements in nerve conduction velocities. Thus, microvascular dysfunction occurs early in diabetes, parallels the progression of neural dysfunction, and may be sufficient to support the severity of structural, functional, and clinical changes observed in diabetic neuropathy. Peripheral neuropathy (legs), sensorimotor neuropathy is a significant component in the pathogenesis of leg ulcers in diabetes.

Nerve conduction studies demonstrate that neuropathy is already present in 10-18% of patients at the time of diabetes diagnosis, suggesting that peripheral nerve injury occurs at early stages of disease and with milder glycemic dysregulation. The concept that neuropathy is an early clinical sign of diabetes was proposed >40 years ago, and most studies report an association between IGT and neuropathy. Most patients with IGT and associated neuropathy have a symmetric, distal sensory polyneuropathy with prominent neuropathic pain. IGT neuropathy (Microvascular complications of impaired glucose tolerance—Perspectives in Diabetes, J. Robinson Singleton, in Diabetes Dec. 1, 2003) is phenotypically similar to early diabetic neuropathy, which also causes sensory symptoms, including pain, and autonomic dysfunction. In a survey of 669 patients with early diabetic neuropathy, sensory symptoms were present in >60%, impotence in nearly 40%, and other autonomic involvement in 33%, but evidence of motor involvement in only 12%. These clinical findings suggest prominent early involvement of the small unmyelinated nerve fibers that carry pain, temperature, and autonomic signals. Direct quantitation of unmyelinated intraepidermal nerve fibers from skin biopsies shows similar fiber loss and altered morphology in patients with neuropathy associated with IGT and early diabetes.

Autonomic dysfunction, particularly erectile dysfunction and altered cardiac vagal response, are common early features of neuropathic injury in diabetes. Work with IGT patients also suggests prevalent vagal dysautonoinia: separate studies have found abnormal heart rate recovery following exercise, blunted R—R interval variability to deep breathing, and reduced expiration to inspiration ratio (all measures of vagal dysautonomia) in a greater fraction of IGT patients than age-matched normoglycemic control subjects.

Nerve damage in diabetes affects the motor, sensory, and autonomic fibers. Motor neuropathy causes muscle weakness, atrophy, and paresis. Sensory neuropathy leads to loss of the protective sensations of pain, pressure, and heat. The absence of pain leads to many problems in the insensate foot, including ulceration, unperceived trauma, and Charcot neuroarthropathy. The patient may not seek treatment until after the wound has advanced. A combination of sensory and motor dysfunction can cause the patient to place abnormal stresses on the foot, resulting in trauma, which may lead to infection. Autonomic sympathetic neuropathy causes vasodilation and decreased sweating, which results in warm, overly dry feet that are particularly prone to skin breakdown, as well as functional alterations in microvascular flow. Autonomic dysfunction (and denervation of dermal structures) also results in loss of skin integrity, which provides an ideal site for microbial invasion. The neuropathic foot does not ulcerate spontaneously; rather, it is the combination of some form of trauma accompanied by neuropathy.

Microvascular dysfunction occurs early in diabetes, parallels the progression of neural dysfunction, and may be sufficient to support the severity of structural, functional, and clinical changes observed in diabetic neuropathy.

In various aspects and embodiments the nucleic acid compounds and pharmaceutical compositions disclosed herein are useful for treating diabetic neuropathy, alone or in combination with other therapies.

Drug-Induced and Toxic Neuropathies

Most toxic neuropathies encountered in routine clinical practice are due to iatrogenic pharmaceutical intoxications; epidemic occupational exposure, as with large pharmaceutical companies, is unusual. The majority, and unfortunately the most difficult, cases of toxic neuropathies are individual intoxications due to small scale, often chance, occupational exposures, or intentional and homicidal ingestion.

Idiopathic polyneuropathy constitutes a significant proportion of peripheral neuropathy cases. In addition, a number of identifiable causes of neuropathy have no preventative or curative interventions available, only symptomatic treatment. Thus, detection of toxic or medication induced neuropathy can be an important diagnosis that impacts quality of life. Medication-induced neuropathies are uncommon (2-4% of cases in one outpatient neurology setting)1, but crucial to recognize because intervention can lead to significant improvement or symptom resolution.

In some embodiments, the dsRNA molecules, compositions, methods and kits provided herein are useful in treating subjects at risk of or suffering from toxic neuropathy. In some embodiments, the dsRNA molecules, compositions, methods and kits provided herein are useful in treating subjects at risk of or suffering from drug-induced neuropathy.

Chemotherapy-Induced Neuropathy

Chemotherapy-induced neuropathy, which can also be considered a drug-induced or toxic neuropathy as well as a cancer-related neuropathy, occurs when the chemicals used in chemotherapy for certain cancer treatments damage or destroy the peripheral nerves.

In some embodiments, the dsRNA molecules, compositions, methods and kits provided herein are useful in treating subjects at risk of or suffering from Chemotherapy-induced neuropathy.

Gastrointestinal and Nutrition-Related Neuropathies

Neuropathy related to the gastrointestinal system has most commonly been recognized to result from nutritional deficiencies. These deficiencies could be due to malnutrition (e.g. alcoholism) or a reduced absorptive surface as a result of physical alteration (e.g. surgical resection/bypass) or intestinal wall infiltration (e.g. Crohn's disease). Immune-mediated mechanisms are suspected to play a role in the development of neuropathy in some gastrointestinal conditions now recognized to have multisystemic manifestations (e.g. celiac disease, inflammatory bowel disease).

In some embodiments, the dsRNA molecules, compositions, methods and kits provided herein are useful in treating subjects at risk of or suffering from gastrointestinal neuropathy. In some embodiments, the dsRNA molecules, compositions, methods and kits provided herein are useful in treating subjects at risk of or suffering from nutrition-related neuropathy.

Hereditary Neuropathies
Charcot-Marie-Tooth Disease

Charcot-Marie-Tooth disease (CMT) refers to the inherited peripheral neuropathies named for the three investigators who described them in the late 1800s. As CMT diseases affect approximately one in 2500 people, they are among the most common inherited neurological disorders. The majority of CMT patients have autosomal dominant inheritance, although X-linked dominant, and autosomal recessive forms also exist. What appear to be sporadic cases also occur, since even dominantly inherited disorders may begin as a new mutation in a given patient. The majority of cases are demyelinating although up to one third appear to be primary axonal or neuronal disorders. Most patients have a "typical" CMT phenotype characterized by distal weakness, sensory loss, foot deformities (pes caus and hammer toes), and absent reflexes. However, some patients develop severe disability in infancy (Dejerine Sottas Disease or congenital hypomyelination), while others develop few if any symptoms of disease.

In various aspects and embodiments the nucleic acid compounds and pharmaceutical compositions disclosed herein are useful for treating hereditary neuropathy, alone or in combination with other therapies. In various aspects and embodiments the nucleic acid compounds and pharmaceutical compositions disclosed herein are useful for treating Charcot-Marie-Tooth disease, alone or in combination with other therapies.

Immune-Mediated Neuropathies and Chronic Immune-Mediated Polyneuropathies

Autoimmune mechanisms are implicated in several chronic neuropathic syndromes that are amenable to immune therapy. Collectively, these neuropathies are relatively common; Barohn et al (1998) and Verghese et al (2001). In practice, however, many of the autoimmune neuropathies are difficult to diagnose, due to a lack of generally accepted clinical diagnostic criteria, or availability of reliable serological tests. Consequently, many patients with autoimmune neuropathies are diagnosed as having "idiopathic neuropathy" instead, and left untreated despite progression of their disease.

The chronic autoimmune neuropathies are a diverse group of syndromes that result from immune-mediated damage to the peripheral nerves. For many of these disorders, there are no definitive diagnostic tests, and only a few or no controlled therapeutic trials. Consequently, the diagnoses may be missed and the patients remain untreated.

In various embodiments the nucleic acid compounds and pharmaceutical compositions disclosed herein are useful for treating immune-mediated neuropathy, alone or in combination with other therapies. In various aspects and embodiments the nucleic acid compounds and pharmaceutical compositions disclosed herein are useful for treating Chronic Immune-Mediated Polyneuropathy, alone or in combination with other therapies.

Infectious Neuropathies

Non-limiting examples of infectious neuropathies include: Neuropathy associated with Human Immunodeficiency Virus (HIV) infection; Lyme neuropathy; Neuropathy associated with leprosy; Herpes zoster neuropathy (shingles and postherpetic neuralgia); Hepatitis C neuropathy; Herpes simplex neuritis; Diphtheric neuritis; and Chagas' disease. In various embodiments the nucleic acid compounds and pharmaceutical compositions disclosed herein are useful for treating infectious neuropathy, alone or in combination with other therapies. In one embodiment the nucleic acid compounds and pharmaceutical compositions disclosed herein are useful for treating Neuropathy associated with Human Immunodeficiency Virus (HIV) infection, alone or in combination with other therapies. In one embodiment the nucleic acid compounds and pharmaceutical compositions disclosed herein are useful for treating Lyme neuropathy, alone or in combination with other therapies. In one embodiment the nucleic acid compounds and pharmaceutical compositions disclosed herein are useful for treating Neuropathy associated with leprosy, alone or in combination with other therapies. In one embodiment the nucleic acid compounds and pharmaceutical compositions disclosed herein are useful for treating Herpes zoster neuropathy, alone or in combination with other therapies. In one embodiment the nucleic acid compounds and pharmaceutical compositions disclosed herein are useful for treating Hepatitis C neuropathy, alone or in combination with other therapies. In one embodiment the nucleic acid compounds and pharmaceutical compositions disclosed herein are useful for treating Herpes simplex neuritis, alone or in combination with other therapies. In one embodiment the nucleic acid compounds and pharmaceutical compositions disclosed herein are useful for treating Diphtheric neuritis, alone or in combination with other therapies. In one embodiment the nucleic acid compounds and pharmaceutical compositions disclosed herein are useful for treating Chagas' disease, alone or in combination with other therapies.

Neuropatic Pain (NP)

The International Association for the Study of Pain (IASP) defines NP as "pains resulting from disease or damage of the peripheral or central nervous systems, and from dysfunction of the nervous system".

Pain is often of mixed nociceptive and neuropathic types, for example, mechanical spinal pain with radiculopathy or myelopathy. It is not generally recognised that nociceptive spinal pain can radiate widely, mimicking a root distribution. It can be difficult to identify the dominant pain type and treat appropriately. Such patients require careful examination, imaging and neurophysiological investigation.

The pathophysiological properties that are responsible for NP can be broadly categorized into five groups: ectopic impulse generation in damaged primary afferent fibers, fiber interactions, central sensitisation, disinhibition (failure or reduction of normal inhibitory mechanisms), and plasticity (degenerative and regenerative changes associated with altered connectivity).

Pain is a frequent symptom of neurological disease and although there have been some advancements in treatment, pain often remains unresponsive to all treatment modalities. For a review on Neuropathic Pain see for example Scadding J. ACNR, v.3 n. 2 MAY/JUNE 2003, pages 8-14. Neuropathic pain is common in cancer as a direct result of the cancer on peripheral nerves (e.g., compression by a tumor) and as a side effect of many chemotherapy drugs.

Allodynia

Allodynia, literally meaning "other power", is a pain due to a stimulus which does not normally provoke pain and can be either thermal or mechanical. Allodynia is a clinical feature of many painful conditions, such as neuropathies, complex regional pain syndrome, postherpetic neuralgia, fibromyalgia, and migraine. Allodynia may also be caused by some populations of stem cells used to treat nerve damage including spinal cord injury.

There are different kinds or types of allodynia, including: Mechanical allodynia (also known as tactile allodynia); Static mechanical allodynia—pain in response to light touch/pressure; Dynamic mechanical allodynia—pain in response to brushing; Thermal (hot or cold) allodynia—pain from normally mild skin temperatures in the affected area.

In various embodiments the nucleic acid compounds and pharmaceutical compositions disclosed herein are useful for treating Neuropatic Pain, alone or in combination with other therapies. In some embodiments the nucleic acid compounds and pharmaceutical compositions disclosed herein are useful for treating allodynia, alone or in combination with other therapies.

Sensorimotor Polyneuropathy

Longer nerve fibers are affected to a greater degree than shorter ones, because nerve conduction velocity is slowed in proportion to a nerve's length. In this syndrome, decreased sensation and loss of reflexes occurs first in the toes bilaterally, then extends upward. It is usually described as glove-stocking distribution of numbness, sensory loss, dysesthesia and nighttime pain. The pain can feel like burning, pricking sensation, achy or dull. Pins and needles sensation is common. Loss of proprioception, that is, the sense of where a limb is in space, is affected early. These patients cannot feel when they are stepping on a foreign body, like a splinter, or when they are developing a callous from an ill-fitting shoe. Consequently, they are at risk for developing ulcers and infections on the feet and legs, which can lead to amputation. Similarly, these patients can get multiple fractures of the knee, ankle or foot, and develop a Charcot joint. Loss of motor function results on dorsiflexion contractures of the toes, so called hammertoes. These contractures occur not only in the foot but also in the hand.

In some embodiments the nucleic acid compounds and pharmaceutical compositions disclosed herein are useful for treating sensorimotor polyneuropathy, alone or in combination with other therapies.

Cytoskeleton Regulation

Cell Motility, Cytoskeleton Regulation, Microtubule Organization

The Rho family GTPases are regulatory molecules that link surface receptors to organisation of the actin cytoskeleton and play major roles in fundamental cellular processes. RhoA has scaffolding properties that function to polymerize actin and affect the formation of microtubules. Actin is regulated by small GTPases of the Rho family. Migrating cells display a characteristic polarization of the actin cytoskeleton. Actin filaments polymerise in the protruding front of the cell whereas actin filament bundles contract in the cell body, which results in retraction of the cell's rear. The actin cytoskeleton provides the driving force for cell migration. Recent studies suggest that, in addition to organizing the actin cytoskeleton, Rho GTPases might also influence the organization and dynamics of microtubules.

In various embodiments the nucleic acid compounds and pharmaceutical compositions disclosed herein are useful for prevention or treatment of disorders or diseases associated with cell motility, cytoskeleton regulation, microtubule organization, alone or in combination with other therapies.

Angiogenesis, Vascular Diseases, Arterial Diseases

Angiogenesis, the formation of new vessels from pre-existing ones, is a complex multistep process. It involves the stimulation of angiogenic growth factor receptors on vascular endothelial cells, proteolytic breakdown of the endothelial cell basal membrane, endothelial cell proliferation and migration, degradation of the surrounding extracellular matrix, vessel maturation, recruitment of supporting cells (e.g. pericytes) and finally closure of the newly formed arteriovenous loops (Folkman J. 1971. Tumour angiogenesis: therapeutic implications. NEJM 285: 1182-1185; Yancopoulos G D et al. 2000. Vascular-specific growth factors and blood vessel formation. Nature 407: 242-248; Carmeliet P. 2003. Angiogenesis in health and disease. Nat Med 9: 653-660). Each of these steps is tightly regulated by the action of both stimulatory (angiogenic factors) and inhibitory (angiogenic inhibitors) molecules (Carmeliet P & Jain J K. 2000. Angiogenesis in cancer and other diseases. Nature 407: 249-257). In the normal state the vessels are quiescent as the action of the angiogenic inhibitors dominates. Under certain conditions, such as hypoxia or inflammation, that activate angiogenic factors, the balance may shift in favour of angiogenesis, an event termed the 'angiogenic switch'.

Suppression of angiogenesis is desirable as a treatment for various pathologies, such as of example, for preventing the blindness associated with proliferative retinopathies and for restricting tumor growth. Studies identify a critical and selective role for Rho activity in regulating endothelial cell assembly into new blood vessels, and identify suppression of Rho activity, as strategy for suppressing the organizational stages of neovascularization.

In the vasculature Rho signalling pathways are intimately involved in the regulation of endothelial barrier function, inflammation and transendothelial leukocyte migration, platelet activation, thrombosis and oxidative stress, as well as smooth muscle contraction, migration, proliferation and differentiation, and are thus implicated in many of the changes associated with atherogenesis. Indeed, it is believed that many of the beneficial, non-lipid lowering effects of statins occur as a result of their ability to inhibit Rho protein activation ((see for example Hoang M V et al. Rho activity critically and selectively regulates endothelial cell organization during angiogenesis. PNAS USA. 2004 Feb. 17; 101(7): 1874-1879; Rolfe B E et al. Rho and Vascular disease. Atherosclerosis. 2005 2005 November; 183(1):1-16.)

In various embodiments the nucleic acid compounds and pharmaceutical compositions disclosed herein are useful for suppression of angiogenesis, alone or in combination with other therapies. In various embodiments the nucleic acid compounds and pharmaceutical compositions disclosed herein are useful for treating vascular diseases, alone or in combination with other therapies.

In various embodiments the nucleic acid compounds and pharmaceutical compositions disclosed herein are useful for treating arterial diseases, alone or in combination with other therapies.

Ocular Angiogenesis—Corneal, Retinal, Choroidal

Ocular angiogenesis, the formation of new vessels from the existing vascular tree, is a major cause of severe vision loss. It can affect different structures in the eye, including the retina, choroid and cornea.

Retinal angiogenesis, typically seen in proliferative diabetic retinopathy, retinal vein occlusion or retinopathy of prematurity, is the consequence of an abnormal vascular response to retinal ischemia or hypoxia. During retinal angiogenesis retinal vascular endothelial cells start to proliferate through the internal limiting membrane into the vitreous, where they may cause vitreous haemorrhage or tractional retinal detachment.

Choroidal (subretinal) angiogenesis. In the neovascular form of age-related macular degeneration (AMD) choroidal vessels grow through the degenerated Bruch's membrane into the subretinal space, causing subretinal exudation and haemorrhage (Ambati J et al. 2003. Age-related macular degeneration: aetiology, pathogenesis and therapeutic strategies. Surv Ophthalmol 48: 257-293). The initial stimulus for this choroidal angiogenic response is still under debate. A model where local inflammation triggers the vascular ingrowth is currently the most favoured (Tezel T H et al. 2004. Pathogenesis of age-related macular degeneration. Trends Mol Med 10: 417-420).

Corneal angiogenesis. Neovascularization of the cornea compromises its transparency and leads to severe visual impairment (Chang J H et al. 2001. Corneal neovascularization. Curr Opin Ophthalmol 12: 242-249). It is a common clinical problem seen in response to chronic hypoxia or various inflammatory stimuli, such as infectious keratitis, alkali burns and graft rejections. Corneal angiogenesis emerges from the limbal vessels and therefore ocular surface disorders predispose to superficial neovascularization, while stromal keratitis causes deep infiltration of vessels.

In various embodiments the nucleic acid compounds and pharmaceutical compositions disclosed herein are useful for prevention or treatment of disease, disorder or injury associated with retinal angiogenesis, alone or in combination with other therapies.

In various embodiments the nucleic acid compounds and pharmaceutical compositions disclosed herein are useful for prevention or treatment of disease, disorder or injury associated with choroidal (subretinal) angiogenesis, alone or in combination with other therapies.

In various embodiments the nucleic acid compounds and pharmaceutical compositions disclosed herein are useful for prevention or treatment of disease, disorder or injury associated with corneal angiogenesis, alone or in combination with other therapies.

Macular Degeneration

The most common cause of decreased best-corrected vision in individuals over 65 years of age in the US is the retinal disorder known as age-related macular degeneration (AMD). As AMD progresses, the disease is characterized by loss of sharp, central vision. The area of the eye affected by AMD is the Macula—a small area in the center of the retina, composed primarily of photoreceptor cells. So-called "dry" AMD, accounting for about 85%-90% of AMD patients, involves alterations in eye pigment distribution, loss of photoreceptors and diminished retinal function due to overall atrophy of cells. So-called "wet" AMD involves proliferation of abnormal choroidal vessels leading to clots or scars in the sub-retinal space. Thus, the onset of wet AMD occurs because of the formation of an abnormal choroidal neovascular network (choroidal neovascularization, CNV) beneath the neural retina. The newly formed blood vessels are excessively leaky. This leads to accumulation of subretinal fluid and blood leading to loss of visual acuity. Eventually, there is total loss of functional retina in the involved region, as a large disciform scar involving choroids and retina forms. While dry AMD patients may retain vision of decreased quality, wet AMD often results in blindness. (Hamdi & Kenney, Age-related Macular degeneration—a new viewpoint, Frontiers in Bioscience, e305-314, May 2003). CNV occurs not only in wet AMD but also in other ocular pathologies such as ocular histoplasmosis syndrome, angiod streaks, ruptures in Bruch's membrane, myopic degeneration, ocular tumors and some retinal degenerative diseases.

In various embodiments the nucleic acid compounds and pharmaceutical compositions disclosed herein are useful for treating retinal degenerative disease, alone or in combination with other therapies. In various embodiments the nucleic acid compounds and pharmaceutical compositions disclosed herein are useful for treating age-related macular degeneration (AMD), alone or in combination with other therapies. In some embodiments the nucleic acid compounds and pharmaceutical compositions disclosed herein are useful for treating wet age-related macular degeneration (AMD), alone or in combination with other therapies. In some embodiments the nucleic acid compounds and pharmaceutical compositions disclosed herein are useful for treating dry age-related macular degeneration (AMD), alone or in combination with other therapies. In some embodiments the nucleic acid compounds and pharmaceutical compositions disclosed herein are useful for treating ocular histoplasmosis syndrome, alone or in combination with other therapies. In some embodiments the nucleic acid compounds and pharmaceutical compositions disclosed herein are useful for treating angiod streaks, alone or in combination with other therapies. In some embodiments the nucleic acid compounds and pharmaceutical compositions disclosed herein are useful for treating ruptures in Bruch's membrane, alone or in combination with other therapies. In some embodiments the nucleic acid compounds and pharmaceutical compositions disclosed herein are useful for treating myopic degeneration, alone or in combination with other therapies. In some embodiments the nucleic acid compounds and pharmaceutical compositions disclosed herein are useful for treating, ocular tumors, alone or in combination with other therapies.

Microvascular Disorders

Microvascular disorders are composed of a broad group of conditions that primarily affect the microscopic capillaries and lymphatics and are therefore outside the scope of direct surgical intervention. Microvascular disease can be broadly grouped into the vasospastic, the vasculitis and lymphatic occlusive. Additionally, many of the known vascular conditions have a microvascular element to them.

Vasospastic Disease

Vasospastic diseases are a group of relatively common conditions where, for unknown reasons, the peripheral vasoconstrictive reflexes are hypersensitive. This results in inappropriate vasoconstriction and tissue ischaemia, even to the point of tissue loss. Vasospastic symptoms are usually related to temperature or the use of vibrating machinery but may be secondary to other conditions.

Vasculitic Disease

Vasculitic diseases are those that involve a primary inflammatory process in the microcirculation. Vasculitis is usually a component of an autoimmune or connective tissue disorder and is not generally amenable to surgical treatment but requires immunosuppressive treatment if the symptoms are severe.

Lymphatic Occlusive Disease

Chronic swelling of the lower or upper limb (lymphoedema) is the result of peripheral lymphatic occlusion. This is a relatively rare condition that has a large number of causes, some inherited, some acquired. The mainstays of treatment are correctly fitted compression garments and the use of intermittent compression devices.

Microvascular Pathologies Associated with Diabetes

Diabetes is the leading cause of blindness, the number one cause of amputations and impotence, and one of the most frequently occurring chronic childhood diseases. Diabetes is also the leading cause of end-stage renal disease in the United States, with a prevalence rate of 31% compared with other renal diseases. Diabetes is also the most frequent indication for kidney transplantation, accounting for 22% of all transplantation operations.

In general, diabetic complications can be classified broadly as microvascular or macrovascular disease. Microvascular complications include neuropathy (nerve damage), nephropathy (kidney disease) and vision disorders (eg retinopathy, glaucoma, cataract and corneal disease). In the retina, glomerulus, and vasa nervorum, similar pathophysiologic features characterize diabetes-specific microvascular disease. Microvascular pathologies associated with diabetes are defined as a disease of the smallest blood vessels (capillaries) that may occur e.g. in people who have had diabetes for a long time. The walls of the vessels become abnormally thick but weak. They, therefore, bleed, leak protein and slow the flow of blood through the body.

Clinical and animal model data indicate that chronic hyperglycemia is the central initiating factor for all types of diabetic microvascular disease. Duration and magnitude of hyperglycemia are both strongly correlated with the extent and rate of progression of diabetic microvascular disease. Although all diabetic cells are exposed to elevated levels of plasma glucose, hyperglycemic damage is limited to those cell types (e.g., endothelial cells) that develop intracellular hyperglycemia. Endothelial cells develop intracellular hyperglycemia because, unlike many other cells, they cannot down-regulate glucose transport when exposed to extracellular hyperglycemia.

Abnormal Endothelial Cell Function: Early in the course of diabetes mellitus, before structural changes are evident, hyperglycemia causes abnormalities in blood flow and vascular permeability in the retina, glomerulus, and peripheral nerve vasa nervorum. The increase in blood flow and intracapillary pressure is thought to reflect hyperglycemia-induced decreased nitric oxide (NO) production on the efferent side of capillary beds, and possibly an increased sensitivity to angiotensin II. As a consequence of increased intracapillary pressure and endothelial cell dysfunction, retinal capillaries exhibit increased leakage of fluorescein and glomerular capillaries have an elevated albumin excretion rate (AER). Comparable changes occur in the vasa vasorum of peripheral nerve. Early in the course of diabetes, increased permeability is reversible; as time progresses, however, it becomes irreversible.

Increased Vessel Wall Protein Accumulation

The common pathophysiologic feature of diabetic microvascular disease is progressive narrowing and eventual occlusion of vascular lumina, which results in inadequate perfusion and function of the affected tissues. Early hyperglycemia-induced microvascular hypertension and increased vascular permeability contribute to irreversible microvessel occlusion by three processes:

The first is an abnormal leakage of periodic acid-Schiff (PAS)-positive, carbohydrate-containing plasma proteins, which are deposited in the capillary wall and which may stimulate perivascular cells such as pericytes and mesangial cells to elaborate growth factors and extracellular matrix.

The second is extravasation of growth factors, such as transforming growth factor β1 (TGF-β1), which directly stimulates overproduction of extracellular matrix components, and may induce apoptosis in certain complication-relevant cell types.

The third is hypertension-induced stimulation of pathologic gene expression by endothelial cells and supporting cells, which include glut-1 glucose transporters, growth factors, growth factor receptors, extracellular matrix components, and adhesion molecules that can activate circulating leukocytes. The observation that unilateral reduction in the severity of diabetic microvascular disease occurs on the side with ophthalmic or renal artery stenosis is consistent with this concept.

Microvascular Cell Loss and Vessel Occlusion

The progressive narrowing and occlusion of diabetic microvascular lumina are also accompanied by microvascular cell loss. In the retina, diabetes mellitus induces programmed cell death of Müller cells and ganglion cells, pericytes, and endothelial cells. In the glomerulus, declining renal function is associated with widespread capillary occlusion and podocyte loss, but the mechanisms underlying glomerular cell loss are not yet known. In the vasa nervorum, endothelial cell and pericyte degeneration occur, and these microvascular changes appear to precede the development of diabetic peripheral neuropathy. The multifocal distribution of axonal degeneration in diabetes supports a causal role for microvascular occlusion, but hyperglycemia-induced decreases in neurotrophins may contribute by preventing normal axonal repair and regeneration.

Another common feature of diabetic microvascular disease has been termed hyperglycemic memory, or the persistence or progression of hyperglycemia-induced microvascular alterations during subsequent periods of normal glucose homeostasis. The most striking example of this phenomenon is the development of severe retinopathy in histologically normal eyes of diabetic dogs that occurred entirely during a 2.5-year period of normalized blood glucose that followed 2.5 years of hyperglycemia. Hyperglycemia-induced increases in selected matrix gene transcription also persist for weeks after restoration of normoglycemia in vivo, and a less pronounced, but qualitatively similar, prolongation of hyperglycemia-induced increase in selected matrix gene transcription occurs in cultured endothelial cells.

For further information, see for example "Shared pathophysiologic features of microvascular complications of diabetes" (Larsen: Williams Textbook of Endocrinology, 10th ed., Copyright© 2003 Elsevier).

Microvascular complications occur not only in overt diabetes but are also due to Impaired Glucose Tolerance (IGT). Microvascular complications of IGT: neuropathy, retinopathy, and renal microproteinuria. In various embodiments the nucleic acid compounds and pharmaceutical compositions disclosed herein are useful for treating microvascular disorders, alone or in combination with other therapies.

Diabetic Limb Ischemia and Diabetic Foot Ulcers

Diabetes and pressure can impair microvascular circulation and lead to changes in the skin on the lower extremities, which in turn, can lead to formation of ulcers and subsequent infection. Microvascular changes lead to limb muscle microangiopathy, as well as a predisposition to develop peripheral ischemia and a reduced angiogenesis compensatory response to ischemic events. Microvascular pathology exacerbates Peripheral Vascular Disease (PVD) (or Peripheral Arterial Disease (PAD) or Lower Extremity Arterial Disease (LEAD)—a MACROvascular complication—narrowing of the arteries in the legs due to atherosclerosis. PVD occurs earlier in diabetics, is more severe and widespread, and often involves intercurrent microcirculatory problems affecting the legs, eyes, and kidneys.

Foot ulcers and gangrene are frequent comorbid conditions of PAD. Concurrent peripheral neuropathy with impaired sensation make the foot susceptible to trauma, ulceration, and infection. The progression of PAD in diabetes is compounded by such comorbidity as peripheral neuropathy and insensitivity of the feet and lower extremities to pain and trauma. With impaired circulation and impaired sensation, ulceration and infection occur. Progression to osteomyelitis and gangrene may necessitate amputation.

In various embodiments the nucleic acid compounds and pharmaceutical compositions disclosed herein are useful for treating diabetic limb ischemia, alone or in combination with other therapies. In various embodiments the nucleic acid compounds and pharmaceutical compositions disclosed herein are useful for treating ulcers, alone or in combination with other therapies. In various embodiments the nucleic acid compounds and pharmaceutical compositions disclosed herein are useful for treating diabetic foot ulcers, alone or in combination with other therapies.

Coronary Microvascular Dysfunction in Diabetes

The correlation between histopathology and microcirculatory dysfunction in diabetes is well known from old experimental studies and from autopsy, where thickening of the basal membrane, perivascular fibrosis, vascular rarefication, and capillary hemorrhage are frequently found. It remains difficult to confirm these data in vivo, although a recent paper demonstrated a correlation between pathology and ocular micorovascular dysfunction (Am J Physiol 2003; 285). A large amount of clinical studies, however, indicate that not only overt diabetes but also impaired metabolic control may affect coronary microcirculation (Hypert Res 2002; 25:893). Werner alluded to the important paper by Sambuceti et al (Circulation 2001; 104:1129) showing the persistence of microvascular dysfunction in patients after successful reopening of the infarct related artery, and which may explain the increased cardiovascular morbidity and mortality in these patients. There is mounting evidence from large acute reperfusion studies that morbidity and mortality are unrelated to the reopening itself of the infarct related artery, but much more dependent on the TIMI flow+/− myocardial blush (Stone 2002; Feldmann Circulation 2003). Herrmann indicated, among others, that the integrity of the coronary microcirculation is probably the most important clinical and prognostic factor in this context (Circulation 2001). The neutral effect of protection devices (no relevant change for TIMI flow, for ST resolution, or for MACE) may indicate that a functional impairment of microcirculation is the major determinant of prognosis. There is also increasing evidence that coronary microvascular dysfunction plays a major role in non obstructive CAD. Coronary endothelial dysfunction remains a strong prognostic predictor in these patients.

In various embodiments the nucleic acid compounds and pharmaceutical compositions disclosed herein are useful for treating coronary microvascular dysfunction, alone or in combination with other therapies.

Diabetic Nephropathy (Renal Dysfunction in Patients with Diabetes)

Diabetic nephropathy encompasses microalbuminuria (a microvascular disease effect), proteinuria and ESRD. Diabetes is the most common cause of kidney failure, accounting for more than 40 percent of new cases. Even when drugs and diet are able to control diabetes, the disease can lead to nephropathy and kidney failure. Most people with diabetes do not develop nephropathy that is severe enough to cause kidney failure. About 16 million people in the United States have diabetes, and about 100,000 people have kidney failure as a result of diabetes.

In various embodiments the nucleic acid compounds and pharmaceutical compositions disclosed herein are useful for treating diabetic nephropathy, alone or in combination with other therapies.

Retinopathy

Retinopathy is a general term that refers to non-inflammatory damage to the retina of the eye. Causes of retinopathy are varied and include for example, diabetes (diabetic retinopathy), artherial hypertension (hypertensive retinopathy), prematurity of a newborn (retinopathy of prematurity), retinal vein or artery occlusion. Many types of retinopathy are progressive and may result in blindness or severe vision loss or impairment.

In various embodiments the nucleic acid compounds and pharmaceutical compositions disclosed herein are useful for prevention or treatment of disease, disorder or injury associated with retinal vein or artery occlusion, alone or in combination with other therapies.

In various embodiments the nucleic acid compounds and pharmaceutical compositions disclosed herein are useful for prevention or treatment of in-stent retinopathy, alone or in combination with other therapies.

In various embodiments the nucleic acid compounds and pharmaceutical compositions disclosed herein are useful for prevention or treatment of in-stent retinopathy, alone or in combination with other therapies.

In various embodiments the nucleic acid compounds and pharmaceutical compositions disclosed herein are useful for prevention or treatment of hypertensive retinopathy, alone or in combination with other therapies.

In various embodiments the nucleic acid compounds and pharmaceutical compositions disclosed herein are useful for prevention or treatment of retinopathy of prematurity, alone or in combination with other therapies.

Diabetic Retinopathy

Diabetic retinopathy is a complication of diabetes and a leading cause of blindness. It occurs when diabetes damages the tiny blood vessels inside the retina. Diabetic retinopathy has four stages:

Mild Nonproliferative Retinopathy: microaneurysms in the retina's blood vessels.

Moderate Nonproliferative Retinopathy. As the disease progresses, some blood vessels that nourish the retina are blocked.

Severe Nonproliferative Retinopathy. Many more blood vessels are blocked, depriving several areas of the retina of a blood supply, which is overcome by the growth of new blood vessels.

Proliferative Retinopathy. The new blood vessels grow along the retina and along the surface of the vitreous gel. When the vessels leak blood, severe vision loss and even blindness can result.

During pregnancy, diabetic retinopathy may be a problem for women with diabetes.

Without wishing to be bound to theory, blood vessels damaged from diabetic retinopathy can cause vision loss in two ways: Fragile, abnormal blood vessels can develop and leak blood into the center of the eye, blurring vision. This is proliferative retinopathy and is the fourth and most advanced stage of the disease. Fluid can leak into the center of the macula, resulting in blurred vision. This condition is called macular edema. It can occur at any stage of diabetic retinopathy, although it is more likely to occur as the disease progresses and is known as diabetic macular edema (DME).

In various embodiments the nucleic acid compounds and pharmaceutical compositions disclosed herein are useful for prevention or treatment of diabetic retinopathy, alone or in combination with other therapies.

Diabetic Macular Edema (DME)

DME is a complication of diabetic retinopathy, a disease affecting the blood vessels of the retina. Diabetic retinopathy results in multiple abnormalities in the retina, including retinal thickening and edema, hemorrhages, impeded blood flow, excessive leakage of fluid from blood vessels and, in the final stages, abnormal blood vessel growth. This blood vessel growth can lead to large hemorrhages and severe retinal damage. When the blood vessel leakage of diabetic retinopathy causes swelling in the macula, it is referred to as DME. The principal symptom of DME is a loss of central vision. Risk factors associated with DME include poorly controlled blood glucose levels, high blood pressure, abnormal kidney function causing fluid retention, high cholesterol levels and other general systemic factors.

According to the World Health Organization, diabetic retinopathy is the leading cause of blindness in working age adults and a leading cause of vision loss in diabetics. The American Diabetes Association reports that there are approximately 18 million diabetics in the United States and approximately 1.3 million newly diagnosed cases of diabetes in the United States each year. Prevent Blindness America and the National Eye Institute estimate that in the United States there are over 5.3 million people aged 18 or older with diabetic retinopathy, including approximately 500,000 with DME. The CDC estimates that there are approximately 75,000 new cases of DME in the United States each year.

In various embodiments the nucleic acid compounds and pharmaceutical compositions disclosed herein are useful for prevention or treatment of diabetic macular edema (DME), alone or in combination with other therapies.

Retinal Microvasculopathy (AIDS Retinopathy)

Retinal microvasculopathy is seen in 100% of AIDS patients. It is characterized by intraretinal hemorrhages, microaneurysms, Roth spots, cotton-wool spots (microinfarctions of the nerve fiber layer) and perivascular sheathing. The etiology of the retinopathy is unknown though it has been thought to be due to circulating immune complexes, local release of cytotoxic substances, abnormal hemorheology, and HIV infection of endothelial cells. There is no specific treatment for AIDS retinopathy.

In various embodiments the nucleic acid compounds and pharmaceutical compositions disclosed herein are useful for prevention or treatment of AIDS retinopathy, alone or in combination with other therapies.

Bone Marrow Transplantation (BMT) Retinopathy

Bone marrow transplantation retinopathy was first reported in 1983. It typically occurs within six months, but it can occur as late as 62 months after BMT. Risk factors such as diabetes and hypertension may facilitate the development of BMT retinopathy by heightening the ischemic microvasculopathy. There is no known age, gender or race predilection for development of BMT retinopathy. Patients present with decreased visual acuity and/or visual field deficit. Posterior segment findings are typically bilateral and symmetric. Clinical manifestations include multiple cotton wool spots, telangiectasia, microaneurysms, macular edema, hard exudates and retinal hemorrhages. Fluorescein angiography demonstrates capillary nonperfusion and dropout, intraretinal microvascular abnormalities, microaneurysms and macular edema. Although the precise etiology of BMT retinopathy has not been elucidated, it appears to be affected by several factors: cyclosporine toxicity, total body irradiation (TBI), and chemotherapeutic agents. Cyclosporine is a powerful immunomodulatory agent that suppresses graft-versus-host immune response. It may lead to endothelial cell injury and neurologic side effects, and as a result, it has been suggested as the cause of BMT retinopathy. However, BMT retinopathy can develop in the absence of cyclosporine use, and cyclosporine has not been shown to cause BMT retinopathy in autologous or syngeneic bone marrow recipients. Cyclosporine does not, therefore, appear to be the sole cause of BMT retinopathy. Total body irradiation (TBI) has also been implicated as the cause of BMT retinopathy. Radiation injures the retinal microvasculature and leads to ischemic vasculopathy. Variables such as the total dose of radiation and the time interval between radiation and bone marrow ablation appear to be important. However, BMT retinopathy can occur in patients who did not receive TBI, and BMT retinopathy is not observed in solid organ transplant recipients who received similar doses of radiation. Thus, TBI is not the sole cause, but it is another contributing factor in development of BMT retinopathy. Chemotherapeutic agents have been suggested as a potential contributing factor in BMT retinopathy. Medications such as cisplatin, carmustine, and cyclophosphamide can cause ocular side effects including papilledema, optic neuritis, visual field deficit and cortical blindness. It has been suggested that these chemotherapeutic drugs may predispose patients to radiation-induced retinal damages and enhance the deleterious effect of radiation. In general, patients with BMT retinopathy have a good prognosis. The retinopathy usually resolves within two to four months after stopping or lowering the dosage of cyclosporine.

In various embodiments the nucleic acid compounds and pharmaceutical compositions disclosed herein are useful for prevention or treatment of Bone marrow transplantation retinopathy, alone or in combination with other therapies.

Corneal Transplantation

One of the most common transplant procedures in humans today is penetrating keratoplasty (corneal transplant or graft). Currently over 40,000 corneal grafts are performed every year worldwide to prevent blindness from acquired (e.g. infection) and inherited (e.g. Stevens-Johnson syndrome) corneal disease. The main aims of a corneal graft are to improve vision, reduce pain and repair structural damage, and a successful visual outcome depends on the long-term survival of the graft. Over time, the likelihood of corneal graft failure increases, thus, in contrast to many vascularized organ grafts, the attrition rate for corneal grafts is typically slow, but inexorable. The need for re-grafting a failed corneal transplant is one of the main indications for corneal transplantation.

The failure of a corneal graft may occur as a result of bad donor tissue (primary failure) or due to early or late postoperative complications. However, one of the most common reasons for corneal graft failure is immunological corneal graft rejection, which occurs in around 30% of cases.

The success of a corneal graft is mainly reliant on maintaining the immune-privileged status of the eye via multiple mechanisms, including the lack of blood vessels, lack of lymphatics, the blood-eye barrier, the relative paucity of mature antigen presenting cells (APCs) in the central cornea, and the presence of immunomodulatory factors in aqueous humor. However, inflammation and trauma in the cornea and the resulting neovascularization leads to a loss of immune privilege in the eye and causes a cell-mediated immune response that results in corneal graft rejection.

Neovascularization within the normally avascular host cornea prevails as the most established and recognized risk factor of corneal graft rejection. A normal cornea is avascular, lacking blood and lymphatic vessels, which is essential for both transparency and vision, and for granting of immune-privilege to the cornea, protecting the donor cornea from being rejected, making it an important prognostic factor for long-term survival of the corneal graft. If neovascularization is present either before or after a corneal graft, the growth of new blood vessels (angiogenesis) provides a route of entry for immune-mediating cells to the graft, while the growth of new lymphatic vessels (lymphangiogenesis) enables the exit of APCs and antigenic material from the graft to regional lymph nodes. Consequently, the cornea becomes infiltrated with and sensitized to immune reaction mediators and although not an immune reaction in itself, neovascularization induces an immune response that can lead to immunological corneal graft rejection.

The risk of a corneal graft rejection rises by two-thirds from an avascular eye to one in which neovascularization is seen in all four quadrants of the eye.

Currently, established therapy involves the use of anti-inflammatory drugs (i.e. corticosteroids) and/or immunosuppressants to manage the immunological response in the eye, which may be helpful in the early phase of rejection but not in the later phases. Therefore, a new approach to the management of corneal graft rejection is needed to ensure that patients retain their vision after a corneal graft. Investigations have been carried out into the possibility of prevention or treatment of neovascularization, rather than treatment of the subsequent immune reaction or of inflammation. However, to date no specific treatment has been licensed to treat corneal neovascularization.

In various embodiments the nucleic acid compounds and pharmaceutical compositions disclosed herein are useful for prevention or treatment of corneal neovascularization, alone or in combination with other therapies.

Inhibition of Neointima Proliferation and Smooth Muscle Cell Migration (Stents)

In-stent restenosis is a pathobiologic process resulting from vascular smooth muscle cell (VSMC) proliferation, migration and excessive matrix production.

Analysis of RhoA activity in an ex vivo organ culture model of human internal mammary arteries (J Vasc Res. 2005 January-February; 42(1):21-8) demonstrated that stenting induced a time-dependent increase in RhoA activity associated with a concomitant decrease in p27 expression. Treatment of stented arteries with the RhoA inhibitors inhibited both neointimal formation and decrease in p27 expression. Stent implantation induced maintained RhoA activation and demonstrates that the inhibitory action of rapamycin on RhoA expression plays a key role in its antirestenotic effect.

In various embodiments the nucleic acid compounds and pharmaceutical compositions disclosed herein are useful for prevention or treatment of in-stent restenosis, alone or in combination with other therapies.

Pulmonary Hypertension

Pulmonary arterial hypertension (PAH) is a devastating disease characterized by progressive elevation of pulmonary arterial pressure and vascular resistance due to pulmonary vasoconstriction and vessel remodeling as well as inflammation.

Pulmonary arterial hypertension (PAH), characterized by an elevated, sustained increase in pulmonary artery pressure greater than 25 mmHg at rest or 30 mmHg upon exertion, is a progressive disease with poor prognosis and death usually occurring within 5 years if left untreated. Further, primary or idiopathic pulmonary hypertension (IPAH) can result in death within a median of 3 years from right ventricular failure without treatment, with a 15% 1-year mortality rate despite current therapy. Factors contributing to PAH include prolonged vasoconstriction, vascular remodeling, inflammatory cell migration, and in situ thrombosis which result in the formation of vascular lesions. It is currently thought that the primary cause of the elevated pulmonary vascular resistance that occurs in PAH is due to mechanical obstruction from vascular remodeling. In addition, pathologic findings show that PAH is associated with intimal and/or medial hypertrophy, intimal fibrosis, and plexiform lesions.

In various embodiments the nucleic acid compounds and pharmaceutical compositions disclosed herein are useful for prevention or treatment of pulmonary hypertension, alone or in combination with other therapies.

Inflammation

Inflammation is part of the complex biological response of vascular tissues to harmful stimuli, such as pathogens, damaged cells, or irritants. Abnormalities associated with inflammation comprise a large, officially unrelated group of disorders which underlie a vast variety of human diseases. The immune system is often involved with inflammatory disorders, demonstrated in both allergic reactions and some myopathies, with many immune system disorders resulting in abnormal inflammation. Non-immune diseases with etiological origins in inflammatory processes are thought to include cancer, atherosclerosis, and ischaemic heart disease.

In various embodiments the nucleic acid compounds and pharmaceutical compositions disclosed herein are useful for prevention or treatment of inflammation, alone or in combination with other therapies. In various embodiments the nucleic acid compounds and pharmaceutical compositions disclosed herein are useful for prevention or treatment of inflammatory disorder, alone or in combination with other therapies.

Oncogenesis

Recently, studies have shown Rho family proteins to be involved in tumor growth, progression, metastasis, and angiogenesis. Though the pathways for Rho proteins involvement are virtually unknown the links between Rho proteins and cancer are substantial. In particular, RhoA proteins seem to have extensive links to certain types of cancer. RhoA over expression has been found to be linked to colon, breast, lung, testicular germ cell, and head and neck squamous-cell carcinoma tumors.

The RhoA level of over expression may correlate to the increased activation of its three known effectors, which in turn give rise to possible functions that may allow for tumorigenesis. The three effectors include the ROCK I,II family. These effectors are kinases that cause actomyosin contraction, transformation, and transcription of the SRF gene. Also, these effectors show scaffolding properties that function to polymerize actin and affect the formation of microtubules. The second effector is the PRK1/PKN proteins that cause endyocytosis. And lastly RhoA binds to the effector Citron causing cytokinesis. These effectors seem to suggest RhoA's involvement in cell motility and cell polarity. The effects of RhoA expression on these two functions would seem to be a likely cause for the formation of tumors. In fact the loss of polarity in epithelial cells, which are the tissues most often causing cancer, and their increased cell motility would seem to create abnormal cell lines Overexpression of RhoA has been associated with colon, breast, lung, and testicular germ cell cancers and in head and neck squamous-cell carcinomas. Different hypotheses regarding RhoA's role in these cancers are being explored. One is that RhoA's GTPase activity provides the energy for processes necessary for tumorigenesis, such as vesicle transport and cell shape change. Another, not incompatible, hypothesis is that metastasis of the cancers may be affected by RhoA's role in cell motility and process formation.

"Cancer and "cancerous disease" are used interchangeably and refer to a disease that is caused by or results in inappropriately high levels of cell division, inappropriately low levels of apoptosis, or both. Examples of cancerous diseases include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangio sarcoma, lymphangioendotheliosarcoma, synovioma, mesothelioma, Ewing's tumor, leiomyo sarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, crailiopharyngioma, ependymoma, pinealoma, hemangioblastoma, acoustic neuroma, oligodenroglioma, schwamioma, meningioma, melanoma, neuroblastoma, and retinoblastoma). In some preferred embodiments the compounds of the present invention are useful in treating lung cancer and metastases in the lung.

As used herein, the term "proliferative disease" refers to a disease in which cellular proliferation, either malignant or benign, contributes to the pathology of the condition. Such unwanted proliferation is the hallmark of cancer and many chronic inflammatory diseases, thus examples of "proliferative disease" include the cancers listed supra and chronic inflammatory proliferative diseases such as psoriasis, inflammatory bowel disease and rheumatoid arthritis; proliferative cardiovascular diseases such as restenosis; proliferative ocular disorders such as diabetic retinopathy; and benign hyperproliferative diseases such as hemangiomas.

In various embodiments the nucleic acid compounds and pharmaceutical compositions disclosed herein are useful for prevention or treatment of cancer, alone or in combination with other therapies. In various embodiments the nucleic acid compounds and pharmaceutical compositions disclosed herein are useful for prevention or treatment of carcinoma, tumor and/or malignant disease, alone or in combination with other therapies.

In one embodiment the nucleic acid compounds and pharmaceutical compositions disclosed herein are useful for prevention or treatment of colon cancer, alone or in combination with other therapies. In one embodiment the nucleic acid compounds and pharmaceutical compositions disclosed herein are useful for prevention or treatment of breast cancer, alone or in combination with other therapies. In one embodiment the nucleic acid compounds and pharmaceutical compositions disclosed herein are useful for prevention or treatment of lung cancer, alone or in combination with other therapies. In one embodiment the nucleic acid compounds and pharmaceutical compositions disclosed herein are useful for prevention or treatment of testicular germ cell cancer, alone or in combination with other therapies. In one embodiment the nucleic acid compounds and pharmaceutical compositions disclosed herein are useful for prevention or treatment of neck squamous-cell carcinoma, alone or in combination with other therapies.

More effective therapies to treat the above mentioned diseases and disorders would be of great therapeutic value.

In conclusion, there are no effective modes of therapy for the prevention and/or treatment of the conditions disclosed herein (e.g., glaucoma, SCI, CNS injury, neurodegenerative) and certainly no effective treatment for contraction of tissues, nor is there effective treatment for ocular scarring. Treatments that are available suffer from, inter alia, the drawbacks of severe side effects due to the lack of selective targeting and there remains a need therefore to develop novel compounds and methods of treatment for these purposes.

In various embodiments the compounds and pharmaceutical compositions of the invention are useful in treating or preventing various diseases, disorders and injury that affect the central nervous system (CNS), such as, without being limited to, the diseases, disorders and injury that are disclosed herein below. Without being bound by theory, it is believed that the therapeutic dsRhoA molecules provided herein, treat CNS disorders, diseases and injury by multiple mechanisms, leading to neuroprotection and neuroregeneration.

RhoA Protein

RhoA is a member of the Ras homology family of small GTPases. These proteins cycle from their active (GTP-bound) to their inactive (GDP-bound) conformation by hydrolyzing GTP to GDP. Specific guanine exchange factors (GEFs) reactivate the GTPases by catalyzing the replacement of GDP with a new GTP. Other regulatory factors include GTPase-activating proteins (GAPs), which deactivate RhoA by enhancing its GTPase activity (thus converting the protein more rapidly to its GDP-bound inactive form) and guanine nucleotide dissociation inhibitors (GDIs), which inhibit GAP's functioning and consequently slow RhoA's GTPase activity.

RhoA's functions in the cell are primarily related to cytoskeletal regulation. Recent studies have shown its indirect involvement (through associated factors) in myosin phosphorylation and cellular responses to stress, such as the formation of focal adhesions and actin stress fibers. It has also been shown to be directly related to myosin chain elongation, actin filament rearrangement, gene expression, cell-shape determination and cell proliferation.

Overexpression of RhoA has been associated with colon, breast, lung, and testicular germ cell cancers and in head and neck squamous-cell carcinomas. Different hypotheses regarding RhoA's role in these cancers are being explored. One is that RhoA's GTPase activity provides the energy for processes necessary for tumorigenesis, such as vesicle transport and cell shape change. Another, not incompatible, hypothesis is that metastasis of the cancers may be affected by RhoA's role in cell motility and process formation.

dsRNA Oligoribonucleotide Compounds

Tables I, II, III, and IV provide nucleic acid sequences of sense and corresponding antisense oligonucleotides, useful in preparing unmodified and chemically modified RhoA dsRNA compounds. The sense and antisense oligonucleotides provided in Tables I, II and III provide the preferred oligonucleotides useful for generation of synthetic siRNA compounds (duplexes) useful in down-regulating RhoA expression and treatment of diseases, disorders and injury disclosed herein.

The selection and synthesis of dsRNA compounds corresponding to known genes has been widely reported; see for example Ui-Tei et al., J Biomed Biotechnol. 2006; 65052; Chalk et al., BBRC. 2004, 319(1):264-74; Sioud and Leirdal, Met. Mol. Biol.; 2004, 252:457-69; Levenkova et al., Bioinform. 2004, 20(3):430-2; Ui-Tei et al., NAR 2004, 32(3):936-48. For examples of the use of, and production of, modified siRNA see Braasch et al., Biochem., 2003, 42(26):7967-75; Chiu et al., RNA, 2003, 9(9):1034-48; PCT publications WO 2004/015107 (atugen); WO 02/44321 (Tuschl et al), and U.S. Pat. Nos. 5,898,031 and 6,107,094.

Several groups have described the development of DNA-based vectors capable of generating siRNA within cells. The method generally involves transcription of short hairpin RNAs that are efficiently processed to form siRNAs within cells (Paddison et al. PNAS USA 2002, 99:1443-1448; Paddison et al. Genes & Dev 2002, 16:948-958; Sui et al. PNAS USA 2002, 8:5515-5520; and Brummelkamp et al. Science 2002, 296:550-553). These reports describe methods of generating siRNAs capable of specifically targeting numerous endogenously and exogenously expressed genes.

The present invention provides double-stranded oligoribonucleotides (e.g. dsRNAs), which down-regulate the expression of RhoA according to the present invention. A dsRNA compound of the invention is a duplex oligoribonucleotide in which the sense strand is derived from the mRNA sequence of RhoA, and the antisense strand is complementary to the sense strand. In general, some deviation from the target mRNA sequence is tolerated without compromising the dsRNA activity (see e.g. Czauderna et al., 2003, NAR 31(11), 2705-2716). A dsRNA compound of the invention down-regulates gene expression on a post-transcriptional level with or without destroying the mRNA. Without being bound by theory, dsRNA may target the mRNA for specific cleavage and degradation and/or may inhibit translation from the targeted message.

The dsRNA compounds disclosed herein are chemically and or structurally modified according to the modifications set forth in the Structures disclosed herein or as tandem dsRNA or RNAstar.

Pharmaceutical Compositions for Inhibiting RhoA

Provided are compositions and methods for down-regulation of RhoA expression by using small nucleic acid molecules, such as short interfering nucleic acid (siNA), interfering RNA (RNAi), short interfering RNA (siRNA), double-stranded RNA (dsRNA), micro-RNA (miRNA), and short hairpin RNA (shRNA) molecules capable of mediating down-regulation of RhoA gene expression or that mediate RNA interference against RhoA gene expression. The composition and methods disclosed herein are also useful in treating various neurodegenerative and neurological disorders and pain.

Nucleic acid molecule(s) and/or methods of the invention are used to down regulate the expression of RhoA that encodes a mRNA referred to, by example, Genbank Accession NM_001664.

While it may be possible for the compounds of the present invention to be administered as the raw chemical, it is preferable to present them as a pharmaceutical composition. Accordingly the present invention provides a pharmaceutical composition comprising one or more of the compounds of the invention; and a pharmaceutically acceptable carrier. This composition may comprise a mixture of two or more different nucleic acid compounds.

Compositions, methods and kits provided herein may include one or more nucleic acid molecules (e.g., dsRNA) and methods that independently or in combination modulate (e.g., downregulate) the expression of RhoA protein and/or genes encoding RhoA protein, proteins and/or genes associated with the maintenance and/or development of diseases, conditions or disorders associated with RhoA, such as e.g., CNS disorders, disease and injury (e.g., genes encoding sequences comprising those sequences referred to by GenBank Accession Nos. NM_001664), or a RhoA gene family member where the genes or gene family sequences share sequence homology. The description of the various aspects and embodiments is provided with reference to exemplary gene RhoA. However, the various aspects and embodiments are also directed to other related RhoA genes, such as homolog genes and transcript variants, and polymorphisms (e.g., single nucleotide polymorphism, (SNPs)) associated with certain RhoA genes. As such, the various aspects and embodiments are also directed to other genes that are involved in RhoA mediated pathways of signal transduction or gene expression that are involved, for example, in the maintenance or development of diseases, traits, or conditions described herein. These additional genes can be analyzed for target sites using the methods described for the RhoA gene herein. Thus, the down-regulation of other genes and the effects of such modulation of the other genes can be performed, determined, and measured as described herein.

The invention further provides a pharmaceutical composition comprising at least one compound of the invention covalently or non-covalently bound to one or more compounds of the invention in an amount effective to down regulate RhoA expression; and a pharmaceutically acceptable carrier. The compound may be processed intracellularly by endogenous cellular complexes to produce one or more oligoribonucleotides of the invention.

The invention further provides a pharmaceutical composition comprising a pharmaceutically acceptable carrier and one or more of the compounds of the invention in an amount effective to inhibit expression in a cell of human RhoA, the compound comprising a sequence which is substantially complementary to the sequence of (N)x.

Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

Additionally, the invention provides a method of inhibiting the expression of RhoA by at least 40%, preferably by 50%, 60% or 70%, more preferably by 75%, 80% or 90% as compared to a control comprising contacting an mRNA transcript of RhoA of the present invention with one or more of the compounds of the invention.

In one embodiment the oligoribonucleotide compounds, compositions and methods disclosed herein inhibit/down-regulate the RhoA gene, whereby the inhibition/down-regulation is selected from the group comprising inhibition/down-regulation of gene function, inhibition/down-regulation of polypeptide and inhibition/down-regulation of mRNA expression.

In one embodiment, compositions and methods provided herein include a double-stranded short interfering nucleic acid (siNA) compound that down-regulates expression of a RhoA gene (e.g., the mRNA coding sequence for human RhoA exemplified by SEQ ID NO:1), where the nucleic acid molecule includes about 15 to about 49 base pairs.

In one embodiment, a nucleic acid disclosed herein may be used to inhibit the expression of the RhoA gene or a RhoA gene family where the genes or gene family sequences share sequence homology. Such homologous sequences can be identified as is known in the art, for example using sequence alignments. Nucleic acid molecules can be designed to target such homologous sequences, for example using perfectly complementary sequences or by incorporating non-canonical base pairs, for example mismatches and/or wobble base pairs, that can provide additional target sequences. In instances where mismatches are identified, non-canonical base pairs (for example, mismatches and/or wobble bases) can be used to generate nucleic acid molecules that target more than one gene sequence. In a non-limiting example, non-canonical base pairs such as UU and CC base pairs are used to generate nucleic acid molecules that are capable of targeting sequences for differing RhoA targets that share sequence homology. As such, one advantage of using dsRNAs disclosed herein is that a single nucleic acid can be designed to include nucleic acid sequence that is complementary to the nucleotide sequence that is conserved between the homologous genes. In this approach, a single nucleic acid can be used to inhibit expression of more than one gene instead of using more than one nucleic acid molecule to target the different genes.

Nucleic acid molecules may be used to target conserved sequences corresponding to a gene family or gene families such as RhoA family genes. As such, nucleic acid molecules targeting multiple RhoA targets can provide increased therapeutic effect. In addition, nucleic acid can be used to characterize pathways of gene function in a variety of applications. For example, nucleic acid molecules can be used to inhibit the activity of target gene(s) in a pathway to determine the function of uncharacterized gene(s) in gene function analysis, mRNA function analysis, or translational analysis. The nucleic acid molecules can be used to determine potential target gene pathways involved in various diseases and conditions toward pharmaceutical development. The nucleic acid molecules can be used to understand pathways of gene expression involved in, for example CNS disorders such as neurodegenerative disorders, and/or inflammatory diseases, disorders, and/or conditions.

In one embodiment the nucleic acid compounds, compositions and methods provided herein, inhibit the RhoA polypeptide, whereby the inhibition is selected from the group comprising inhibition of function (which may be examined by an enzymatic assay or a binding assay with a known interactor of the native gene/polypeptide, inter alia), inhibition of protein (which may be examined by Western blotting, ELISA or immuno-precipitation, inter alia) and inhibition of mRNA expression (which may be examined by Northern blotting, quantitative RT-PCR, in-situ hybridisation or microarray hybridisation, inter alia).

In one embodiment, the compositions and methods provided herein include a nucleic acid molecule having RNAi activity against RhoA RNA, where the nucleic acid molecule includes a sequence complementary to any RNA having RhoA encoding sequence, such as that sequence set forth in SEQ ID NO: 1. In another embodiment, a nucleic acid molecule may have RNAi activity against RhoA RNA, where the nucleic acid molecule includes a sequence complementary to an RNA having variant RhoA encoding sequence, for example other mutant RhoA genes not shown in SEQ ID NO: 1 but known in the art to be associated with the onset and/or maintenance and/or development of neurodegeneration and/or neuropathy, for example a SNP. Chemical modifications as described herein can be applied to any nucleic acid construct disclosed herein. In another embodiment, a nucleic acid molecule disclosed herein includes a nucleotide sequence that can interact with nucleotide sequence of a RhoA gene and thereby mediate down-regulation or silencing of RhoA gene expression, for example, wherein the nucleic acid molecule mediates regulation of RhoA gene expression by cellular processes that modulate the chromatin structure or methylation patterns of the RhoA gene and prevent transcription of the RhoA gene.

In additional embodiments the invention provides methods of treating a subject suffering from a disease accompanied by an elevated level of RhoA, the method comprising administering to the subject a compound of the invention in a therapeutically effective dose thereby treating the subject.

More particularly, the invention provides an oligoribonucleotide wherein one strand includes consecutive nucleotides having, from 5' to 3', the compounds set forth in Tables I, II, III and IV or a homologs thereof wherein in up to two of the ribonucleotides in each terminal region is altered.

Delivery of Nucleic Acid Molecules and Pharmaceutical Formulations

Nucleic acid molecules of the present invention may be delivered to the target tissue by direct application of the naked molecules prepared with a carrier or a diluent.

The terms "naked nucleic acid" or "naked dsRNA" or "naked siRNA" refers to nucleic acid molecules that are free from any delivery vehicle that acts to assist, promote or facilitate entry into the cell, including viral sequences, viral particles, liposome formulations, lipofectin or precipitating agents and the like. For example, dsRNA in PBS is "naked dsRNA".

Nucleic acid molecules may be adapted for use to prevent or CNS disorders (e.g., neurodegenerative, ocular, otic) diseases, traits, conditions and/or disorders, and/or any other trait, disease, disorder or condition that is related to or will respond to the levels of RhoA in a cell or tissue, alone or in combination with other therapies.

Nucleic acid molecules disclosed herein may be delivered or administered directly with a carrier or diluent but not any delivery vehicle that acts to assist, promote or facilitate entry to the cell, including viral vectors, viral particles, liposome formulations, lipofectin or precipitating agents and the like.

A nucleic acid molecule may include a delivery vehicle, including liposomes, for administration to a subject, carriers and diluents and their salts, and/or can be present in pharmaceutically acceptable formulations. In some embodiments the dsRNA molecules of the invention are delivered in liposome formulations and lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al., FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003. 327: 761-766; Lewis et al., Nat. Gen. 2002, 32: 107-108 and Simeoni et al., NAR 2003, 31, 11: 2717-2724). siRNA has recently been successfully used for inhibition of gene expression in primates (see for example, Tolentino et al., Retina 24(4):660).

Polypeptides that facilitate introduction of nucleic acid into a desired subject are known in the art, e.g. such as those described in US. Application Publication No. 20070155658 (e.g., a melamine derivative such as 2,4,6-Triguanidino Traizine and 2,4,6-Tramidosarcocyl Melamine, a polyarginine polypeptide, and a polypeptide including alternating glutamine and asparagine residues).

The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169, 383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

Methods for the delivery of nucleic acid molecules are described in Akhtar et al., Trends Cell Bio., 2: 139 (1992); Delivery Strategies for Antisense Oligonucleotide Therapeutics, ed. Akhtar, (1995), Maurer et al., Mol. Membr. Biol., 16: 129-140 (1999); Hofland and Huang, Handb. Exp. Pharmacol., 137: 165-192 (1999); and Lee et al., ACS Symp. Ser., 752: 184-192 (2000); U.S. Pat. Nos. 6,395,713; 6,235,310; 5,225,182; 5,169,383; 5,167,616; 4,959217; 4,925,678; 4,487,603; and 4,486,194 and Sullivan et al., PCT WO 94/02595; PCT WO 00/03683 and PCT WO 02/08754; and U.S. Patent Application Publication No. 2003077829. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see e.g., Gonzalez et al., Bioconjugate Chem., 10: 1068-1074 (1999); Wang et al., International PCT publication Nos. WO 03/47518 and WO 03/46185), poly(lactic-co-glycolic)acid (PLGA) and PLCA microspheres (see for example U.S. Pat. No. 6,447,796 and U.S. Application Publication No. 2002130430), biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether intravitreal, subcutaneous, transtympanic, intramuscular, or intradermal, can take place using standard needle and syringe methodologies, or by needle-free technologies such as those described in Conry et al., Clin. Cancer Res., 5: 2330-2337 (1999) and Barry et al., International PCT Publication No. WO 99/31262. The molecules of the instant invention can be used as pharmaceutical agents. Pharmaceutical agents prevent, modulate the occurrence, or treat or alleviate a symptom to some extent (preferably all of the symptoms) of a disease state in a subject. In one specific embodiment of this invention topical and transdermal formulations may be selected.

The dsRNAs or pharmaceutical compositions of the present invention are administered and dosed in accordance with good medical practice, taking into account the clinical condition of the individual subject, the disease to be treated, the site and method of administration, scheduling of administration, patient age, sex, body weight and other factors known to medical practitioners.

In another embodiment the administration comprises topical or local administration such as via eye drops, eardrops or ointment. In a non-limiting example, dsRNA compounds that target RhoA are useful in treating a subject suffering from damage to the neural retina, wherein the dsRNA compounds are delivered to the eye via topical delivery (e.g., eye drops, ear drops or ointments). In a non-limiting example, dsRNA compounds that target RhoA are useful in treating a subject suffering from Retinal Ganglion Cell (RGC) loss wherein the dsRNA compounds are delivered to the eye via topical delivery (e.g., eye drops, ear drops or ointments). In a non-limiting example, dsRNA compounds that target RhoA are useful in treating a subject suffering from glaucoma wherein the dsRNA compounds are delivered to the eye via topical delivery (e.g., eye drops, ear drops or ointment).

Nucleic acid molecules may be complexed with cationic lipids, packaged within liposomes, or otherwise delivered to target cells or tissues. The nucleic acid or nucleic acid complexes can be locally administered to relevant tissues ex vivo, or in vivo through direct dermal application, transdermal application, or injection, with or without their incorporation in biopolymers. The nucleic acid molecules of the invention may include sequences shown herein in Tables I-IV. Examples of such nucleic acid molecules consist essentially of sequences provided in Tables I-IV.

Delivery systems may include surface-modified liposomes containing poly(ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011).

Nucleic acid molecules may be formulated or complexed with polyethylenimine (e.g., linear or branched PEI) and/or polyethylenimine derivatives, including for example polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives, grafted PEIs such as galactose PEI, cholesterol PEI, antibody derivatized PEI, and polyethylene glycol PEI (PEG-PEI) derivatives thereof (see for example Ogris et al., 2001, AAPA PharmSci, 3, 1-11; Furgeson et al., 2003, Bioconjugate Chem., 14, 840-847; Kunath et al., 2002, Pharmaceutical Research, 19, 810-817; Choi et al., 2001, Bull. Korean Chem. Soc., 22, 46-52; Bettinger et al., 1999, Bioconjugate Chem., 10, 558-561; Peterson et al., 2002, Bioconjugate Chem., 13, 845-854; Erbacher et al., 1999, Journal of Gene Medicine Preprint, 1, 1-18; Godbey et al., 1999., PNAS USA, 96, 5177-5181; Godbey et al., 1999, Journal of Controlled Release, 60, 149-160; Diebold et al., 1999, Journal of Biological Chemistry, 274, 19087-19094; Thomas and Klibanov, 2002, PNAS USA, 99, 14640-14645; Sagara, U.S. Pat. No. 6,586,524 and United States Patent Application Publication No. 20030077829.

Nucleic acid molecules may be complexed with membrane disruptive agents such as those described in U.S. Patent Application Publication No. 20010007666. The membrane disruptive agent or agents and the nucleic acid molecule may also be complexed with a cationic lipid or helper lipid molecule, such as those lipids described in U.S. Pat. No. 6,235,310.

Nucleic acid molecules disclosed herein may be administered to the central nervous system (CNS) or peripheral nervous system (PNS). Experiments have demonstrated the efficient in vivo uptake of nucleic acids by neurons. See e.g., Sommer et al., 1998, Antisense Nuc. Acid Drug Dev., 8, 75; Epa et al., 2000, Antisense Nuc. Acid Drug Dev., 10, 469; Broaddus et al., 1998, J. Neurosurg., 88(4), 734; Karle et al., 1997, Eur. J. Pharmacol., 340(2/3), 153; Bannai et al., 1998, Brain Research, 784(1,2), 304; Rajakumar et al., 1997, Synapse, 26(3), 199; Wu-pong et al., 1999, BioPharm, 12(1), 32; Bannai et al., 1998, Brain Res. Protoc., 3(1), 83; and Simantov et al., 1996, Neuroscience, 74(1), 39. Nucleic acid molecules are therefore amenable to delivery to and uptake by cells in the CNS and/or PNS, e.g. neurons, macrophages, white matter axons and endothelial cells.

Delivery of nucleic acid molecules to the CNS is provided by a variety of different strategies. Traditional approaches to CNS delivery that can be used include, but are not limited to, intrathecal and intracerebroventricular administration, implantation of catheters and pumps, direct injection or perfusion at the site of injury or lesion, injection into the brain arterial system, or by chemical or osmotic opening of the blood-brain barrier. Non-invasive methods of delivery of nucleic acid molecules to the CNS are also know and may include, e.g. intranasal, ocular (e.g. eyedrops) or otic (e.g. eardrops) administration. A combination of invasive and non-invasive administration methods may also be used. Other approaches can include the use of various transport and carrier systems, for example though the use of conjugates and biodegradable polymers. Furthermore, gene therapy approaches, e.g., as described in Kaplitt et al., U.S. Pat. No. 6,180,613 and Davidson, WO 04/013280, can be used to express nucleic acid molecules in the CNS.

Delivery systems may include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer. Non-limiting examples of liposomes which can be used with the compounds of this invention include the following: (1) CellFectin, 1:1.5 (M/M) liposome formulation of the cationic lipid N,NI,NII,NIII-tetramethyl-N,NI,NII,NIII-tetrapalmit-y-spermine and dioleoyl phosphatidylethanolamine (DOPE) (GIBCO BRL); (2) Cytofectin GSV, 2:1 (M/M) liposome formulation of a cationic lipid and DOPE (Glen Research); (3) DOTAP (N-[1-(2,3-dioleoyloxy)-N,N,N-trimethyl-ammoniummethylsulfate) (Boehringer Manheim); and (4) Lipofectamine, 3:1 (M/M) liposome formulation of the polycationic lipid DOSPA, the neutral lipid DOPE (GIBCO BRL) and Di-Alkylated Amino Acid (DiLA2).

Delivery systems may include patches, tablets, suppositories, pessaries, gels, s aqueous and nonaqueous solutions, lotions and creams, and can contain excipients such as solubilizers and enhancers (e.g., propylene glycol, bile salts and amino acids), and other vehicles (e.g., polyethylene glycol, glycerol, fatty acid esters and derivatives, and hydrophilic polymers such as hydroxypropylmethylcellulose and hyaluronic acid).

Nucleic acid molecules may include a bioconjugate, for example a nucleic acid conjugate as described in Vargeese et al., U.S. Ser. No. 10/427,160; U.S. Pat. No. 6,528,631; U.S. Pat. No. 6,335,434; U.S. Pat. No. 6,235,886; U.S. Pat. No. 6,153,737; U.S. Pat. No. 5,214,136; U.S. Pat. No. 5,138,045.

Compositions, methods and kits disclosed herein may include an expression vector that includes a nucleic acid sequence encoding at least one nucleic acid molecule of the invention in a manner that allows expression of the nucleic acid molecule. Methods of introducing nucleic acid molecules or one or more vectors capable of expressing the strands of dsRNA into the environment of the cell will depend on the type of cell and the make up of its environment. The nucleic acid molecule or the vector construct may be directly introduced into the cell (i.e., intracellularly); or introduced extracellularly into a cavity, interstitial space, into the circulation of an organism, introduced orally, or may be introduced by bathing an organism or a cell in a solution containing dsRNA. The cell is preferably a mammalian cell; more preferably a human cell. The nucleic acid molecule of the expression vector can include a sense region and an antisense region. The antisense region can include a sequence complementary to a RNA or DNA sequence encoding RhoA and the sense region can include a sequence complementary to the antisense region. The nucleic acid molecule can include two distinct strands having complementary sense and antisense regions. The nucleic acid molecule can include a single strand having complementary sense and antisense regions.

Nucleic acid molecules that interact with target RNA molecules and down-regulate gene encoding target RNA molecules (e.g., RhoA mRNA, SEQ ID NO:1) may be expressed from transcription units inserted into DNA or RNA vectors. Recombinant vectors can be DNA plasmids or viral vectors. Nucleic acid molecule expressing viral vectors can be constructed based on, but not limited to, adeno-associated virus, retrovirus, adenovirus, or alphavirus. The recombinant vectors capable of expressing the nucleic acid molecules can be delivered as described herein, and persist in target cells. Alternatively, viral vectors can be used that provide for transient expression of nucleic acid molecules. Such vectors can be repeatedly administered as necessary. Once expressed, the nucleic acid molecules bind and down-regulate gene function or expression, e.g., via RNA interference (RNAi). Delivery of nucleic acid molecule expressing vectors can be systemic, such as by intravenous or intramuscular administration, by local administration, by administration to target cells explanted from a subject followed by reintroduction into the subject, or by any other means that would allow for introduction into the desired target cell.

Expression vectors may include a nucleic acid sequence encoding at least one nucleic acid molecule disclosed herein, in a manner which allows expression of the nucleic acid molecule. For example, the vector may contain sequence(s) encoding both strands of a nucleic acid molecule that include a duplex. The vector can also contain sequence(s) encoding a single nucleic acid molecule that is self-complementary and thus forms a nucleic acid molecule. Non-limiting examples of such expression vectors are described in Paul et al., 2002, Nature Biotechnology, 19, 505; Miyagishi and Taira, 2002, Nature Biotechnology, 19, 497; Lee et al., 2002, Nature Biotechnology, 19, 500; and Novina et al., 2002, Nature Medicine, advance online publication doi:10.1038/nm725. Expression vectors may also be included in a mammalian (e.g., human) cell.

An expression vector may include a nucleic acid sequence encoding two or more nucleic acid molecules, which can be the same or different. Expression vectors may include a sequence for a nucleic acid molecule complementary to a nucleic acid molecule referred to by a Genbank Accession number NM_001664, for example those shown in Tables I, II, III and IV.

An expression vector may encode one or both strands of a nucleic acid duplex, or a single self-complementary strand that self hybridizes into a nucleic acid duplex. The nucleic acid sequences encoding nucleic acid molecules can be operably linked in a manner that allows expression of the nucleic acid molecule (see for example Paul et al., 2002, Nature Biotechnology, 19, 505; Miyagishi and Taira, 2002, Nature Biotechnology, 19, 497; Lee et al., 2002, Nature Biotechnology, 19, 500; and Novina et al., 2002, Nature Medicine, advance online publication doi:10.1038/nm725).

An expression vector may include one or more of the following: a) a transcription initiation region (e.g., eukaryotic pol I, II or III initiation region); b) a transcription termination region (e.g., eukaryotic pol I, II or III termination region); c) an intron and d) a nucleic acid sequence encoding at least one of the nucleic acid molecules, wherein said sequence is operably linked to the initiation region and the termination region in a manner that allows expression and/or delivery of the nucleic acid molecule. The vector can optionally include an open reading frame (ORF) for a protein operably linked on the 5'-side or the 3'-side of the sequence encoding the nucleic acid molecule; and/or an intron (intervening sequences).

Transcription of the nucleic acid molecule sequences can be driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA, 87, 6743-7; Gao and Huang 1993, Nucleic Acids Res., 21, 2867-72; Lieber et al., 1993, Methods Enzymol., 217, 47-66; Zhou et al., 1990, Mol. Cell. Biol., 10, 4529-37). Several investigators have demonstrated that nucleic acid molecules expressed from such promoters can function in mammalian cells (e.g. Kashani-Sabet et al., 1992, Antisense Res. Dev., 2, 3-15; Ojwang et al., 1992, Proc. Natl. Acad. Sci. USA, 89, 10802-6; Chen et al., 1992, Nucleic Acids Res., 20, 4581-9; Yu et al., 1993, Proc. Natl. Acad. Sci. USA, 90, 6340-4; L'Huillier et al., 1992, EMBO J., 11, 4411-8; Lisziewicz et al., 1993, Proc. Natl. Acad. Sci. U.S.A, 90, 8000-4; Thompson et al., 1995, Nucleic Acids Res., 23, 2259; Sullenger & Cech, 1993, Science, 262, 1566). More specifically, transcription units such as the ones derived from genes encoding U6 small nuclear (snRNA), transfer RNA (tRNA) and adenovirus VA RNA are useful in generating high concentrations of desired RNA molecules such as siNA in cells (Thompson et al., supra; Couture and Stinchcomb, 1996, supra; Noonberg et al., 1994, Nucleic Acid Res., 22, 2830; Noonberg et al., U.S. Pat. No. 5,624,803; Good et al., 1997, Gene Ther., 4, 45; Beigelman et al., International PCT Publication No. WO 96/18736. The above nucleic acid transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (see Couture and Stinchcomb, 1996 supra).

Nucleic acid molecule may be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591-5; Kashani-Sabet et al., 1992, Antisense Res. Dev., 2, 3-15; Dropulic et al., 1992, J. Virol., 66, 1432-41; Weerasinghe et al., 1991, J. Virol., 65, 5531-4; Ojwang et al., 1992, Proc. Natl. Acad. Sci. USA, 89, 10802-6; Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45. Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., 1992, Nucleic Acids Symp. Ser., 27, 15-6; Taira et al., 1991, Nucleic Acids Res., 19, 5125-30; Ventura et al., 1993, Nucleic Acids Res., 21, 3249-55; Chowrira et al., 1994, J. Biol. Chem., 269, 25856.

A viral construct packaged into a viral particle would accomplish both efficient introduction of an expression construct into the cell and transcription of dsRNA construct encoded by the expression construct.

Methods for oral introduction include direct mixing of RNA with food of the organism, as well as engineered approaches in which a species that is used as food is engineered to express an RNA, then fed to the organism to be affected. Physical methods may be employed to introduce a nucleic acid molecule solution into the cell. Physical methods of introducing nucleic acids include injection of a solution containing the nucleic acid molecule, bombardment by particles covered by the nucleic acid molecule, soaking the cell or organism in a solution of the RNA, or electroporation of cell membranes in the presence of the nucleic acid molecule.

Other methods known in the art for introducing nucleic acids to cells may be used, such as chemical mediated transport, such as calcium phosphate, and the like. Thus the nucleic acid molecules may be introduced along with components that perform one or more of the following activities: enhance RNA uptake by the cell, promote annealing of the duplex strands, stabilize the annealed strands, or other-wise increase inhibition/down-regulation of the target gene.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Nucleic acid molecules may be formulated as a microemulsion. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Delivery formulations can include water soluble degradable crosslinked polymers that include one or more degradable crosslinking lipid moiety, one or more PEI moiety, and/or one or more mPEG (methyl ether derivative of PEG (methoxypoly(ethylene glycol)).

Dosages

The useful dosage to be administered and the particular mode of administration will vary depending upon such factors as the cell type, or for in vivo use, the age, weight and the particular animal and region thereof to be treated, the particular nucleic acid and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

Suitable amounts of nucleic acid molecules may be introduced and these amounts can be empirically determined using standard methods. Effective concentrations of individual nucleic acid molecule species in the environment of a cell may be about 1 femtomolar, about 50 femtomolar, 100 femtomolar, 1 picomolar, 1.5 picomolar, 2.5 picomolar, 5 picomolar, 10 picomolar, 25 picomolar, 50 picomolar, 100 picomolar, 500 picomolar, 1 nanomolar, 2.5 nanomolar, 5 nanomolar, 10 nanomolar, 25 nanomolar, 50 nanomolar, 100 nanomolar, 500 nanomolar, 1 micromolar, 2.5 micromolar, 5 micromolar, 10 micromolar, 100 micromolar or more.

In general, the active dose of nucleic acid compound for humans is in the range of from 1 ng/kg to about 20-100 milligrams per kilogram (mg/kg) body weight of the recipient per day, preferably about 0.01 mg to about 2-10 mg/kg body weight of the recipient per day, in a regimen of a single dose, a one dose per day or twice or three or more times per day for a period of 1-4 weeks or longer. A suitable dosage unit of nucleic acid molecules may be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Dosage may be from 0.01 ug to 1 g per kg of body weight (e.g., 0.1 ug, 0.25 ug, 0.5 ug, 0.75 ug, 1 ug, 2.5 ug, 5 ug, 10 ug, 25 ug, 50 ug, 100 ug, 250 ug, 500 ug, 1 mg, 2.5 mg, 5 mg, 10 mg, 25 mg, 50 mg, 100 mg, 250 mg, or 500 mg per kg of body weight).

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, intranasal, ocular and/or otic administration as well as intrathecal and infusion techniques. Implants of the compounds are also useful. Liquid forms may be prepared for injection, the term including subcutaneous, transdermal, intravenous, intramuscular, intrathecal, transtympanic injection and other parental routes of administration. The liquid compositions include aqueous solutions, with and without organic co-solvents, aqueous or oil suspensions, emulsions with edible oils, as well as similar pharmaceutical vehicles. In one embodiment, the administration comprises intravenous administration. In preferred embodiments the administration comprises topical administration, in particular topical administration to the ear canal, topical administration to the tympanic membrane, topical administration to the eye or a combination thereof. In some embodiments the compounds of the present application are applied to the tympanic membrane as an ear drop. In some embodiments the compounds of the present application are applied to the eye as an eye drop. In some preferred embodiments the dsRNA molecules disclosed herein are adminstered by transtympanic injection or by ear drops. In other embodiments the dsRNA molecules disclosed herein are adminstered by epidural or intrathecal administration.

Pharmaceutical compositions that include the nucleic acid molecule disclosed herein may be administered once daily (QD), twice a day (bid), three times a day (tid), four times a day (qid), or at any interval and for any duration that is medically appropriate. However, the therapeutic agent may also be dosed in dosage units containing two, three, four, five, six or more sub-doses administered at appropriate intervals throughout the day. In that case, the nucleic acid molecules contained in each sub-dose may be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. The dosage unit may contain a corresponding multiple of the daily dose. The composition can be compounded in such a way that the sum of the multiple units of a nucleic acid together contain a sufficient dose.

Pharmaceutical Compositions, Kits, and Containers

Also provided are compositions, kits, containers and formulations that include a nucleic acid molecule (e.g., an siNA molecule) as provided herein for down-regulating expression of RhoA for administering or distributing the nucleic acid molecule to a patient. A kit may include at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s) and/or any other component required for relevant laboratory, prognostic, diagnostic, prophylactic and therapeutic purposes. Indications and/or directions for such uses can be included on or with such container, as can reagents and other compositions or tools used for these purposes.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be a nucleic acid molecule capable of specifically binding RhoA mRNA and/or down-regulating the function of RhoA.

A kit may further include a second container that includes a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

Federal law requires that the use of pharmaceutical compositions in the therapy of humans be approved by an agency of the Federal government. In the United States, enforcement is the responsibility of the Food and Drug Administration, which issues appropriate regulations for securing such approval, detailed in 21 U.S.C. §301-392. Regulation for biologic material, including products made from the tissues of animals is provided under 42 U.S.C. §262. Similar approval is required by most foreign countries. Regulations vary from country to country, but individual procedures are well known to those in the art and the compositions and methods provided herein preferably comply accordingly.

The nucleic acid molecules disclosed herein can be used to treat diseases, conditions or disorders associated with RhoA, such as such as disease, injury, condition or pathology in the CNS, PNS, vestibular sensory system, visual system and/or circulatory (vascular, arterial) system and any other disease or conditions that are related to or will respond to the levels of RhoA in a cell or tissue (e.g. disease or disorder associated with aberrant and/or disrupted cell motility, cytoskeleton regulation and/or microtubule organization), alone or in combination with other therapies. As such, compositions, kits and methods disclosed herein may include packaging a nucleic acid molecule disclosed herein that includes a label or package insert. The label may include indications for use of the nucleic acid molecules such as use for treatment or prevention of, diseases, disorders, injuries and conditions of the central nervous system (CNS), peripheral nervous system (PNS), ocular system, circulatory (vascular, arterial) system or vestibular system, including, without being limited to, spinal cord injury (SCI), glaucoma, NAION, Alzheimer's disease, Meniere's disease and any other disease or condition disclosed herein. The label may include indications for use of the nucleic acid molecules such as use for treatment or prevention of attenuation of neuronal degeneration. Neuronal degeneration includes for example degeneration of the optic nerve and retina including retinal ganglion cells; the auditory nerve, (also known as the vestibulocochlear nerve or acoustic nerve and responsible for transmitting sound and equilibrium information from the inner ear to the brain); the hair cells of the inner ear that transmit information to the brain via the auditory nerve, which consists of the cochlear nerve, and the vestibular nerve, and emerges from the medulla oblongata and enters the inner skull via the internal acoustic meatus (or internal auditory meatus) in the temporal bone, along with the facial nerve. The label may include indications for use of the nucleic acid molecules such as use for treatment or prevention of malignancy or cancer. The label may include indications for use of the nucleic acid molecules such as use for treatment or prevention of any other disease or conditions that are related to or will respond to the levels of RhoA in a cell or tissue, alone or in combination with other therapies. A label may include an indication for use in reducing and/or down-regulating expression of RhoA. A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

Those skilled in the art will recognize that other treatments, drugs and therapies known in the art can be readily combined with the nucleic acid molecules herein (e.g. dsNA molecules) and are hence contemplated herein.

Methods of Treatment

In another aspect, the present invention relates to a method for the treatment of a subject in need of treatment for a disease or disorder associated with the abnormal expression of RhoA, comprising administering to the subject an amount of an inhibitor, which reduces or inhibits expression of RhoA.

RhoA is a GTPase that is involved in regulation of cytoskeleton and hence in all processes that are associated with cytoskeleton remodeling, including e.g., cell motility, invasion, proliferation. Its relevance to neuroregeneration directly stems from these properties.

In one embodiment, nucleic acid molecules may be used to down regulate or inhibit the expression of RhoA and/or RhoA proteins arising from RhoA and/or RhoA haplotype polymorphisms that are associated with a disease or condition, (e.g., neurodegeneration). Analysis of RhoA and/or RhoA genes, or RhoA and/or RhoA protein or RNA levels can be used to identify subjects with such polymorphisms or those subjects who are at risk of developing traits, conditions, or diseases described herein. These subjects are amenable to treatment, for example, treatment with nucleic acid molecules disclosed herein and any other composition useful in treating diseases related to RhoA and/or RhoA gene expression. As such, analysis of RhoA and/or RhoA protein or RNA levels can be used to determine treatment type and the course of therapy in treating a subject. Monitoring of RhoA and/or RhoA protein or RNA levels can be used to predict treatment outcome and to determine the efficacy of compounds and compositions that modulate the level and/or activity of certain RhoA and/or RhoA proteins associated with a trait, condition, or disease.

Provided are compositions and methods for inhibition of RhoA expression by using small nucleic acid molecules as provided herein, such as short interfering nucleic acid (siNA), interfering RNA (RNAi), short interfering RNA (siRNA), double-stranded RNA (dsRNA), micro-RNA (miRNA), and short hairpin RNA (shRNA) molecules capable of down-regulating RhoA gene expression or of mediating RNA interference against RhoA gene expression. The composition and methods disclosed herein are also useful in treating various conditions or diseases, such as, e.g. CNS, PNS and vestibular sensory system disorders, disease and injury, ocular disorders, Meniere's disease and pain.

The nucleic acid molecules disclosed herein individually, or in combination or in conjunction with other drugs, can be use for preventing or treating diseases, traits, conditions and/or disorders associated with RhoA, such as diseases, disorders and injury described herein.

The nucleic acid molecules disclosed herein are able to down-regulate the expression of RhoA in a sequence specific manner. The nucleic acid molecules may include a sense strand and an antisense strand which include contiguous nucleotides that are at least partially complementary (antisense) to a portion of RhoA mRNA.

In some embodiments, dsRNA specific for RhoA can be used in conjunction with other therapeutic agents and/or dsRNA specific for other molecular targets, that assist in neuroprotection and/or neuro-regeneration and/or neurogenesis, such as, without being limited to, neurosteroids (e.g., progesterone, pregnenolone), anxiolytic drugs (e.g., Etifoxin), growth factors, neurotrophic factors (e.g., CNTF), intraocular pressure (IOP) lowering drugs (e.g., latanoprost (Xalatan®)), stem cells.

Neurodegenerative, neurological, oncological and cerebrovascular disorders can be treated by RNA interference using nucleic acid molecules as disclosed herein. Exemplary neurodegenerative disorders include Alzheimer's disease, Parkinson's disease, spinal cord injury and ocular neurodegenerative disorders. The nucleic acid molecules disclosed herein may down-regulate the expression of RhoA in a sequence specific manner.

A method for treating or preventing RhoA associated disease or condition in a subject or organism may include contacting the subject or organism with a nucleic acid molecule as provided herein under conditions suitable to down-regulate the expression of the RhoA gene in the subject or organism.

A method for treating or preventing neurodegeneration in a subject or organism may include contacting the subject or organism with a nucleic acid molecule under conditions suitable to down-regulate the expression of the RhoA gene in the subject or organism.

A method for treating or preventing a neurodegenerative disorder, selected from the group consisting of Alzheimer's Alzheimer's Disease (AD), Amyotrophic Lateral Sclerosis (ALS), Parkinson's Disease (PD), Ataxia-telangiectasia (AT), Post Stroke Dementia (PSD), Ocular neurodegenerative disease, and/or Auditory neurodegenerative disease in a subject or organism may include contacting the subject or organism with a nucleic acid molecule under conditions suitable to down-regulate the expression of the RhoA gene in the subject or organism.

A method for treating or preventing Injury of the central nervous system, selected from the group consisting of Spinal Cord Injury (SCI), brain injury, neurological disorder, stroke and Parkinsonism in a subject or organism may include contacting the subject or organism with a nucleic acid molecule under conditions suitable to down-regulate the expression of the RhoA gene in the subject or organism.

A method for treating or preventing cerebrovascular disorders selected from the group consisting of ocula ischemic conditions, e.g. Anterior Ischemic Optic Neuropathy in a subject or organism may include contacting the subject or organism with a nucleic acid molecule under conditions suitable to down-regulate the expression of the RhoA gene in the subject or organism.

A method for treating or preventing neuropathy in a subject or organism may include contacting the subject or organism with a nucleic acid molecule under conditions suitable to down-regulate the expression of the RhoA gene in the subject or organism.

A method of treating or preventing a neuropathy in a subject selected from the group consisting of autonomic neuropathy, cancer-related neuropathy, compressive neuropathy, diabetic neuropathy, drug-induced neuropathy, toxic neuropathy, chemotherapy-induced neuropathy, gastrointestinal neuropathy, nutrition-related neuropathy, hereditary neuropathy, immune-mediated neuropathy and chronic immune-mediated poly neuropathy, infectious neuropathy and neuropatic pain may include contacting the subject or organism with a nucleic acid molecule under conditions suitable to down-regulate the expression of the RhoA gene in the subject or organism. In some embodiments the present invention provides a method of treating a subject suffering from diabetic neuropathy. In some embodiments the subject is afflicted with allodynia.

A method for promoting neuroregeneration in a subject or organism may include contacting the subject or organism with a nucleic acid molecule under conditions suitable to down-regulate the expression of the RhoA gene in the subject or organism.

A method for conferring neuroprotection to a subject or organism may include contacting the subject or organism with a nucleic acid molecule under conditions suitable to down-regulate the expression of the RhoA gene in the subject or organism.

A method for conferring neuroprotection to a subject or organism at risk or suffering from a neuropathy selected from the group consisting of autonomic neuropathy, cancer-related neuropathy, compressive neuropathy, diabetic neuropathy, drug-induced neuropathy, toxic neuropathy, chemotherapy-induced neuropathy, gastrointestinal neuropathy, nutrition-related neuropaty, hereditary neuropathy, immune-mediated neuropathy, infectious disease-mediated neuropathy, neuropatic pain and allodynia may include contacting the subject or organism with a nucleic acid molecule under conditions suitable to down-regulate the expression of the RhoA gene in the subject or organism.

A method for conferring neuroprotection to a subject or organism afflicted with a neurological injury or neurodegenerative disease may include contacting the subject or organism with a nucleic acid molecule under conditions suitable to down-regulate the expression of the RhoA gene in the subject or organism.

A method for treating or preventing a disease or disorder associated with aberrant and/or disrupted cell motility, cytoskeleton regulation and/or microtubule organization in a subject or organism may include contacting the subject or organism with a nucleic acid molecule under conditions suitable to down-regulate the expression of the RhoA gene in the subject or organism.

A method for treating or preventing an angiogenic disorder, vascular diseases and/or arterial diseases in a subject or organism may include contacting the subject or organism with a nucleic acid molecule under conditions suitable to down-regulate the expression of the RhoA gene in the subject or organism.

A method for treating or preventing ocular angiogenic disease or disorder in a subject or organism may include contacting the subject or organism with a nucleic acid molecule under conditions suitable to down-regulate the expression of the RhoA gene in the subject or organism.

A method for treating or preventing ocular angiogenic disease or disorder selected from the group consisting of corneal angiogenic disease or disorder, retinal angiogenic disease or disorder, choroidal angiogenic disease or disorder or a combination thereof may include contacting the subject or organism with a nucleic acid molecule under conditions suitable to down-regulate the expression of the RhoA gene in the subject or organism.

A method for treating or preventing retinopathy in a subject or organism may include contacting the subject or organism with a nucleic acid molecule under conditions suitable to down-regulate the expression of the RhoA gene in the subject or organism.

A method for treating or preventing diabetic retinopathy in a subject or organism may include contacting the subject or organism with a nucleic acid molecule under conditions suitable to down-regulate the expression of the RhoA gene in the subject or organism.

A method for treating or preventing corneal graft rejection in a corneal transplant subject or organism may include contacting the subject or organism with a nucleic acid molecule under conditions suitable to down-regulate the expression of the RhoA gene in the subject or organism.

A method for treating or preventing restenosis in a subject or organism may include contacting the subject or organism with a nucleic acid molecule under conditions suitable to down-regulate the expression of the RhoA gene in the subject or organism.

A method for treating or preventing cancer or malignancy or carcinoma or tumoriginesis in a subject or organism may include contacting the subject or organism with a nucleic acid molecule under conditions suitable to down-regulate the expression of the RhoA gene in the subject or organism.

In preferred embodiments the subject being treated is a warm-blooded animal and, in particular, mammals including human.

The methods of the invention comprise administering to the subject one or more inhibitory compounds which down-regulate expression of RhoA; and in particular siRNA in a therapeutically effective dose so as to thereby treat the subject.

The term "treatment" refers to both therapeutic treatment and prophylactic or preventative measures, wherein the object is to prevent or slow down (lessen) related disorders as listed above. Those in need of treatment include those already experiencing the disease or condition, those prone to having the disease or condition, and those in which the disease or condition is to be prevented. The compounds of the invention may be administered before, during or subsequent to the onset of the disease or condition or symptoms associated therewith. In cases where treatment is for the purpose of prevention, then the present invention relates to a method for delaying the onset of or averting the development of the disease or disorder.

The present invention relates to the use of compounds which down-regulate the expression of RhoA, particularly to novel double stranded RNA compounds (dsRNAs), in the treatment of diseases or conditions in which down-regulation of the expression of RhoA is beneficial.

Methods, molecules and compositions which down-regulate RhoA are discussed herein at length, and any of said molecules and/or compositions may be beneficially employed in the treatment of a subject suffering from any of said conditions. Preferred oligomer sequences useful in the preparation of siRNA directed to RhoA are listed in Tables I, II, III or IV.

Details of certain indications in which the compounds of the present invention are useful as therapeutics are described herein.

The present invention is illustrated in detail below with reference to examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

General Methods in Molecular Biology

Standard molecular biology techniques known in the art and not specifically described were generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry can be used for detection of cells containing specific DNA and mRNA sequences (Testoni et al., 1996, Blood 87:3822.) Methods of performing RT-PCR are also well known in the art.

Example 1

Generation of Sequences for Active dsRNA Compounds to RhoA and Production of the dsRNA Compounds Using proprietary algorithms and the sequence of human RhoA mRNA (SEQ ID NO:1), the sequences of many potential dsRNA compounds were generated. The sequences that have been generated using this method are either fully complementary to the corresponding human RhoA mRNA sequence (Table I "18 mers", Tables III and IV "19-mers") or include a mismatch between the 5' terminal nucleotide of the antisense strand and the target mRNA (Table II, "18+1-mer"). Candidate dsRNA compounds predicted in silico using proprietary algorithm to be most active against human RhoA mRNA, and at least one more species including rat, mouse, Rhesus monkey and/or chimpanzee RhoA mRNA, were selected.

The polynucleotide sequence of human RhoA mRNA is identified in NCBI Reference Sequence: NM_001664.2, and is set forth in SEQ ID NO:1. The RhoA mRNA encodes a polypeptide identified in the NCBI Reference Sequence NP_001655.1, set forth in SEQ ID NO:2. The SEQ ID NO. of each sense and antisense oligonucleotide is set forth in the tables. The following abbreviations are used in the Tables herein: "X=-species" refers to cross species identity with other animals: Rt-rat, Rh-rhesus monkey, Ms-Mouse; Cp-Chimpanzee. ORF: open reading frame. 19-mers, and 18+1-mers refer to oligomers of 19 and 18+1 (U at position 1 of Antisense, A at position 19 of sense strand) ribonucleic acids in length, respectively.

Each selected sequence pair (duplex) is tested as a 19-mer duplex with a 3' terminal dinucleotide dTdT overhang (_S709 compound).

TABLE I

| | | | | | | |
|---|---|---|---|---|---|---|
| | | 18-mer oligonucleotide pairs | | | | |
| Name | Sense 5->3 (18) | SEQ ID NO | AntiSense 5->3 (18) | SEQ ID NO | mRNA position | Human X-sp |
| RHOA_32-1 | GGAUCUUCGGAAUGAUGA | 3 | UCAUCAUUCCGAAGAUCC | 35 | 633-650 | Ms, Rt, Rh, Cp |
| RHOA_34-1 | CAUGCUUGCUCAUAGUCU | 4 | AGACUAUGAGCAAGCAUG | 36 | 332-349 | Rh, Cp |

TABLE I-continued

18-mer oligonucleotide pairs

| Name | Sense 5->3 (18) | SEQ ID NO | AntiSense 5->3 (18) | SEQ ID NO | mRNA position | Human X-sp |
|---|---|---|---|---|---|---|
| RHOA_35-1 | GGAAGAAACUGGUGAUUG | 5 | CAAUCACCAGUUUCUUCC | 37 | 290-307 | Rt, Rh, Cp |
| RHOA_36-1 | GGGUACAUGGAGUGUUCA | 6 | UGAACACUCCAUGUACCC | 38 | 739-756 | Rt, Rh, Cp |
| RHOA_39-1 | GAAGGAUCUUCGGAAUGA | 7 | UCAUUCCGAAGAUCCUUC | 39 | 630-647 | Ms, Rt, Rh, Cp |
| RHOA_40-1 | GGAAUGAUGAGCACACAA | 8 | UUGUGUGCUCAUCAUUCC | 40 | 641-658 | Rt, Rh, Cp |
| RHOA_41-1 | CUGAAGAAGGCAGAGAUA | 9 | UAUCUCUGCCUUCUUCAG | 41 | 698-615 | Ms, Rt, Rh, Cp |
| RHOA_42-1 | GCAGAGAUAUGGCAAACA | 10 | UGUUUGCCAUAUCUCUGC | 42 | 707-724 | Ms, Rt, Rh, Cp |
| RHOA_44-1 | GAACUAUGUGGCAGAUAU | 11 | AUAUCUGCCACAUAGUUC | 43 | 396-413 | Cp |
| RHOA_45-1 | CCAUCGACAGCCCUGAUA | 12 | UAUCAGGGCUGUCGAUGG | 44 | 530-547 | Rt, Rh, Cp |
| RHOA_46-1 | CCCAGAAGUCAAGCAUUU | 13 | AAAUGCUUGACUUCUGGG | 45 | 576-593 | Cp |
| RHOA_47-1 | GGCGCUUUUGGGUACAUG | 14 | CAUGUACCCAAAAGCGCC | 46 | 730-747 | Ms, Rt, Cp |
| RHOA_48-1 | CAGAAGUCAUCUUGCUAC | 15 | GUAGCAAGAUGACUUCUG | 47 | 973-990 | Rt, Rh, Cp |
| RHOA_49-1 | UAAGAAGGAUCUUCGGAA | 16 | UUCCGAAGAUCCUUCUUA | 48 | 627-644 | Rh, Cp |
| RHOA_50-1 | GUGGCAGAGUUACAGUUC | 17 | GAACUGUAACUCUGCCAC | 49 | 1351-1368 | Rt, Rh, Cp |
| RHOA_51-1 | CAGAGAUAUGGCAAACAG | 18 | CUGUUUGCCAUAUCUCUG | 50 | 708-725 | Ms, Rt, Rh, Cp |
| RHOA_53-1 | GAUUGGCGCUUUUGGGUA | 19 | UACCCAAAAGCGCCAAUC | 51 | 726-743 | Ms, Rt, Cp |
| RHOA_54-1 | GACAGCCCUGAUAGUUUA | 20 | UAAACUAUCAGGGCUGUC | 52 | 535-552 | Ms, Rt, Rh, Cp |
| RHOA_55-1 | GAAUGAUGAGCACACAAG | 21 | CUUGUGUGCUCAUCAUUC | 53 | 642-659 | Rt, Rh, Cp |
| RHOA_59-1 | CAAACAGGAUUGGCGCUU | 22 | AAGCGCCAAUCCUGUUUG | 54 | 719-736 | Ms, Rt, Cp |
| RHOA_60-1 | CAUCGACAGCCCUGAUAG | 23 | CUAUCAGGGCUGUCGAUG | 55 | 531-548 | Rt, Rh, Cp |
| RHOA_61-1 | GAUCUUCGGAAUGAUGAG | 24 | CUCAUCAUUCCGAAGAUC | 56 | 634-651 | Rt, Rh, Cp |
| RHOA_62-1 | CUGUGGCAGAGUUACAGU | 25 | ACUGUAACUCUGCCACAG | 57 | 1349-1366 | Rt, Rh, Cp |
| RHOA_63-1 | UCUUCGGAAUGAUGAGCA | 26 | UGCUCAUCAUUCCGAAGA | 58 | 636-653 | Rt, Rh, Cp |
| RHOA_64-1 | UGUGGCAGAGUUACAGUU | 27 | AACUGUAACUCUGCCACA | 59 | 1350-1367 | Rt, Rh, Cp |
| RHOA_65-1 | UGAUGAGCACACAAGGCG | 28 | CGCCUUGUGUGCUCAUCA | 60 | 645-662 | Rt, Rh, Cp |
| RHOA_66-1 | GUUUUCCAUCGACAGCC | 29 | GGCUGUCGAUGGAAAAAC | 61 | 524-541 | Rt, Rh, Cp |

TABLE I-continued

18-mer oligonucleotide pairs

| Name | Sense 5->3 (18) | SEQ ID NO | AntiSense 5->3 (18) | SEQ ID NO | mRNA position | Human X-sp |
|---|---|---|---|---|---|---|
| RHOA_67-1 | UUCGGAAUGAUGAGCACA | 30 | UGUGCUCAUCAUUCCGAA | 62 | 638-655 | Rt, Rh, Cp |
| RHOA_71-1 | CGAUGUUAUACUGAUGUG | 31 | CACAUCAGUAUAACAUCG | 63 | 507-524 | Rh, Cp |
| RHOA_72-1 | GUGUUUUCCAUCGACAG | 32 | CUGUCGAUGGAAAAACAC | 64 | 522-539 | Rt, Rh, Cp |
| RHOA_74-1 | AGCUGUGGCAGAGUUACA | 33 | UGUAACUCUGCCACAGCU | 65 | 1347-1364 | Rt, Rh, Cp |
| RHOA_75-1 | UCGACAGCCCUGAUAGUU | 34 | AACUAUCAGGGCUGUCGA | 66 | 533-550 | Rt, Rh, Cp |

TABLE II

18 + 1 -mer oligonucleotide pairs

| Name | Sense 5' > 3' (18 + A/U) (N')y-N$^2$ | SEQ ID NO | AntiSense 5' > 3' (18 + U/A) (N)x-N$^1$ | SEQ ID NO |
|---|---|---|---|---|
| RHOA_32 | GGAUCUUCGGAAUGAUGAA | 67 | UUCAUCAUUCCGAAGAUCC | 101 |
| RHOA_34 | CAUGCUUGCUCAUAGUCUA | 68 | UAGACUAUGAGCAAGCAUG | 102 |
| RHOA_35 | GGAAGAAACUGGUGAUUGA | 69 | UCAAUCACCAGUUUCUUCC | 103 |
| RHOA_36 | GGGUACAUGGAGUGUUCAA | 70 | UUGAACACUCCAUGUACCC | 104 |
| RHOA_39 | GAAGGAUCUUCGGAAUGAA | 71 | UUCAUUCCGAAGAUCCUUC | 105 |
| RHOA_40 | GGAAUGAUGAGCACACAAA | 72 | UUUGUGUGCUCAUCAUUCC | 106 |
| RHOA_41 | CUGAAGAAGGCAGAGAUAA | 73 | UUAUCUCUGCCUUCUUCAG | 107 |
| RHOA_42 | GCAGAGAUAUGGCAAACAA | 74 | UUGUUUGCCAUAUCUCUGC | 108 |
| RHOA_44 | GAACUAUGUGGCAGAUAUA | 75 | UAUAUCUGCCACAUAGUUC | 109 |
| RHOA_45 | CCAUCGACAGCCCUGAUAA | 76 | UUAUCAGGGCUGUCGAUGG | 110 |
| RHOA_46 | CCCAGAAGUCAAGCAUUUA | 77 | UAAAUGCUUGACUUCUGGG | 111 |
| RHOA_47 | GGCGCUUUUGGGUACAUGA | 78 | UCAUGUACCCAAAAGCGCC | 112 |
| RHOA_48 | CAGAAGUCAUCUUGCUACA | 79 | UGUAGCAAGAUGACUUCUG | 113 |
| RHOA_48u | CAGAAGUCAUCUUGCUACU | 80 | AGUAGCAAGAUGACUUCUG | 114 |
| RHOA_49 | UAAGAAGGAUCUUCGGAAA | 81 | UUUCCGAAGAUCCUUCUUA | 115 |
| RHOA_50 | GUGGCAGAGUUACAGUUCA | 82 | UGAACUGUAACUCUGCCAC | 116 |
| RHOA_51 | CAGAGAUAUGGCAAACAGA | 83 | UCUGUUUGCCAUAUCUCUG | 117 |
| RHOA_53 | GAUUGGCGCUUUUGGGUAA | 84 | UUACCCAAAAGCGCCAAUC | 118 |
| RHOA_54 | GACAGCCCUGAUAGUUUAA | 85 | UUAAACUAUCAGGGCUGUC | 119 |
| RHOA_55 | GAAUGAUGAGCACACAAGA | 86 | UCUUGUGUGCUCAUCAUUC | 120 |
| RHOA_59 | CAAACAGGAUUGGCGCUUA | 87 | UAAGCGCCAAUCCUGUUUG | 121 |
| RHOA_60 | CAUCGACAGCCCUGAUAGA | 88 | UCUAUCAGGGCUGUCGAUG | 122 |
| RHOA_61 | GAUCUUCGGAAUGAUGAGA | 89 | UCUCAUCAUUCCGAAGAUC | 123 |
| RHOA_61u | GAUCUUCGGAAUGAUGAGU | 90 | ACUCAUCAUUCCGAAGAUC | 124 |
| RHOA_62 | CUGUGGCAGAGUUACAGUA | 91 | UACUGUAACUCUGCCACAG | 125 |

TABLE II-continued

18 + 1 -mer oligonucleotide pairs

| Name | Sense 5' > 3' (18 + A/U) (N')y-N² | SEQ ID NO | AntiSense 5' > 3' (18 + U/A) (N)x-N¹ | SEQ ID NO |
|---|---|---|---|---|
| RHOA_63 | UCUUCGGAAUGAUGAGCAA | 92 | UUGCUCAUCAUUCCGAAGA | 126 |
| RHOA_64 | UGUGGCAGAGUUACAGUUA | 93 | UAACUGUAACUCUGCCACA | 127 |
| RHOA_65 | UGAUGAGCACACAAGGCGA | 94 | UCGCCUUGUGUGCUCAUCA | 128 |
| RHOA_66 | GUUUUUCCAUCGACAGCCA | 95 | UGGCUGUCGAUGGAAAAAC | 129 |
| RHOA_67 | UUCGGAAUGAUGAGCACAA | 96 | UUGUGCUCAUCAUUCCGAA | 130 |
| RHOA_71 | CGAUGUUAUACUGAUGUGA | 97 | UCACAUCAGUAUAACAUCG | 131 |
| RHOA_72 | GUGUUUUUCCAUCGACAGA | 98 | UCUGUCGAUGGAAAAACAC | 132 |
| RHOA_74 | AGCUGUGGCAGAGUUACAA | 99 | UUGUAACUCUGCCACAGCU | 133 |
| RHOA_75 | UCGACAGCCCUGAUAGUUA | 100 | UAACUAUCAGGGCUGUCGA | 134 |

TABLE III

19-mer oligonucleotide pairs

| Name | Sense 5' > 3' (N')y | SEQ ID NO | Antisense 5' > 3' (N)x | SEQ ID NO | position in mRNA |
|---|---|---|---|---|---|
| RHOA_31 | GCUUCUUUCUAGAAAGAGA | 135 | UCUCUUUCUAGAAAGAAGC | 149 | 1134-1152 |
| RHOA_33 | ACCAGUAUUUAGAAGCCAA | 136 | UUGGCUUCUAAAUACUGGU | 150 | 989-1007 |
| RHOA_37 | GCCCUGAUAGUUUAGAAAA | 137 | UUUUCUAAACUAUCAGGGC | 151 | 539-557 |
| RHOA_38 | CGACAGCCCUGAUAGUUUA | 138 | UAAACUAUCAGGGCUGUCG | 152 | 534-552 |
| RHOA_43 | CAGCCCUGAUAGUUUAGAA | 139 | UUCUAAACUAUCAGGGCUG | 153 | 537-555 |
| RHOA_52 | AGAAGGAUCUUCGGAAUGA | 140 | UCAUUCCGAAGAUCCUUCU | 154 | 629-647 |
| RHOA_56 | UAAGAAGGAUCUUCGGAAU | 141 | AUUCCGAAGAUCCUUCUUA | 155 | 627-645 |
| RHOA_57 | GGAUCUUCGGAAUGAUGAG | 142 | CUCAUCAUUCCGAAGAUCC | 156 | 633-651 |
| RHOA_58 | GUGGCAGAGUUACAGUUCU | 143 | AGAACUGUAACUCUGCCAC | 157 | 1351-1369 |
| RHOA_68 | CUUCGGAAUGAUGAGCACA | 144 | UGUGCUCAUCAUUCCGAAG | 158 | 637-655 |
| RHOA_69 | CUGUGGCAGAGUUACAGUU | 145 | AACUGUAACUCUGCCACAG | 159 | 1349-1367 |
| RHOA_70 | CAUCGACAGCCCUGAUAGU | 146 | ACUAUCAGGGCUGUCGAUG | 160 | 531-549 |
| RHOA_73 | CAGCUGUGGCAGAGUUACA | 147 | UGUAACUCUGCCACAGCUG | 161 | 1346-1364 |
| RHOA_76 | GAUCUUCGGAAUGAUGAGC | 148 | GCUCAUCAUUCCGAAGAUC | 162 | 634-652 |

Table IV provides oligonucleotide pairs useful in generating chemically modified dsRNA molecules. These oligonucleotide pairs were disclosed in WO 2009/044392, to the assignees of the present application.

TABLE IV

| Name | Sense 5->3 | SEQ ID NO | AntiSense 5->3 | SEQ ID NO | position in mRNA |
|---|---|---|---|---|---|
| RHOA_23 | CGGAAUGAUGAGCACACAA | 163 | UUGUGUGCUCAUCAUUCCG | 167 | [640-658] |
| RHOA_24 | GAAGGAUCUUCGGAAUGAU | 164 | AUCAUUCCGAAGAUCCUUC | 168 | [630-648] |

TABLE IV-continued

| Name | Sense 5->3 | SEQ ID NO | AntiSense 5->3 | SEQ ID NO | position in mRNA |
|---|---|---|---|---|---|
| RHOA_26 | UCGGAAUGAUGAGCACACA | 165 | UGUGUGCUCAUCAUUCCGA | 169 | [639-657] |
| RHOA_29 | UCGACAGCCCUGAUAGUUU | 166 | AAACUAUCAGGGCUGUCGA | 170 | [533-551] |

Table V provides oligonucleotide pairs for comparative activity studies.

TABLE V

| Name | Sense 5->3 | SEQ ID NO | AntiSense 5->3 | SEQ ID NO |
|---|---|---|---|---|
| RHOA_78 | AAGUCAUCUUGCUACCAGU | 171 | ACUGGUAGCAAGAUGACUU | 178 |
| RHOA_79 | GGCAGAGUUACAGUUCUGU | 172 | ACAGAACUGUAACUCUGCC | 179 |
| RHOA_80 | AGAAGUCAUCUUGCUACCA | 173 | UGGUAGCAAGAUGACUUCU | 180 |
| RHOA_81 | GCAGAGUUACAGUUCUGUG | 174 | CACAGAACUGUAACUCUGC | 181 |
| RHOA_82 | UGGCAGAGUUACAGUUCUG | 175 | CAGAACUGUAACUCUGCCA | 182 |
| RHOA_83 | CAGAGUUACAGUUCUGUGG | 176 | CCACAGAACUGUAACUCUG | 183 |
| RHOA_84 | GAAGUCAUCUUGCUACCAG | 177 | CUGGUAGCAAGAUGACUUC | 184 |

These RhoA dsRNA (dsRhoA) molecules, as well as active dsRhoA compounds previously identified and compatible with at least human and rat species, were synthesized and screened for in-vitro RNAi activity using qPCR analysis of residual RhoA mRNA levels in a human cell line. dsRNA compounds producing at least 85% knockdown at =<5 nM concentrations (<15% residual mRNA at 5 mM) were re-tested in rat cell line and advanced to further optimization. The selected candidate dsRNA molecules were optimized by incorporating chemical modifications to confer nuclease resistance, to reduce off-target activity, while preserving or increasing the on-target activity, and to reduce pro-inflammatory responses. Different types of chemical modifications and dsRNA sequence were evaluated. The chemically modified dsRNA that were synthesized are shown in FIG. 1. These modified dsRNA compounds were synthesized and screened in cell culture for RNAi activity. Those with similar or improved activity relative to the parent molecules were advanced to further characterization. First, nuclease resistance of dsRNA compounds was assessed in human plasma, human serum, CSF (cerebrospinal fluid) and/or cell lysates. dsRNA compounds exhibiting at least 10 hours stability in plasma, serum, CSF and or cell lysates were advanced to off-target assays for which the psiCHECK™ (Promega) luciferase reporter system was used. RNAi-mediated inhibition of luciferase expression was analyzed in cell culture.

Testing for potential activation of innate immunity by dsRNA compounds is performed using three different in vitro methods: (a) assessment of dsRNA activation of TLR/RIG-I/Mda5-dependent luciferase reporter; (b) assessment of cytokine production in dsRNA-treated human peripheral blood mononuclear cells (PBMC); (c) assessment of activation of interferon (IFN) response by analyzing expression of IFN-responsive genes in dsRNA-treated human PBMCs. These methods are familiar to, and easily carried out by, a person with skill in the art.

In Vitro Testing of Control Set

The control set includes dsRNA compounds with a 19-mer duplex and the dinucleotide dTdT covalently attached to the 3' terminus of the sense and antisense strands. The control compounds are named RHOA_X_S709.

About $2 \times 10^5$ human PC3 cells endogenously expressing RhoA gene, were inoculated in 1.5 mL growth medium in order to reach 30-50% confluence after 24 hours. Cells were transfected with dsRNA Lipofectamine™2000 reagent to a final concentration of 0.3-5 nM per transfected cells. Cells were incubated at 37±1° C., 5% $CO_2$ for 48 hours. Cy3-labeled dsRNA duplexes were used as positive control for transfection efficiency. Cells treated only with Lipofectamine™2000 reagent were used as negative control for knock down activity. dsRNA transfected cells were harvested and RNA was isolated using EZ-RNA™ kit [Biological Industries (#20-410-100)]. The dsRNA compounds that were tested using this protocol include pairs set forth in Tables I, II, III and V. Activity data for unmodified 18+A duplexes is provided below in Table A. 18+A refers to a 19-base pair duplex wherein the oligonucleotide (N')y-N2 having full match to the target mRNA at positions 1-18 [(N')y] and an A (N2, adenosine) at position 19, is duplexed with the complementary oligonucleotide (N)x—N1. The compounds were unmodified and were synthesized with 3' dTdT overhangs for testing of activity in vitro. The activity results in Table A and in Table B are provided as % residual target after application of dsRNA at a concentration of 5 nM, 0.5 nM and 0.1 nM.

TABLE A knock down activity results (% residual mRNA) for 18 + 1 mer dsRNA which include unmodified ribonucleotides in both strands and the dTdT dinucleotide overhang at the 3' termini of the sense and antisense strands.

| Name _S709 | Sense 5' > 3' (18 + A) (N')y-N2 | AntiSense 5' > 3' (18 + U) (N)x-N1 | 5 nM | 0.5 nM | 0.1 nM |
|---|---|---|---|---|---|
| RHOA_32 | GGAUCUUCGGAAUGAUGAA (SEQ ID NO: 67) | UUCAUCAUUCCGAAGAUCC (SEQ ID NO: 101) | 6.4 | 13.8 | |
| RHOA_34 | CAUGCUUGCUCAUAGUCUA (SEQ ID NO: 68) | UAGACUAUGAGCAAGCAUG (SEQ ID NO: 102) | 2.8 | 4.4 | 6.1 |
| RHOA_35 | GGAAGAAACUGGUGAUUGA (SEQ ID NO: 69) | UCAAUCACCAGUUUCUUCC (SEQ ID NO: 103) | 4.6 | 6.4 | 13.1 |
| RHOA_36 | GGGUACAUGGAGUGUUCAA (SEQ ID NO: 70) | UUGAACACUCCAUGUACCC (SEQ ID NO: 104) | 4.4 | 8.4 | 18.6 |
| RHOA_39 | GAAGGAUCUUCGGAAUGAA (SEQ ID NO: 71) | UUCAUUCCGAAGAUCCUUC (SEQ ID NO: 105) | 2.4 | 6.0 | 26.1 |
| RHOA_40 | GGAAUGAUGAGCACACAAA (SEQ ID NO: 72) | UUUGUGUGCUCAUCAUUCC (SEQ ID NO: 106) | 5.4 | 18.4 | 30.6 |
| RHOA_41 | CUGAAGAAGGCAGAGAUAA (SEQ ID NO: 73) | UUAUCUCUGCCUUCUUCAG (SEQ ID NO: 107) | 2.1 | 5.2 | 14.5 |
| RHOA_42 | GCAGAGAUAUGGCAAACAA (SEQ ID NO: 74) | UUGUUUGCCAUAUCUCUGC (SEQ ID NO: 108) | 2.6 | 5.0 | 10.6 |
| RHOA_44 | GAACUAUGUGGCAGAUAUA (SEQ ID NO: 75) | UAUAUCUGCCACAUAGUUC (SEQ ID NO: 109) | 1.9 | 11.4 | 15.3 |
| RHOA_45 | CCAUCGACAGCCCUGAUAA (SEQ ID NO: 76) | UUAUCAGGGCUGUCGAUGG (SEQ ID NO: 110) | 3.1 | 5.3 | 50.3 |
| RHOA_46 | CCCAGAAGUCAAGCAUUUA (SEQ ID NO: 77) | UAAAUGCUUGACUUCUGGG (SEQ ID NO: 111) | 4.2 | 15.7 | 36.4 |
| RHOA_47 | GGCGCUUUUGGGUACAUGA (SEQ ID NO: 78) | UCAUGUACCCAAAAGCGCC (SEQ ID NO: 112) | 2.0 | 6.2 | 18.5 |
| RHOA_48 | CAGAAGUCAUCUUGCUACA (SEQ ID NO: 79) | UGUAGCAAGAUGACUUCUG (SEQ ID NO: 113) | 2.6 | 3.9 | 15.6 |
| RHOA_49 | UAAGAAGGAUCUUCGGAAA (SEQ ID NO: 81) | UUUCCGAAGAUCCUUCUUA (SEQ ID NO: 115) | 3.6 | 3.6 | 17.5 |
| RHOA_50 | GUGGCAGAGUUACAGUUCA (SEQ ID NO: 82) | UGAACUGUAACUCUGCCAC (SEQ ID NO: 116) | 2.3 | 12.3 | 17.5 |
| RHOA_51 | CAGAGAUAUGGCAAACAGA (SEQ ID NO: 83) | UCUGUUUGCCAUAUCUCUG (SEQ ID NO: 117) | 1.6 | 12.5 | 35.9 |
| RHOA_53 | GAUUGGCGCUUUUGGGUAA (SEQ ID NO: 84) | UUACCCAAAAGCGCCAAUC (SEQ ID NO: 118) | 2.7 | 5.2 | 10.6 |
| RHOA_54 | GACAGCCCUGAUAGUUUAA (SEQ ID NO: 85) | UUAAACUAUCAGGGCUGUC (SEQ ID NO: 119) | 2.5 | 3.1 | 19.5 |
| RHOA_55 | GAAUGAUGAGCACACAAGA (SEQ ID NO: 86) | UCUUGUGUGCUCAUCAUUC (SEQ ID NO: 120) | 3.0 | 10.5 | 22.6 |
| RHOA_59 | CAAACAGGAUUGGCGCUUA (SEQ ID NO: 87) | UAAGCGCCAAUCCUGUUUG (SEQ ID NO: 121) | 2.9 | 4.9 | 11.3 |
| RHOA_60 | CAUCGACAGCCCUGAUAGA (SEQ ID NO: 88) | UCUAUCAGGGCUGUCGAUG (SEQ ID NO: 122) | 1.8 | 5.1 | 11.4 |
| RHOA_61 | GAUCUUCGGAAUGAUGAGA (SEQ ID NO: 89) | UCUCAUCAUUCCGAAGAUC (SEQ ID NO: 123) | 6.1 | 26.4 | 49.3 |
| RHOA_62 | CUGUGGCAGAGUUACAGUA (SEQ ID NO: 91) | UACUGUAACUCUGCCACAG (SEQ ID NO: 125) | 8.3 | 25.1 | 52.8 |
| RHOA_63 | UCUUCGGAAUGAUGAGCAA (SEQ ID NO: 92) | UUGCUCAUCAUUCCGAAGA (SEQ ID NO: 126) | 2.7 | 6.2 | 43.4 |

TABLE A-continued knock down activity results (% residual mRNA) for 18 + 1 mer dsRNA which include unmodified ribonucleotides in both strands and the dTdT dinucleotide overhang at the 3' termini of the sense and antisense strands.

| Name _S709 | Sense 5' > 3' (18 + A) (N')y-N2 | AntiSense 5' > 3' (18 + U) (N)x-N1 | 5 nM | 0.5 nM | 0.1 nM |
|---|---|---|---|---|---|
| RHOA_64 | UGUGGCAGAGUUACAGUUA (SEQ ID NO: 93) | UAACUGUAACUCUGCCACA (SEQ ID NO: 127) | 12.6 | 39.2 | 51.9 |
| RHOA_65 | UGAUGAGCACACAAGGCGA (SEQ ID NO: 94) | UCGCCUUGUGUGCUCAUCA (SEQ ID NO: 128) | 2.0 | 4.6 | 22.5 |
| RHOA_66 | GUUUUCCAUCGACAGCCA (SEQ ID NO: 95) | UGGCUGUCGAUGGAAAAAC (SEQ ID NO: 129) | 1.3 | 2.8 | 19.2 |
| RHOA_67 | UUCGGAAUGAUGAGCACAA (SEQ ID NO: 96) | UUGUGCUCAUCAUUCCGAA (SEQ ID NO: 130) | 8.3 |  | 31.9 |
| RHOA_71 | CGAUGUUAUACUGAUGUGA (SEQ ID NO: 97) | UCACAUCAGUAUAACAUCG (SEQ ID NO: 131) | 2.3 | 5.7 | 15.5 |
| RHOA_72 | GUGUUUUCCAUCGACAGA (SEQ ID NO: 98) | UCUGUCGAUGGAAAAACAC (SEQ ID NO: 132) | 2.0 | 4.1 | 6.3 |
| RHOA_74 | AGCUGUGGCAGAGUUACAA (SEQ ID NO: 99) | UUGUAACUCUGCCACAGCU (SEQ ID NO: 133) | 9.5 | 41.3 |  |
| RHOA_75 | UCGACAGCCCUGAUAGUUA (SEQ ID NO: 100) | UAACUAUCAGGGCUGUCGA (SEQ ID NO: 134) | 1.8 | 5.6 |  |

TABLE B

Knock down activity results (% residual mRNA) for 19 mer dsRNA which include unmodified ribonucleotides in both strands and the dTdT dinucleotide overhang at the 3' terminus of both strands.

| Name | Sense 5' > 3' (N')y | AntiSense 5' > 3' (N)x | 5 nM | 0.5 nM | 0.1 nM |
|---|---|---|---|---|---|
| RHOA_23 | CGGAAUGAUGAGCACACAA (SEQ ID NO: 163) | UUGUGUGCUCAUCAUUCCG (SEQ ID NO: 167) | 1.6 | 17.5 | 26.8 |
| RHOA_24 | GAAGGAUCUUCGGAAUGAU (SEQ ID NO: 164) | AUCAUUCCGAAGAUCCUUC (SEQ ID NO: 168) | 5.3 | 20.8 | 4.4 |
| RHOA_26 | UCGGAAUGAUGAGCACACA (SEQ ID NO: 165) | UGUGUGCUCAUCAUUCCGA (SEQ ID NO: 169) | 6.4 | 28.5 | 59.6 |
| RHOA_29 | UCGACAGCCCUGAUAGUUU (SEQ ID NO: 166) | AAACUAUCAGGGCUGUCGA (SEQ ID NO: 170) | 2.1 | 7.3 | 10.0 |
| RHOA_31 | GCUUCUUUCUAGAAAGAGA (SEQ ID NO: 135) | UCUCUUUCUAGAAAGAAGC (SEQ ID NO: 149) | 2.3 | 8.7 | 37.0 |
| RHOA_33 | ACCAGUAUUUAGAAGCCAA (SEQ ID NO: 136) | UUGGCUUCUAAAUACUGGU (SEQ ID NO: 150) | 2.4 | 3.7 | 5.7 |
| RHOA_37 | GCCCUGAUAGUUUAGAAAA (SEQ ID NO: 137) | UUUUCUAAACUAUCAGGGC (SEQ ID NO: 151) | 1.8 | 5.1 | 18.7 |
| RHOA_38 | CGACAGCCCUGAUAGUUUA (SEQ ID NO: 138) | UAAACUAUCAGGGCUGUCG (SEQ ID NO: 152) | 4.9 | 5.2 | 8.8 |
| RHOA_43 | CAGCCCUGAUAGUUUAGAA (SEQ ID NO: 139) | UUCUAAACUAUCAGGGCUG (SEQ ID NO: 153) | 3.4 | 20.4 | 17.0 |
| RHOA_52 | AGAAGGAUCUUCGGAAUGA (SEQ ID NO: 140) | UCAUUCCGAAGAUCCUUCU (SEQ ID NO: 154) | 3.5 | 6.5 | 9.9 |
| RHOA_56 | UAAGAAGGAUCUUCGGAAU (SEQ ID NO: 141) | AUUCCGAAGAUCCUUCUUA (SEQ ID NO: 155) | 3.4 | 21.2 | 39.1 |
| RHOA_57 | GGAUCUUCGGAAUGAUGAG (SEQ ID NO: 142) | CUCAUCAUUCCGAAGAUCC (SEQ ID NO: 156) | 6.1 | 23.0 | 32.8 |

TABLE B-continued

Knock down activity results (% residual mRNA) for 19 mer dsRNA which include unmodified ribonucleotides in both strands and the dTdT dinucleotide overhang at the 3' terminus of both strands.

| Name | Sense 5' > 3' (N')y | AntiSense 5' > 3' (N)x | 5 nM | 0.5 nM | 0.1 nM |
|---|---|---|---|---|---|
| RHOA_58 | GUGGCAGAGUUACAGUUCU (SEQ ID NO: 143) | AGAACUGUAACUCUGCCAC (SEQ ID NO: 157) | 4.5 | 10.3 | 22.7 |
| RHOA_68 | CUUCGGAAUGAUGAGCACA (SEQ ID NO: 144) | UGUGCUCAUCAUUCCGAAG (SEQ ID NO: 158) | 2.8 | 7.9 | 38.5 |
| RHOA_69 | CUGUGGCAGAGUUACAGUU (SEQ ID NO: 145) | AACUGUAACUCUGCCACAG (SEQ ID NO: 159) | 10.7 | 25.3 | 55.6 |
| RHOA_70 | CAUCGACAGCCCUGAUAGU (SEQ ID NO: 146) | ACUAUCAGGGCUGUCGAUG (SEQ ID NO: 160) | 1.2 | 1.9 | 8.3 |
| RHOA_73 | CAGCUGUGGCAGAGUUACA (SEQ ID NO: 147) | UGUAACUCUGCCACAGCUG (SEQ ID NO: 161) | 2.0 | 22.6 | 45.1 |

Activity of certain preferred molecules (48, 50 58) compared to control molecules (78-84) is shown in Table C.

TABLE C

| | Residual % 20 nM | Residual % 5 nM | Residual % 1.25 nM | Residual % 0.3125 nM |
|---|---|---|---|---|
| RHOA_48_S709 | 11 | 13 | 30 | 25 |
| RHOA_50_S709 | 16 | 21 | | |
| RHOA_58_S709 | 10 | 10 | 18 | 21 |
| RHOA_78_S709 | | | | |
| RHOA_79_S709 | 26 | 23 | 39 | 61 |
| RHOA_80_S709 | | 20 | 22 | 58 |
| RHOA_81_S709 | 47 | 62 | 74 | 60 |
| RHOA_82_S709 | 23 | 44 | 77 | 81 |
| RHOA_83_S709 RHOA_84_S709 | 42 | 63 | 66 | 62 |

Chemically modified dsRNA molecules and activity (knock down) profiled are provided in FIG. 1. The legend for the modifications is as follows: a prefix "z" indicates a moiety (nucleotide or non-nucleotide) covalently attached to the 3' or 5' terminal nucleotide. For example zdT refers to a dT overhang; zdT; zdT refers to a dTdT overhang. A prefix "y" indicates a nucleotide substitution, for example yLdA refers to a L-deoxyriboadenine substituted for a ribonucleotide in the sense strand or antisense strand; and yrU refers to a uridine substituted for another ribonucleotide in the sense or antisense oligonucleotide. A prefix "m" refers to a 2'OMe sugar modified ribonucleotide. Additional codes are set forth hereinbelow in Table D.

TABLE D legend for chemically modified dsRNA molecules

| Code | Description |
|---|---|
| rA | riboadenosine-3'-phosphate; 3'-adenylic acid |
| rC | ribocytidine-3'-phosphate; 3'-cytidylic acid |
| rG | riboguanosine-3'-phosphate; 3'-guanylic acid |
| rU | ribouridine-3'-phosphate; 3'-uridylic acid |
| mA | 2'-O-methyladenosine-3'-phosphate; 2'-O-methyl-3'-adenylic acid |
| mC | 2'-O-methylcytidine-3'-phosphate; 2'-O-methyl-3'-cytidylic acid |
| mG | 2'-O-methylguanosine-3'-phosphate; 2'-O-methyl-3'-guanylic acid |
| mU | 2'-O-methyluridine-3'-phosphate; 2'-O-methyl-3'-uridylic acid |
| dA | deoxyriboadenosine-3'-phosphate; 2'-deoxyribo-3'-adenylic acid |
| dC | deoxyribocytidine-3'-phosphate; 2'-deoxyribo-3'-cytidylic acid |
| dG | deoxyriboguanosine-3'-phosphate; 2'-deoxyribo-3'-guanylic acid |
| dT | thymidine-3'-phosphate; 3'-thymidylic acid |
| rA2p | riboadenosine-2'-phosphate; 2'-adenylic acid |
| rC2p | ribocytidine-2'-phosphate; 2'-cytidylic acid |
| rG2p | riboguanosine-2'-phosphate; 2'-guanylic acid |
| rU2p | ribouridine-2'-phosphate; 2'-uridylic acid |
| LdA | L-deoxyriboadenosine-3'-phosphate (mirror dA) |
| LdC | L-deoxyribocytidine-3'-phosphate (mirror dC) |
| LdG | L-deoxyriboguanosine-3'-phosphate (mirror dG) |
| LdT | L-deoxyribothymidine-3'-phosphate (mirror dT) |
| zVEp | Vitamin E |

TABLE D-continued legend for chemically modified dsRNA molecules

| Code | Description |
|---|---|
| dB | abasic deoxyribose-3'-phosphate; 1,2-dideoxy-D-ribofuranose-3-phosphate; 1,4-anhydro-2-deoxy-D-ribitol-3-phosphate |
| zidB | Inverted abasic deoxyribose-5'-phosphate at terminus; 5' = 5'-5' idAb; At 3' = 3'-3' idAb |
| p | 5' phosphate |
| s | 5' phosphorothioate |
| $ | lacking a 3' linker (used together with above nucleotides at the 3' end of the sequence) |
| 3mN2p | 3'-O-methyl ribo-nucleotide-2'-phosphate |
| y8Oxo-dG | substitute a ribonucleotide with with 8-Oxo-dG (Glen Research: 10-1028-xx) |
| yC3p | substitute a ribonucleotide with with 3-Hydroxypropane-1-phosphate |
| ydA | substitute a ribonucleotide with with deoxyriboAdenosine-3'-phosphate; |
| ydT | substitute a ribonucleotide with with deoxyriboThymidine-3'-phosphate; |
| ydU | substitute a ribonucleotide with with deoxyUridine |
| yLdA | substitute a ribonucleotide with with L-deoxyriboAdenosine-3'-phosphate |
| yLdC | substitute a ribonucleotide with with L-deoxyriboCytidine-3'-phosphate |
| yLdG | substitute a ribonucleotide with with L-deoxyriboGuanosine-3'-phosphate |
| ymA | substitute a ribonucleotide with with 2'-O-methylAdenosine-3'-phosphate; |
| ymC | substitute a ribonucleotide with with 2'-O-methylCytidine-3'-phosphate; |
| ymU | substitute a ribonucleotide with with 2'-O-methylUridine-3'-phosphate; |
| yrA | substitute a ribonucleotide with with riboAdenosine-3'-phosphate; |
| yrC | substitute a ribonucleotide with with riboCytidine-3'-phosphate; |
| yrG | substitute a ribonucleotide with with riboGuanosine-3'-phosphate; |
| yrU | substitute a ribonucleotide with with riboUridine-3'-phosphate; |
| zC3p | $(CH2)3$-Pi = 3-Hydroxypropane-1-phosphate |
| zC3p; zC3p | $(CH2)3$-Pi x2; =3-Hydroxypropane-1-phosphate; |
| zC5Np | Amino-C5-Phosphate |
| zC6Np | Amino-C6-Phosphate |
| zdC(N4al) | deoxy Cytidine N4 Amino linker (ChemGenes: CLP-1329) |
| zdT; zdT | 3' terminal dTdToverhang |
| zidB | Inverted abasic deoxyribose-5'-phosphate; At 5' = 5'-5' idAb; At 3' = 3'-3' idAb |
| zidT | Inverted-Deoxy-Thymidine-5'-Phosphate |
| ziLd | Inverted L-DNA |
| zLdA | L-deoxyriboAdenosine-3'-phosphate |
| zLdC | L-deoxyriboCytidine-3'-phosphate |
| zLdG | L-deoxyriboGuanosine-3'-phosphate |
| zLdT | L-deoxyriboThymidine-3'-phosphate |

In Vitro Testing of RhoA Nucleic Acid Compounds

Cell Lines: Human prostate adenocarcinoma PC3 cells (ATCC, Cat# CRL-1435) were grown in RPMI medium supplemented with 10% FBS and 2 mM L-Glutamine and human epithelial cervical cancer HeLa cells (ATCC, Cat#CCL-2) were maintained in Dulbecco's modified Eagle's medium (DMEM) supplemented with 10% FBS, 2 mM L-glutamine. Cells were maintained at 37° C. in 5% $CO2$.

About $2\times10^5$ human PC-3 cells endogenously expressing RhoA gene, were inoculated in 1.5 mL growth medium in order to reach 30-50% confluence after 24 hours. Cells were transfected with dsRNA and Lipofectamine™2000 reagent to a final concentration of 0.1-5 nM per transfected cells. Cells were incubated at 37±1° C., 5% $CO_2$ for 48 hours. Cy3-labeled dsRNA duplexes were used as positive control for transfection efficiency. Cells treated with Lipofectamine™2000 reagent were used as negative control for siRNA activity. dsRNA transfected cells were harvested and RNA was isolated using EZ-RNA™ kit [Biological Industries (#20-410-100)].

The percent of inhibition of target gene expression by each tested dsRNA duplex was determined by qPCR analysis of a target mRNA from cells. Reverse transcription was performed by synthesizing cDNA from the cells and determining target gene mRNA levels by Real Time qPCR. Measured cell mRNA levels were normalized to those of the Cyclophilin A (CYNA, PPIA) mRNA for each sample. Knock down activity was determined based on the ratio of the target gene mRNA quantity in dsRNA-treated samples versus non-transfected control samples.

The percent of inhibition of target gene expression by each tested dsRNA duplex was determined by qPCR analysis of a target mRNA from cells. Reverse transcription was performed by synthesizing cDNA from the cells and determining target gene mRNA levels by Real Time qPCR. Measured cell mRNA levels were normalized to those of the Cyclophilin A (CYNA, PPIA) mRNA for each sample. Knock down activity was determined based on the ratio of the target gene mRNA quantity in dsRNA-treated samples versus non-transfected control samples.

Characterization of Nuclease Stability of RhoA dsRNAs

Endo- and exonuclease stability of dsRNA RhoA compounds were determined as follows (1) Human plasma and/or human Cerebrospinal fluid (CSF) (endonuclease stability)

Assessment of dsRNA integrity by ethidium bromide (EthBr) staining of non-denaturing gels Assessment of stability of each dsRNA strand in the duplex by hybridization of sequence-specific probes to Northern blots obtained from denaturing gels (2) Extracts of human HCT116 (exonuclease stability)

Assessment of stability of each dsRNA strand in the duplex by hybridization of sequence-specific probes to Northern blots obtained from denaturing gels.

(3) Stability in plasma (endonuclease resistance)

RhoA dsRNA compounds were incubated in complete human plasma or CSF at 37° C. for up to 24 hours. 3 μL aliquots were collected and snap-frozen in liquid $N_2$ at 1, 3, 6, 12 and 24 hours of incubation. dsRNA integrity was analyzed (1) by electrophoresis (~40 ng/lane) through native 15% native polyacrylamide gel (PAGE) followed by Ethidium bromide (EthBr) staining (human plasma samples only) and (2) by electrophoresis (of 1 ng/lane) (1:87 dilution in Formamide) through a denaturing 8M urea 8% PAGE followed by electro-blotting to Nylon membranes (Hybond-XL) and hybridization with radioactively labeled oligonucleotide probes detecting either sense or antisense strands of the dsRNA duplex. 40 ng or 1 ng dsRNA dissolved in 5 μL PBS and loaded on native or denaturing PAGE, respectively, served as a migration references for the intact untreated dsRNA molecule. Non-modified dsRNA counterparts, i.e. dsRNA compounds having the same nucleotide sequence with all of the ribonucleotides being unmodified, were used as negative control for endonuclease stability.

Stability in human HCT116 cytosolic extracts (exonuclease resistance): Exonuclease resistance of dsRNA RhoA compounds was evaluated in cytosolic extracts of human HCT116 by incubation at 37° C. for different time intervals (1, 3, 6, 12 or 24 hours). dsRNA integrity after various incubation times was analyzed by electrophoresis through denaturing gels (PAGE), blotting and subsequent hybridization to radioactively labeled strand-specific probes (oligonucleotide probes detecting either sense or antisense strands of the dsRNA compound duplex.

Stability results of compounds tested is shown herein below in Tables E, F and G. Stability data is presented in hours, i.e. 24 refers to 24 hours. Some of the preferred molecules are stable in plasma and or serum for more than 3 hours.

Table E shows stability for control compounds (RHOA_48, 50 and 58 (S709)) and for chemically modified dsRNA based on RHOA48 and RHOA_48u.

TABLE E

| Compound name | Plasma | | Extract HCT116 | | CSF | |
|---|---|---|---|---|---|---|
| | Sense | Antisense | Sense | Antisense | Sense | Antisense |
| RHOA_48_S709 | <3 | <3 | <3 | <3 | 6 | 6 |
| RHOA_50_S709 | <3 | <3 | <3 | <3 | | |
| RHOA_58_S709 | <3 | <3 | <3 | <3 | 6 | 6 |
| RHOA_48_S1626 | <3 | | | | | |
| RHOA_48_S1631 | <3 | | | | | |
| RHOA_48_S1632 | <3 | | | | | |
| RHOA_48_S1633 | <3 | | | | | |
| RHOA_48_S1634 | <3 | | | | | |
| RHOA_48u_S1635 | <3 | | | | | |
| RHOA_48u_S1812 | <3 | 24 | | 24 | 24 | |
| RHOA_48u_S1813 | <3 | 24 | | 24 | 24 | |
| RHOA_48_S1814 | <3 | 24 | | | | |
| RHOA_48_S1815 | <3 | 24 | | | | |
| RHOA_48_S1833 | <3 | 24 | | 24 | 24 | |
| RHOA_48_S1834 | <3 | 24 | | | | |
| RHOA_48_S1850 | <3 | 24 | | | | |
| RHOA_48_S1851 | <3 | 24 | | | | |
| RHOA_48_S1852 | <3 | 24 | | | | |
| RHOA_48_S1853 | <3 | 24 | | | | |
| RHOA_48_S1854 | <3 | 24 | | | | |
| RHOA_48_S1855 | 24 | 24 | | | | |
| RHOA_48_S1856 | 24 | 24 | 24 | 24 | | |
| RHOA_48_S1857 | 24 | 24 | 10 | 10 | | |
| RHOA_48_S1858 | 24 | 24 | | | | |
| RHOA_48_S1859 | 24 | 24 | | | | |
| RHOA_48_S1860 | 24 | 24 | | | | |
| RHOA_48u_S1870 | 24 | 24 | 24 | 24 | | |
| RHOA_48u_S1871 | 24 | 24 | 24 | 24 | | |
| RHOA_48_S1872 | 24 | 24 | 24 | 24 | | |
| RHOA_48_S1873 | 24 | 24 | 24 | 24 | | |
| RHOA_48_S1874 | 24 | 24 | | | | |
| RHOA_48_S1875 | 24 | 24 | | | | |
| RHOA_48_S1876 | 24 | 24 | | | | |
| RHOA_48_S1884 | 24 | 24 | | | | |

TABLE E-continued

| Compound name | Plasma | | Extract HCT116 | | CSF | |
|---|---|---|---|---|---|---|
| | Sense | Antisense | Sense | Antisense | Sense | Antisense |
| RHOA_48_S1885 | 24 | 24 | | | | |
| RHOA_48_S1886 | 24 | 24 | | | | |
| RHOA_48_S1887 | 24 | 24 | | | | |

Table F shows stability data for chemically modified dsRNA based on RHOA_50.

TABLE F

| Compound name | Plasma | | Extract HCT116 | | CSF | |
|---|---|---|---|---|---|---|
| | Sense | Antisense | Sense | Antisense | Sense | Antisense |
| RHOA_50_S1639 | 8 | | | | | |
| RHOA_50_S1640 | 8 | | | | | |
| RHOA_50_S1641 | 8 | | | | | |
| RHOA_50_S1642 | 8 | | | | | |
| RHOA_50_S1787 | 12 | 12 | | | | |
| RHOA_50_S1793 | 24 | 24 | | | | |
| RHOA_50_S1794 | 12 | 24 | | | | |
| RHOA_50_S1795 | 24 | 24 | | | | |
| RHOA_50_S1796 | 12 | 24 | 12 | 12 | 24 | 24 |
| RHOA_50_S1797 | 24 | 24 | | | | |
| RHOA_50_S1798 | 24 | 24 | 12 | 12 | 24 | 24 |
| RHOA_50_S1799 | 12 | 12 | 12 | 12 | 24 | 24 |
| RHOA_50_S1800 | 12 | 24 | | | | |
| RHOA_50_S1835 | 24 | 24 | | | | |
| RHOA_50_S1836 | 24 | 24 | | | | |
| RHOA_50_S1837 | 24 | 24 | | | | |
| RHOA_50_S1838 | 24 | 24 | | | | |
| RHOA_50_S1839 | 24 | 24 | 12 | 12 | | |
| RHOA_50_S1840 | 24 | 24 | | | | |
| RHOA_50_S1865 | 24 | 24 | <3 | <3 | | |
| RHOA_50_S1866 | 24 | 24 | <3 | <3 | | |
| RHOA_50_S1882 | 24 | 24 | 3 | 3 | | |
| RHOA_50_S1883 | 24 | 24 | 3 | 3 | | |

Table G shows stability data for chemically modified dsRNA based on RHOA_58.

TABLE G

| Compound name | Plasma | | Extract HCT116 | | CSF | |
|---|---|---|---|---|---|---|
| | Sense | Antisense | Sense | Antisense | Sense | Antisense |
| RHOA_58_S1782 | 12 | 12 | | | | |
| RHOA_58_S1801 | 24 | 24 | 24 | 24 | 24 | 24 |
| RHOA_58_S1802 | 24 | 24 | | | | |
| RHOA_58_S1803 | 12 | 12 | | | | |
| RHOA_58_S1804 | 24 | 24 | 24 | 24 | 24 | 24 |
| RHOA_58_S1805 | 12 | 24 | | | | |
| RHOA_58_S1806 | 24 | 24 | <3 (24) | 10 (24) | 24 | 24 |
| RHOA_58_S1807 | 24 | 24 | | | | |
| RHOA_58_S1808 | 24 | 24 | | | | |
| RHOA_58_S1809 | 24 | 24 | | | | |
| RHOA_58_S1810 | 24 | 24 | | | | |
| RHOA_58_S1811 | 24 | 24 | | | | |
| RHOA_58_S1861 | 24 | 24 | <3 | 10 | | |
| RHOA_58_S1862 | 24 | 24 | <3 | 3 | | |
| RHOA_58_S1863 | 24 | 24 | | | | |
| RHOA_58_S1864 | 24 | 24 | | | | |
| RHOA_58_S1867 | 24 | 24 | | | | |
| RHOA_58_S1877 | 6 | 6 | 6 | 24 | | |
| RHOA_58_S1878 | 24 | 24 | <3 | 6 | | |
| RHOA_58_S1879 | 24 | 24 | <3 | 6 | | |
| RHOA_58_S1880 | 24 | 24 | <3 | 6 | | |
| RHOA_58_S1881 | 24 | 24 | | | | |

Assessment of on-Target Vs. Off-Target Knockdown Activity of RhoA Compounds

Activity in human HeLa cells: The knockdown efficiency of dsRNA RhoA compounds (vs. non-modified counterparts) was tested using the "on-target" psi-CHECK test in human HeLa cells (analyzing the activity of Luciferase reporter plasmid constructs containing the corresponding matched complementary target sequences for the guide strands of the dsRNA compounds). Each dsRNA was transfected at 5 concentrations from 4 µM to 100 nM. Lipofectamine-exposed cells served as negative control.

Off-target activity: Potential seed-mediated off-target effects of dsRNA RHOA compounds were analyzed in psi-CHECK plasmid reporter system (Promega™). This system enables the evaluation of the intrinsic potency of
Guide strand (GS)—"on-target" activity towards a completely matched sequence;
Guide strand seed region—"off-target" miRNA-like activity;
Passenger strand (PS)—"off-target" effects due to passenger strand competitive loading into RISC (PS-CM).

All target sequences were inserted into the 3'-UTR of luciferase reporter construct and siRNA activity was determined as specific reduction of luciferase reporter luminescence following dsRNA transfections. Four psiCHECK™-2-based constructs were prepared for each candidate dsRNA primary sequence. The psiCHECK constructs contained single copies of matched complementary guide (GS-CM) or passenger (PS-CM) strand sequences, or three copies of sequences complementary to the guide strand seed regions (GS-SM) cloned at optimal distances between them (for testing potential seed-mediated off-target effects in most stringent conditions) or "full sensor" psiCHECK constructs contain four tandem copies of the "full-sensor" sequence of the guide strand, this sequence is comprised of the seed region, position 2-8 (5'>3') of the sense strand and the antisense RNA strand, followed by a spacer of 4 non-target nucleotides and then by the central region of the antisense strand, positions 13-19 (These constructs were generated in order to mimic very extensive base pairing off-targets).

Results of the on-target and off-target activity is provided in Tables H, J, K, L, M, N, P, Q, R, S, T and U below.

TABLE H

Complete match of antisense strand of dsRHOA_48 and dsRHOA_48u molecules to target (on-target)

| AS_CM_X1 [complete match (on-target of AS)] dsRNA conc | Residual % of Ctrl 100 nM | Residual % of Ctrl 20 nM | Residual % of Ctrl 4 nM | Residual % of Ctrl 0.4 nM | Residual % of Ctrl 0.04 nM | Residual % of Ctrl 0.004 nM | Residual % of Ctrl 0.0004 nM |
|---|---|---|---|---|---|---|---|
| RHOA_48_S1833 | 14 | 16 | 23 | 32 | 43 | | |
| RHOA_48_S1834 | 14 | 15 | 25 | 52 | 71 | | |
| RHOA_48_S1815 | 7 | 11 | 16 | 24 | 38 | | |
| RHOA_48_S1814 | 10 | 15 | 18 | 27 | 38 | | |
| RHOA_48u_S1812 | 9 | 17 | 21 | 33 | 39 | | |
| RHOA_48u_S1812 | 14 | 19 | 26 | 34 | 47 | | |
| RHOA_48u_S1813 | 11 | 14 | 18 | 25 | 36 | | |
| RHOA_48_S1632 | 11 | 20 | 29 | 39 | 47 | | |
| RHOA_48_S1850 | 10 | 19 | 31 | 41 | 46 | | |
| RHOA_48_S1851 | 9 | 15 | 23 | 30 | 35 | | |
| RHOA_48_S1852 | 15 | 26 | 35 | 45 | 38 | | |
| RHOA_48_S1853 | 17 | 24 | 36 | 45 | 49 | | |
| RHOA_48_S1854 | 26 | 42 | 57 | 57 | 62 | | |
| RHOA_48_S709 | 6 | 10 | 17 | 34 | 45 | | |
| RHOA_48_S709 | 16 | 14 | 17 | 21 | 23 | | |
| RHOA_48_S709 | 7 | 9 | 13 | 18 | 48 | | |
| RHOA_48_S709 | | | 15 | 48 | 68 | 63 | 68 |
| RHOA_48_S1855 | 12 | 22 | 36 | 45 | 51 | | |
| RHOA_48_S1856 | 13 | 24 | 36 | 40 | 50 | | |
| RHOA_48_S1856 | 20 | 20 | 31 | 44 | 54 | | |
| RHOA_48_S1856 | 15 | 15 | 24 | 36 | 36 | | |
| RHOA_48_S1857 | 14 | 21 | 29 | 44 | 62 | | |
| RHOA_48_S1857 | 9 | 11 | 17 | 29 | 38 | | |
| RHOA_48_S1857 | | | 26 | 53 | 80 | 87 | 81 |
| RHOA_48_S1858 | 21 | 33 | 43 | 59 | 79 | | |
| RHOA_48_S1859 | 14 | 23 | 33 | 41 | 69 | | |
| RHOA_48_S1860 | 34 | 53 | 60 | 70 | 81 | | |
| RHOA_48u_S1870 | | 15 | 16 | 21 | 44 | 39 | |
| RHOA_48_S1872 | | 9 | 14 | 26 | 39 | 51 | |
| RHOA_48_S1873 | | 10 | 10 | 15 | 20 | 24 | |
| RHOA_48_S1873 | | | 15 | 39 | 61 | 77 | 66 |
| RHOA_48u_S1871 | | 7 | 11 | 18 | 28 | 35 | |
| RHOA_48u_S1871 | | | 21 | 48 | 64 | 71 | 73 |
| RHOA_48_S1884 | | 21 | 38 | 73 | 93 | 92 | |
| RHOA_48_S1885 | | 11 | 14 | 31 | 59 | 64 | |
| RHOA_48_S1886 | | 21 | 41 | 76 | 79 | 83 | |
| RHOA_48_S1887 | | 6 | 6 | 12 | 20 | 26 | |

TABLE J

Seed match of antisense strand of dsRHOA_48 and dsRHOA_48u molecules to its target (off-target)

AS_SM_X3 [seed-match (off-target of AS)]

| dsRNA conc | Residual % of Ctrl 100 nM | Residual % of Ctrl 20 nM | Residual % of Ctrl 4 nM | Residual % of Ctrl 0.4 nM | Residual % of Ctrl 0.04 nM |
|---|---|---|---|---|---|
| RHOA_48_S1833 | 24 | 36 | 58 | 79 | 90 |
| RHOA_48_S1834 | 50 | 46 | 78 | 81 | 81 |
| RHOA_48_S1815 | 35 | 47 | 61 | 70 | 73 |
| RHOA_48_S1814 | 48 | 60 | 72 | 72 | 67 |
| RHOA_48u_S1812 | 48 | 75 | 88 | 93 | 92 |
| RHOA_48u_S1813 | 58 | 64 | 81 | 87 | 82 |
| RHOA_48_S1632 | 31 | 66 | 76 | 81 | 80 |
| RHOA_48_S1850 | 79 | 85 | 93 | 92 | 87 |
| RHOA_48_S1851 | 67 | 73 | 77 | 77 | 75 |
| RHOA_48_S1852 | 70 | 73 | 73 | 75 | 77 |
| RHOA_48_S1853 | 69 | 91 | 92 | 91 | 90 |
| RHOA_48_S1854 | 70 | 84 | 87 | 87 | 85 |
| RHOA_48_S709 | 38 | 60 | 62 | 69 | 66 |
| RHOA_48_S1855 | 72 | 78 | 81 | 82 | 80 |
| RHOA_48_S1856 | 74 | 76 | 79 | 77 | 77 |
| RHOA_48_S1857 | 76 | 85 | 91 | 95 | 88 |
| RHOA_48_S1858 | 83 | 87 | 84 | 89 | 85 |
| RHOA_48_S1859 | 67 | 76 | 81 | 75 | 78 |
| RHOA_48_S1860 | 72 | 77 | 80 | 78 | 81 |
| RHOA_48u_S1870 | 61 | 73 | 79 | 79 | 87 |
| RHOA_48_S1872 | 57 | 69 | 76 | 76 | 75 |
| RHOA_48_S1873 | 43 | 57 | 68 | 64 | 66 |
| RHOA_48u_S1871 | 37 | 60 | 60 | 63 | 68 |

TABLE K

Complete match of sense strand of dsRHOA_48 and dsRHOA_48u molecules to target (off-target)

S_CM_x1 [complete match sense (off-target of S)]

| dsRNA conc | Residual % of Ctrl 100 nM | Residual % of Ctrl 20 nM | Residual % of Ctrl 4 nM | Residual % of Ctrl 0.4 nM | Residual % of Ctrl 0.04 nM |
|---|---|---|---|---|---|
| RHOA_48_S1812 | 75 | 100 | 98 | 94 | 88 |
| RHOA_48u_S1813 | 88 | 62 | 53 | 70 | 89 |
| RHOA_48_S1833 | 61 | 71 | 77 | 81 | 79 |
| RHOA_48u_S1870 | 81 | 90 | 87 | 84 | 85 |
| RHOA_48_S1872 | 81 | 83 | 82 | 81 | 79 |
| RHOA_48_S1873 | 69 | 73 | 78 | 73 | 71 |
| RHOA_48u_S1871 | 69 | 72 | 75 | 71 | 41 |
| RHOA_48_S1856 | 90 | 92 | 92 | 87 | 89 |
| RHOA_48_S1857 | 76 | 85 | 85 | 82 | 83 |
| RHOA_48_S709 | 69 | 71 | 67 | 68 | 65 |

TABLE L

Match of antisense strand of dsRHOA_48 and dsRHOA_48u molecules to its seed nucleotides and nucleotides 13-17 (off-target)

Full-sensor (AS)

| dsRNA conc | Residual % of Ctrl 100 nM | Residual % of Ctrl 20 nM | Residual % of Ctrl 4 nM | Residual % of Ctrl 0.4 nM | Residual % of Ctrl 0.04 nM |
|---|---|---|---|---|---|
| RHOA_48_S1833 | 9 | 12 | 17 | 31 | 55 |
| RHOA_48_S1834 | 18 | 17 | 28 | 65 | 81 |
| RHOA_48_S1815 | 6 | 8 | 14 | 36 | 57 |
| RHOA_48_S1814 | 9 | 16 | 31 | 63 | 70 |
| RHOA_48u_S1812 | 8 | 13 | 30 | 57 | 70 |
| RHOA_48u_S1813 | 9 | 9 | 16 | 49 | 73 |
| RHOA_48_S1632 | 7 | 13 | 28 | 45 | 60 |
| RHOA_48_S1850 | 38 | 53 | 73 | 89 | 84 |
| RHOA_48_S1851 | 14 | 30 | 55 | 56 | 64 |
| RHOA_48_S1852 | 18 | 31 | 46 | 49 | 60 |
| RHOA_48_S1853 | 36 | 38 | 55 | 67 | 79 |
| RHOA_48_S1854 | 21 | 41 | 63 | 67 | 76 |
| RHOA_48_S709 | 13 | 26 | 47 | 52 | 59 |
| RHOA_48_S1855 | 35 | 65 | 74 | 80 | 81 |
| RHOA_48_S1856 | 38 | 69 | 77 | 74 | 78 |
| RHOA_48_S1857 | 27 | 47 | 69 | 78 | 87 |
| RHOA_48_S1858 | 34 | 60 | 70 | 76 | 83 |
| RHOA_48_S1859 | 16 | 33 | 47 | 61 | 76 |
| RHOA_48_S1860 | 31 | 50 | 62 | 73 | 70 |
| RHOA_48u_S1870 | 81 | 90 | 87 | 84 | 85 |
| RHOA_48_S1872 | 81 | 83 | 82 | 81 | 79 |
| RHOA_48_S1873 | 69 | 73 | 78 | 73 | 71 |
| RHOA_48u_S1871 | 69 | 72 | 75 | 71 | 41 |

TABLE M

Complete match of antisense strand of dsRHOA_50 molecules to its target (on-target)

| AS_CM_X1 [antisense on-target] dsRNA conc | Residual % of Ctrl 100 nM | Residual % of Ctrl 20 nM | Residual % of Ctrl 4 nM | Residual % of Ctrl 0.4 nM | Residual % of Ctrl 0.04 nM | Residual % of Ctrl 0.004 nM |
|---|---|---|---|---|---|---|
| RHOA_50_S1793 | 6 | 6 | 7 | 9 | 14 | |
| RHOA_50_S1787 | 9 | 8 | 9 | 11 | 17 | |
| RHOA_50_S1794 | 6 | 7 | 7 | 10 | 15 | |
| RHOA_50_S1795 | 7 | 6 | 6 | 8 | 12 | |
| RHOA_50_S1796 | 8 | 6 | 7 | 9 | 10 | |
| RHOA_50_S1797 | 9 | 9 | 8 | 8 | 13 | |
| RHOA_50_S1798 | 7 | 6 | 5 | 7 | 10 | |
| RHOA_50_S1865 | 12 | 18 | 26 | 44 | 57 | |
| RHOA_50_S1866 | 11 | 16 | 27 | 41 | 51 | |
| RHOA_50_S1799 | 6 | 7 | 7 | 7 | 11 | |
| RHOA_50_S1800 | 10 | 9 | 11 | 15 | 19 | |
| RHOA_50_S1835 | 18 | 14 | 20 | 66 | 79 | |
| RHOA_50_S1836 | 9 | 13 | 14 | 24 | 46 | |
| RHOA_50_S1837 | 12 | 12 | 18 | 45 | 70 | |

TABLE M-continued

Complete match of antisense strand of dsRHOA_50 molecules to its target (on-target)

| AS_CM_X1 [antisense on-target] dsRNA conc | Residual % of Ctrl 100 nM | Residual % of Ctrl 20 nM | Residual % of Ctrl 4 nM | Residual % of Ctrl 0.4 nM | Residual % of Ctrl 0.04 nM | Residual % of Ctrl 0.004 nM |
|---|---|---|---|---|---|---|
| RHOA_50_S1838 | 12 | 15 | 20 | 42 | 76 | |
| RHOA_50_S1839 | 12 | 10 | 16 | 49 | 81 | |
| RHOA_50_S1840 | 13 | 10 | 13 | 23 | 48 | |
| RHOA_50_S709 | 7 | 7 | 12 | 14 | 16 | |
| RHOA_50_S1862 | 46 | 13 | 15 | 22 | 23 | |
| RHOA_50_S1862 | 13 | 15 | 54 | 79 | 91 | 81 |
| RHOA_50_S1882 | 8 | 8 | 11 | 13 | 23 | |
| RHOA_50_S1883 | 6 | 7 | 8 | 11 | 22 | |
| RHOA_50_S1865 | 4 | 5 | 6 | 7 | 14 | |
| RHOA_50_S1865 | | 9 | 30 | 71 | 84 | 80 |
| RHOA_50_S1866 | 5 | 6 | 8 | 10 | 21 | |
| RHOA_50_S1866 | | 13 | 45 | 75 | 96 | 106 |
| RHOA_50_S1798 | 12 | 10 | 11 | 14 | 35 | |
| RHOA_50_S1798 | | 6 | 32 | 61 | 73 | 76 |
| RHOA_50_S1799 | 6 | 7 | 8 | 14 | 32 | |
| RHOA_50_S1799 | | 13 | 43 | 78 | 87 | 95 |

TABLE N

Seed match of antisense strand of ds RHOA_50 molecules to seed (off-target)

| | AS_SM_X3 | | | | |
|---|---|---|---|---|---|
| dsRNA conc | Residual % of Ctrl 100 | Residual % of Ctrl 20 nM | Residual % of Ctrl 4 nM | Residual % of Ctrl 0.4 nM | Residual % of Ctrl 0.04 nM |
| RHOA_50_S1793 | 57 | 68 | 78 | 88 | 89 |
| RHOA_50_S1787 | 51 | 67 | 74 | 83 | 80 |
| RHOA_50_S1794 | 41 | 52 | 67 | 77 | 78 |
| RHOA_50_S1795 | 50 | 50 | 60 | 73 | 72 |
| RHOA_50_S1796 | 43 | 48 | 66 | 83 | 90 |
| RHOA_50_S1797 | 47 | 46 | 66 | 89 | 85 |
| RHOA_50_S1798 | 47 | 50 | 64 | 76 | 79 |
| RHOA_50_S1865 | 85 | 94 | 94 | 97 | 96 |
| RHOA_50_S1866 | 60 | 69 | 72 | 73 | 76 |
| RHOA_50_S1799 | 37 | 41 | 59 | 73 | 75 |
| RHOA_50_S1800 | 43 | 54 | 73 | 87 | 83 |
| RHOA_50_S1835 | 69 | 76 | 83 | 85 | 64 |
| RHOA_50_S1836 | 33 | 58 | 70 | 76 | 75 |

TABLE N-continued

Seed match of antisense strand of ds RHOA_50 molecules to seed (off-target)

| | AS_SM_X3 | | | | |
|---|---|---|---|---|---|
| dsRNA conc | Residual % of Ctrl 100 | Residual % of Ctrl 20 nM | Residual % of Ctrl 4 nM | Residual % of Ctrl 0.4 nM | Residual % of Ctrl 0.04 nM |
| RHOA_50_S1837 | 56 | 61 | 75 | 77 | 74 |
| RHOA_50_S1838 | 63 | 67 | 79 | 87 | 89 |
| RHOA_50_S1839 | 53 | 51 | 78 | 86 | 79 |
| RHOA_50_S1840 | 35 | 39 | 63 | 74 | 77 |
| RHOA_50_S709 | 33 | 56 | 72 | 80 | 77 |
| RHOA_50_S1862 | 44 | 39 | 55 | 63 | 74 |
| RHOA_50_S1882 | 51 | 60 | 74 | 91 | 86 |
| RHOA_50_S1883 | 41 | 51 | 69 | 74 | 78 |
| RHOA_50_S1865 | 42 | 55 | 64 | 71 | 75 |
| RHOA_50_S1866 | 36 | 40 | 57 | 67 | 68 |
| RHOA_50_S1798 | 59 | 70 | 75 | 80 | 82 |
| RHOA_50_S1799 | 39 | 51 | 65 | 81 | 83 |

TABLE P

Complete match of sense strand of dsRHOA_50 molecules to its target (off-target)

| S_CM_x1 dsRNA conc | Residual % of Ctrl 100 | Residual % of Ctrl 20 nM | Residual % of Ctrl 4 nM | Residual % of Ctrl 0.4 nM | Residual % of Ctrl 0.04 nM |
|---|---|---|---|---|---|
| RHOA_50_S1862 100 nM | 53 | 52 | 63 | 74 | 82 |
| RHOA_50_S1882 100 nM | 47 | 58 | 68 | 76 | 71 |
| RHOA_50_S1883 100 nM | 36 | 47 | 67 | 77 | 80 |
| RHOA_50_S1865 100 nM | 35 | 49 | 71 | 64 | 65 |
| RHOA_50_S1866 100 nM | 51 | 56 | 59 | 67 | 71 |
| RHOA_50_S1798 100 nM | 58 | 60 | 71 | 76 | 85 |
| RHOA_50_S1799 100 nM | 53 | 57 | 63 | 73 | 86 |
| RHOA_50_S709 100 nM | 14 | 20 | 33 | 40 | 47 |

TABLE Q

Match of antisense strand of dsRHOA 50 molecules to seed nucleotides + nucleotides 13-17 (off- target)

Full sensor (OFF TARGET SEED + 13-17)

| dsRNA conc | Residual % of Ctrl 100 | Residual % of Ctrl 20 nM | Residual % of Ctrl 4 nM | Residual % of Ctrl 0.4 nM | Residual % of Ctrl 0.04 nM |
|---|---|---|---|---|---|
| RHOA_50_S1793 | 16 | 51 | 67 | 81 | 84 |
| RHOA_50_S1787 | 12 | 33 | 59 | 74 | 76 |
| RHOA_50_S1794 | 7 | 16 | 46 | 69 | 73 |
| RHOA_50_S1795 | 10 | 13 | 40 | 69 | 71 |
| RHOA_50_S1796 | 10 | 12 | 32 | 79 | 91 |
| RHOA_50_S1797 | 9 | 10 | 21 | 78 | 92 |
| RHOA_50_S1798 | 10 | 15 | 40 | 78 | 80 |
| RHOA_50_S1865 | 36 | 68 | 70 | 81 | 85 |
| RHOA_50_S1866 | 12 | 38 | 60 | 70 | 75 |
| RHOA_50_S1799 | 8 | 10 | 27 | 68 | 77 |
| RHOA_50_S1800 | 7 | 9 | 20 | 73 | 85 |
| RHOA_50_S1835 | 65 | 59 | 81 | 84 | 83 |
| RHOA_50_S1836 | 13 | 38 | 59 | 74 | 78 |
| RHOA_50_S1837 | 40 | 5- | 72 | 76 | 73 |
| RHOA_50_S1838 | 49 | 45 | 67 | 91 | 93 |
| RHOA_50_S1839 | 42 | 40 | 75 | 89 | 87 |
| RHOA_50_S1840 | 20 | 23 | 55 | 74 | 78 |
| RHOA_50_S709 | 19 | 42 | 62 | 73 | 72 |

TABLE S

Seed match of antisense strand of ds RHOA_58 molecules to seed (off-target)

AS_SM_X3

| dsRNA conc | Residual % of Ctrl 100 | Residual % of Ctrl 20 nM | Residual % of Ctrl 4 nM | Residual % of Ctrl 0.4 nM | Residual % of Ctrl 0.04 nM |
|---|---|---|---|---|---|
| RHOA_58_S1782 | 43 | 54 | 67 | 72 | 71 |
| RHOA_58_S1801 | 57 | 75 | 74 | 87 | 92 |
| RHOA_58_S1802 | 54 | 68 | 84 | 90 | 91 |
| RHOA_58_S1806 | 39 | 45 | 61 | 71 | 79 |
| RHOA_58_S1807 | 67 | 66 | 74 | 75 | 77 |
| RHOA_58_S1807 | 66 | | | | |
| RHOA_58_S1808 | 47 | 49 | 64 | 87 | 91 |
| RHOA_58_S1809 | 45 | 50 | 68 | 82 | 79 |
| RHOA_58_S1810 | 44 | 50 | 65 | 74 | 73 |
| RHOA_58_S1811 | 41 | 43 | 61 | 74 | 72 |
| RHOA_58_S1803 | 56 | 63 | 79 | 90 | 96 |
| RHOA_58_S1804 | 57 | 62 | 71 | 90 | 88 |
| RHOA_58_S1805 | 41 | 44 | 55 | 82 | 85 |
| RHOA_58_S1806 | 90 | 95 | 95 | 97 | 98 |
| RHOA_58_S1806 | 54 | 54 | 66 | 83 | 69 |
| RHOA_58_S1861 | 85 | 94 | 94 | 97 | 96 |
| RHOA_58_S1861 | 56 | 61 | 66 | 80 | 75 |
| RHOA_58_S1862 | 52 | 66 | 73 | 73 | 75 |
| RHOA_58_S1863 | 57 | 77 | 80 | 77 | 75 |

TABLE R

Complete match of antisense strand of dsRHOA_58 molecules to target.

| AS_CM_X1 (on target activity) dsRNA conc | Residual % of Ctrl 100 nM | Residual % of Ctrl 20 nM | Residual % of Ctrl 4 nM | Residual % of Ctrl 0.4 nM | Residual % of Ctrl 0.04 nM | Residual % of Ctrl 0.004 nM | Residual % of Ctrl 0.0004 nM |
|---|---|---|---|---|---|---|---|
| RHOA_58_S1782 | 11 | 9 | 11 | 15 | 26 | | |
| RHOA_58_S1801 | 6 | 9 | 9 | 10 | 17 | | |
| RHOA_58_S1802 | 8 | 8 | 10 | 12 | 21 | | |
| RHOA_58_S1806 | 7 | 6 | 9 | 12 | 21 | | |
| RHOA_58_S1807 | 6 | 7 | 7 | 9 | 17 | | |
| RHOA_58_S1808 | 7 | 8 | 9 | 13 | 26 | | |
| RHOA_58_S1809 | 8 | 10 | 9 | 16 | 27 | | |
| RHOA_58_S1810 | 7 | 6 | 7 | 10 | 15 | | |
| RHOA_58_S1811 | 7 | 8 | 9 | 13 | 29 | | |
| RHOA_58_S1803 | 7 | 7 | 10 | 13 | 26 | | |
| RHOA_58_S1804 | 8 | 7 | 8 | 10 | 16 | | |
| RHOA_58_S1805 | 9 | 7 | 8 | 12 | 17 | | |
| RHOA_58_S1806 | 14 | 24 | 28 | 50 | 70 | | |
| RHOA_58_S1806 | 6 | 5 | 10 | 18 | 20 | | |
| RHOA_58_S1806 | | | 11 | 46 | 69 | 86 | 90 |
| RHOA_58_S1861 | 14 | 16 | 26 | 41 | 57 | | |
| RHOA_58_S1861 | 14 | 13 | 15 | 21 | 29 | | |
| RHOA_58_S1861 | | | 6 | 30 | 61 | 68 | 61 |
| RHOA_58_S1862 | 7 | 12 | 22 | 36 | 55 | | |
| RHOA_58_S1862 | | | 15 | 54 | 79 | 91 | 81 |
| RHOA_58_S1863 | 16 | 56 | 62 | 75 | 75 | | |
| RHOA_58_S1864 | 18 | 24 | 32 | 52 | 78 | | |
| RHOA_58_S709 | 65 | 20 | 31 | 46 | 61 | | |
| RHOA_58_S709 | 10 | 15 | 19 | 19 | 21 | | |
| RHOA_58_S709 | | | 17 | 62 | 80 | 87 | 79 |
| RHOA_58_S1877 | 10 | 13 | 13 | 16 | 22 | | |
| RHOA_58_S1877 | | | 19 | 43 | 68 | 79 | 82 |
| RHOA_58_S1878 | 6 | 8 | 9 | 12 | 16 | | |
| RHOA_58_S1879 | | 5 | 6 | 9 | 12 | 15 | |
| RHOA_58_S1879 | | | 9 | 30 | 51 | 63 | 55 |

TABLE S-continued

Seed match of antisense strand of ds RHOA_58 molecules to seed (off-target)

| | AS_SM_X3 | | | | |
|---|---|---|---|---|---|
| | Residual % of Ctrl | Residual % of Ctrl | Residual % of Ctrl | Residual % of Ctrl | Residual % of Ctrl |
| dsRNA conc | 100 | 20 nM | 4 nM | 0.4 nM | 0.04 nM |
| RHOA_58_S1864 | 90 | 95 | 95 | 97 | 98 |
| RHOA_58_S709 | 73 | 68 | 72 | 78 | 75 |
| RHOA_58_S1877 | 69 | 69 | 71 | 90 | 85 |
| RHOA_58_S1878 | 57 | 63 | 70 | 90 | 96 |
| RHOA_58_S1879 | 50 | 49 | 61 | 83 | 84 |

TABLE T

Complete match of sense strand of dsRHOA_58 molecules to its target (off-target)

| | S_CM_xl | | | | |
|---|---|---|---|---|---|
| | Residual % of Ctrl | Residual % of Ctrl | Residual % of Ctrl | Residual % of Ctrl | Residual % of Ctrl |
| dsRNA conc | 100 | 20 nM | 4 nM | 0.4 nM | 0.04 nM |
| RHOA_58_S1801 | 78 | 78 | 90 | 88 | 81 |
| RHOA_58_S1804 | 79 | 71 | 74 | 67 | 84 |
| RHOA_58_S1806 | 82 | 52 | 64 | 80 | 90 |
| RHOA_58_S1806 | 31 | 36 | 48 | 68 | 65 |
| RHOA_58_S1877 | 36 | 43 | 61 | 80 | 75 |
| RHOA_58_S1878 | 43 | 44 | 55 | 70 | 78 |
| RHOA_58_S1879 | 35 | 46 | 59 | 61 | 73 |
| RHOA_58_S1861 | 43 | 48 | 63 | 75 | 85 |
| RHOA_58_S709 | 14 | 20 | 33 | 40 | 47 |

TABLE U

Match of antisense strand of dsRHOA_58 molecules to seed nucleotides + nucleotides 13-17 (off-target)

| | full sensor | | | | |
|---|---|---|---|---|---|
| | Residual % of Ctrl | Residual % of Ctrl | Residual % of Ctrl | Residual % of Ctrl | Residual % of Ctrl |
| dsRNA conc | 100 | 20 nM | 4 nM | 0.4 nM | 0.04 nM |
| RHOA_58_S1782 | 13 | 31 | 59 | 74 | 73 |
| RHOA_58_S1801 | 21 | 52 | 73 | 85 | 88 |
| RHOA_58_S1802 | 11 | 23 | 63 | 82 | 78 |
| RHOA_58_S1806 | 8 | 11 | 32 | 69 | 76 |
| RHOA_58_S1806 | 31 | 36 | 48 | 68 | 65 |
| RHOA_58_S1807 | 13 | 14 | 47 | 72 | 74 |
| RHOA_58_S1808 | 11 | 13 | 24 | 74 | 87 |
| RHOA_58_S1809 | 11 | 13 | 43 | 80 | 84 |
| RHOA_58_S1810 | 11 | 18 | 52 | 76 | 77 |
| RHOA_58_S1811 | 8 | 10 | 33 | 70 | 76 |
| RHOA_58_S1803 | 15 | 17 | 52 | 84 | 86 |
| RHOA_58_S1804 | 15 | 16 | 43 | 83 | 86 |
| RHOA_58_S1805 | 7 | 8 | 15 | 65 | 77 |
| RHOA_58_S1864 | 32 | 60 | 73 | 83 | 92 |
| RHOA_58_S709 | 70 | 61 | 66 | 71 | 72 |
| RHOA_58_S1877 | 36 | 43 | 61 | 80 | 75 |
| RHOA_58_S1878 | 43 | 44 | 55 | 79 | 78 |
| RHOA_58_S1879 | 35 | 6 | 59 | 61 | 73 |
| RHOA_58_S1861 | 43 | 48 | 63 | 75 | 85 |

Candidate Molecules

Certain currently preferred dsRNA (dsRHOA) molecules are set forth in Table W, with knock down activity (qPCR), on-target (Psi-AS-CM), off-target (Psi-AS-SM and Psi-S-SM) and antisense strand stability data provided for each molecule.

TABLE W

| dsRHOA | qPCR | Psi-AS-CM (20-mM) | Psi-AS-SM (20 mM) | Psi-S-SM (20 mM) | AS stability Plasma/extract/CSF |
|---|---|---|---|---|---|
| RHOA_48_S1833 | ++ | 16 | 36 | 71 | 24/na/24 |
| RHOA_48_S1856 | ++ | 24/20/15 | 76 | 92 | 24/24/na |
| RHOA_48_S1857 | +++ | 21/11 | 85 | 85 | 24/24/na |
| RHOA_48_S1872 | ++ | 9 | 69 | 83 | 24/24/na |
| RHOA_48_S1873 | ++ | 10 | 57 | 73 | 24/24/na |
| RHOA_48u_S1812 | ++ | 19 | 75 | 100 | 24/na/24 |
| RHOA_48u_S1813 | ++ | 14 | 64 | 62 | 24/na/24 |
| RHOA_50_S1796 | ++ | 6 | 48 | na | 24/12/24 |
| RHOA_50_S1798 | +++ | 6 | 50 | 60 | 24/12/24 |
| RHOA_50_51799 | +++ | 7 | 41 | 57 | 12/12/24 |
| RHOA_50_S1839 | ++ | 10 | 51 | na | 24/12/na |
| RHOA_50_S1865 | +++ | 5/9 | 94 | 49 | 23/<3/na |
| RHOA_50_S1866 | na | 6/13 | 69 | 56 | 23/<3/na |
| RHOA_58_51801 | +++ | 9 | 75 | 78 | 24/24/24 |
| RHOA_58_51804 | ++ | 7 | 62 | 71 | 24/24/24 |
| RHOA_58_51806 | +++ | 6 | 45 | 52/36 | 24/24/24 |
| RHOA_58_51861 | +++ | 16/13 | 94/61 | 48 | 24/10/na |
| RHOA_58_S1862 | +++ | 12 | 66 | na | 24/<3/na |
| RHOA_58_S1877 | +++ | 13 | 69 | 43 | 6/24/na |
| RHOA_58_S1878 | +++ | 8 | 63 | 44 | 24/6/na |
| RHOA_58_S1879 | +++ | 5 | 49 | 46 | 24/6/na | na: not available. Either not tested or assay did not pass QC.
qPCR knock down at 5 nM: +++ ≤ 15 %; ++15 < 30%; + 31 < 50%

Innate Immune Response to RHOA dsRNA Molecules:

Fresh human blood (at RT) is mixed at 1:1 ratio with sterile 0.9% NaCl at RT, and gently loaded (1:2 ratio) on Ficoll (Lymphoprep, Axis-Shield cat#1114547). Samples are centrifuged at RT (22° C., 800 g) in a swinging centrifuge for 30 minutes, washed with RPMI1640 medium and centrifuged (RT, 250 g) for 10 minutes. Cells are counted and seeded at final concentration of $1.5 \times 10^6$ cell/ml in growth medium (RPMI1640+10% FBS+2 mM L-glutamine+1% Pen-Strep) and incubated for 1 hour at 37° C. before dsRNA treatment.

Cells are contacted with test dsRNAs at different concentrations using Lipofectamine™2000 reagent (Invitrogen) according to manufacturer's instructions and incubated at 37° C. in a 5% $CO_2$ incubator for 24 hours.

As a positive control for IFN response, cells are treated with either poly(I:C), a synthetic analog of double strand RNA (dsRNA) which is a TLR3 ligand (InvivoGen Cat# tlrl-pic) at final concentrations of 0.25-5.0 µg/mL or to Thiazolaquinolone (CLO75), a TLR 7/8 ligand (InvivoGen Cat# tlrl-c75) at final concentrations of 0.075-2 µg/mL. Cell treated with Lipofectamine™2000 reagent were used as negative (reference) control for IFN response.

At about 24 hours following incubation, cells are collected and supernatant transferred to new tubes. Samples are frozen immediately in liquid nitrogen and secretion of IL-6 and TNF-α cytokines is tested using IL-6, DuoSet ELISA kit (R&D System DY2060), and TNF-α, DuoSet ELISA kit (R&D System DY210), according to manufacturer's instructions. RNA is extracted from the cell pellets and mRNA levels of human genes IFIT1 (interferon-induced protein with tetratricopeptide repeats 1) and MX1 (myxovirus (influenza virus) resistance 1, interferon-inducible protein p78) were measured by qPCR. Measured mRNA quantities were normalized to the mRNA quantity of the reference gene peptidylprolyl isomerase A (cyclophilin A; CycloA). Induction of IFN-signaling is evaluated by comparing the quantity of mRNA from IFIT1 and MX1 genes from treated cells, compared to their quantities in non-treated cells. The qPCR results are those that passed QC standards, i.e. the value of the standard curve slope was in the interval [−4, −3], $R^2 > 0.99$, no primer dimers. Results that do not pass the QC requirements are disqualified from analysis.

Example 2

Animal Models

Model Systems of Glaucoma

Testing the active dsRNA compounds of the invention for treating or preventing glaucoma is preformed in rat animal model for optic nerve crush described for example in: Maeda, K. et al., "*A Novel Neuroprotectant against Retinal Ganglion Cell Damage in a Glaucoma Model and an Optic Nerve Crush Model in the rat*", Investigative Ophthalmology and visual Science (IOVS), March 2004, 45(3)851. Specifically, for optic nerve transection the orbital optic nerve (ON) of anesthetized rats is exposed through a supraorbital approach, the meninges severed and all axons in the ON transected by crushing with forceps for 10 seconds, 2 mm from the lamina cribrosa.

RhoA dsRNA compounds disclosed herein are tested in this animal model and the results show that these RhoA dsRNA compounds are useful in treating and/or preventing glaucoma.

Rat Optic Nerve Crush (ONC) Model: Intravitreal (IVT) dsRNA Delivery and Eye Drop dsRNA Delivery For optic nerve transection the orbital optic nerve (ON) of anesthetized rats is exposed through a supraorbital approach, the meninges severed and all axons in the ON transected by crushing with forceps for 10 seconds, 2 mm from the lamina cribrosa.

The dsRNA compounds are delivered alone or in combination in 5 uL volume (10 ug/uL) as eye drops. Immediately after optic nerve crush (ONC), 20 ug/10 ul test dsRNA compound or 10 ul PBS is administered to one or both eyes of adult Wistar rats and the levels of dsRNA taken up into the dissected and snap frozen whole retinae at 5 hours and 1 day, and later at 2, 4, 7, 14 and 21 days post injection is determined. Similar experiments are performed in order to test activity and efficacy of dsRNA compounds administered via eye drops.

MASCIS Rat Model for Spinal Cord Injury

Most human spinal cord injuries involve contusions of the spinal cord. The Impactor model of rat spinal cord contusion produces consistent injuries and provides an invaluable in vivo model for testing drug candidates as reflected in a variety of measures including extracellular potassium and calcium shifts, descending evoked responses, and spinal cord lesion volumes (Pinzon et al., 2008a; Pinzon et al., 2008b). The model can detect significant lesion volume changes due to methylprednisolone (MP) treatment with only 7 rats (reviewed in (Young, 2002)). In addition, the MASCIS group validated the Basso-Beattie-Bresnahan (BBB) locomotor score, a 21-point ordinal scale that correlated linearly with histological changes at the impact site (Basso et al., 1995). The model yields very consistent chronic histological changes (Beattie et al., 1997). In recent years, the trend has been towards use of rats for spinal cord injury studies. The MASCIS Impactor is a well-standardized rat spinal cord contusion model that produces very consistent graded spinal cord damage that linearly predicts 24-hour lesion volumes, 6-week white matter sparing, and locomotor recovery in rats (Young, 2002). Whereas other spinal injury models have been useful for studying multiple mechanisms associated with these injuries, transections of the spinal cord do not generate the extensive traumatic damage that is associated with the worst aspects of secondary damage. Thus, treatments that are effective in transactions may not be effective in contusive injuries (Iseda et al., 2008).

The dsRNA compounds disclosed herein are tested in this animal model and the results show that these dsRNA compounds are useful in treating and/or preventing spinal cord injury.

Example 3

In-Vivo Study of dsRhoA Compounds in Treatment of SCI

RhoA Immunohistochemistry Following Contusive SCI

The immunolocalization of RhoA following SCI at 1, 2 and 4 weeks following injury to confirm upregulation of the protein in RhoA dsRNA compound non-treated animals is investigated. Increases in RhoA protein following SCI relative to uninjured control animals is observed. The increase in RhoA protein is maintained through 4 weeks and appears to peak somewhere between 1 and 2 weeks. Dorsal and ventral roots show strong immunolocalization of RhoA as well as endothelial cells lining blood vessels. Confocal microscopic analysis suggests that much of the RhoA is located near the plasma membrane (D'Alessandro et al., 2004) suggesting that it is in its active state following SCI.

Cellular Localization of dsRNA Compound in Rat Spinal Cord Following Spinal Cord Injury and Intraparenchymal Delivery Naked nuclease-stabilized dsRNA conjugated with Cy3.5 fluorophore demonstrate incorporation into motor neurons, macrophages, white matter axons, as well as neurons in the dorsal root and endothelial cells. Thus, when injected immediately after contusive injury, the dsRNA can be taken up by many of the cells in which RhoA action has been implicated in SCI including neurons, astrocytes, microglia, macrophages and endothelial cells. All these cells therefore represent potential targets for inhibition of RhoA, which is anticipated to be neuroprotective (Dubreuil et al., 2003; Lord-Fontaine et al., 2008), anti-inflammatory (Schwab et al., 2004) and neuroregenerative (Bertrand et al., 2007; McKerracher and Higuchi, 2006).

Inhibition of RhoA Protein Induction after SCI

To analyze the ability of the RhoA dsRNA compound disclosed herein to alter RhoA protein levels, proteins are extracted from 5 mm segments of spinal cord tissues and relative levels of RhoA protein are measured after immunblotting. The levels of RhoA proteins are lower in the injected contusion sites that are treated with dsRhoA compound in comparison to siGFP controls, indicating inhibition of RhoA protein induction. Immunoblotting of the same extracts with anti-RhoA antibodies shows a similar decrease in immunoreactivity with the RhoA dsRNA compound against Rho by comparison to the siGFP control.

Functional Recovery of Rat Hindlimb Walking (Basso, Beattie and Bresnahan (BBB) Score Test) Following SCI and Intraparenchymal Injections of siRNA A locomotor BBB analysis for 6 weeks is carried out using dsRNA compounds disclosed herein against RhoA. Significant locomotor improvement, following intraspinal injections of dsRhoA compound compared to dsGFP compound as a control, are observed. The effect indicating improvement of BBB walking scores is observed at the earliest times tested, suggesting that the siRNA effect may be due to protective mechanisms in addition to promoting regeneration, which may require longer times for axons to grow.

Uptake of dsRNA at SCI Sites after Lumbar Puncture Injection dsRNA compounds disclosed herein are introduced into the cerebrospinal fluid intrathecally. Cy3.5-labeled naked dsRNA compound is administered to the lumbar enlargement one day after contusion using bolus administration, in order to compare intraparenchymal with intrathecal delivery. Results show widespread dye incorporation into the spinal cord at the injury center as well as in adjacent rostral and caudal regions of the spinal cord. Cryosectioning shows that the dsRNA penetrated into the white matter as well as the gray matter most robustly near in and around the injury site. Weak parenchymal signals are observed more distally although the signals re intense both in the central canal and surrounding the spinal cord. The results suggests greater uptake in the parenchyma near the injury site perhaps because of increased penetration of the dsRNA in the injured region. Intrathecal delivery in the lumbar region yields preferential uptake of dsRNA in and around the injury site in the thoracic region of the spinal cord.

Inhibition of RhoA mRNA Expression 3 Days after dsRNA Injection Via Lumbar Puncture.

The ability of the RhoA dsRNA compound disclosed herein to inhibit the SCI-induced increase in RhoA mRNA is measured by Quantitative RT-PCR. One day after contusion, RhoA dsRNA compound is injected via lumbar puncture and three days later spinal cord tissues are analyzed for relative levels of RhoA mRNA. Results show that relative levels of RhoA mRNA increase in the injury site by 4 days after SCI and that dsRhoA compound treatment reduces this increase when 40 µg and 100 µg are injected.

Functional Recovery of Rat Hindlimb Walking (BBB) Following Lumbar Puncture

The therapeutic effects of lumbar puncture injection of dsRhoA compound disclosed herein compared to dsGFP controls administered one day after contusion injury are measured using BBB scoring. The dsRhoA compound treatment yields higher scores than the dsGFP controls.

dsRhoA compounds utilizing the oligonucleotide sequences and structures provided in the present application are useful in treating SCI.

Example 4

Model Systems and Results Relating to Eye Diseases, Disorders and Injury

Model Systems Include the Optic Nerve Crush (ONC), Elevated IOP and Optic Nerve Axotomy Models.

IOP Reducing Activity of dsRhoA Compounds Following Delivery Via Intravitreal Injection (IVT) or as Eye Drops (ED) in the Rat Glaucoma Model To induce elevated IOP, microbeads are injected into the anterior chamber of the Wistar rat eye once a week until IOP is raised by more than 30% (time designated as Day 0). IOP is measured three times a week using a TonoPen XL tonometer to assess the relative efficacy of dsRhoA compounds in IOP reduction. Delivery by eye drop (ED): 100 µg of dsRhoA compound or control dsRNA compound (siCNL), or 60 ng of latanoprost (positive control) in 3 µl 2% methylcellulose (MC) or 3 µl 2% MC alone are delivered daily between the doses as eye drops for 14 days after induction of elevated IOP (n=4). Delivery by intravitreal injection: 20 µg of dsRhoA or siCNL or 60 ng of latanoprost in 10 µl PBS or 10 µl PBS alone are delivered on day 0 and 7 by intravitreal injection (IVT) (n=4). Combined IVT-ED treatment: 20 µg of dsRhoA or siCNL in 10 µl PBS or 10 µl PBS alone is delivered on day 0 by intravitreal injection (IVT) and followed with daily 100 µg of dsRhoA compound or control dsRNA compound (siCNL) in 3 µl 2% methylcellulose (MC) or 3 µl 2% MC alone as ED for 14 days.

dsRhoA Neuroprotective Efficacy in Rat ONC Model:

The orbital optic nerve (ON) of anaesthetized adult Wistar rats is exposed, the meninges are severed and all axons in the ON crushed with calibrated forceps for 10 seconds, 2 mm from the lamina cribrosa. 10 µg of dsRhoA compound or control dsRNA compound (siCNL) in 10 µl PBS or 10 µl PBS alone are delivered by IVT injection at day 0 after ONC (n=4). Eyes similarly injected with 5 µg Brain-derived neurotrophic factor (BDNF) serve as positive control. Two days prior to termination, retinal ganglion cells (RGC) are retrogradely labelled by Fluorogold injection into the ON. At termination (day 7 after ONC), experimental animals are perfused transcardially with 4% paraformaldehyde. The eyes with the ON are enucleated, the cornea dissected with the blade and lens/vitreous gently removed. Retinas are then dissected out, fixed for an additional 30 minutes in 4% paraformaldehyde and prepared for examination of the labelled RGC under the fluorescence microscope with a UV filter (365/420 nm). The number of retrograde labeled, fluorescent RGC is determined from captured images from each of the 4 quadrants of each retinal whole mount. RGC density in intact eyes serves as baseline control.

dsRhoA Efficacy in the ONC Model:

The ON of adult Fischer rats is crushed as described above and simultaneously a freshly excised segment of sciatic nerve is grafted into the vitreous body of the eye to drive axon regeneration. 20 μg of dsRhoA compound or control dsRNA compound (siCNL) in 10 μl PBS or 10 μl PBS alone are delivered by three IVT injections on days 0, 7 and 14 after ONC (n=4). A group injected with 5 μg BDNF serves as positive control. The experiment is terminated on day 21. Immunohistochemistry of ON sections with GAP43 antibody allows quantitative and qualitative measurement of the extent of RGC axon regeneration beyond the crush point in each treatment group dsRhoA Compound IOP Reducing Efficacy in the Glaucoma Model:

Increased IOP is induced as described. Each of dsRhoA test compound or control dsRNA compound (siCNL) or 60 ng of latanoprost or excipient alone are delivered by one of the delivery routes that showed the best results in experiments performed (e.g. IVT injection, eye drops, ear drops or any combination thereof). IOP is measured three times a week using a TonoPen XL tonometer to assess the relative efficacy of the tested RhoA dsRNA compounds for IOP reduction.

The lead drug candidate is selected as showing the best in vivo efficacy based on the results of the three animal models. The dsRhoA compounds utilizing the oligonucleotide sequences and structures provided herein are useful in treating eye diseases, disorders and injury (e.g., glaucoma).

Optimization of treatment regiments using lead dsRhoA drug candidate (dose response studies in optic nerve crush (ONC) injury model, retinal ganglion cell (RGC) axon regeneration model, elevated intraocular pressure (IOP) model). Measurement of the Ability of Escalating Doses of Lead dsRhoA Compound to Reduce IOP in Glaucoma Model:

Increased IOP is induced and results analyzed as described above. Escalating doses of lead dsRhoA compound are delivered either IVT (5, 10, 20 and 40 μg of 10 μl, as a single dose) or by eye drops (ED) when 100 μg siRNA is delivered in 3 μL volume once, twice or 3 times daily with 20 minute intervals between the doses for 14 days or by ear drops (ErD) when XX μg siRNA is delivered in X μL volume once, twice or 3 times daily with XX minute intervals between the doses for 14 days (n=4). siCNL serves as negative control and latanoprost—as positive control. IOP is measured three times a week using a TonoPen XL tonometer to assess efficacy of the dsRhoA compound in IOP reduction.

Measuring the Ability of Escalating Doses of dsRhoA Compound to Elicit RGC Survival Following ONC in Rats:

The ONC model is performed and results analyzed as described above. Escalating doses of 5, 10, 20 or 40 μg of dsRhoA test compound or 40 ug siCNL in 10 μl PBS or 10 μl PBS alone are delivered by single IVT injection on day 0 after ONC (n=4). BDNF-injected eyes serve as positive control. The study is terminated on day 7 after ONC.

Example 5

In-vivo Study Measuring the Ability of Escalating Doses of dsRhoA Compound to Induce RGC Axon Regeneration Following Optic Nerve Crush in Rats The study was performed and results analyzed as described for ONC model above. Escalating doses of 10, 20 and 40 μg of test dsRhoA compound or 40 ug dsEGFP compound in 10 μl PBS or 10 μl PBS alone, were delivered by intravitreal (IVT) injection at 0, 10 and 20 days after ONC (n=4). Ciliary neurotrophic factor (CNTF)-injected group served as positive control. The experiment was terminated on day 30.

ONC and dsRNA Injection

Adult, female 200-250 g Wistar rats were anaesthetised intraperitoneally with Hypnorm/Hypnovel anaesthetic (Janssen Pharmaceuticals, Oxford, UK) and the optic nerves (ON) of both eyes were crushed (ONC model) intraorbitally to completely transect all RGC axons. All reagents were intravitreally injected using glass micropipettes in a final volume of 10 μl. Animals were treated with either:

(i) PBS;

(ii) 20 μg dsEGFP control compound EGFP_5_S763_L1 dsRNA;

Sense strand:
rG;mG;rC;mU;rA;mC;rG;mU;rC;mC;rA;mG;rG;mA;rG; mC;rG;mC;rA;mC;rC$;

AntiSense strand:
mG;rG;mU;rG;mC;rG;mC;rU;mC;rC;mU;rG;mG;rA;mC; rG;mU;rA;mG;rC;mC$;

(mC, mG, mA and mU designate 2'OMe sugar modified ribonucleotides; C, G, A and U designate unmodified ribonucleotides; $ designates no terminal Pi), (iii) 10 μg, 20 μg or 40 μg of dsRhoA compound RHOA_4_S500, also designated as "RhoA Batch 1":

Sense strand:
rG;mC;rC;mA;rC;mU;rU;mA;rA;mU;rG;mU;rA;mU;rG; mU;rU;mA;rC

AntiSense strand:
mG;rU;mA;rA;mC;rA;mU;rA;mC;rA;mU;rU;mA;rA;mG; rU;mG;rG;mC (mC, mG, mA and mU designate 2'OMe sugar modified ribonucleotides; C, G, A and U designate unmodified ribonucleotides);

(iv) 10 μg, 20 μg or 40 μg of dsRhoA compound RHOA_29_S73, "RhoA Batch 2":

```
Sense strand:
                                                    (SEQ ID NO: 166)
U; mC; G; mA; C; mA; G; mC; C; mC; U; mG; A; mU; A; mG; U; mU; U$ AntiSense strand:
                                                    (SEQ ID NO: 170)
mA; A; mA; C; mU; A; mU; C; mA; G; mG; G; mC; U; mG; U; mC; G; mA$
```

(mC, mG, mA and mU designate 2'OMe sugar modified ribonucleotides; C, G, A and U designate unmodified ribonucleotides; $ designates no terminal Pi); or (v) 5 μg CNTF (Peprotech Ltd, London, UK);

at day 0, 10 and 20 post ONC.

At 30 days post-ONC, animals were sacrificed by exposure to $CO_2$ and intracardially perfused with 4% formaldehyde (TAAB Laboratories, Aldermaston, UK). Retinas were dissected out and immersion fixed in 4% formaldehyde (TAAB Laboratories) for 30 minutes followed by 3 washes in PBS for 30 minutes each. Eyes and ON were then cryoprotected in 10, 20 and 30% sucrose for 2 hours each, prior to blocking up samples in O.C.T. compound and frozen on dry ice. Sections 15 μm thick were cut using a cryostat and adhered onto Superfrost slides and stored at −20° C. until required.

RGC Counts

Sections of eyes taken at the point of where the optic disc was visible were allowed to thaw at room temperature for 30 minutes prior to staining in Haemotoxylin (Sigma, Poole, UK) for 2 minutes, washed in running tap water for 2 minutes, washed in Scotts tap water for 1 minute, prior to staining in Eosin (Sigma) for 30 seconds. Sections were then washed in running tap water for 2 minutes and dehydrated through a graded series of alcohols for 1 minute each and immersed in Histoclear for 1 and 3 minutes prior to mounting in Vectamount (Vector Labs, Peterborough, UK). Five areas of each retina equidistant from each other and covering the entire circumference of the retina were used to count the number of RGCs present in the ganglion cell layer. Counts from 4 retinas, 5 areas/condition were added together and averaged to represent the mean RGC count/retina±SD.

Immunohistochemistry

For double immunofluorescent staining, sections were post-fixed in 100% ethanol for 1 minute, washed ×3 in phosphate buffered saline (PBS), permeabilized in 0.1% Triton X-100, washed, blocked and incubated with the appropriate primary antibody (Table 3) diluted in PBS containing 0.5% bovine serum albumin (BSA; Sigma) and 0.05% Tween 20 (PBST-BSA) (Sigma), overnight at 4° C.

TABLE 3

Properties of antibodies used.

| Antibody | Source | Dilution |
|---|---|---|
| Mouse anti GAP43 | Zymed Labs | 1:500 |
| Rabbit anti Laminin | Sigma | 1:200 |
| Mouse anti rat CD68 (ED1) | Serotec | 1:500 |
| Rabbit anti human Fibronectin | Sigma | 1:500 |
| Rabbit anti NG2 | Chemicon | 1:500 |
| Mouse anti GFAP | Sigma | 1:500 |

Sections were then washed in PBS and incubated with the appropriate fluorescent labelled secondary antibody (either Alexa-488 or Texas Red; Molecular Probes, Oregon, USA) diluted 1:400 in PBST-BSA for 1 hour at room temperature and after further washed in PBS, were mounted in Vectashield containing DAPI (Vector Labs, Peterborough, UK). Controls included sections that omitted the primary antibody or specific IgG controls. Sections were viewed under a Zeiss epifluorescent microscope (Zeiss, Hertfordshire, UK) and images captured using an AxioCam® HRc controlled by Axiovision® Software (Zeiss, Version 4,2) at ×10 magnification (×100 original magnification). All images were compiled in Adobe Photoshop CS3 (Adobe Systems, San Jose, Calif., USA).

Results: Mean RGC survival after dsRhoA treatment is shown in FIG. 2.

Figure 3:
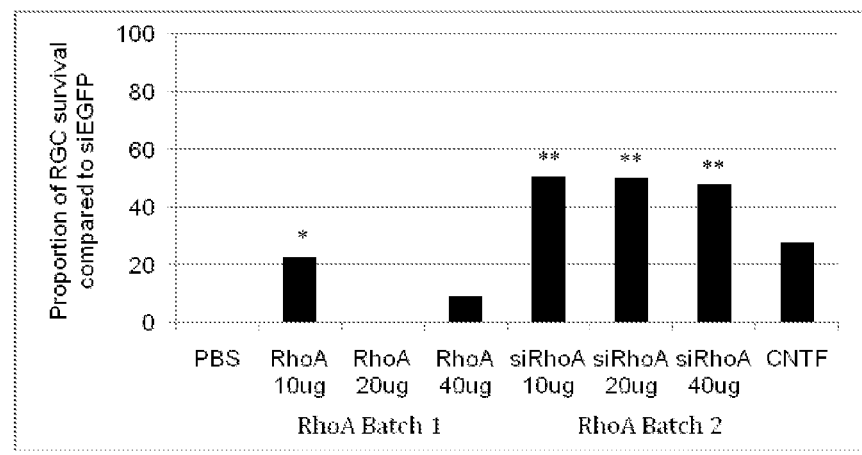
FIG. 3: Promotion of RGC survival compared to dsEGFP in in-vivo Study Measuring the Ability of Escalating Doses of dsRhoA Compound to Induce RGC Axon Regeneration Following Optic Nerve Crush in Rats

Promotion of RGC survival by RhoA dsRNA compounds as compared to dsEGFP compound is shown in FIG. 3.

The results show that the dsRhoA compound RHOA_29_S73, also designated as "RhoA Batch 2", promoted significant RGC survival at 30 days. Upon treatment with this dsRhoA compound, >50% more RGC survival was observed compared to PBS treated controls and ca 20% more RGC survival was observed compared to CNTF treated controls, at 30 days post injury, this represents a significant advance on current neuroprotective therapies.

Dose-Dependent Pharmacodynamic Effect of Test dsRhoA Compound in Rat Retina and its Tissue Distribution:

Groups of 8 intact rats (n=8) are injected IVT with escalating doses of test dsRhoA compound or control dsRNA compound (siCNL) (5, 10, 20 and 40 μg) and sacrificed 24 hours later. Eyes of 6 rats per group are enucleated, retinas dissected and used for dsRNA quantification, mRNA knockdown measurement and RNAi confirmation using RLM-RACE. Two remaining rats per group are transcardially perfused with 4% PFA, eyes enucleated, post fixed, paraffin embedded and used for in situ hybridization detection of dsRNA distribution in the eye.

Example 6

Selection of Optimal Dose Per Model Per Route of Delivery

Evaluation of Duration of dsRNA Effect:

Duration of therapeutic effect of a single administration of test dsRhoA compound is analyzed under the optimal conditions found as described above. The end point for evaluation is duration of IOP-lowering activity in the glaucoma model and duration of RhoA knockdown effect in the retina.

Duration of dsRhoA Test Compound Effect in High IOP Model:

High IOP model is induced as described above. Rats (n=4) are treated with the optimal dose of test dsRhoA compound via IVT injection or with an optimal ED regiment (over one day) found as described above. Control animals are similarly treated with siCNL. Efficacy and duration of effect of the test dsRhoA candidate compound is examined by daily monitoring IOP until it is raised again in dsRhoA group after the drug ceases to work. Without being bound by theory, it is believed that this time interval is equivalent to the duration of dsRhoA RNAi effect in the trabecular meshwork.

Duration of dsRhoA Test Compound Pharmacodynamic (RNAi) Effect in the Retina:

To establish the duration of effect of the test dsRhoA candidate compound in the retina, dsRhoA compound at the best IVT dose found as described above is administered via single IVT injection into naïve rats. siCNL is administered at the same IVT dose to a separate group of rats. The animals are sacrificed at 1, 2, 3, 5, 7, 10 and 14 days after injection (n=6 per time point). The eyes are enucleated, retinas dissected and used for (1) dsRNA quantification using Stem&Loop qPCR; (2) target knockdown measurement using qPCR; and (3) RNAi confirmation using RLM-RACE.

Example 7

Effect of dsRNA Compounds Targeting RhoA on Neuronal Survival and Axon Regeneration in the Rat Optic Nerve Crush (ONC) Model Study design: Termination for groups is 30 or 50 days post ONC. dsRNA administration for all groups is via bilateral intravitreal injection (IVT) every 10 days.

Groups 1-12 undergo bilateral ONC. Each pair eyes receive the same treatment.

TABLE 4

Study Design

| Group number | Compound administered (dose per administration) | Lens Injury | Termination (days post ONC) | Post-termination analysis | N (rats) | Total siRNA quantity (ug) |
|---|---|---|---|---|---|---|
| 1 | dsRHOA (20 ug) | Yes | 30 | Axon regrowth RGC counts | 4 | 480 + 480 |
| 2 | dsRHOA (20 ug) | Yes | 50 | Axon regrowth RGC counts | 4 | 800 + 800 |
| 3 | dsRHOA (20 ug) + dsEGFP (20 μg) | No | 30 | Axon regrowth RGC counts | 4 | 480 + 480 |
| 4 | dsRHOA (20 μg) + dsEGFP (20 μg) | Yes | 30 | Axon regrowth RGC counts | 4 | 480 + 480 |
| 5 | dsEGFP (40 ug) | No | 30 | Axon regrowth RGC counts | 4 | 960 |
| 6 | Lens Injury + dsEGFP (40 ug) | Yes | 30 | Axon regrowth RGC counts | 4 | 960 |
| 7 | PBS vehicle | No | 30 | Axon regrowth RGC counts | 4 | 0 |
| 8 | Intact | N/A | N/A | RGC counts | 4 | 0 |

Experimental Design:

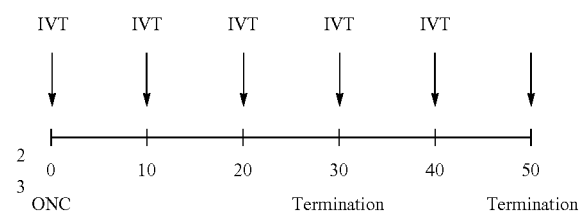

Measured End-Points:
Histology fixed and frozen tissue sections:
a) GAP43 for RGC axon regeneration in optic nerve
b) TUJ1 for RGC survival in retina Test dsRNA are disclosed throughout this application. CNTF-injected group serves as positive control. The experiment is terminated on day 30 for all groups except for group 2, which is terminated on day 50.

ONC and siRNA Injection

Adult, female 200-250 g Wistar rats are anesthetized intraperitoneally with Hypnorm/Hypnovel anaesthetic (Janssen Pharmaceuticals, Oxford, UK) and the ONs of both eyes are crushed (ONC) intraorbitally to completely transect all RGC axons. All reagents are intravitreally injected using glass micropipettes in a final volume of 10 μl. Animals are treated according to the study design in Table 4.

At 30 days post-ONC or 50 days post-ONC (according to the study design), animals are sacrificed by exposure to $CO_2$ and intracardially perfused with 4% formaldehyde (TAAB Laboratories, Aldermaston, UK). Retinas are dissected out and immersion fixed in 4% formaldehyde (TAAB Laboratories) for 30 minutes followed by 3 washes in PBS for 30 minutes each. Eyes and ON are then cryoprotected in 10, 20 and 30% sucrose for 2 hours each prior to blocking up samples in OCT and frozen on dry ice. Sections 15 μm thick are cut using a cryostat and adhered onto Superfrost slides and stored at −20° C. until required.

RGC Counts

Sections of eyes taken at the point of where the optic disc is visible are allowed to thaw at room temperature for 30 minutes prior to staining in Haemotoxylin (Sigma, Poole, UK) for 2 minutes, washed in running tap water for 2 minutes, washed in Scotts tap water for 1 minute, prior to staining in Eosin (Sigma) for 30 seconds. Sections are then washed in running tap water for 2 minutes and dehydrated through a graded series of alcohols for 1 minute each and immersed in Histoclear for 1 and 3 minutes prior to mounting in Vectamount (Vector Labs, Peterborough, UK). Five areas of each retina equidistant from each other and covering the entire circumference of the retina are used to count the number of RGC present in the ganglion cell layer. Counts from 4 retinas, 5 areas/condition are added together and averaged to represent the mean RGC count/retina±SD.

Immunohistochemistry

For double immunofluorescent staining, sections are post-fixed in 100% ethanol for 1 minute, washed ×3 in phosphate buffered saline (PBS), permeabilized in 0.1% Triton X-100, washed, blocked and incubated with the appropriate primary antibody (Table 3) diluted in PBS containing 0.5% bovine serum albumin (BSA; Sigma) and 0.05% Tween 20 (PBST-BSA) (Sigma), overnight at 4° C.

Sections are then washed in PBS and incubated with the appropriate fluorescent labelled secondary antibody (either Alexa-488 or Texas Red; Molecular Probes, Oregon, USA) diluted 1:400 in PBST-BSA for 1 hour at room temperature and after further washes in PBS, are mounted in Vectashield containing DAPI (Vector Labs, Peterborough, UK). Controls include sections that omit the primary antibody or specific IgG controls. Sections are viewed under a Zeiss epifluorescent microscope (Zeiss, Hertfordshire, UK) and images captured using an AxioCam® HRc controlled by Axiovision® Software (Zeiss, Version 4,2) at ×10 magnification (×100 original magnification). All images are compiled in Adobe Photoshop CS3 (Adobe Systems, San Jose, Calif., USA).

dsRhoA compounds disclosed herein are tested in this experiment and are shown to induce neuroprotection. The number of RGCs rescued after ONC is significantly higher in the dsRhoA treated groups than in the group treated with dsEGFP control dsRNA.

Example 8

Cortical Neuron Protection

To assess the in vitro neuroprotectant effect of dsRhoA compound, mouse cortical neurons grown in culture are exposed for 5 minutes to NMDA, and cell death after 24 hours is monitored by measuring the release of lactate dehydrogenase, (LDH) (Choi et al., J. Neurosci. 7: 357, 1987). Additional testing to determine potential therapeutic efficacy involves in vivo stroke models. In these models, the blood supply is temporarily blocked by clamping the main arteries to the brain.

Example 9

Model Systems for Meniere's Disease dsRhoA compounds disclosed herein are effective in attenuating or treating hearing loss in patients suffering from Meniere's disease and, without wishing to be bound to theory, act to protect the auditory neurons from neuronal damage associated with Meniere's disease. Exemplary models for testing efficacy of dsRhoA compounds in treating Meniere's disease/as a neuroprotectant and or neural regeneration factor in Meniere's disease are as follows:

Sheykholeslami K, Megerian C A, Zheng Q Y. Vestibular evoked myogenic potentials in normal mice and Phex mice with spontaneous endolymphatic hydrops. Otol Neurotol. 2009 June; 30(4):535-44; Megerian C A, Semaan M T, Aftab S, Kisley L B, Zheng Q Y, Pawlowski K S, Wright C G, Alagramam K N. A mouse model with postnatal endolymphatic hydrops and hearing loss. Hear Res. 2008 March; 237(1-2):90-105; Semaan M T, Alagramam K N, Megerian C A. The basic science of Meniere's disease and endolymphatic hydrops. Curr Opin Otolaryngol Head Neck Surg. 2005 October; 13(5):301-7.

Example 10

In-Vivo Study Measuring the Efficacy of dsRhoA Compounds in Attenuating or Treating Hearing Loss in a Mice Model of Meniere's Disease Study Objectives:

Assessment of efficacy of four selected dsRNA compounds in mouse genetic model of Meniere's disease by using functional and histological evaluation.

Study Design

Functional tests are performed weekly from day 29 on the day of test or control articles administration and prior to their administration. dsRNA administration requires animal immobilization (anesthesia) for 40-60 minutes. Functional tests in intact non-treated mice of the same age serve as baseline control.

Application of Test Items by Ear Drops

Anesthesia: The mice are anesthetized with 4 ml/kg body weight of Equithesine (Intraperitoneal, I.P.).

External Auditory Canal (Right (REAC) eardrops (ErD) delivery: A 3 µl sample volume (warm 10% glycerol based eardrops, 37° C.) is slowly instilled into the right external auditory canal (REAC), using a blunt pipette tip. During and after REAC ErD administration, the mice are kept on the contra lateral recumbence for one hour, and are returned to their cage after they regain consciousness.

Preparation of the Formulated Test Item in 10% Glycerol—Description of the Test Material:

dsRNA is precipitated by lyophilization under sterile conditions.

10% Glycerol solution is added to the test compound and left to stand for 15 minutes. Then it is vortexed for 10 seconds. Prior to application the eardrops are brought to a temperature of 37° C.

Upon termination, inner ears of mice are dissected, fixed, embedded in paraffin and sectioned to have representation of both auditory and vestibular compartments as well as of spiral ganglion. The slides are used for histological evaluation of inner ear morphology.

Six slides per ear including two 5 micron sections per slide are used for in-situ hybridization analysis of dsRNA distribution in the inner ear. Fifteen (15) slides of a non-treated, intact mouse ear are used for calibration of the system.

RhoA dsRNA compounds disclosed herein are tested in this study, that shows that at 6 weeks of model induction, RhoA dsRNA induces a significant improvement in all functional tests of the RhoA dsRNA treated mice, as compared to the vehicle treated group and as compared to the control dsRNA treated group. This improvement is maintained till the

TABLE 5

Study design

| Group (n = 12) | Test Compound | Treatment frequency | Functional tests | Termination |
|---|---|---|---|---|
| 1 | dsCASP2 compound (test 1) | P15, P22, P29, P36, P42, P49, P56, P63, P70, P77, P84 | P29, P36, P42, P49, P56, P63, P70, P77, P84, P90 | P90 |
| 2 | dsNOX3 compound (test 2) | P15, P22, P29, P36, P42, P49, P56, P63, P70, P77, P84 | P29, P36, P42, P49, P56, P63, P70, P77, P84, P90 | P90 |
| 3 | dsCAPNS compound (test 3) | P15, P22, P29, P36, P42, P49, P56, P63, P70, P77, P84 | P29, P36, P42, P49, P56, P63, P70, P77, P84, P90 | P90 |
| 4 | dsRHOA compound (test 4) | P15, P22, P29, P36, P42, P49, P56, P63, P70, P77, P84 | P29, P36, P42, P49, P56, P63, P70, P77, P84, P90 | P90 |
| 5 | dsEGFP compound (negative control) | P15, P22, P29, P36, P42, P49, P56, P63, P70, P77, P84 | P29, P36, P42, P49, P56, P63, P70, P77, P84, P90 | P90 |
| 6 | Vehicle (negative control) | P15, P22, P29, P36, P42, P49, P56, P63, P70, P77, P84 | P29, P36, P42, P49, P56, P63, P70, P77, P84, P90 | P90 |
| 7 | Intact (negative control) | none | P29, P36, P42, P49, P56, P63, P70, P77, P84, P90 | P90 |

Note:
"P" is the abbreviation of "postnatal day".

end of the study. These results indicated that RhoA dsRNA compounds disclosed herein are useful in treating Ménière's Disease.

Example 11

Model Systems for Corneal Neovascularization

The aim of this study is the assessment of the therapeutic effect of RhoA dsRNA compound applied by subconjunctival injection in a murine suture model of corneal neovascularization.

The study design includes 9 experimental groups containing 6 mice each. The cornea of both eyes of each mouse are sutured at 2 points with 11-0 nylon to induce corneal neovascularization. In contrast to scraping, sutures provide neovascularization in about 2 weeks, they provide greater consistency between eyes in the vessel growth; and induce more neovascularization. One day after corneal suturing the test item dsRhoA compound or control PBS vehicle are injected subconjunctivally into both eyes. Thereafter dsRhoA compound or control PBS vehicle is injected twice per week, on days 3, 7 and 10 (a total of 4 applications).

To control for the possibility that subconjunctival injection induces neovascularization, control group #9 is included, using vehicle injection without dsRNA compound (Table 6).

TABLE 6

Study Design

| Group # | Targeted Gene | Dose/injection (µg)- Bilateral | # Applications/ Week | Termination (days) | Group size |
|---|---|---|---|---|---|
| 1 | dsRhoA | 10 | 3 | 35 | 6 |
| 2 | dsRhoA | 30 | 3 | 35 | 6 |
| 3 | dsRhoA | 50 | 3 | 35 | 6 |
| 4 | dsRhoA | 100 | 3 | 35 | 6 |
| 5 | dsEGFP | 10 | 3 | 35 | 6 |
| 6 | dsEGFP | 30 | 3 | 35 | 6 |
| 7 | dsEGFP | 50 | 3 | 35 | 6 |
| 8 | dsEGFP | 100 | 3 | 35 | 6 |
| 9 | Vehicle PBS | — | 3 | 35 | 6 |

Anesthesia: Mice are anesthetized with ketamine/xylazine or avertine. The cornea of all mice is anesthetized with 5 microliters proparacaine (topical anesthetics).

Corneal Sutures Procedure: The cornea (of both eyes of each mouse) is sutured at 2 points with a 11-0 nylon thread. The purpose of cornea suturing is to induce corneal neovascularization. Sutures provide neovascularization in about 2 weeks. (As opposed to scraping, sutures provide greater consistency between eyes in the vessel growth and they induce more neovascularization).

Surgery Procedures:
A) Mice are anesthetized with avertine.
B) Mice whisker and excessive long eye lashes are cut by scissors.
C) The first 11-0 nylon suture is performed at a 12 o'clock position between center of cornea and limbus using a 2-1-1 knot. Corneal endothelium-puncture suture is intended to induce neovascularization and maintains suture in place.
D) The second 11-0 nylon suture is done at 6 o'clock position (opposite position to the first suture) between center of cornea and limbus using 2-1-1 knot.
E) Topical bacitracin antibiotic ointment is applied to the eye surface.
F) Mouse is returned to their cage and monitored until ambulatory.
G) Mice are checked the following day and antibiotic ointment is re-applied.

Subconjunctival Injections:
One day after suturing and thereafter twice a week of days 3, 7, and 10. The mice are given bilateral subconjunctival injections as follows:
a. Mice are anesthetized with avertine.
b. Mice are placed on a water re-circulating heating pad under a surgical microscope in JMEC A0612
c. 5 microliters of tropicamide (dialation) & 5 microliters of propericaine (topical anesthetic) is topically administered to each eye using a micropipette.
d. Any excessively long eyelashes are trimmed with vannas scissors.
e. A 32 gauge gas-tight micro-syringe (Hamilton Company) is inserted into the subconjunctiva to deliver dsRhoA compound or PBS (control group) at 1 mm behind the limbus, in both eyes.
f. The needle is removed and topical bacitracin antibiotic ointment is applied to the eye surface.
g. Mouse is returned to cage and monitored until ambulatory.
h. Mice are checked the following day and antibiotic ointment is re-applied.

Evaluation
Data Generation and Analysis
Image of corneal vasculature (neovascularization): Microscopic pictures are captured with a camera attached to a surgical microscope. The same position is compared at each step of the study (each week, around cornea suture in both eyes). Corneal neovascularization is graded according to area and intensity of vessel from 0 to 5:
a. 0—(no neovascularization);
b. 1—(weak and tiny vessels from the limbus);
c. 2—(new vessels engrowing between limbus and corneal suture);
d. 3—(new vessels up until and around suture);
e. 4—(thick tortous new vessels up until and around suture), and
f. 5—(thick tortous new vessels over suture and toward corneal center).

Immunohistochemical staining for vascular endothelial cells: The mice eyes (both eyes) are harvested and the cornea is trimmed of remaining limbus and iris. Immunohistochemical staining for vascular endothelial cells is performed on corneal flat mounts by a masked investigator. Fresh corneas are dissected, rinsed in phosphate-buffered saline (PBS) for 30 minutes, and fixed in 100% acetone (Sigma) for 20 minutes. After washing in PBS, nonspecific binding is blocked with 0.1M PBS and 2% albumin (Sigma) for 3 nights at 4° C. temperature. Incubation with fluorescein isothiocyanate (FITC)—conjugated monoclonal anti-mouse CD31 antibody (BD Pharmingen) at a concentration of 1:500 and LYVE-1 (rabbit,ab 14917) at a concentration 1:200 in 0.1 M PBS and 2% albumin at 4° C. overnight, are followed by 1:1000 anti rabbit antibody-A546(A11010) for 1 hour and subsequent washes in PBS at room temperature. Corneas are mounted with an antifading agent (Gelmount; Biomeda, San Francisco, Calif.) and visualized with a fluorescent microscope.

Digital quantification of neovascularization: After immunochemical staining for vascular endothelial cells and flat mounting of cornea, images of the corneal vasculature are captured with a camera attached to a fluorescence microscope. The image is analyzed on a computer with commercial software (Microscope Software AxioVision LE) and the corneal neovascularization is quantified. Digital quantification of corneal neovascularization is performed. Images of the corneal vasculature are captured using a CD-330 charge-coupled device (CCD) camera attached to a fluorescent microscope. The images are analyzed using LSM-5 Image Examiner (Zeiss, Hamburg, Germany), resolved at 624 3 480 pixels, and converted to tagged image file format (TIFF) files. The neovascularization and lymphangiogenesis are quantified by setting a threshold level of fluorescence above which only vessels are captured. The entire mounted cornea is analyzed to minimize sampling bias. The quantification of the neovascularization and lymphangiogenesis is performed in masked fashion. The total corneal area is outlined using the innermost vessel of the limbal (rim of the cornea) arcade as the border. The total area of neovascularization and lymphangiogenesis is normalized to the total corneal area.

dsRhoA compounds utilizing the oligonucleotide sequences and structures provided herein are tested in this model and found useful in inducing a decrease in neovascularisation in the CNV induced eyes. The number of blood vessels counted in the dsRhoA compound treated group is significantly lower when compared to the dsEGFP compound treated groups.

Example 12

Assessment of RhoA mRNA Cleavage by dsRNA Compound Targeting RhoA in Retinal Ganglion Cells (RGCs) Following Different Administration Modes in Normal Rat The aim of this study is to obtain evidence of directed cleavage of RhoA mRNA in rat retinal ganglion cells (RGC) using dsRhoA compounds described herein. RACE (Rapid Amplification of cDNA Ends) assay is performed following three different modes of administration of dsRhoA compounds described herein: transtympanic (TT), Ear Drops (ErD) or Intravitreal Injections (IVT).

Test Articles
(i) Substance (unformulated compound) dsRNA compound described herein against RhoA mRNA
(ii) Formulated (formulated compound) 2 mg/ml of dsRNA compound in PBS for IVT groups 1-6 (1344 µg dsRNA compound in 672 µl PBS solution (2 mg/ml) divided into six tubes of 112 µl)
(iii) Formulated (formulated compound) (400 µg/30 µl/ear) dsRNA compound in PBS—for TT groups 7-10 (Four tubes containing 4.48 mg siRNA in 168 µl PBS solution (13.3 mg/ml))
(iv) Formulated (formulated compound) (200 µg/10 µl/ear) dsRNA compound in 10% glycerol—For ErD Groups 11-14 (Four tubes, each containing 2.24 mg siRNA in 56 µl 10% glycerol solution (20 mg/ml)).

Control Article(s) (Including Positive/Negative Controls and Vehicle)
(i) Vehicle PBS×1—For TT and IVT
(ii) Vehicle—10% sterile Glycerol solution in pyrogen free water fresh prepared for experiment—For ErD Test System
Animals used:
10-12 week old Sprague Dawley™ Hsd: Sprague Dawley™ SD™ (SD) Rats
Source: Harlan, Jerusalem Israel
Body Weight Range: 270-320 gr
Sex: Male
Group Size: n=4/12
Total number of animals: 80
Animal Husbandry Diet: Animals are provided an ad libitum commercial rodent diet (Harlan Teklad diet for rodents), and free access to drinking water.
Environment: (i) Acclimatization of at least 5 days. (ii) All animals are confined in a limited access facility with environmentally-controlled housing conditions throughout the entire study period, and maintained in accordance with approved standard operating procedures (SOPs). Automatically controlled environmental conditions are set to maintain temperature at 20-24° C. with a relative humidity (RH) of 30-70%, a 12-hour light/12-hour dark cycle and 15-30 air changes/hour in the study room. Temperature, RH and the light cycle are monitored by the control.

Experimental Design
General: The experimental setup includes 16 experimental groups (4/or 12 rats each; (study design Table 7)). Rats from experimental groups 1-6 are bilaterally injected (IVT) with 20 µg/10 µl of RhoA dsRNA compound. Rats from experimental groups 7-10 are injected unilaterally TT (Left ear) with 400 µg RhoA dsRNA compound in 30 µl PBS×1. Rats from experimental groups 11-14 are treated with single unilateral applications of eardrops (ErD) in the right ear (REAC): with 200 µg RhoA dsRNA compound in 10 µl glycerol 10%. Group 15-16 are carried out as intact control. Euthanasia and specimens harvesting are accomplished according to the study design (Table 7). Dissected retinas are transferred to positive cells separation or to qPCR analysis as described in Table 7.

TABLE 7

Study Design

| Group No.: | Application Mode | dsRNA Type | Dose/ Volume µg/30 | Vehicle | Time Point (hrs) | Group Size | Analytical Processing |
|---|---|---|---|---|---|---|---|
| 1 | IVT (Bilateral) | RhoA dsRNA compound | 20 µg/10 µl | PBSx1 | 24 | 4 | Disintegrated retinas (A) |
| 2 | IVT (Bilateral) | RhoA dsRNA compound | 20 µg/10 µl | PBSx1 | 24 | 4 | Whole Retinas (B) |
| 3 | IVT (Bilateral) | RhoA dsRNA compound | 20 µg/10 µl | PBSx1 | 48 | 4 | Disintegrated retinas (A) |
| 4 | IVT (Bilateral) | RhoA dsRNA compound | 20 µg/10 µl | PBSx1 | 48 | 4 | Whole Retinas (B) |
| 5 | IVT (Bilateral) | RhoA dsRNA compound | 20 µg/10 µl | PBSx1 | 72 | 4 | Disintegrated retinas (A) |
| 6 | IVT (Bilateral) | RhoA dsRNA compound | 20 µg/10 µl | PBSx1 | 72 | 4 | Whole Retinas (B) |

TABLE 7-continued

Study Design

| Group No.: | Application Mode | dsRNA Type | Dose/ Volume µg/30 | Vehicle | Time Point (hrs) | Group Size | Analytical Processing |
|---|---|---|---|---|---|---|---|
| 7 | TT Single (Left ear) | RhoA dsRNA compound | 400 µg/30 µl | PBSx1 | 48 | 4 | Disintegrated retinas (A) |
| 8 | TT Single (Left ear) | RhoA dsRNA compound | 400 µg/30 µl | PBSx1 | 48 | 4 | Whole Retinas (B) |
| 9 | TT Single (Left ear) | RhoA dsRNA compound | 400 µg/30 µl | PBSx1 | 72 | 4 | Disintegrated retinas (A) |
| 10 | TT Single (Left ear) | RhoA dsRNA compound | 400 µg/30 µl | PBSx1 | 72 | 4 | Whole Retinas (B) |
| 11 | ErD Single (REAC) | RhoA dsRNA compound | 200 µg/10 µl | Glycerol 10% | 48 | 4 | Disintegrated retinas (A) |
| 12 | ErD Single (REAC) | RhoA dsRNA compound | 200 µg/10 µl | Glycerol 10% | 48 | 4 | Whole Retinas (B) |
| 13 | ErD Single (REAC) | RhoA dsRNA compound | 200 µg/10 µl | Glycerol 10% | 72 | 4 | Disintegrated retinas (A) |
| 14 | ErD Single (REAC) | RhoA dsRNA compound | 200 µg/10 µl | Glycerol 10% | 72 | 4 | Whole Retinas (B) |
| 15 | Intact | N/A | N/A | N/A | 48 | 12 | Disintegrated retinas (A) |
| 16 | Intact | N/A | N/A | N/A | 48 | 12 | Whole Retinas (B) |

Anesthesia & Premedication:

For IVT injections: Animals are anesthetized by using an Isoflurane special circuit system (Stoelting, USA); working setup: 3-4.5% Isoflurane in $O_2$ at 600-200 ml/min O2 flow rate.

For ErD and TT treatments: Before general anesthesia all animals are inducted to the light anaesthetization using an Isoflurane special circuit system (Stoelting, USA); working setup: 3-4.5% Isoflurane in $O_2$ at 600-800 ml/min $O_2$ flow rate (3-4 minutes), and thereafter are deeply anesthetized by Equithesin (Intraperitoneal, I.P; 4 ml/kg)

Transtympanic injections (TT): A 30 µl sample volume (warm test article) is slowly instilled TT, using 0.3 ml syringes. This volume is delivered into left middle ear cavity. During and after TT instillations, rats are kept on the contra lateral recumbency for about one hour, and are returned to cage after regaining consciousness. TT instillation is performed under binocular microscope.

ErD application Right External Auditory Canal (REAC): A 10 µl sample volume (warm 10% glycerol based eardrops) is slowly instilled into REAC, using blunt pipette tip. During and after REAC instillations, rats are kept on the contra lateral recumbency following caone hour, and are returned to cage after regaining consciousness capability.

Scheduled euthanasia: All animals are deeply anaesthetized by Equithesin (4 ml/kg; I.P) and euthanized according to the study design (Table 7; time point)

Tissue Collection: Both Eyes will be enucleated and retinas will be dissected and processed for further analysis as follows:

"Disintegration processing": Both eyes from groups "retinas analytical processing A" are enucleated and stored on ice. The eyes are dissected. Each tube contains 2 dissected retinas from one animal. Dissected retinas are transferred into 15 ml tubes filled with 6 ml PBS containing $Ca^{+2}$ and $Mg^{+2}$. The tubes are transferred at room temperature for isolation of RGCs.

RGC isolation: Cells from Retinae tubes are dissociated using the "Neural Tissue—Dissociation Kit—Postnatal Neurons" Miltenyi Biotec Cat#130-094-202, as described in the manufacturing protocol. Macrophages are then eliminated using anti CD11b Microbeads (BD IMag™, Cat# IMAG558013) and the cells from the "CD11b Unbound" fraction are stained with anti CD90.1-PE Ab (eBioscience, Cat N 12-0900-83, Lot N E0138-253) for RGC separation by PE_Microbeads (BD IMag™, Cat#557899) to have "CD90.1 Bound" and "CD90.1 Unbound" populations, as described in the manufacturing protocol. Purity of RGCs is determined by FACS (Disqualification of samples TBD according CD90.1 purity level in "Bound" population).

Whole retina processing Dissected retinas from groups "retinas analytical processing B"" are enucleated and stored on ice. The eyes are dissected and collected into appropriate test tubes (each tube contains 2 dissected retinas from one animal) and immediately frozen in liquid nitrogen, and transferred for extraction of total RNA and further analysis.

Evaluation

All samples from analytical processing A & B, of each pooled retinal pairs are transferred for RNA extraction followed by either RACE analysis of the RhoA cleavage product or gene expression assessments.

RACE analysis: dsRNA compound directed cleavage of RhoA in rat retina is determined by the detection of the cleavage product using RACE (Rapid Amplification of cDNA Ends) assay in pooled retinal pairs from all study groups. The cleavage site is be verified by sequence analysis.

Samples RNA Isolation: From all groups RNA is processed from both RGCs (bound) and unbound samples according. Total RNA Isolation With EZ RNA" by double extraction. Part of the RNA is transferred cDNA preparation and qPCR analyses.

dsRNA compounds described herein are tested in this study and are found to generate direct cleavage of RhoA mRNA.

Example 13

In-Vivo Study of the Anti-Nociceptive and Analgesic Activity of dsRhoA Compounds in Spinal Nerve Ligation (SNL or Chung) Model of Neuropathic Pain in Rats The aim of this study is to evaluate the antinociceptive and analgesic activity of dsRhoA compounds disclosed herein in a spinal nerve ligation (SNL or Chung) model for neuropathic pain in rats.

On study day 0, all animals are subject to Chung surgery, which consists of an operation where the left L5-L6 spinal nerves are isolated and cut. Animals from groups 1M, 5M, 7M and 9M are implanted subcutaneously with ALZET osmotic pumps on the day of surgery and continuously treated with test items. Duration of pump performance is 28 days, while the pump releases test item from days 0 till 14 and saline from day 14 till 28 or the pump releases saline from day 0 till 14 and test item from days 14 till 28. Animals from groups 2M, 4M, 6M and 8M are dosed with test items on either day 1 or on day 14 after the insult, slowly in bolus via intrathecal (IT) tube which is inserted in spinal space at L4-L5 level.

Study design is provided in Table 8. Abbreviations: IT Pump—intrathecal pump implantation; IT single lumbar injection—intrathecal injection in the lumbar region.

TABLE 8

Study Design

| Group # | Group Size | Test Item | Route | Dose per animal | Volume | Dosing Regime | Testing Regime |
|---|---|---|---|---|---|---|---|
| 1M | N = 12 | Vehicle 1 (Saline) | IT Pump | 0 | 12 µl/day** | From day 0 until day 28 continuously | On study days 1, 14, 21 and 28 |
| 2M | N = 12 | Vehicle 2 (Saline) | IT Single lumbar injection | 0 | 40 µl bolus injection (slowly) | Once on day 1, 24 hours after surgery | On study days 1, 14, 16, 21 and 28 |
| 3M | N = 12 | Positive Control (Gabapentin) | IP | 150 mg/kg | 5 ml/kg | Once daily, 2 hours prior to testing on study days 14, 21 and 28 | On study days 1, 14, 21 and 28 |
| 4M | N = 12 | dsRNA1 (dsRhoA compound 1) | IT Single lumbar injection | 100 µg | 40 µl bolus injection (slowly) | Once on day 1, 24 hours after surgery | On study days 1, 14, 21 and 28 |
| 5M | N = 12 | dsRNA1 (dsRhoA compound 1) | IT Pump | 20 µg/day (total 280 µg) | 12 µl/day** | From day 0 until day 14* continuously | On study days 1, 14, 21 and 28 |
| 6M | N = 12 | dsRNA1 (dsRhoA compound 1) | IT Single lumbar injection | 100 µg | 40 µl bolus injection (slowly) | Once on day 14, post VF testing | On study days- 1, 14, 16, 21 and 28 |
| 7M | N = 12 | dsRNA1 (dsRhoA compound 1) | IT Pump | 20 µg/day (total 280 µg) | 12 µl/day** | From day 14 until day 28* continuously | On study days- 1, 14, 21 and 28 |
| 8M | N = 12 | dsRNA2 (dsRhoA compound 2) | IT Single lumbar injection | 100 µg | 40 µl bolus injection (slowly) | Once on day 1, 24 hours after surgery | On study days- 1, 14, 21 and 28 |
| 9M | N = 12 | dsRNA2 (dsRhoA compound 2) | IT Pump | 30 µg/day (total 420 µg) | 12 µl/day** | From day 0 until day 14* continuously | On study days- 1, 14, 21 and 28 |

*NOTE:
The animals from these groups are given saline via intrathecal pump implantation on days when TI is not administered. Groups 5M and 9M are administered 12 µl/day 0.9% saline IT from day 15 until day 28. Group 7M is administered 12 µl/day 0.9% saline IT from day 0 until day 13.

**NOTE:
The pumping rate is 0.5 µl/hr (±0.1 µl/hr). Duration of pump performance is 14 days. Reservoir volume is 200 µl.

Test Procedures:

Principles of the Chung Induced Model: The Chung model is a reliable model for neuropathic pain that enables the measurement of the animal's pain threshold immediately after the animal awakes from surgery.

Figure 4:
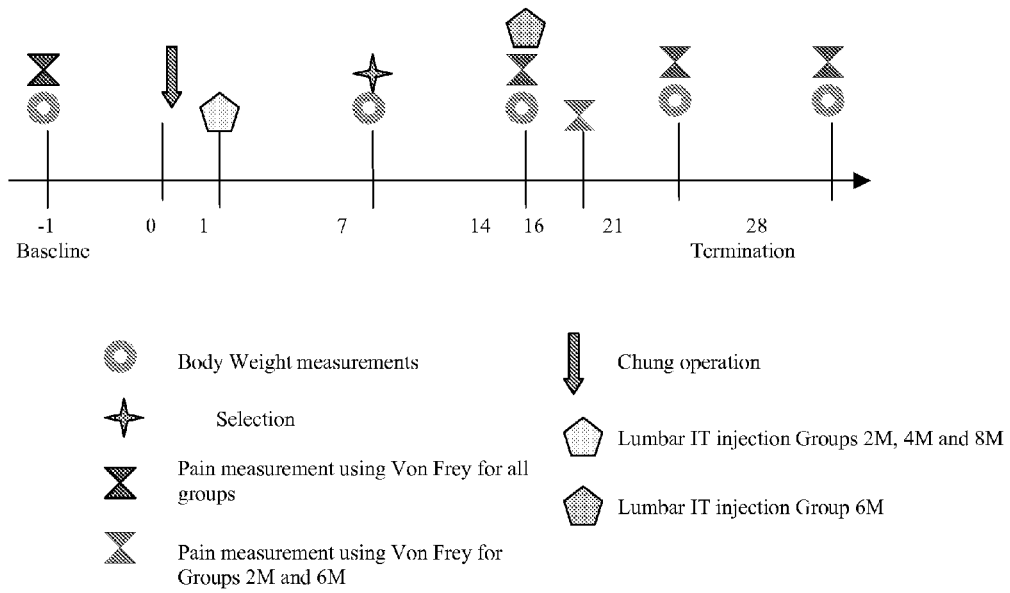
FIG. 4: Test Items administered via IT Pump Implantation and Gabapentin treatment
Figure 5:
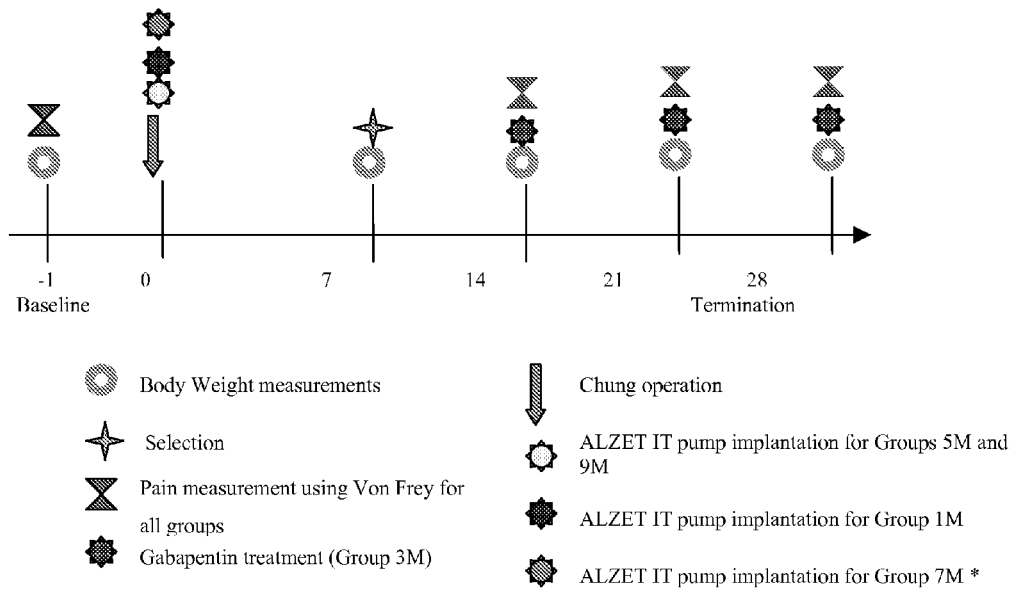
FIG. 5: Test Items administered via IT Single Lumbar Injection.

Schematic Description of Operation and Treatment are shown in FIGS. 4 and 5.

FIG. 4 for test items administered via it pump implantation and gabapentin treatment. (*NOTE: Saline drops are applied during the first 14 days (from day 0 until day 14) and the drug then is applied for further 14 days from day 14 until day 28 (Group 7M).)

FIG. 5 for test items administered via it single lumbar injection.

taneously with osmotic pumps on the day of surgery. The skin incision is then closed with 4-0 silk sutures. A polyethylene tubing is implanted in the intrathecal space of the spinal cord, ending at spinal L4 level. A cannula is then connected to the osmotic pump and filled with saline in the amount required for 2 weeks administration. Then, the cannula is filled with a small amount of air. The pumping rate is 0.5 µl/hr (±0.1 µl/hr). Duration of pump performance is 14 days. The pump is filled with TI at a volume of 200 µl. The intrathecal catheter is inserted in a length that matches as far as possible the length between Cisterna Magna to L4 vertebra so that the TI is administered at the area of L4. Animals from groups 1M, 5M, 7M and 9M are treated as specified in Table 8.

TABLE 9

Study Schedule (study day 1 through study day 28):

| Day | Task |
|---|---|
| −1 | Von Frey response measurements (baseline); Body weight measurements (baseline). |
| 0 | Chung operation, AlZET IT pump implantation (Groups 1M, 5M, 7M and 9M). |
| 1 | Lumbar TT injection (Groups 4M and 8M) |
| 7 | Body weight measurements. Selection. |
| 14 | Body weight measurements, Von Frey response measurements. Lumbar injection (Group 6M). |
| 16 | Von Frey response measurements for Groups 2M and 6M only. |
| 21 | Body weight measurements, Von Frey response measurements. |
| 28 | Body weight measurements, Von Frey response measurements, Termination |

Neuropathic Pain Induction: While under anesthesia using ketamine/xylazine sodium and after the area is shaved, the rat is placed in a prone position and the left paraspinal muscles are separated from the spinous process at the L4-S2 levels. The L6 vertebral transverse process is carefully removed with a small rongeur to visually identify the L5-L6 spinal nerves. The left L5-L6 spinal nerves are cut. The muscle is then closed with 4-0 silk sutures and the skin is closed by a clamp. Following surgery, the rats are returned to the cage and remain under a heating lamp until they are awake.

Inclusion/Exclusion Criteria for Pre-Selection:
a. Selection is performed on study day 7.
b. Pain is detected when one or more of the criteria below are met:
c. Licking of the operated paw, accompanied by gentle biting or pulling on the nails with the mouth;
d. Placing the leg in the air;
e. Boring weight on the side contra-lateral to the nerve injury;
f. Deformities of the hind paw and abnormal posture and walking;
g. Weakness of the left hind paw.
h. All of these are inclusion criteria.
i. The animal has to be able to move its leg to ensure that the L4 is intact. If the animal is unable to move its leg, it is excluded from the study.

In addition, careful clinical examinations are carried out on testing days. Observations include changes in skin, fur, eyes, mucous membranes, occurrence of secretions and excretions (e.g. diarrhea) and autonomic activity (e.g. lacrimation, salivation, piloerection, pupil size, unusual respiratory pattern). Changes in gait, posture and response to handling, as well as the presence of strange behavior, tremors, convulsions, sleep and coma are also observed. Animals showing one or more of the above signs are removed from the study.

ALZET Osmotic Pump Preparation and implantation: Animals from groups 1M, 5M, 7M and 9M are implanted subcu- Lumbar injections: Intrathecal tube is inserted in spinal space at L4-L5 level and the Test Items are dosed slowly in bolus.

Treatment

Treatment Commencement: Continuous treatment for 14 days via IT route using ALZET pump (Groups 5M, 7M and 9M). Continuous treatment for 28 days via IT route using ALZET pump (Group 1M).

Acute single treatment via IT route in lumbar regions.

Prophylactic treatment once on study day 1, using transtechal injection in the lumbar regions, 24 hours after surgery (Groups 4M and 8M).

Therapeutical treatment once on study day 14, using lumbar injections, prior to VF testing (Group 6M).

The positive control, gabapentin, (Group 3M) is administered once daily, 2 hours prior to pain testing on study days 14, 21 and 28.

Route of Administration

Routes of administration that are used in this study are described in Table 10.

TABLE 10

| Routes of Administration | |
|---|---|
| (i) Test Items dsRNA 1 and dsRNA 2 | IT Pump |
| (i) Test Items dsRNA 1 and dsRNA 2 | IT Lumbar injections |
| (ii) Vehicle 1 | IT Pump |
| (iv) Vehicle 2 | IT Lumbar injections |
| (iv) Positive Control (Gabapentin) | IP |

Termination

At the end of the study, the animals are euthanized with $CO_2$.

Observations and Calculations

Pain Response Evaluation: Pain response was evaluated using Von Frey test for mechanical allodynia. The Von Frey test for mechanical allodynia is based on applying short pulses of pressure that are not painful to a naïve animal. In fact, in order to achieve paw withdrawal from a naïve animal, the pressure applied is sometimes higher than 60 g. This often requires the researcher to apply enough pressure with the Von Frey filament to actually lift the paw of the naïve animal. However, in disease conditions, the animals are sensitive to much lower pressure and experience pain as a result of a normally non-painful stimulus.

Mechanical Allodynia Evaluation (Von Frey testing): Allodynic response to tactile stimulation is assessed using the Von Frey apparatus (Touch®). The rats are placed in an enclosure and positioned on a metal mesh surface, but allowed to move freely. The rats' cabins are covered with red cellophane to diminish environmental disturbances. The test begins after cessation of exploratory behavior. The set of Von Frey monofilaments provides an approximate logarithmic scale of actual force and a linear scale of perceived intensity as provided by the manufacturer of the Von Frey apparatus (Ugo Basil).

The operating principle: When the tip of a fiber of given length and diameter is pressed against the skin at right angles, the force of application increases as long as the researcher continues to advance the probe until the fiber bends. After the fiber bends, the probe continues to advance, causing the fiber to bend more, but without additional force being applied to the paw.

Table 11 shows the force (g) and its corresponding size of monofilaments.

TABLE 11

| Force (g) and its corresponding size of monofilaments | | | | | | | | | |
|---|---|---|---|---|---|---|---|---|---|
| Size | 1.65 | 2.36 | 2.44 | 2.83 | 3.22 | 3.61 | 3.84 | 4.08 | 4.17 | 4.31 |
| Force (g) | 0.008 | 0.02 | 0.04 | 0.07 | 0.16 | 0.40 | 0.60 | 1.00 | 1.40 | 2.00 |
| Size | 4.56 | 4.74 | 4.93 | 5.07 | 5.18 | 5.46 | 5.88 | 6.10 | 6.45 | 6.65 |
| Force (g) | 4.00 | 6.00 | 8.00 | 10 | 15 | 26 | 60 | 100 | 180 | 300 |

Rodents exhibit a paw withdrawal reflex when its paw is unexpectedly touched. The Touch Test™ Sensory Evaluator can be used on the plantar surfaces of the rat's foot. The animal will indicate sensation by pulling back its paw. The minimal force needed to elevate the withdrawal reflex is designated/considered as the value of reference.

Statistics/Data Evaluation:

All data are presented as means±SEM. Each treatment group is compared to its relevant Vehicle group using one way ANOVA followed by a Tukey post-test (Software: GraphPad Prism). One-way ANOVA repeated measures followed by a Tukey post-test is used to compare pre-treatment pain response to post-treatment pain response for each test group. A p value <0.05 is considered to represent a significant difference.

Results

Body Weight: Body weights are measured on study days −1, 7, 14, 21 and 28.

Von Frey Test: Results are presented as the mean force of withdrawal of left leg (g). The mechanical allodynia is observed as an increase in the animal sensitivity to the Von Frey filaments at different time points on study days 14, 16, 21 and 28.

Von Frey Response of animals treated via IT route using ALZET pump: The baseline average force required for withdrawal of the left operated leg of the Vehicle treated animals (Group 1M) is measured. On study days 14, 21 and 28, the withdrawal force of the left leg is measured again and compared to the baseline measurement.

dsRhoA compound disclosed herein are tested in this study and are found to be effective in reducing SNL induced neuropathic pain when administered via IT Pump using prophylactic treatment.

dsRhoA compound disclosed herein are tested in this study and are found to be effective in reducing SNL induced neuropathic pain when administered via IT Pump using therapeutic treatment.

Example 14

Model Systems of Diabetic Neuropathy

The aim of this study is the assessment of the therapeutic effect of RhoA dsRNA compound applied by intrathecal (IT) pump implantation or IT single lumbar injection—intrathecal injection in the lumbar region in a rodent suture model of corneal neovascularization.
Species/Strain: SD rats
Total population: 120; Population per group: 12
Test groups: 1 Vehicle Group
2 dsRNA control Group
6 Test Item (including dsRhoA and dsTLR4 compounds or a combination in different dosing regimes/routes)
1 Positive Control Group
Dosing regime: Once on study day 16 after selection Streptozocin (STZ)-induced diabetic rat study outline. STZ is dosed IV on study day 0. BGL is tested on study day 3 and there after once weekly. Pain threshold is tested on study day 16. Animals that show pain response are included in the study and are dosed with Test Item using IT route. Then pain threshold is re-tested on study day 21 and 28.

At termination the spinal cord and DRG are taken for further analysis as follows: The tissue for 6 animals are harvested for histology and the tissue from 6 animals are harvested for RNA analysis.

Body weight: Animal body weights is measured once weekly.

Read outs: Response to Von Frey dsRhoA compounds disclosed herein are tested in this model system and are shown to be effective in reducing neuropathic pain when administered alone, or in combination with another dsRNA compound that targets the TLR4 gene.

Example 15

Model Systems of Microvascular Disorders dsRhoA compounds disclosed herein are tested in animal models of a range of microvascular disorders as described below.
1. Diabetic Retinopathy Diabetes is induced in C57Bl6 mice, which are subsequently used for intravitreal injection of dsRhoA compound of the invention and control dsRNA compound. For diabetes induction, the mice are injected with streptozotocin (STZ 90 mg/kg/d for 2 days after overnight fast). Animal physiology is monitored throughout the study for changes in blood glucose, body weight, and hematocrit. Vehicle-injected mice serve as controls. The appropriate animals are treated by intravitreal injections of 1 ug of anti-RhoA dsRNA compound of the invention or 1 ug of anti-GFP control dsRNA compound. dsRNA compounds are injected twice in the course of the study—on day 0, when the first STZ injection was performed, and on day 14 after the STZ injection.

Retinal vascular leakage is measured using the Evans-blue (EB) dye technique on the animals after 4 weeks duration of diabetes. Mice have a catheter implanted into the right jugular vein 24 hours prior to Evans Blue (EB) measurements. Retinal permeability measurements in both eyes of each animal follow a standard Evans-blue protocol.

dsRhoA compounds disclosed herein are tested in this model system and are shown to be effective in reducing diabetes-induced retinal blood vessel leakage.

2. Retinopathy of Prematurity

Retinopathy of prematurity is induced by exposing the test animals to hypoxic and hyperoxic conditions, and subsequently testing the effects on the retina. dsRhoA compounds disclosed herein are tested in this model system and are shown to be effective in protecting the animal from retinopathy of prematurity.

3. Myocardial Infarction

Myocardial infarction is induced by Left Anterior Descending artery ligation in mice, both short term and long term. dsRhoA compounds disclosed herein are tested in this model system and are shown to be effective in reducing troponin-T (TnT) and MB fraction of total creatine phoshokinase (CPK-MB) levels at 24 hrs postinfarct in the blood of tested animals. Animals treated with dsRhoA compounds disclosed herein are having a better echocardiogram (ejection fraction volume) at 28 days postinfarct as compared to animals treated with control dsRNA compounds.

4. Closed Head Injury (CHI)

Experimental TBI produces a series of events contributing to neurological and neurometabolic cascades, which are related to the degree and extent of behavioral deficits. CHI is induced under anesthesia, while a weight is allowed to free-fall from a prefixed height (Chen et al, J. Neurotrauma 13, 557, 1996) over the exposed skull covering the left hemisphere in the midcoronal plane.

dsRhoA compounds disclosed herein are tested in this model system and are shown to be effective in treating TBI.

Example 16

Model Systems of Macular Degeneration dsRhoA compounds disclosed herein are tested in the following animal model of Choroidal neovascularization (CNV). This hallmark of wet AMD is induced in model animals by laser treatment.

Mouse model: Choroidal neovascularization (CNV) induction

Choroid neovascularization (CNV), a hallmark of wet AMD, is triggered by laser photocoagulation (532 nm, 200 mW, 100 ms, 75 μm) (OcuLight GL, Iridex, Mountain View, Calif.) performed on both eyes of each mouse on day 0 by a single individual masked to drug group assignment. Laser spots are applied in a standardized fashion around the optic nerve, using a slit lamp delivery system and a cover slip as a contact lens.

Treatment groups: CNV is induced in the following groups of mice (males 6-8 weeks of age):

12 WT mice;

12 WT mice injected (IVT) with 0.25 μg of RhoA dsRNA compound described herein in one eye and inactive anti-GFP dsRNA compound (negative control) in the fellow eye at days 0 and 7;

12 WT mice injected (IVT) with either 0.1 μg of RhoA dsRNA compound described herein in one eye and PBS (negative control) in the fellow eye at days 0 and 7;

12 WT mice injected (IVT) with either 0.05 μg of RhoA dsRNA compound described herein in one eye and PBS (negative control) in the fellow eye at days 0 and 7.

Both eyes of each mouse are laser-treated. The volume injected is 2 μl.

Evaluation

The experiment is terminated at day 14. For evaluation, the eyes are enucleated and fixed with 4% paraformaldehyde for 30 minutes at 4° C. The neurosensory retina is detached and severed from the optic nerve. The remaining RPE-choroid-sclera complex is flat mounted in Immu-Mount (Vectashield Mounting Medium, Vector) and coverslipped. Flat mounts are examined with a scanning laser confocal microscope (TCS SP, Leica, Germany). Vessels are visualized by exciting with blue argon laser. Horizontal optical sections (1 μm step) are obtained from the surface of the RPE-choroid-sclera complex. The deepest focal plane in which the surrounding choroidal vascular network connecting to the lesion could be identified is judged to be the floor of the lesion. Any vessel in the laser treated area and superficial to this reference plane is judged as CNV. Images of each section are digitally stored. The area of CNV-related fluorescence is measured by computerized image analysis using the Leica TCS SP software. The summation of whole fluorescent area in each horizontal section is used as an index for the volume of CNV.

Separate WT mice (5 eyes per group) were used for evaluating RhoA mRNA expression in CNV (as well as the expression of other genes relevant to AMD) (untreated and treated with dsRNA compounds disclosed herein) using real-time PCR on RNA extracted from RPE/choroids, or from neural retina.

dsRhoA compounds disclosed herein are tested in this model system and are shown to elicit reduction of the CNV volume.

Example 17

Assessment of dsRNA to RHOA for Attenuation of Tumor Growth

Methods:

(a) Subcutaneous tumor xenografts: About $5 \times 10^6$ A549 cells are injected into the hind leg of male athymic nude mice and the subcutaneous tumor is measured weekly. The tumor volumes are measured using the following formula: [length (mm)×width (mm)×width (mm)×0.52]. For in vivo delivery of dsiRNA into subcutaneous tumors, the test dsRNA duplexes are diluted in PBS and injected into the hind leg tumors using insulin syringes at a concentration of 10 μg/ml. In other animals intraperitoneal injections of carboplatin are given at a dose of 40 mg/kg body weight. The dsRNA and carboplatin are administered twice weekly for 4 weeks. In order to test the anti-tumor activity of the dsRNA of the invention in vivo, mice bearing subcutaneous tumors are treated with test dsRNA, by direct injection into the tumor and by carboplatin twice a week for 4 weeks and tumor weight is measured at the termination of the experiment.

(b) Lung metastasis experiments: About 2×10⁶ A549-C8-luc cells are injected into SCID-Beige mice (Charles River, Mass.) intravenously and the developing lung tumor is measured weekly. For aerosol delivery of test or control dsRNA into lung tumors, 100 µg of dsRNA diluted in PBS is aerosolized using a nebulizer. Mice are given three dose of dsRNA (100 µg/dose) every week, for 4 weeks, using a nebulizer. In control mice Intraperitoneal injections of carboplatin are given at a dose of 30 mg/kg body weight twice/week. Tumor weight is measured at the termination of the experiment.

The dsRNA molecules disclosed herein are tested in these animal models, and are effective at reducing tumor load in vivo and in the treatment of cancer.

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of chemical modifications described herein toward generating nucleic acid constructs with improved activity for mediating RNAi activity. Such improved activity can include improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifying nucleic acid molecules with improved RNAi activity.

The inventions illustratively described herein may suitably be practiced in the absence of any element or elements, limitation or limitations, not specifically disclosed herein. Thus, for example, the terms "a" and "an" and "the" and similar referents in the context of describing the invention (especially in the context of the following claims) are to be construed to cover both the singular and the plural, unless otherwise indicated herein or clearly contradicted by context. The terms "comprising", "having," "including," containing", etc. shall be read expansively and without limitation (e.g., meaning "including, but not limited to,"). Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

That which is claimed is:

1. A double-stranded ribonucleic acid molecule having the structure:

```
5'    UGUAGCAAGAUGACUUCUG-Z   3'  (antisense
      |||||||||||||||||||         SEQ ID NO: 113)
3' Z'-ACAUCGUUCUACUGAAGAC-z" 5'  (sense
                                  SEQ ID NO: 79)
``` wherein each "|" represents base pairing;

wherein each of A, C, G and U is independently an unmodified ribonucleotide, a modified ribonucleotide, or an unconventional moiety;

provided that on the antisense strand a mirror nucleotide or a 2'-5' linked ribonucleotide is present in at least one of positions 5, 6, 7 or 8 (5'>3'), 2'-O-Methyl sugar-modified ribonucleotides are present at positions 1, 3, 11, 14, 15, 17 and 18 (5'>3'), and Z is a C3Pi-C3OH moiety or a C3Pi-C3Pi moiety covalently attached at the 3' terminus of the antisense strand;

provided that on the sense strand a 2'-O-Methyl sugar-modified ribonucleotide is present at position 1, 2'-5' linked ribonucleotides are present at positions 15, 16, 17, 18 and 19 (5'>3'); and Z' is 1-5 consecutive nucleotides or non-nucleotide or unconventional moieties or a combination thereof covalently attached at the 3' terminus of the sense strand;

and wherein z" is a capping moiety covalently attached at the 5' terminus of the sense strand; or a pharmaceutically acceptable salt of such ribonucleic acid molecule.

2. The double-stranded ribonucleic acid molecule of claim 1, wherein the antisense strand is phosphorylated at the 5' terminus;

or a pharmaceutically acceptable salt of such ribonucleic acid molecule.

3. The double-stranded ribonucleic acid molecule of claim 1, wherein on the antisense strand a 2'-5' linked ribonucleotide is present at position 6, at position 7 or at positions 6 and 7; or a pharmaceutically acceptable salt of such ribonucleic acid molecule.

4. The double-stranded ribonucleic acid molecule of claim 3, wherein on the antisense strand a 2'-5' linked ribonucleotide is present at position 6; or a pharmaceutically acceptable salt of such ribonucleic acid molecule.

5. The double-stranded ribonucleic acid molecule of claim 1, wherein Z' is a non-nucleotide C3Pi moiety; or a pharmaceutically acceptable salt of such ribonucleic acid molecule.

6. The double-stranded ribonucleic acid molecule of claim 1, wherein z" is an inverted abasic deoxyribonucleotide; or a pharmaceutically acceptable salt of such ribonucleic acid molecule.

7. The double-stranded ribonucleic acid molecule of claim 1, wherein on the antisense strand 2'-O-Methyl sugar-modified ribonucleotides are present at positions 1, 3, 11, 14, 15, 17 and 18 (5'>3'), a 2'-5' linked ribonucleotide is present at position 6, and Z is a C3Pi-C3Pi non-nucleotide moiety; and wherein on the sense strand a 2'-O-Methyl sugar-modified ribonucleotide is present at position 1 (5'>3'), 2'-5' linked ribonucleotides are present at positions 15, 16, 17, 18 and 19 (5'>3'), Z' is a C3Pi non-nucleotide moiety, and z" is an inverted abasic deoxyribonucleotide capping moiety; or a pharmaceutically acceptable salt of such ribonucleic acid molecule.

8. The double-stranded ribonucleic acid molecule of claim 1, wherein on the antisense strand 2'-O-Methyl sugar-modified ribonucleotides are present at positions 1, 3, 11, 14, 15, 17 and 18 (5'>3'), a 2'-5' linked ribonucleotide is present at position 6, Z is a C3Pi-C3OH non-nucleotide moiety, and the 5' terminus is phosphorylated; and wherein on the sense strand a 2'-O-Methyl sugar-modified ribonucleotide is present at position 1 (5'>3'), 2'-5' linked ribonucleotides are present at positions 15, 16, 17, 18 and 19 (5'>3'), Z' is a C3Pi non-nucleotide moiety, and z" is an inverted abasic deoxyribonucleotide capping moiety; or a pharmaceutically acceptable salt of such ribonucleic acid molecule.

9. A pharmaceutical composition comprising the ribonucleic acid molecule or a pharmaceutically acceptable salt of such ribonucleic acid molecule of claim 1; and a pharmaceutically acceptable carrier.

* * * * *